US011970815B2

(12) United States Patent
Altman et al.

(10) Patent No.: US 11,970,815 B2
(45) Date of Patent: Apr. 30, 2024

(54) SILK PROTEIN BONDED LAYERED MATERIALS AND METHODS OF MAKING AND USING THEREOF

(71) Applicant: EVOLVED BY NATURE, INC., Medford, MA (US)

(72) Inventors: Gregory H. Altman, Providence, RI (US); Carlos J. Bosques, Arlington, MA (US); Enrico Mortarino, Hickory, NC (US)

(73) Assignee: EVOLVED BY NATURE, INC., Medford, MA (US)

( * ) Notice: Subject to any disclaimer, the term of this patent is extended or adjusted under 35 U.S.C. 154(b) by 278 days.

(21) Appl. No.: 17/628,471

(22) PCT Filed: Jul. 18, 2020

(86) PCT No.: PCT/US2020/042690
§ 371 (c)(1),
(2) Date: Jan. 19, 2022

(87) PCT Pub. No.: WO2021/016139
PCT Pub. Date: Jan. 28, 2021

(65) Prior Publication Data
US 2022/0275573 A1   Sep. 1, 2022

Related U.S. Application Data

(60) Provisional application No. 62/903,657, filed on Sep. 20, 2019, provisional application No. 62/876,386, filed on Jul. 19, 2019.

(51) Int. Cl.
*D06N 3/14*   (2006.01)
*D06N 3/12*   (2006.01)

(52) U.S. Cl.
CPC ............ *D06N 3/126* (2013.01); *D06N 3/128* (2013.01); *D06N 3/14* (2013.01);
(Continued)

(58) Field of Classification Search
CPC ............ C07K 14/43586; C08L 89/00; D06N 2201/042; D06N 2201/06; D06N 2211/28;
(Continued)

(56) References Cited

U.S. PATENT DOCUMENTS

| 2006/0222816 A1 | 10/2006 | Yoshida et al. |
| 2015/0033442 A1 | 2/2015 | Hasegawa |
| 2020/0256009 A1† | 8/2020 | Altman |

FOREIGN PATENT DOCUMENTS

| CN | 102505476 A | 6/2012 |
| CN | 107724079 A | 2/2018 |

(Continued)

OTHER PUBLICATIONS

PCT International Search Report and Written Opinion issued for corresponding PCT Application No. PCT/US2020/042690 dated Nov. 25, 2020 (12 pages).
(Continued)

*Primary Examiner* — Lawrence D Ferguson
(74) *Attorney, Agent, or Firm* — Morgan, Lewis & Bockius LLP

(57) ABSTRACT

Silk processed, coated, repaired, and/or infused faux or bonded leather, or faux or bonded leather articles, and methods of preparing the same are disclosed herein.

18 Claims, 26 Drawing Sheets

Specification includes a Sequence Listing.

(52) U.S. Cl.
CPC ... *D06N 2201/042* (2013.01); *D06N 2201/06* (2013.01); *D06N 2211/28* (2013.01)

(58) Field of Classification Search
CPC .......... D06N 3/126; D06N 3/128; D06N 3/14; D06N 2203/02; D06N 3/00; D06M 15/15
See application file for complete search history.

(56) References Cited

FOREIGN PATENT DOCUMENTS

| | | | |
|---|---|---|---|
| WO | 2013119551 | A1 † | 8/2013 |
| WO | 2017011679 | A1 † | 1/2017 |
| WO | 2019/067745 | A1 | 4/2019 |
| WO | 2019067745 | A1 † | 4/2019 |

OTHER PUBLICATIONS

Zhang et al. "Applications of natural silk protein sericin in biomaterials" Biotechnology Advances, vol. 20 (2002): pp. 91-100.

† cited by third party

FIG. 25

# SILK PROTEIN BONDED LAYERED MATERIALS AND METHODS OF MAKING AND USING THEREOF

CROSS-REFERENCE TO RELATED APPLICATION

This application is a National Stage of International Application No. PCT/US2020/042690, filed Jul. 18, 2020, which claims the benefit of U.S. Provisional Application Nos. 62/876,386, filed Jul. 19, 2019, and 62/903,657, filed Sep. 20, 2019, which are hereby incorporated by reference in their entirety.

REFERENCE TO SEQUENCE LISTING SUBMITTED ELECTRONICALLY

The sequence listing contained in the file named "032272-5018-US.txt", created on Dec. 7, 2022, and having a size of 13.5 kilobytes, has been submitted electronically herewith via EFS-Web, and the contents of the txt file are hereby incorporated by reference in their entirety.

FIELD

In some embodiments, the disclosure relates to faux or bonded leather including silk fibroin-based proteins or protein fragments thereof. In some embodiments, the present disclosure relates to novel silk protein bonded layered or spun materials, and specifically the non-woven materials, fibers, yarns and fabric formed of thereof, and methods of making thereof.

BACKGROUND

Silk is a natural polymer produced by a variety of insects and spiders, and comprises a filament core protein, silk fibroin, and a glue-like coating consisting of a non-filamentous protein, sericin. Silk fibers are lightweight, breathable, and hypoallergenic.

During the leather-making process, only 20-40 percent rawhide is finally processed to form leather, the rest becomes leftover wastes due to various defects, such as brand, crimple, hurt by grass thorns present in rawhide and other reasons. Additionally, a great mount of fractional materials generated during processing the leather products makes the availability of the sources very low. There are numerous reports on utilizing the scrap leather in the development of products that strive to simulate genuine leather texture. A typical product is bonded leather composed of polyvinyl chloride (PVC) or polyurethane and leather fiber. In such a material, scrap leather fiber is placed beneath the surface of the product, and dense overlay coats of PVC are applied. The product is then stamped to render a leather-like appearance. The majority of bonded leather products are board or paper-like, due to a failure to establish a true connection between the new material and leather.

This disclosure provides novel silk protein bonded layered or spun materials, and specifically the fibers, yarns and fabric formed of thereof that overcome the deficiencies of the typical bonded leather products as described above.

SUMMARY

In an embodiment, this disclosure provides a single or multilayered material including a plurality of fibers, filaments, powders, particles, or yarns, and a silk derived protein. In some embodiments, the material is a bonded leather. In some embodiments, the material is a faux or bonded leather. In some embodiments, the plurality of fibers, filaments, powders, particles, or yarns includes natural fibers, filaments, powders, particles, or yarns. In some embodiments, the plurality of fibers, filaments, powders, particles, or yarns includes synthetic fibers, filaments, powders, particles, or yarns. In some embodiments, the plurality of fibers, filaments, powders, particles, or yarns includes natural leather. In some embodiments, the plurality of fibers, filaments, powders, particles, or yarns includes leather waste. In some embodiments, the plurality of fibers, filaments, powders, particles, or yarns includes recycled leather. In some embodiments, the plurality of fibers, filaments, powders, particles, or yarns includes one or more of bovine wet blue shaving, bovine post-industrial waste, or sheep post-industrial waste. In some embodiments, the plurality of fibers, filaments, powders, particles, or yarns includes synthetic leather. In some embodiments, the plurality of fibers, filaments, powders, particles, or yarns includes one or more of silk, cotton, alpaca fleece, alpaca wool, lama fleece, lama wool, cashmere, sheep fleece, and sheep wool. In some embodiments, the plurality of fibers, filaments, powders, particles, or yarns includes one or more of polyester, nylon, and polyester-polyurethane copolymer. In some embodiments, the plurality of fibers, filaments, powders, particles, or yarns includes one or more of Lyocell and/or cellulose. In some embodiments, the plurality of fibers, filaments, powders, particles, or yarns includes one or more of acrylic, anidex, aramid, fluorocarbon, modacrylic, novoloid, nylon, nytril, olefin, PBI, polycarbonate, polyester, rubber, saran, spandex, vinal vinvon. In some embodiments, the plurality of fibers, filaments, powders, particles, or yarns includes one or more of non-woven or woven fibers or filaments, non-woven or woven mat or fabric, a woven, knitted, or crochet fabric, or any combination thereof.

In some embodiments, the silk derived protein includes sericin.

In some embodiments, the silk derived protein includes silk fibroin proteins or fragments thereof having an average weight average molecular weight in a range selected from between about 1 kDa and about 5 kDa, between about 5 kDa and about 10 kDa, between about 6 kDa and about 17 kDa, between about 10 kDa and about 15 kDa, between about 15 kDa and about 20 kDa, between about 17 kDa and about 39 kDa, between about 20 kDa and about 25 kDa, between about 25 kDa and about 30 kDa, between about 30 kDa and about 35 kDa, between about 35 kDa and about 40 kDa, between about 39 kDa and about 80 kDa, between about 40 kDa and about 45 kDa, between about 45 kDa and about 50 kDa, between about 60 kDa and about 100 kDa, and between about 80 kDa and about 144 kDa, and a polydispersity between 1 and about 5.

In some embodiments, the silk derived protein comprises one or more of low molecular weight silk fibroin proteins or fragments thereof, medium molecular weight silk fibroin proteins or fragments thereof, or high molecular weight silk fibroin proteins or fragments thereof. In some embodiments, the silk fibroin proteins or fragments thereof do not spontaneously or gradually gelate and do not visibly change in color or turbidity when in an aqueous solution for at least 10 days prior to being formulated into the material. In some embodiments, the amount by weight of the plurality of fibers, filaments, powders, particles, or yarns in the material is between about 40% and about 95%. In some embodiments, the amount by weight of the plurality of fibers, filaments, powders, particles, or yarns in the material is about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, or about 90%. In some embodiments, the amount by weight of the silk derived protein in the material is between about 0.01% and about 25%. In some embodiments, the amount by weight of the silk derived protein in the material is between about 25% and about 50%. In some embodiments, the amount by weight of the silk derived protein in the material is about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, or about 20%. In some embodiments, the amount by weight of the silk derived protein in the material is about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, or about 50%. In some embodiments, the material further includes one or more of a polymer, a pigment, a dye, or any combinations thereof. In some embodiments, the material further includes one or more of a silicone, a dye, a pigment, and a polyurethane.

In an embodiment, this disclosure provides an article including the material of the disclosure including a layer of material having a thickness between about 0.01 mm and about 10 mm. In some embodiments, the article includes a layer of material having a thickness of about 0.1 mm, about 0.2 mm, about 0.3 mm, about 0.4 mm, about 0.5 mm, about 0.6 mm, about 0.7 mm, about 0.8 mm, about 0.9 mm, about 1.0 mm, about 1.1 mm, about 1.2 mm, about 1.3 mm, about 1.4 mm, about 1.5 mm, about 1.6, mm, about 1.7 mm, about 1.8 mm, about 1.9 mm, about 2.0 mm, about 2.1 mm, about 2.2 mm, about 2.3 mm, about 2.4 mm, about 2.5 mm, about 2.6, mm, about 2.7 mm, about 2.8 mm, about 2.9 mm, about 3.0 mm, about 3.1 mm, about 3.2 mm, about 3.3 mm, about 3.4 mm, about 3.5 mm, about 3.6 mm, about 3.7 mm, about 3.8 mm, about 3.9 mm, about 4.0 mm, about 4.1 mm, about 4.2 mm, about 4.3 mm, about 4.4 mm, about 4.5 mm, about 4.6, mm, about 4.7 mm, about 4.8 mm, about 4.9 mm, or about 5.0 mm.

In some embodiments, the article includes a layer of material having a thickness of about 1 mm, about 2 mm, about 3 mm, about 4 mm, about 5 mm, about 6, mm, about 7 mm, about 8 mm, about 9 mm, or about 10 mm. In some embodiment, the article includes one or more of a coating, a laminated film, or a combination thereof. In some embodiments, the coating or the laminated film include one or more polymers selected from polyglycolide (PGA), polyethylene glycols, copolymers of glycolide, glycolide/L-lactide copolymers (PGA/PLLA), glycolide/trimethylene carbonate copolymers (PGA/TMC), polylactides (PLA), stereocopolymers of PLA, poly-L-lactide (PLLA), poly-DL-lactide (PDLLA), L-lactide/DL-lactide copolymers, co-polymers of PLA, lactide/tetramethylglycolide copolymers, lactide/trimethylene carbonate copolymers, lactide/δ-valerolactone copolymers, lactide/ε-caprolactone copolymers, polydepsipeptides, PLA/polyethylene oxide copolymers, unsymmetrically 3,6-substituted poly-1,4-dioxane-2,5-diones, poly-β-hydroxybutyrate (PHBA), PHBA/β-hydroxyvalerate copolymers (PHBA/HVA), poly-β-hydroxypropionate (PHPA), poly-p-dioxanone (PDS), poly-δ-valerolactone, poly-ε-caprolactone, methylmethacrylate-N-vinyl pyrrolidine copolymers, polyesteramides, polyesters of oxalic acid, polydihydropyrans, polyalkyl-2-cyanoacrylates, polyurethanes (PU), polyvinylalcohols (PVA), polypeptides, poly-β-malic acid (PMLA), poly-β-alkanoic acids, polyvinylalcohol (PVA), polyethyleneoxide (PEO), chitine polymers, polyethylene, polypropylene, polyasetal, polyamides, polyesters, polysulphone, polyether ether ketone, polyethylene terephthalate, polycarbonate, polyaryl ether ketone, and polyether ketone ketone. In some embodiments, the coating or the laminated film comprises silk fibroin proteins or fragments thereof having an average weight average molecular weight in a range selected from between about 1 kDa and about 5 kDa, between about 5 kDa and about 10 kDa, between about 6 kDa and about 17 kDa, between about 10 kDa and about 15 kDa, between about 15 kDa and about 20 kDa, between about 17 kDa and about 39 kDa, between about 20 kDa and about 25 kDa, between about 25 kDa and about 30 kDa, between about 30 kDa and about 35 kDa, between about 35 kDa and about 40 kDa, between about 39 kDa and about 80 kDa, between about 40 kDa and about 45 kDa, between about 45 kDa and about 50 kDa, between about 60 kDa and about 100 kDa, and between about 80 kDa and about 144 kDa, and a polydispersity between 1 and about 5. In some embodiments, the coating or the laminated film comprises silk fibroin proteins or fragments thereof having one or more of low molecular weight silk fibroin proteins or fragments thereof, medium molecular weight silk fibroin proteins or fragments thereof, or high molecular weight silk fibroin proteins or fragments thereof. In some embodiments, the silk fibroin proteins or fragments thereof do not spontaneously or gradually gelate and do not visibly change in color or turbidity when in an aqueous solution for at least 10 days prior to being formulated into the coating or the laminated film.

In an embodiment, this disclosure provides a method of making a material of the disclosure, or an article of the disclosure. In some embodiments, the method includes providing or obtaining the plurality of fibers, filaments, powders, particles, or yarns, and formulating with a silk derived protein composition.

In some embodiments, the concentration of silk derived protein in the silk derived protein composition is between about 0.1% w/v and about 15% w/v. In some embodiments, the concentration of silk derived protein in the silk derived protein composition is between about 5 mg/mL and about 125 mg/mL. In some embodiments, the silk derived protein composition further comprises a pH adjusting agent. In some embodiments, the pH adjusting agent is selected from ammonium hydroxide, citric acid, and hydrochloric acid. In some embodiments, the silk derived protein composition has a pH of about 2, about 3, about 4, about 5, about 6, about 7, about 8, about 9, about 10, about 11, or about 12. In some embodiments, the method further includes one or more additional steps selected from grinding, fibrillating, dyeing, drying, water annealing, mechanical stretching, trimming, performing one or more polishing steps, applying a pigment, applying a colorant, applying an acrylic formulation, chemical fixing, stamping, applying a silicone finish, providing a Uniflex treatment, and/or providing a Finiflex treatment.

In an embodiment, this disclosure provides an article comprising a plurality of fibers or yarns and a silk derived protein or fragments thereof. In some embodiments, the plurality of fibers are natural fibers, synthetic fibers, or a combination thereof. In some embodiments, the natural fibers or yarns include one or more of silk, cotton, alpaca fleece, alpaca wool, lama fleece, lama wool, cashmere, sheep fleece, and sheep wool. In some embodiments, the natural fibers or yarns include one or more of alpaca fiber, alpaca fleece, alpaca wool, lama fiber, lama fleece, lama wool, cotton, cashmere and sheep fiber, sheep fleece, sheep wool, byssus, chiengora, quiviut, yak, rabbit, lambswool, mohair wool, camel hair, angora wool, silkworm silk, abaca fiber, coir fiber, flax fiber, jute fiber, kapok fiber, kenaf fiber, raffia fiber, bamboo fiber, hemp, modal fiber, pina, ramie, sisal, and soy protein fiber.

In some embodiments, the synthetic fibers or yarns include one or more of polyester, nylon, and polyester-polyurethane copolymer. In some embodiments, the synthetic fibers or yarns include one or more of acrylic, anidex, aramid, fluorocarbon, modacrylic, novoloid, nylon, nytril, olefin, PBI, polycarbonate, polyester, rubber, saran, spandex, vinal vinvon.

In some embodiments, the silk derived protein includes sericin.

In some embodiments, the silk derived protein includes silk fibroin proteins or fragments thereof having an average weight average molecular weight in a range selected from between about 1 kDa and about 5 kDa, between about 5 kDa and about 10 kDa, between about 6 kDa and about 17 kDa, between about 10 kDa and about 15 kDa, between about 15 kDa and about 20 kDa, between about 17 kDa and about 39 kDa, between about 20 kDa and about 25 kDa, between about 25 kDa and about 30 kDa, between about 30 kDa and about 35 kDa, between about 35 kDa and about 40 kDa, between about 39 kDa and about 80 kDa, between about 40 kDa and about 45 kDa, between about 45 kDa and about 50 kDa, between about 60 kDa and about 100 kDa, and between about 80 kDa and about 144 kDa, and a polydispersity between 1 and about 5.

In an embodiment, this disclosure provides an article comprising a plurality of fibers or yarns and a silk derived protein or fragments thereof. In an embodiment, the disclosure provides an article comprising a plurality of fibers or yarns and a silk derived protein or fragments thereof, wherein a portion of the silk derived protein or fragments thereof are coated onto a plurality of fibers.

In some embodiments, the plurality of fibers are natural fibers, synthetic fibers, or a combination thereof. In some embodiments, the natural fibers or yarns include one or more of silk, cotton, alpaca fleece, alpaca wool, lama fleece, lama wool, cashmere, sheep fleece, and sheep wool. In some embodiments, the natural fibers or yarns include one or more of alpaca fiber, alpaca fleece, alpaca wool, lama fiber, lama fleece, lama wool, cotton, cashmere and sheep fiber, sheep fleece, sheep wool, byssus, chiengora, quiviut, yak, rabbit, lambswool, mohair wool, camel hair, angora wool, silkworm silk, abaca fiber, coir fiber, flax fiber, jute fiber, kapok fiber, kenaf fiber, raffia fiber, bamboo fiber, hemp, modal fiber, pina, ramie, sisal, and soy protein fiber.

In some embodiments, the synthetic fibers or yarns include one or more of polyester, nylon, and polyester-polyurethane copolymer. In some embodiments, the synthetic fibers or yarns include one or more of acrylic, anidex, aramid, fluorocarbon, modacrylic, novoloid, nylon, nytril, olefin, PBI, polycarbonate, polyester, rubber, saran, spandex, vinal vinvon.

In some embodiments, the silk derived protein includes sericin.

In some embodiments, the silk derived protein includes silk fibroin proteins or fragments thereof having an average weight average molecular weight in a range selected from between about 1 kDa and about 5 kDa, between about 5 kDa and about 10 kDa, between about 6 kDa and about 17 kDa, between about 10 kDa and about 15 kDa, between about 15 kDa and about 20 kDa, between about 17 kDa and about 39 kDa, between about 20 kDa and about 25 kDa, between about 25 kDa and about 30 kDa, between about 30 kDa and about 35 kDa, between about 35 kDa and about 40 kDa, between about 39 kDa and about 80 kDa, between about 40 kDa and about 45 kDa, between about 45 kDa and about 50 kDa, between about 60 kDa and about 100 kDa, and between about 80 kDa and about 144 kDa, and a polydispersity between 1 and about 5.

In some embodiments, the silk derived protein includes silk fibroin proteins or fragments thereof having one or more of low molecular weight silk fibroin proteins or fragments thereof, medium molecular weight silk fibroin proteins or fragments thereof, or high molecular weight silk fibroin proteins or fragments thereof.

In some embodiments, the silk fibroin proteins or fragments thereof do not spontaneously or gradually gelate and do not visibly change in color or turbidity when in an aqueous solution for at least 10 days prior to being formulated into the coating or the laminated film.

In some embodiments, the article is a spun yarn. In some embodiments, the spun yarn comprises one or more slivers comprising the plurality of fibers or yarns.

In some embodiments, the article further comprising one or more materials selected from ground up leather, ground up faux or bonded leather, rubber, a polymer, a pigment, a dye, or any combinations thereof.

In some embodiments, the article further comprising a coating.

In some embodiments, the coating includes one or more polymers selected from polyglycolide (PGA), polyethylene glycols, copolymers of glycolide, glycolide/L-lactide copolymers (PGA/PLLA), glycolide/trimethylene carbonate copolymers (PGA/TMC), polylactides (PLA), stereocopolymers of PLA, poly-L-lactide (PLLA), poly-DL-lactide (PDLLA), L-lactide/DL-lactide copolymers, co-polymers of PLA, lactide/tetramethylglycolide copolymers, lactide/trimethylene carbonate copolymers, lactide/δ-valerolactone copolymers, lactide/ε-caprolactone copolymers, polydepsipeptides, PLA/polyethylene oxide copolymers, unsymmetrically 3,6-substituted poly-1,4-dioxane-2,5-diones, poly-β-hydroxybutyrate (PHBA), PHBA/β-hydroxyvalerate copolymers (PHBA/HVA), poly-β-hydroxypropionate (PHPA), poly-p-dioxanone (PDS), poly-δ-valerolactone, poly-ε-caprolactone, methylmethacrylate-N-vinyl pyrrolidine copolymers, polyesteramides, polyesters of oxalic acid, polydihydropyrans, polyalkyl-2-cyanoacrylates, polyurethanes (PU), polyvinylalcohols (PVA), polypeptides, poly-β-malic acid (PMLA), poly-β-alkanoic acids, polyvinylalcohol (PVA), polyethyleneoxide (PEO), chitine polymers, polyethylene, polypropylene, polyasetal, polyamides, polyesters, polysulphone, polyether ether ketone, polyethylene terephthalate, polycarbonate, polyaryl ether ketone, and polyether ketone.

In some embodiments, the coating includes silk fibroin proteins or fragments thereof having an average weight average molecular weight in a range selected from between about 1 kDa and about 5 kDa, between about 5 kDa and about 10 kDa, between about 6 kDa and about 17 kDa, between about 10 kDa and about 15 kDa, between about 15 kDa and about 20 kDa, between about 17 kDa and about 39 kDa, between about 20 kDa and about 25 kDa, between about 25 kDa and about 30 kDa, between about 30 kDa and about 35 kDa, between about 35 kDa and about 40 kDa, between about 39 kDa and about 80 kDa, between about 40 kDa and about 45 kDa, between about 45 kDa and about 50 kDa, between about 60 kDa and about 100 kDa, and between about 80 kDa and about 144 kDa, and a polydispersity between 1 and about 5.

In some embodiments, the silk derived proteins or fragments thereof do not spontaneously or gradually gelate and do not visibly change in color or turbidity when in an aqueous solution for at least 10 days prior to being added to the article.

In some embodiments, the article further comprises one or more polysaccharides selected from starch, cellulose, gum arabic, guar gum, xanthan gum, alginate, pectin, chitin, chitosan, carrageenan, inulin, and gellan gum.

In some embodiments, the gellan gum comprises low-acyl content gellan gum.

In some embodiments, the w/w ratio between the silk derived proteins or fragments thereof and the polysaccharide is selected from about 99:1, about 98:2, about 97:3, about 96:4, about 95:5, about 94:6, about 93:7, about 92:8, about 91:9, about 90:10, about 89:11, about 88:12, about 87:13, about 86:14, about 85:15, about 84:16, about 83:17, about 82:18, about 81:19, about 80:20, about 79:21, about 78:22, about 77:23, about 76:24, about 75:25, about 74:26, about 73:27, about 72:28, about 71:29, about 70:30, about 69:31, about 68:32, about 67:33, about 66:34, about 65:35, about 64:36, about 63:37, about 62:38, about 61:39, about 60:40, about 59:41, about 58:42, about 57:43, about 56:44, about 55:45, about 54:46, about 53:47, about 52:48, about 51:49, about 50:50, about 49:51, about 48:52, about 47:53, about 46:54, about 45:55, about 44:56, about 43:57, about 42:58, about 41:59, about 40:60, about 39:61, about 38:62, about 37:63, about 36:64, about 35:65, about 34:66, about 33:67, about 32:68, about 31:69, about 30:70, about 29:71, about 28:72, about 27:73, about 26:74, about 25:75, about 24:76, about 23:77, about 22:78, about 21:79, about 20:80, about 19:81, about 18:82, about 17:83, about 16:84, about 15:85, about 14:86, about 13:87, about 12:88, about 11:89, about 10:90, about 9:91, about 8:92, about 7:93, about 6:94, about 5:95, about 4:96, about 3:97, about 2:98, or about 1:99, about 100:1, about 50:1, about 25:1, about 24:1. about 23:1, about 22:1, about 21:1, about 20:1, about 19:1, about 18:1, about 17:1, about 16:1, about 15:1, about 14:1, about 13:1, about 12:1, about 11:1, abut 10:1, about 9:1, about 8:1, about 7:1, about 6:1, about 5:1, about 4:1, about 3:1, about 2:1, about 1:1, about 1:2, about 1:3, about 1:4, and about 1:5.

In some embodiments, the w/w ratio between the silk derived proteins or fragments thereof and the polysaccharide is selected from about 12:1, about 11.9:1, about 11.8:1, about 11.7:1, about 11.6:1, about 11.5:1, about 11.4:1, about 11.3:1, about 11.2:1, about 11.1:1, about 11:1, abut 10.9:1, abut 10.8:1, abut 10.7:1, abut 10.6:1, abut 10.5:1, abut 10.4:1, abut 10.3:1, abut 10.2:1, abut 10.1:1, abut 10:1, about 9.9:1, about 9.8:1, about 9.7:1, about 9.6:1, about 9.5:1, about 9.4:1, about 9.3:1, about 9.2:1, about 9.1:1, about 9:1, about 8.9:1, about 8.8:1, about 8.7:1, about 8.6:1, about 8.5:1, about 8.4:1, about 8.3:1, about 8.2:1, about 8.1:1, about 8:1, about 7.9:1, about 7.8:1, about 7.7:1, about 7.6:1, about 7.5:1, about 7.4:1, about 7.3:1, about 7.2:1, about 7.1:1, about 7:1, about 6.9:1, about 6.8:1, about 6.7:1, about 6.6:1, about 6.5:1, about 6.4:1, about 6.3:1, about 6.2:1, about 6.1:1, about 6:1, about 5.9:1, about 5.8:1, about 5.7:1, about 5.6:1, about 5.5:1, about 5.4:1, about 5.3:1, about 5.2:1, about 5.1:1, about 5:1, about 4.9:1, about 4.8:1, about 4.7:1, about 4.6:1, about 4.5:1, about 4.4:1, about 4.3:1, about 4.2:1, about 4.1:1, about 4:1, about 3.9:1, about 3.8:1, about 3.7:1, about 3.6:1, about 3.5:1, about 3.4:1, about 3.3:1, about 3.2:1, about 3.1:1, about 3:1, about 2.9:1, about 2.8:1, about 2.7:1, about 2.6:1, about 2.5:1, about 2.4:1, about 2.3:1, about 2.2:1, about 2.1:1, about 2:1, about 1.9:1, about 1.8:1, about 1.7:1, about 1.6:1, about 1.5:1, about 1.4:1, about 1.3:1, about 1.2:1, about 1.1:1, about 1:1, about 0.9:1, about 0.8:1, about 0.7:1, about 0.6:1, about 0.5:1, about 0.4:1, about 0.3:1, about 0.2:1, and about 0.1:1.

In some embodiments, the article further comprises one or more polyols, and/or one or more polyethers. In some embodiments, the polyols comprise one or more of glycol, glycerol, sorbitol, glucose, sucrose, and dextrose. In some embodiments, the polyethers comprise one or more polyethyleneglycols (PEGs).

In some embodiments, the w/w ratio between the silk derived proteins or fragments thereof and the one or more polyols and/or one or more polyethers is selected from about 5:1, about 4.9:1, about 4.8:1, about 4.7:1, about 4.6:1, about 4.5:1, about 4.4:1, about 4.3:1, about 4.2:1, about 4.1:1, about 4:1, about 3.9:1, about 3.8:1, about 3.7:1, about 3.6:1, about 3.5:1, about 3.4:1, about 3.3:1, about 3.2:1, about 3.1:1, about 3:1, about 2.9:1, about 2.8:1, about 2.7:1, about 2.6:1, about 2.5:1, about 2.4:1, about 2.3:1, about 2.2:1, about 2.1:1, about 2:1, about 1.9:1, about 1.8:1, about 1.7:1, about 1.6:1, about 1.5:1, about 1.4:1, about 1.3:1, about 1.2:1, about 1.1:1, about 1:1, about 0.9:1, about 0.8:1, about 0.7:1, about 0.6:1, about 0.5:1, about 0.4:1, about 0.3:1, about 0.2:1, about 0.1:1, about 1:0.1, about 1:0.2, about 1:0.3, about 1:0.4, about 1:0.5, about 1:0.6, about 1:0.7, about 1:0.8, about 1:0.9, about 1:1.1, about 1:1.2, about 1:1.3, about 1:1.4, about 1:1.5, about 1:1.6, about 1:1.7, about 1:1.8, about 1:1.9, about 1:2, about 1:2.1, about 1:2.2, about 1:2.3, about 1:2.4, about 1:2.5, about 1:2.6, about 1:2.7, about 1:2.8, about 1:2.9, about 1:3, about 1:3.1, about 1:3.2, about 1:3.3, about 1:3.4, about 1:3.5, about 1:3.6, about 1:3.7, about 1:3.8, about 1:3.9, about 1:4, about 1:4.1, about 1:4.2, about 1:4.3, about 1:4.4, about 1:4.5, about 1:4.6, about 1:4.7, about 1:4.8, about 1:4.9, and about 1:5.

In some embodiments, the article further comprises one or more of a silicone, a dye, a pigment, and a polyurethane.

In some embodiments, the article is a single or multilayered faux or bonded leather article.

In some embodiments, the plurality of fibers or yarns are assembled in one or more of a nonwoven mat or fabric; a woven, knitted, or crochet fabric; or a combination thereof.

In some embodiments, the plurality of fibers or yarns and the silk derived protein or fragments thereof are included in a layer having a thickness of about 0.1 mm, about 0.2 mm, about 0.3 mm, about 0.4 mm, about 0.5 mm, about 0.6, mm, about 0.7 mm, about 0.8 mm, about 0.9 mm, about 1.0 mm, about 1.1 mm, about 1.2 mm, about 1.3 mm, about 1.4 mm, about 1.5 mm, about 1.6, mm, about 1.7 mm, about 1.8 mm, about 1.9 mm, about 2.0 mm, about 2.1 mm, about 2.2 mm, about 2.3 mm, about 2.4 mm, about 2.5 mm, about 2.6, mm, about 2.7 mm, about 2.8 mm, about 2.9 mm, about 3.0 mm, about 3.1 mm, about 3.2 mm, about 3.3 mm, about 3.4 mm, about 3.5 mm, about 3.6, mm, about 3.7 mm, about 3.8 mm, about 3.9 mm, about 4.0 mm, about 4.1 mm, about 4.2 mm, about 4.3 mm, about 4.4 mm, about 4.5 mm, about 4.6, mm, about 4.7 mm, about 4.8 mm, about 4.9 mm, or about 5.0 mm.

In some embodiments, the plurality of fibers or yarns and the silk derived protein or fragments thereof are included in a layer having a thickness of about 1 mm, about 2 mm, about 3 mm, about 4 mm, about 5 mm, about 6, mm, about 7 mm, about 8 mm, about 9 mm, or about 10 mm.

In some embodiments, the article further comprising a laminated film. In some embodiments, the laminated film includes one or more polymers selected from polyglycolide (PGA), polyethylene glycols, copolymers of glycolide, glycolide/L-lactide copolymers (PGA/PLLA), glycolide/trimethylene carbonate copolymers (PGA/TMC), polylactides (PLA), stereocopolymers of PLA, poly-L-lactide (PLLA), poly-DL-lactide (PDLLA), L-lactide/DL-lactide copolymers, co-polymers of PLA, lactide/tetramethylglycolide copolymers, lactide/trimethylene carbonate copolymers, lactide/δ-valerolactone copolymers, lactide/ε-caprolactone copolymers, polydepsipeptides, PLA/polyethylene oxide copolymers, unsymmetrically 3,6-substituted poly-1,4-dioxane-2,5-diones, poly-β-hydroxybutyrate (PHBA), PHBA/β-hydroxyvalerate copolymers (PHBA/HVA), poly-β-hydroxypropionate (PHPA), poly-p-dioxanone (PDS), poly-δ-valerolactone, poly-ε-caprolactone, methylmethacrylate-N-vinyl pyrrolidine copolymers, polyesteramides, polyesters of oxalic acid, polydihydropyrans, polyalkyl-2-cyanoacrylates, polyurethanes (PU), polyvinylalcohols (PVA), polypeptides, poly-β-malic acid (PMLA), poly-β-alkanoic acids, polyvinylalcohol (PVA), polyethyleneoxide (PEO), chitine polymers, polyethylene, polypropylene, polyasetal, polyamides, polyesters, polysulphone, polyether ether ketone, polyethylene terephthalate, polycarbonate, polyaryl ether ketone, and polyether ketone ketone.

In an embodiments, a method of making the article as described above, the method comprising providing a plurality of fibers or yarns, making a woven or nonwoven layer of fibers or yarns, and adding to the layer a formulation comprising a silk derived protein or fragments thereof.

In some embodiments, the concentration of silk derived protein or fragments thereof in the formulation is between about 0.1% w/v and about 15% w/v.

In some embodiments, the concentration of silk derived protein or fragments thereof in the formulation is between about 5 mg/mL and about 125 mg/mL.

In some embodiments, the formulation further comprises a pH adjusting agent. In some embodiments, the pH adjusting agent is selected from ammonium hydroxide and citric acid. In some embodiments, the formulation has a pH of about 2, about 3, about 4, about 5, about 6, about 7, about 8, about 9, about 10, about 11, or about 12.

In some embodiments, the method further comprising one or more additional steps selected from dyeing, drying, water annealing, mechanical stretching, trimming, performing one or more polishing steps, applying a pigment, applying a colorant, applying an acrylic formulation, chemical fixing, stamping, applying a silicone finish, providing a Uniflex treatment, and/or providing a Finiflex treatment.

In some embodiments, the article is a spun yarn. In some embodiments, the spun yarn comprises one or more slivers comprising the plurality of fibers or yarns.

In an embodiment, this disclosure provides a method of making a spun yarn comprising providing a plurality of fibers, carding the fibers into sliver, spinning the sliver into the spun yarn. In some embodiments, the method further comprising scouring the spun yarn.

In some embodiments, the method further comprising threating the spun yarn with a formulation comprising a silk derived protein or fragments thereof.

In some embodiments, the concentration of silk derived protein or fragments thereof in the formulation is between about 0.1% w/v and about 15% w/v.

In some embodiments, the concentration of silk derived protein or fragments thereof in the formulation is between about 5 mg/mL and about 125 mg/mL.

In some embodiments, the formulation further comprises a pH adjusting agent. In some embodiments, the pH adjusting agent is selected from ammonium hydroxide and citric acid. In some embodiments, the formulation has a pH of about 2, about 3, about 4, about 5, about 6, about 7, about 8, about 9, about 10, about 11, or about 12.

In some embodiments, the method further comprising one or more additional steps selected from dyeing, drying, water annealing, mechanical stretching, trimming, performing one or more polishing steps, applying a pigment, applying a colorant, applying an acrylic formulation, chemical fixing, stamping, applying a silicone finish, providing a Uniflex treatment, and/or providing a Finiflex treatment.

In an embodiment, this disclosure provides silk protein bonded leather fibers comprises leather fibers, binder resin, and silk fibroin protein fragments having an average weight average molecular weight selected from between about 1 kDa and about 5 kDa, between about 5 kDa and about 10 kDa, between about 6 kDa and about 17 kDa, between about 10 kDa and about 15 kDa, between about 15 kDa and about 20 kDa, between about 17 kDa and about 39 kDa, between about 20 kDa and about 25 kDa, between about 25 kDa and about 30 kDa, between about 30 kDa and about 35 kDa, between about 35 kDa and about 40 kDa, between about 39 kDa and about 80 kDa, between about 40 kDa and about 45 kDa, between about 45 kDa and about 50 kDa, between about 60 kDa and about 100 kDa, and between about 80 kDa and about 144 kDa, and a polydispersity between 1 and about 5.

In some embodiments, the silk fibroin fragments in silk protein bonded leather fibers have a polydispersity between 1 and about 1.5. In some embodiments, the silk fibroin fragments in the silk protein bonded leather fibers have a polydispersity between about 1.5 and about 2.0. In some embodiments, the silk fibroin fragments in the silk protein bonded leather fibers have a polydispersity between about 1.5 and about 3.0. In some embodiments, the silk fibroin fragments in the silk protein bonded leather fibers have a polydispersity between about 2.0 and about 2.5. In some embodiments, the silk fibroin fragments in the silk protein bonded leather fibers have a polydispersity between about 2.5 and about 3.0.

In some embodiments, the silk fibroin protein fragments have an average weight average molecular weight selected from between about 6 kDa and about 17 kDa, between about 17 kDa and about 39 kDa, between about 39 kDa and about 80 kDa, and a polydispersity between 1.5 and about 3.0.

In some embodiments, the silk fibroin fragments in the silk protein bonded leather fibers are obtained from a precursor solution comprising silk fibroin fragments having an average weight average molecular weight selected from between about 1 kDa and about 5 kDa, between about 5 kDa and about 10 kDa, between about 6 kDa and about 17 kDa, between about 10 kDa and about 15 kDa, between about 15 kDa and about 20 kDa, between about 17 kDa and about 39 kDa, between about 20 kDa and about 25 kDa, between about 25 kDa and about 30 kDa, between about 30 kDa and about 35 kDa, between about 35 kDa and about 40 kDa, between about 39 kDa and about 80 kDa, between about 40 kDa and about 45 kDa, between about 45 kDa and about 50 kDa, between about 60 kDa and about 100 kDa, and between about 80 kDa and about 144 kDa, and a polydispersity between 1.0 and about 5.0.

In some embodiments, the silk bonded leather fibers comprise low molecular weight silk fibroin protein fragments having a weight average molecular weight selected from between about 5 kDa to about 20 kDa, and a polydispersity between 1.5 and about 3.0.

In some embodiments, the silk bonded leather fibers comprise low molecular weight silk fibroin protein fragments having a weight average molecular weight selected from the group consisting of from about 5 kDa to 10 kDa, about 10 kDa to about 20 kDa, and about 20 kDa to about 25 kDa, and a polydispersity between 1.5 and about 3.0.

In some embodiments, the silk bonded leather fibers comprise low molecular weight silk fibroin fragments (low-MW silk) having a weight average molecular weight (Mw) 6 kDa and about 17 kDa and a polydispersity between about 1.5 and about 3.0.

In some embodiments, the silk bonded leather fibers comprise low molecular weight silk fibroin protein fragments having a weight average molecular weight selected from between about 10 kDa to about 20 kDa and a polydispersity between 1 and about 5.0, or between about 1.5 and about 3.0.

In some embodiments, the silk bonded leather fibers comprise low molecular weight silk fibroin fragments (low-MW silk) having a weight average molecular weight (Mw) selected from between 14 kDa and about 30 kDa and a polydispersity between about 1.5 and about 3.0. In some embodiments, the silk bonded leather fibers comprise Mid-MW silk fibroin protein fragments having an average weight average molecular weight selected from about 25 kDa to about 30 kDa, about 30 kDa to about 35 kDa, from about 35 kDa to about 40 kDa, from about 17 kDa to about 39 kDa, from about 45 kDa to about 50 kDa, and from about 50 kDa to about 55 kDa, and a polydispersity between 1 and about 5.0, or between about 1.5 and about 3.0.

In some embodiments, the silk bonded leather fibers comprise Mid-MW silk fibroin protein fragments having a weight average molecular weight ranging from about 39 kDa to about 54 kDa and a polydispersity between 1 and about 5.0, or between about 1.5 and about 3.0.

In some embodiments, the silk bonded leather fibers comprise mid-molecular weight silk fibroin protein fragments having a weight average molecular weight ranging from about 40 kDa to about 55 kDa, and a polydispersity between 1 and about 5.0, or between about 1.5 and about 3.0.

In some embodiments, the silk bonded leather fibers comprise mid-molecular weight silk fibroin protein fragments having a weight average molecular weight ranging from about 39 kDa to about 54 kDa, and a polydispersity between 1 and about 5.0, or between about 1.5 and about 3.0.

In some embodiments, the silk bonded leather fibers comprise high-MW silk fibroin protein fragments having an average weight average molecular weight selected from about 55 kDa to about 60 kDa, from about 60 kDa to about 65 kDa, from about 40 kDa to about 65 kDa, from 65 kDa to about 70 kDa, from about 70 kDa to about 75 kDa, from about 75 kDa to about 80 kDa, from about 39 kDa to about 80 kDa, from about 80 kDa to about 85 kDa, from about 85 kDa to about 90 kDa, from about 90 kDa to about 95 kDa, from about 95 kDa to about 100 kDa, from about 100 kDa to about 105 kDa, from about 105 kDa to about 110 kDa, from about 60 kDa to about 100 kDa, and from about 80 kDa to about 144 kDa, and a polydispersity between 1 and about 5.0, or between about 1.5 and about 3.0.

In some embodiments, the silk bonded leather fibers comprise high-molecular weight silk fibroin protein fragments having a weight average molecular weight ranging from about 80 kDa to about 144 kDa, and a polydispersity between 1 and about 5.0, or between about 1.5 and about 3.0.

In some embodiments, the binder resin is selected from the group consisting of thermoplastic resin, latex, polyvinyl chloride, polyurethane, butadiene acrylonitrile copolymer, anionic copolymer of ester and urethane, and combinations thereof. In some embodiments, the binder resin is polyvinyl chloride. In some embodiments, the binder resin is polyurethane. In some embodiments, the binder resin is butadiene acrylonitrile copolymer (Chemigum® Latex 6387). In some embodiments, the binder resin is anionic copolymer of ester and urethane (Baybond® PU 401).

In some embodiments, the silk protein bonded leather fibers further comprising about 0.01% (w/w) to about 10% (w/w) sericin relative to the silk fibroin fragments.

In some embodiments, the silk fibroin fragments in the precursor solution do not spontaneously or gradually gelate and do not visibly change in color or turbidity when in the precursor solution for at least 10 days prior to obtaining the silk fibroin fragments in the substantially solid silk composition.

In an embodiment, this disclosure provides a method for making silk protein bonded leather fibers from waste leather materials comprising the steps: (1) obtaining waste leather materials; (2) cutting the waste leather material to form ground leather having size ranging from 3 mm to 10 mm in length; (3) forming a suspension of the ground leather in water; (4) beating the suspension with a laboratory beater for at least 2 hours to form a ground leather fiber suspension; (5) adding a polymer binder and silk solution as described herein to the ground leather fiber suspension to form a blend of leather fibers with silk fibroin protein fragments; (6) adding a flocculant to the blend of leather fibers with silk fibroin protein fragments to form a flocked silk leather material; (7) adjusting pH in the leather fiber aqueous suspension with a pH adjusting agent to a value ranging from about 3 to 5; (8) feeding the flocked silk leather materials directly onto a screen for draining out water; (9) drying the flocked silk leather materials under heat to form silk bonded leather fibers.

In some embodiments, the pH value of the leather fiber aqueous suspension is selected from the group consisting of about 3.0, about 3.1, about 3.2, about 3.3, about 3.4, about 3.5, about 3.6, about 3.7, about 3.8, about 3.9, about 4.0, about 4.1, about 4.2, about 4.3, about 4.4, about 4.5, about 4.6, about 4.7, about 4.8, about 4.9, and about 5.0. In some embodiments, the pH-adjusting agent is hydrochloric acid.

In some embodiments, the leather fiber concentration in the leather fiber aqueous suspension is of about 0.1 wt. % to about 1.0 wt. % by the total weight of the leather fiber aqueous suspension. In some embodiments, the leather fiber concentration is of about 0.3 wt. % to about 0.5 wt. % by the total weight of the leather fiber aqueous suspension. In some embodiments, the leather fiber concentration is selected from the group consisting of about 0.1 wt. %, 0.2 wt. %, 0.3 wt. %, 0.4 wt. %, 0.5 wt. %, 0.6 wt. %, 0.7 wt. %, 0.8 wt. %, 0.9 wt. %, and 1.0 wt. % by the total weight of the leather fiber aqueous suspension. In some embodiments, the leather fiber concentration in the aqueous suspension is of about 0.42 wt. % by the total weight of the leather fiber aqueous suspension.

In some embodiments, the silk fibroin protein fragments have a concentration of about 0.05 wt. % to about 1.0 wt. % by the total weight of the leather fiber suspension. In some embodiments, the silk fibroin protein fragments have a concentration selected from the group consisting of about 0.1 wt. %, 0.2 wt. %, 0.3 wt. %, 0.4 wt. %, 0.5 wt. %, 0.6 wt. %, 0.7 wt. %, 0.8 wt. %, 0.9 wt. %, and 1.0 wt. % by the total weight of the leather fiber aqueous suspension. In some embodiments, the silk fibroin protein fragments have a concentration of about 0.6 wt. % by the total weight of the leather fiber aqueous suspension. In some embodiments, the silk fibroin protein fragments have a concentration of about 0.12 wt. % by the total weight of the leather fiber aqueous suspension.

In some embodiments, the binder resin has a concentration of about 0.05 wt. % to about 1.0 wt. % by the total weight of the leather fiber suspension. In some embodiments, the binder resin has a concentration selected from the group consisting of about 0.1 wt. %, 0.2 wt. %, 0.3 wt. %, 0.4 wt. %, 0.5 wt. %, 0.6 wt. %, 0.7 wt. %, 0.8 wt. %, 0.9 wt. %, and 1.0 wt. % by the total weight of the leather fiber aqueous suspension. In some embodiments, the binder resin has a concentration of about 0.36 wt. % by the total weight of the leather fiber aqueous suspension.

In some embodiments, the flocculant is selected form cationic polyacrylamide, and nonionic polyacrylamide. In some embodiments, the flocculant is high molecular weight nonionic polyacrylamide (Percol® 351, also known as Magnafloc® 351).

In some embodiments, the flocculant is Percol® 351. In some embodiments, the flocculant is present in the leather fiber aqueous suspension at a concentration ranging from 0.0005 wt. % to about 1.0 wt. % by the total weight of the leather fiber aqueous suspension. In some embodiments, the flocculant has a concentration of about 0.0005 wt. % to about 0.005 wt. % by the total weight of the leather fiber suspension. In some embodiments, the flocculant has a concentration selected from the group consisting of about 0.0005 wt. %, about 0.00075 wt. %, about 0.001 wt. %, 0.0015 wt. %, about 0.002 wt. %, about 0.0025 wt. %, about 0.003 wt. %, about 0.0035 wt. %, about 0.004 wt. %, about 0.0045 wt. %, and about 0.005 wt. % by the total weight of the leather fiber aqueous suspension. In some embodiments, the flocculant has a concentration of about 0.001 wt. % by the total weight of the leather fiber aqueous suspension.

Silk bonded layered materials comprise the silk bonded leather fibers as described above. Silk bonded spun materials or yarns comprise the silk bonded leather fibers as described above.

BRIEF DESCRIPTION OF THE DRAWINGS

The presently disclosed embodiments will be further explained with reference to the attached drawings. The drawings shown are not necessarily to scale, with emphasis instead generally being placed upon illustrating the principles of the presently disclosed embodiments.

FIG. 25 is a table showing the dyeing procedure for panels prepared from control yarn (T-12-3) and yarn of the disclosure (T11-3).

DETAILED DESCRIPTION

Figure 1:
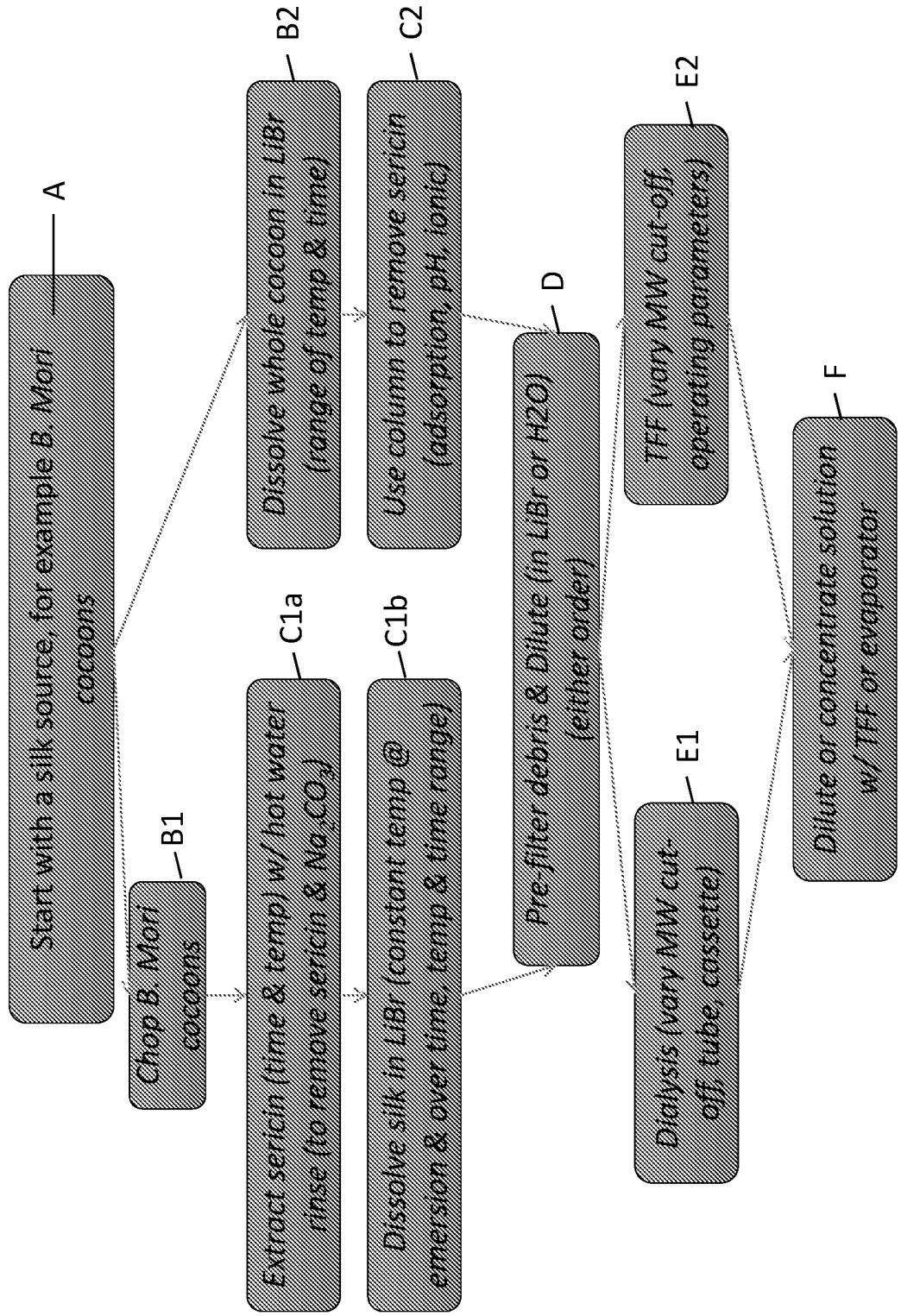
FIG. 1 is a flow chart showing various embodiments for producing silk fibroin protein fragments (SPFs) of the present disclosure.

Leather is a material manufactured by treating the skin peeled off from an animal body with a series of physical mechanic and chemical methods, followed by tanning. The leather materials are composed of weaved collagen fiber bundles and trace amount of elastic fibers and reticular fibers, of which the collagen fiber is between 95 and 98 percent. The natural weaving structure of collagen fiber in natural leather is that the thicker fiber bundles sometimes are divided into several strands of thinner fiber bundles and the resulting thinner fiber bundles sometimes incorporate other fiber bundles to form another larger fiber bundle. That collagen fibers are capable to form bundles is one of characteristics that differ from other textile fibers and non-woven fabric and textiles prepared by the same.

Recently, some leftover materials are opened or smashed under natural state using the current technology to obtain non-spinning fractional fibers with the length lower than several millimeters, and the resulting fractional fibers conjugate other raw materials to produce low value-added products, such as non-woven fabric and regenerated leather, and so on. However, the collagen fibers are still short, poor in spinnability, only used for producing low-level textiles or as the raw materials for "waste textile".

This disclosure provides novel silk protein bonded layered or spun materials and processes that convert the waste leather materials into luxury fabrics exhibiting good dyeability, high brilliance, and excellent color fastness.

Silk bonded and/or faux or bonded leather products and methods of preparing the same are disclosed herein. Utilize recycled fiber in 100% polyester and/or a blend containing at least 40% wool to achieve a non-woven fabric having a thickness between 0.7-1.5 mm and an average fabric weight 200-220 gr/m$^2$. The process of choice to achieve this fabric properties is with carding and needle punch. In some embodiments, to the final fabric Activated Silk solution will be applied followed by a lamination with a polyurethane film to achieve a faux leather appearance.

Utilize recycled fiber in 100% polyester and/or a blend containing at least 40% wool to achieve a non-woven fabric having a thickness between 0.7-1.5 mm and an average fabric weight 200-220 gr/m$^2$. In some embodiments, the process of choice to achieve this fabric properties is with wet laid and Activated Silk will be blended in with the fibers before the fabric is formed or after the fabric is dried. The final fabric will be laminated with a polyurethane film to achieve a faux leather appearance.

Utilize recycled fiber in 100% polyester and/or a blend containing at least 40% wool to achieve a non-woven fabric having a thickness between 1.0-1.5 mm. The process of choice to achieve this fabric properties is wet laid and Activated Silk with recycled ground up faux leather waste will be blended in with the fibers or applied after the fabric is formed.

Description of the Faux or Bonded Leather

The faux or bonded leather substrate can be prepared with the 3 methods above. A Silk derived protein, either fibroin based or sericin based or a combination of fibroin and sericin at different concentration will be used in combination with the textile fibers.

Silk derived protein can be applied by:
 treating the fibers before the fabric is formed in wet laid or carding process
 mixing with the fibers during the wet laid process
 treating the fibers already formed into a fabric mat by
  applying with standard textile wet processing, spraying one or both surfaces or nebulizing one or both sides.

The added value of silk derived protein is to provide a binder to the fibers for improving mechanical properties, and to provide a natural touch to the final substrate.

Other ingredients can be used in combination with silk in the previously described methods:
 ground up faux leather from the shaving process in wet blue state
 ground up faux leather from the retanned faux leather hides not meeting specifications
 ground up faux leather from the remnant after cut and sew
 natural rubber from the latex tree
 polyurethane based
 pigments
 dyes Finishing of the Faux or Bonded Leather The fabric substrate can be finished to further reproduce a natural feel of faux leather on the faux leather. Finishing can include but not limiting to standard textile and faux leather processing or a combination of:
 sueding the fabric on one side or both sides
 applying a polyurethane layer on one of the substrates face
 applying a silk and gellan gum layer on of the substrates face
 applying standard faux leather finishing in combination with silk
 mechanical finishing such as milling/tumblering
 embossing
 digital printing or screen printing
 lamination
 laser engraving
 shaving The faux or bonded leather finishing will modify the surface to impart properties like water repellency, softening and hand, fire proof, antibacterial, tearing and abrasion resistance, dye fading resistance, washability, flex cracking resistance, antistatic, stain resistance, oil resistance, breathability and liquid transport.

The final thickness of the faux or bonded leather may have a range, without limitation, between 0.5 mm to 4 mm.

Definitions

As used in the preceding sections and throughout the rest of this specification, unless defined otherwise, all technical and scientific terms used herein have the same meaning as is commonly understood by one skilled in the art to which this disclosure belongs. All patents and publications referred to herein are incorporated by reference in their entireties.

All percentages, parts and ratios are based upon the total weight of the collagen boosting compositions of the present disclosure, unless otherwise specified. All such weights as they pertain to listed ingredients are based on the active level and, therefore, do not include solvents or by-products that may be included in commercially available materials, unless otherwise specified. The term "weight percent" may be denoted as "wt. %" or % w/w herein.

As used herein, the term "a", "an", or "the" generally is construed to cover both the singular and the plural forms.

As used herein, the term "about" generally refers to a particular numeric value that is within an acceptable error range as determined by one of ordinary skill in the art, which will depend in part on how the numeric value is measured or determined, i.e., the limitations of the measurement system. For example, "about" can mean a range of ±20%, ±10%, or ±5% of a given numeric value.

As used herein, the term "dermatologically acceptable carrier" means a carrier suitable for use in contact with mammalian keratinous tissue without causing any adverse effects such as undue toxicity, incompatibility, instability, allergic response, for example. A dermatologically acceptable carrier may include, without limitations, water, liquid or solid emollients, humectants, solvents, and the like.

As used herein, the term "hydrophilic-lipophilic balance" (HLB) of a surfactant is a measure of the degree to which it is hydrophilic or hydrophobic, as determined by calculating values for the different regions of the molecule, as described by Griffin's method HLB=20*$M_h$/M, where $M_h$ is the molecular mass of the hydrophilic portion of the surfactant, and M is the molecular mass of the entire surfactant molecule, giving a result on a scale of 0 to 20. A HLB value of 0 corresponds to a completely lipophilic molecule, and a value of 20 corresponds to a completely hydrophilic molecule. The HLB value can be used to predict the surfactant properties of a molecule: HLB K 10: Lipid-soluble (water-insoluble), HLB>10: Water-soluble (lipid-insoluble), HLB=1–3: anti-foaming agent, 3-6: W/O (water-in-oil) emulsifier, 7-9: wetting and spreading agent, 8-16: O/W (oil-in-water) emulsifier, 13-16: detergent, 16-18: solubilizer or hydrotrope.

As used herein, "average weight average molecular weight" refers to an average of two or more values of weight average molecular weight of silk fibroin or fragments thereof of the same compositions, the two or more values determined by two or more separate experimental readings.

As used herein, the term polymer "polydispersity (PD)" is generally used as a measure of the broadness of a molecular weight distribution of a polymer, and is defined by the formula polydispersity $$PD = \frac{Mw}{Mn}.$$

As used herein, the term "substantially homogeneous" may refer to silk fibroin-based protein fragments that are distributed in a normal distribution about an identified molecular weight. As used herein, the term "substantially homogeneous" may refer to an even distribution of a component or an additive, for example, silk fibroin fragments, dermatologically acceptable carrier, etc., throughout a composition of the present disclosure.

As used herein, the terms "silk fibroin peptide," "silk fibroin protein fragment," and "silk fibroin fragment" are used interchangeably. Molecular weight or number of amino acids units are defined when molecular size becomes an important parameter.

As used herein, the term "plasticizer" refers to a chemical added to polymers and resins to impart flexibility or stretchability, or a bonding agent that acts by solvent action on fibers. Water may act as a plasticizer, and a plasticizer means other substances that, owing to their intrinsic characteristics or by aiding in water retention, improve the ductility and plasticity of a fiber.

SPF Definitions and Properties

As used herein, "silk protein fragments" (SPF) and "silk derived proteins" include, without limitation, one or more of: "silk fibroin fragments" as defined herein; "recombinant silk fragments" as defined herein; "spider silk fragments" as defined herein; "silk fibroin-like protein fragments" as defined herein; "chemically modified silk fragments" as defined herein; and/or "sericin or sericin fragments" as defined herein. SPF and silk derived proteins may have any molecular weight values or ranges described herein, and any polydispersity values or ranges described herein. As used herein, in some embodiments the term "silk protein fragment" and/or "silk derived proteins" also refers to a silk protein that comprises or consists of at least two identical repetitive units which each independently selected from naturally-occurring silk polypeptides or of variations thereof, amino acid sequences of naturally-occurring silk polypeptides, or of combinations of both.

SPF Molecular Weight and Polydispersity

In an embodiment, a composition of the present disclosure includes SPF having an average weight average molecular weight selected from between about 1 to about 5 kDa. In an embodiment, a composition of the present disclosure includes SPF having an average weight average molecular weight selected from between about 5 to about 10 kDa. In an embodiment, a composition of the present disclosure includes SPF having an average weight average molecular weight selected from between about 10 to about 15 kDa. In an embodiment, a composition of the present disclosure includes SPF having an average weight average molecular weight selected from between about 15 to about 20 kDa. In an embodiment, a composition of the present disclosure includes SPF having an average weight average molecular weight selected from between about 14 to about 30 kDa. In an embodiment, a composition of the present disclosure includes SPF having an average weight average molecular weight selected from between about 20 to about 25 kDa. In an embodiment, a composition of the present disclosure includes SPF having an average weight average molecular weight selected from between about 25 to about 30 kDa. In an embodiment, a composition of the present disclosure includes SPF having an average weight average molecular weight selected from between about 30 to about 35 kDa. In an embodiment, a composition of the present disclosure includes SPF having an average weight average molecular weight selected from between about 35 to about 40 kDa. In an embodiment, a composition of the present disclosure includes SPF having an average weight average molecular weight selected from between about 39 to about 54 kDa. In an embodiment, a composition of the present disclosure includes SPF having an average weight average molecular weight selected from between about 40 to about 45 kDa. In an embodiment, a composition of the present disclosure includes SPF having an average weight average molecular weight selected from between about 45 to about 50 kDa. In an embodiment, a composition of the present disclosure includes SPF having an average weight average molecular weight selected from between about 50 to about 55 kDa. In an embodiment, a composition of the present disclosure includes SPF having an average weight average molecular weight selected from between about 55 to about 60 kDa. In an embodiment, a composition of the present disclosure includes SPF having an average weight average molecular weight selected from between about 60 to about 65 kDa. In an embodiment, a composition of the present disclosure includes SPF having an average weight average molecular weight selected from between about 65 to about 70 kDa. In an embodiment, a composition of the present disclosure includes SPF having an average weight average molecular weight selected from between about 70 to about 75 kDa. In an embodiment, a composition of the present disclosure includes SPF having an average weight average molecular weight selected from between about 75 to about 80 kDa. In an embodiment, a composition of the present disclosure includes SPF having an average weight average molecular weight selected from between about 80 to about 85 kDa. In an embodiment, a composition of the present disclosure includes SPF having an average weight average molecular weight selected from between about 85 to about 90 kDa. In an embodiment, a composition of the present disclosure includes SPF having an average weight average molecular weight selected from between about 90 to about 95 kDa. In an embodiment, a composition of the present disclosure includes SPF having an average weight average molecular weight selected from between about 95 to about 100 kDa. In an embodiment, a composition of the present disclosure includes SPF having an average weight average molecular weight selected from between about 100 to about 105 kDa. In an embodiment, a composition of the present disclosure includes SPF having an average weight average molecular weight selected from between about 105 to about 110 kDa. In an embodiment, a composition of the present disclosure includes SPF having an average weight average molecular weight selected from between about 110 to about 115 kDa. In an embodiment, a composition of the present disclosure includes SPF having an average weight average molecular weight selected from between about 115 to about 120 kDa. In an embodiment, a composition of the present disclosure includes SPF having an average weight average molecular weight selected from between about 120 to about 125 kDa. In an embodiment, a composition of the present disclosure includes SPF having an average weight average molecular weight selected from between about 125 to about 130 kDa. In an embodiment, a composition of the present disclosure includes SPF having an average weight average molecular weight selected from between about 130 to about 135 kDa. In an embodiment, a composition of the present disclosure includes SPF having an average weight average molecular weight selected from between about 135 to about 140 kDa. In an embodiment, a composition of the present disclosure includes SPF having an average weight average molecular weight selected from between about 140 to about 145 kDa. In an embodiment, a composition of the present disclosure includes SPF having an average weight average molecular weight selected from between about 145 to about 150 kDa. In an embodiment, a composition of the present disclosure includes SPF having an average weight average molecular weight selected from between about 150 to about 155 kDa. In an embodiment, a composition of the present disclosure includes SPF having an average weight average molecular weight selected from between about 155 to about 160 kDa. In an embodiment, a composition of the present disclosure includes SPF having an average weight average molecular weight selected from between about 160 to about 165 kDa. In an embodiment, a composition of the present disclosure includes SPF having an average weight average molecular weight selected from between about 165 to about 170 kDa. In an embodiment, a composition of the present disclosure includes SPF having an average weight average molecular weight selected from between about 170 to about 175 kDa. In an embodiment, a composition of the present disclosure includes SPF having an average weight average molecular weight selected from between about 175 to about 180 kDa. In an embodiment, a composition of the present disclosure includes SPF having an average weight average molecular weight selected from between about 180 to about 185 kDa. In an embodiment, a composition of the present disclosure includes SPF having an average weight average molecular weight selected from between about 185 to about 190 kDa. In an embodiment, a composition of the present disclosure includes SPF having an average weight average molecular weight selected from between about 190 to about 195 kDa. In an embodiment, a composition of the present disclosure includes SPF having an average weight average molecular weight selected from between about 195 to about 200 kDa. In an embodiment, a composition of the present disclosure includes SPF having an average weight average molecular weight selected from between about 200 to about 205 kDa. In an embodiment, a composition of the present disclosure includes SPF having an average weight average molecular weight selected from between about 205 to about 210 kDa. In an embodiment, a composition of the present disclosure includes SPF having an average weight average molecular weight selected from between about 210 to about 215 kDa. In an embodiment, a composition of the present disclosure includes SPF having an average weight average molecular weight selected from between about 215 to about 220 kDa. In an embodiment, a composition of the present disclosure includes SPF having an average weight average molecular weight selected from between about 220 to about 225 kDa. In an embodiment, a composition of the present disclosure includes SPF having an average weight average molecular weight selected from between about 225 to about 230 kDa. In an embodiment, a composition of the present disclosure includes SPF having an average weight average molecular weight selected from between about 230 to about 235 kDa. In an embodiment, a composition of the present disclosure includes SPF having an average weight average molecular weight selected from between about 235 to about 240 kDa. In an embodiment, a composition of the present disclosure includes SPF having an average weight average molecular weight selected from between about 240 to about 245 kDa. In an embodiment, a composition of the present disclosure includes SPF having an average weight average molecular weight selected from between about 245 to about 250 kDa. In an embodiment, a composition of the present disclosure includes SPF having an average weight average molecular weight selected from between about 250 to about 255 kDa. In an embodiment, a composition of the present disclosure includes SPF having an average weight average molecular weight selected from between about 255 to about 260 kDa. In an embodiment, a composition of the present disclosure includes SPF having an average weight average molecular weight selected from between about 260 to about 265 kDa. In an embodiment, a composition of the present disclosure includes SPF having an average weight average molecular weight selected from between about 265 to about 270 kDa. In an embodiment, a composition of the present disclosure includes SPF having an average weight average molecular weight selected from between about 270 to about 275 kDa. In an embodiment, a composition of the present disclosure includes SPF having an average weight average molecular weight selected from between about 275 to about 280 kDa. In an embodiment, a composition of the present disclosure includes SPF having an average weight average molecular weight selected from between about 280 to about 285 kDa. In an embodiment, a composition of the present disclosure includes SPF having an average weight average molecular weight selected from between about 285 to about 290 kDa. In an embodiment, a composition of the present disclosure includes SPF having an average weight average molecular weight selected from between about 290 to about 295 kDa. In an embodiment, a composition of the present disclosure includes SPF having an average weight average molecular weight selected from between about 295 to about 300 kDa. In an embodiment, a composition of the present disclosure includes SPF having an average weight average molecular weight selected from between about 300 to about 305 kDa. In an embodiment, a composition of the present disclosure includes SPF having an average weight average molecular weight selected from between about 305 to about 310 kDa. In an embodiment, a composition of the present disclosure includes SPF having an average weight average molecular weight selected from between about 310 to about 315 kDa. In an embodiment, a composition of the present disclosure includes SPF having an average weight average molecular weight selected from between about 315 to about 320 kDa. In an embodiment, a composition of the present disclosure includes SPF having an average weight average molecular weight selected from between about 320 to about 325 kDa. In an embodiment, a composition of the present disclosure includes SPF having an average weight average molecular weight selected from between about 325 to about 330 kDa. In an embodiment, a composition of the present disclosure includes SPF having an average weight average molecular weight selected from between about 330 to about 335 kDa. In an embodiment, a composition of the present disclosure includes SPF having an average weight average molecular weight selected from between about 335 to about 340 kDa. In an embodiment, a composition of the present disclosure includes SPF having an average weight average molecular weight selected from between about 340 to about 345 kDa. In an embodiment, a composition of the present disclosure includes SPF having an average weight average molecular weight selected from between about 345 to about 350 kDa.

In some embodiments, compositions of the present disclosure include SPF compositions selected from compositions #1001 to #2450, having weight average molecular weights selected from about 1 kDa to about 145 kDa, and a polydispersity selected from between 1 and about 5 (including, without limitation, a polydispersity of 1), between 1 and about 1.5 (including, without limitation, a polydispersity of 1), between about 1.5 and about 2, between about 1.5 and about 3, between about 2 and about 2.5, between about 2.5 and about 3, between about 3 and about 3.5, between about 3.5 and about 4, between about 4 and about 4.5, and between about 4.5 and about 5:

| MW (about) | PDI (about) | | | | | | | | | |
|---|---|---|---|---|---|---|---|---|---|---|
| | 1-5 | 1-1.5 | 1.5-2 | 1.5-3 | 2-2.5 | 2.5-3 | 3-3.5 | 3.5-4 | 4-4.5 | 4.5-5 |
| 1 kDa | 1001 | 1002 | 1003 | 1004 | 1005 | 1006 | 1007 | 1008 | 1009 | 1010 |
| 2 kDa | 1011 | 1012 | 1013 | 1014 | 1015 | 1016 | 1017 | 1018 | 1019 | 1020 |
| 3 kDa | 1021 | 1022 | 1023 | 1024 | 1025 | 1026 | 1027 | 1028 | 1029 | 1030 |
| 4 kDa | 1031 | 1032 | 1033 | 1034 | 1035 | 1036 | 1037 | 1038 | 1039 | 1040 |
| 5 kDa | 1041 | 1042 | 1043 | 1044 | 1045 | 1046 | 1047 | 1048 | 1049 | 1050 |
| 6 kDa | 1051 | 1052 | 1053 | 1054 | 1055 | 1056 | 1057 | 1058 | 1059 | 1060 |
| 7 kDa | 1061 | 1062 | 1063 | 1064 | 1065 | 1066 | 1067 | 1068 | 1069 | 1070 |
| 8 kDa | 1071 | 1072 | 1073 | 1074 | 1075 | 1076 | 1077 | 1078 | 1079 | 1080 |
| 9 kDa | 1081 | 1082 | 1083 | 1084 | 1085 | 1086 | 1087 | 1088 | 1089 | 1090 |
| 10 kDa | 1091 | 1092 | 1093 | 1094 | 1095 | 1096 | 1097 | 1098 | 1099 | 1100 |
| 11 kDa | 1101 | 1102 | 1103 | 1104 | 1105 | 1106 | 1107 | 1108 | 1109 | 1110 |
| 12 kDa | 1111 | 1112 | 1113 | 1114 | 1115 | 1116 | 1117 | 1118 | 1119 | 1120 |
| 13 kDa | 1121 | 1122 | 1123 | 1124 | 1125 | 1126 | 1127 | 1128 | 1129 | 1130 |
| 14 kDa | 1131 | 1132 | 1133 | 1134 | 1135 | 1136 | 1137 | 1138 | 1139 | 1140 |
| 15 kDa | 1141 | 1142 | 1143 | 1144 | 1145 | 1146 | 1147 | 1148 | 1149 | 1150 |
| 16 kDa | 1151 | 1152 | 1153 | 1154 | 1155 | 1156 | 1157 | 1158 | 1159 | 1160 |
| 17 kDa | 1161 | 1162 | 1163 | 1164 | 1165 | 1166 | 1167 | 1168 | 1169 | 1170 |
| 18 kDa | 1171 | 1172 | 1173 | 1174 | 1175 | 1176 | 1177 | 1178 | 1179 | 1180 |
| 19 kDa | 1181 | 1182 | 1183 | 1184 | 1185 | 1186 | 1187 | 1188 | 1189 | 1190 |
| 20 kDa | 1191 | 1192 | 1193 | 1194 | 1195 | 1196 | 1197 | 1198 | 1199 | 1200 |
| 21 kDa | 1201 | 1202 | 1203 | 1204 | 1205 | 1206 | 1207 | 1208 | 1209 | 1210 |
| 22 kDa | 1211 | 1212 | 1213 | 1214 | 1215 | 1216 | 1217 | 1218 | 1219 | 1220 |
| 23 kDa | 1221 | 1222 | 1223 | 1224 | 1225 | 1226 | 1227 | 1228 | 1229 | 1230 |
| 24 kDa | 1231 | 1232 | 1233 | 1234 | 1235 | 1236 | 1237 | 1238 | 1239 | 1240 |
| 25 kDa | 1241 | 1242 | 1243 | 1244 | 1245 | 1246 | 1247 | 1248 | 1249 | 1250 |
| 26 kDa | 1251 | 1252 | 1253 | 1254 | 1255 | 1256 | 1257 | 1258 | 1259 | 1260 |
| 27 kDa | 1261 | 1262 | 1263 | 1264 | 1265 | 1266 | 1267 | 1268 | 1269 | 1270 |
| 28 kDa | 1271 | 1272 | 1273 | 1274 | 1275 | 1276 | 1277 | 1278 | 1279 | 1280 |
| 29 kDa | 1281 | 1282 | 1283 | 1284 | 1285 | 1286 | 1287 | 1288 | 1289 | 1290 |
| 30 kDa | 1291 | 1292 | 1293 | 1294 | 1295 | 1296 | 1297 | 1298 | 1299 | 1300 |
| 31 kDa | 1301 | 1302 | 1303 | 1304 | 1305 | 1306 | 1307 | 1308 | 1309 | 1310 |
| 32 kDa | 1311 | 1312 | 1313 | 1314 | 1315 | 1316 | 1317 | 1318 | 1319 | 1320 |
| 33 kDa | 1321 | 1322 | 1323 | 1324 | 1325 | 1326 | 1327 | 1328 | 1329 | 1330 |
| 34 kDa | 1331 | 1332 | 1333 | 1334 | 1335 | 1336 | 1337 | 1338 | 1339 | 1340 |
| 35 kDa | 1341 | 1342 | 1343 | 1344 | 1345 | 1346 | 1347 | 1348 | 1349 | 1350 |
| 36 kDa | 1351 | 1352 | 1353 | 1354 | 1355 | 1356 | 1357 | 1358 | 1359 | 1360 |
| 37 kDa | 1361 | 1362 | 1363 | 1364 | 1365 | 1366 | 1367 | 1368 | 1369 | 1370 |
| 38 kDa | 1371 | 1372 | 1373 | 1374 | 1375 | 1376 | 1377 | 1378 | 1379 | 1380 |
| 39 kDa | 1381 | 1382 | 1383 | 1384 | 1385 | 1386 | 1387 | 1388 | 1389 | 1390 |
| 40 kDa | 1391 | 1392 | 1393 | 1394 | 1395 | 1396 | 1397 | 1398 | 1399 | 1400 |
| 41 kDa | 1401 | 1402 | 1403 | 1404 | 1405 | 1406 | 1407 | 1408 | 1409 | 1410 |
| 42 kDa | 1411 | 1412 | 1413 | 1414 | 1415 | 1416 | 1417 | 1418 | 1419 | 1420 |
| 43 kDa | 1421 | 1422 | 1423 | 1424 | 1425 | 1426 | 1427 | 1428 | 1429 | 1430 |
| 44 kDa | 1431 | 1432 | 1433 | 1434 | 1435 | 1436 | 1437 | 1438 | 1439 | 1440 |
| 45 kDa | 1441 | 1442 | 1443 | 1444 | 1445 | 1446 | 1447 | 1448 | 1449 | 1450 |
| 46 kDa | 1451 | 1452 | 1453 | 1454 | 1455 | 1456 | 1457 | 1458 | 1459 | 1460 |
| 47 kDa | 1461 | 1462 | 1463 | 1464 | 1465 | 1466 | 1467 | 1468 | 1469 | 1470 |
| 48 kDa | 1471 | 1472 | 1473 | 1474 | 1475 | 1476 | 1477 | 1478 | 1479 | 1480 |
| 49 kDa | 1481 | 1482 | 1483 | 1484 | 1485 | 1486 | 1487 | 1488 | 1489 | 1490 |
| 50 kDa | 1491 | 1492 | 1493 | 1494 | 1495 | 1496 | 1497 | 1498 | 1499 | 1500 |
| 51 kDa | 1501 | 1502 | 1503 | 1504 | 1505 | 1506 | 1507 | 1508 | 1509 | 1510 |
| 52 kDa | 1511 | 1512 | 1513 | 1514 | 1515 | 1516 | 1517 | 1518 | 1519 | 1520 |
| 53 kDa | 1521 | 1522 | 1523 | 1524 | 1525 | 1526 | 1527 | 1528 | 1529 | 1530 |
| 54 kDa | 1531 | 1532 | 1533 | 1534 | 1535 | 1536 | 1537 | 1538 | 1539 | 1540 |
| 55 kDa | 1541 | 1542 | 1543 | 1544 | 1545 | 1546 | 1547 | 1548 | 1549 | 1550 |

-continued

| MW (about) | PDI (about) | | | | | | | | | |
|---|---|---|---|---|---|---|---|---|---|---|
| | 1-5 | 1-1.5 | 1.5-2 | 1.5-3 | 2-2.5 | 2.5-3 | 3-3.5 | 3.5-4 | 4-4.5 | 4.5-5 |
| 56 kDa | 1551 | 1552 | 1553 | 1554 | 1555 | 1556 | 1557 | 1558 | 1559 | 1560 |
| 57 kDa | 1561 | 1562 | 1563 | 1564 | 1565 | 1566 | 1567 | 1568 | 1569 | 1570 |
| 58 kDa | 1571 | 1572 | 1573 | 1574 | 1575 | 1576 | 1577 | 1578 | 1579 | 1580 |
| 59 kDa | 1581 | 1582 | 1583 | 1584 | 1585 | 1586 | 1587 | 1588 | 1589 | 1590 |
| 60 kDa | 1591 | 1592 | 1593 | 1594 | 1595 | 1596 | 1597 | 1598 | 1599 | 1600 |
| 61 kDa | 1601 | 1602 | 1603 | 1604 | 1605 | 1606 | 1607 | 1608 | 1609 | 1610 |
| 62 kDa | 1611 | 1612 | 1613 | 1614 | 1615 | 1616 | 1617 | 1618 | 1619 | 1620 |
| 63 kDa | 1621 | 1622 | 1623 | 1624 | 1625 | 1626 | 1627 | 1628 | 1629 | 1630 |
| 64 kDa | 1631 | 1632 | 1633 | 1634 | 1635 | 1636 | 1637 | 1638 | 1639 | 1640 |
| 65 kDa | 1641 | 1642 | 1643 | 1644 | 1645 | 1646 | 1647 | 1648 | 1649 | 1650 |
| 66 kDa | 1651 | 1652 | 1653 | 1654 | 1655 | 1656 | 1657 | 1658 | 1659 | 1660 |
| 67 kDa | 1661 | 1662 | 1663 | 1664 | 1665 | 1666 | 1667 | 1668 | 1669 | 1670 |
| 68 kDa | 1671 | 1672 | 1673 | 1674 | 1675 | 1676 | 1677 | 1678 | 1679 | 1680 |
| 69 kDa | 1681 | 1682 | 1683 | 1684 | 1685 | 1686 | 1687 | 1688 | 1689 | 1690 |
| 70 kDa | 1691 | 1692 | 1693 | 1694 | 1695 | 1696 | 1697 | 1698 | 1699 | 1700 |
| 71 kDa | 1701 | 1702 | 1703 | 1704 | 1705 | 1706 | 1707 | 1708 | 1709 | 1710 |
| 72 kDa | 1711 | 1712 | 1713 | 1714 | 1715 | 1716 | 1717 | 1718 | 1719 | 1720 |
| 73 kDa | 1721 | 1722 | 1723 | 1724 | 1725 | 1726 | 1727 | 1728 | 1729 | 1730 |
| 74 kDa | 1731 | 1732 | 1733 | 1734 | 1735 | 1736 | 1737 | 1738 | 1739 | 1740 |
| 75 kDa | 1741 | 1742 | 1743 | 1744 | 1745 | 1746 | 1747 | 1748 | 1749 | 1750 |
| 76 kDa | 1751 | 1752 | 1753 | 1754 | 1755 | 1756 | 1757 | 1758 | 1759 | 1760 |
| 77 kDa | 1761 | 1762 | 1763 | 1764 | 1765 | 1766 | 1767 | 1768 | 1769 | 1770 |
| 78 kDa | 1771 | 1772 | 1773 | 1774 | 1775 | 1776 | 1777 | 1778 | 1779 | 1780 |
| 79 kDa | 1781 | 1782 | 1783 | 1784 | 1785 | 1786 | 1787 | 1788 | 1789 | 1790 |
| 80 kDa | 1791 | 1792 | 1793 | 1794 | 1795 | 1796 | 1797 | 1798 | 1799 | 1800 |
| 81 kDa | 1801 | 1802 | 1803 | 1804 | 1805 | 1806 | 1807 | 1808 | 1809 | 1810 |
| 82 kDa | 1811 | 1812 | 1813 | 1814 | 1815 | 1816 | 1817 | 1818 | 1819 | 1820 |
| 83 kDa | 1821 | 1822 | 1823 | 1824 | 1825 | 1826 | 1827 | 1828 | 1829 | 1830 |
| 84 kDa | 1831 | 1832 | 1833 | 1834 | 1835 | 1836 | 1837 | 1838 | 1839 | 1840 |
| 85 kDa | 1841 | 1842 | 1843 | 1844 | 1845 | 1846 | 1847 | 1848 | 1849 | 1850 |
| 86 kDa | 1851 | 1852 | 1853 | 1854 | 1855 | 1856 | 1857 | 1858 | 1859 | 1860 |
| 87 kDa | 1861 | 1862 | 1863 | 1864 | 1865 | 1866 | 1867 | 1868 | 1869 | 1870 |
| 88 kDa | 1871 | 1872 | 1873 | 1874 | 1875 | 1876 | 1877 | 1878 | 1879 | 1880 |
| 89 kDa | 1881 | 1882 | 1883 | 1884 | 1885 | 1886 | 1887 | 1888 | 1889 | 1890 |
| 90 kDa | 1891 | 1892 | 1893 | 1894 | 1895 | 1896 | 1897 | 1898 | 1899 | 1900 |
| 91 kDa | 1901 | 1902 | 1903 | 1904 | 1905 | 1906 | 1907 | 1908 | 1909 | 1910 |
| 92 kDa | 1911 | 1912 | 1913 | 1914 | 1915 | 1916 | 1917 | 1918 | 1919 | 1920 |
| 93 kDa | 1921 | 1922 | 1923 | 1924 | 1925 | 1926 | 1927 | 1928 | 1929 | 1930 |
| 94 kDa | 1931 | 1932 | 1933 | 1934 | 1935 | 1936 | 1937 | 1938 | 1939 | 1940 |
| 95 kDa | 1941 | 1942 | 1943 | 1944 | 1945 | 1946 | 1947 | 1948 | 1949 | 1950 |
| 96 kDa | 1951 | 1952 | 1953 | 1954 | 1955 | 1956 | 1957 | 1958 | 1959 | 1960 |
| 97 kDa | 1961 | 1962 | 1963 | 1964 | 1965 | 1966 | 1967 | 1968 | 1969 | 1970 |
| 98 kDa | 1971 | 1972 | 1973 | 1974 | 1975 | 1976 | 1977 | 1978 | 1979 | 1980 |
| 99 kDa | 1981 | 1982 | 1983 | 1984 | 1985 | 1986 | 1987 | 1988 | 1989 | 1990 |
| 100 kDa | 1991 | 1992 | 1993 | 1994 | 1995 | 1996 | 1997 | 1998 | 1999 | 2000 |
| 101 kDa | 2001 | 2002 | 2003 | 2004 | 2005 | 2006 | 2007 | 2008 | 2009 | 2010 |
| 102 kDa | 2011 | 2012 | 2013 | 2014 | 2015 | 2016 | 2017 | 2018 | 2019 | 2020 |
| 103 kDa | 2021 | 2022 | 2023 | 2024 | 2025 | 2026 | 2027 | 2028 | 2029 | 2030 |
| 104 kDa | 2031 | 2032 | 2033 | 2034 | 2035 | 2036 | 2037 | 2038 | 2039 | 2040 |
| 105 kDa | 2041 | 2042 | 2043 | 2044 | 2045 | 2046 | 2047 | 2048 | 2049 | 2050 |
| 106 kDa | 2051 | 2052 | 2053 | 2054 | 2055 | 2056 | 2057 | 2058 | 2059 | 2060 |
| 107 kDa | 2061 | 2062 | 2063 | 2064 | 2065 | 2066 | 2067 | 2068 | 2069 | 2070 |
| 108 kDa | 2071 | 2072 | 2073 | 2074 | 2075 | 2076 | 2077 | 2078 | 2079 | 2080 |
| 109 kDa | 2081 | 2082 | 2083 | 2084 | 2085 | 2086 | 2087 | 2088 | 2089 | 2090 |
| 110 kDa | 2091 | 2092 | 2093 | 2094 | 2095 | 2096 | 2097 | 2098 | 2099 | 2100 |
| 111 kDa | 2101 | 2102 | 2103 | 2104 | 2105 | 2106 | 2107 | 2108 | 2109 | 2110 |
| 112 kDa | 2111 | 2112 | 2113 | 2114 | 2115 | 2116 | 2117 | 2118 | 2119 | 2120 |
| 113 kDa | 2121 | 2122 | 2123 | 2124 | 2125 | 2126 | 2127 | 2128 | 2129 | 2130 |
| 114 kDa | 2131 | 2132 | 2133 | 2134 | 2135 | 2136 | 2137 | 2138 | 2139 | 2140 |
| 115 kDa | 2141 | 2142 | 2143 | 2144 | 2145 | 2146 | 2147 | 2148 | 2149 | 2150 |
| 116 kDa | 2151 | 2152 | 2153 | 2154 | 2155 | 2156 | 2157 | 2158 | 2159 | 2160 |
| 117 kDa | 2161 | 2162 | 2163 | 2164 | 2165 | 2166 | 2167 | 2168 | 2169 | 2170 |
| 118 kDa | 2171 | 2172 | 2173 | 2174 | 2175 | 2176 | 2177 | 2178 | 2179 | 2180 |
| 119 kDa | 2181 | 2182 | 2183 | 2184 | 2185 | 2186 | 2187 | 2188 | 2189 | 2190 |
| 120 kDa | 2191 | 2192 | 2193 | 2194 | 2195 | 2196 | 2197 | 2198 | 2199 | 2200 |
| 121 kDa | 2201 | 2202 | 2203 | 2204 | 2205 | 2206 | 2207 | 2208 | 2209 | 2210 |
| 122 kDa | 2211 | 2212 | 2213 | 2214 | 2215 | 2216 | 2217 | 2218 | 2219 | 2220 |
| 123 kDa | 2221 | 2222 | 2223 | 2224 | 2225 | 2226 | 2227 | 2228 | 2229 | 2230 |
| 124 kDa | 2231 | 2232 | 2233 | 2234 | 2235 | 2236 | 2237 | 2238 | 2239 | 2240 |
| 125 kDa | 2241 | 2242 | 2243 | 2244 | 2245 | 2246 | 2247 | 2248 | 2249 | 2250 |
| 126 kDa | 2251 | 2252 | 2253 | 2254 | 2255 | 2256 | 2257 | 2258 | 2259 | 2260 |
| 127 kDa | 2261 | 2262 | 2263 | 2264 | 2265 | 2266 | 2267 | 2268 | 2269 | 2270 |
| 128 kDa | 2271 | 2272 | 2273 | 2274 | 2275 | 2276 | 2277 | 2278 | 2279 | 2280 |
| 129 kDa | 2281 | 2282 | 2283 | 2284 | 2285 | 2286 | 2287 | 2288 | 2289 | 2290 |
| 130 kDa | 2291 | 2292 | 2293 | 2294 | 2295 | 2296 | 2297 | 2298 | 2299 | 2300 |

-continued

| MW | PDI (about) | | | | | | | | | |
|---|---|---|---|---|---|---|---|---|---|---|
| (about) | 1-5 | 1-1.5 | 1.5-2 | 1.5-3 | 2-2.5 | 2.5-3 | 3-3.5 | 3.5-4 | 4-4.5 | 4.5-5 |
| 131 kDa | 2301 | 2302 | 2303 | 2304 | 2305 | 2306 | 2307 | 2308 | 2309 | 2310 |
| 132 kDa | 2311 | 2312 | 2313 | 2314 | 2315 | 2316 | 2317 | 2318 | 2319 | 2320 |
| 133 kDa | 2321 | 2322 | 2323 | 2324 | 2325 | 2326 | 2327 | 2328 | 2329 | 2330 |
| 134 kDa | 2331 | 2332 | 2333 | 2334 | 2335 | 2336 | 2337 | 2338 | 2339 | 2340 |
| 135 kDa | 2341 | 2342 | 2343 | 2344 | 2345 | 2346 | 2347 | 2348 | 2349 | 2350 |
| 136 kDa | 2351 | 2352 | 2353 | 2354 | 2355 | 2356 | 2357 | 2358 | 2359 | 2360 |
| 137 kDa | 2361 | 2362 | 2363 | 2364 | 2365 | 2366 | 2367 | 2368 | 2369 | 2370 |
| 138 kDa | 2371 | 2372 | 2373 | 2374 | 2375 | 2376 | 2377 | 2378 | 2379 | 2380 |
| 139 kDa | 2381 | 2382 | 2383 | 2384 | 2385 | 2386 | 2387 | 2388 | 2389 | 2390 |
| 140 kDa | 2391 | 2392 | 2393 | 2394 | 2395 | 2396 | 2397 | 2398 | 2399 | 2400 |
| 141 kDa | 2401 | 2402 | 2403 | 2404 | 2405 | 2406 | 2407 | 2408 | 2409 | 2410 |
| 142 kDa | 2411 | 2412 | 2413 | 2414 | 2415 | 2416 | 2417 | 2418 | 2419 | 2420 |
| 143 kDa | 2421 | 2422 | 2423 | 2424 | 2425 | 2426 | 2427 | 2428 | 2429 | 2430 |
| 144 kDa | 2431 | 2432 | 2433 | 2434 | 2435 | 2436 | 2437 | 2438 | 2439 | 2440 |
| 145 kDa | 2441 | 2442 | 2443 | 2444 | 2445 | 2446 | 2447 | 2448 | 2449 | 2450 |

As used herein, "low molecular weight," "low MW," or "low-MW" SPF may include SPF having a weight average molecular weight, or average weight average molecular weight selected from between about 5 kDa to about 38 kDa, about 14 kDa to about 30 kDa, or about 6 kDa to about 17 kDa. In some embodiments, a target low molecular weight for certain SPF may be weight average molecular weight of about 5 kDa, about 6 kDa, about 7 kDa, about 8 kDa, about 9 kDa, about 10 kDa, about 11 kDa, about 12 kDa, about 13 kDa, about 14 kDa, about 15 kDa, about 16 kDa, about 17 kDa, about 18 kDa, about 19 kDa, about 20 kDa, about 21 kDa, about 22 kDa, about 23 kDa, about 24 kDa, about 25 kDa, about 26 kDa, about 27 kDa, about 28 kDa, about 29 kDa, about 30 kDa, about 31 kDa, about 32 kDa, about 33 kDa, about 34 kDa, about 35 kDa, about 36 kDa, about 37 kDa, or about 38 kDa.

As used herein, "medium molecular weight," "medium MW," or "mid-MW" SPF may include SPF having a weight average molecular weight, or average weight average molecular weight selected from between about 31 kDa to about 55 kDa, or about 39 kDa to about 54 kDa. In some embodiments, a target medium molecular weight for certain SPF may be weight average molecular weight of about 31 kDa, about 32 kDa, about 33 kDa, about 34 kDa, about 35 kDa, about 36 kDa, about 37 kDa, about 38 kDa, about 39 kDa, about 40 kDa, about 41 kDa, about 42 kDa, about 43 kDa, about 44 kDa, about 45 kDa, about 46 kDa, about 47 kDa, about 48 kDa, about 49 kDa, about 50 kDa, about 51 kDa, about 52 kDa, about 53 kDa, about 54 kDa, or about 55 kDa.

As used herein, "high molecular weight," "high MW," or "high-MW" SPF may include SPF having a weight average molecular weight, or average weight average molecular weight selected from between about 55 kDa to about 150 kDa. In some embodiments, a target high molecular weight for certain SPF may be about 55 kDa, about 56 kDa, about 57 kDa, about 58 kDa, about 59 kDa, about 60 kDa, about 61 kDa, about 62 kDa, about 63 kDa, about 64 kDa, about 65 kDa, about 66 kDa, about 67 kDa, about 68 kDa, about 69 kDa, about 70 kDa, about 71 kDa, about 72 kDa, about 73 kDa, about 74 kDa, about 75 kDa, about 76 kDa, about 77 kDa, about 78 kDa, about 79 kDa, or about 80 kDa.

In some embodiments, the molecular weights described herein (e.g., low molecular weight silk, medium molecular weight silk, high molecular weight silk) may be converted to the approximate number of amino acids contained within the respective SPF, as would be understood by a person having ordinary skill in the art. For example, the average weight of an amino acid may be about 110 daltons (i.e., 110 g/mol). Therefore, in some embodiments, dividing the molecular weight of a linear protein by 110 daltons may be used to approximate the number of amino acid residues contained therein.

In an embodiment, SPF in a composition of the present disclosure have a polydispersity selected from between 1 to about 5.0, including, without limitation, a polydispersity of 1. In an embodiment, SPF in a composition of the present disclosure have a polydispersity selected from between about 1.5 to about 3.0. In an embodiment, SPF in a composition of the present disclosure have a polydispersity selected from between 1 to about 1.5, including, without limitation, a polydispersity of 1. In an embodiment, SPF in a composition of the present disclosure have a polydispersity selected from between about 1.5 to about 2.0. In an embodiment, SPF in a composition of the present disclosure have a polydispersity selected from between about 2.0 to about 2.5. In an embodiment, SPF in a composition of the present disclosure have a polydispersity selected from between about 2.5 to about 3.0. In an embodiment, SPF in a composition of the present disclosure have a polydispersity selected from between about 3.0 to about 3.5. In an embodiment, SPF in a composition of the present disclosure have a polydispersity selected from between about 3.5 to about 4.0. In an embodiment, SPF in a composition of the present disclosure have a polydispersity selected from between about 4.0 to about 4.5. In an embodiment, SPF in a composition of the present disclosure have a polydispersity selected from between about 4.5 to about 5.0.

In an embodiment, SPF in a composition of the present disclosure have a polydispersity of 1. In an embodiment, SPF in a composition of the present disclosure have a polydispersity of about 1.1. In an embodiment, SPF in a composition of the present disclosure have a polydispersity of about 1.2. In an embodiment, SPF in a composition of the present disclosure have a polydispersity of about 1.3. In an embodiment, SPF in a composition of the present disclosure have a polydispersity of about 1.4. In an embodiment, SPF in a composition of the present disclosure have a polydispersity of about 1.5. In an embodiment, SPF in a composition of the present disclosure have a polydispersity of about 1.6. In an embodiment, SPF in a composition of the present disclosure have a polydispersity of about 1.7. In an embodiment, SPF in a composition of the present disclosure have a polydispersity of about 1.8. In an embodiment, SPF in a composition of the present disclosure have a polydispersity of about 1.9. In an embodiment, SPF in a composition of the present disclosure have a polydispersity of about 2.0. In an embodiment, SPF in a composition of the present disclosure have a polydispersity of about 2.1. In an embodiment, SPF in a composition of the present disclosure have a polydispersity of about 2.2. In an embodiment, SPF in a composition of the present disclosure have a polydispersity of about 2.3. In an embodiment, SPF in a composition of the present disclosure have a polydispersity of about 2.4. In an embodiment, SPF in a composition of the present disclosure have a polydispersity of about 2.5. In an embodiment, SPF in a composition of the present disclosure have a polydispersity of about 2.6. In an embodiment, SPF in a composition of the present disclosure have a polydispersity of about 2.7. In an embodiment, SPF in a composition of the present disclosure have a polydispersity of about 2.8. In an embodiment, SPF in a composition of the present disclosure have a polydispersity of about 2.9. In an embodiment, SPF in a composition of the present disclosure have a polydispersity of about 3.0. In an embodiment, SPF in a composition of the present disclosure have a polydispersity of about 3.1. In an embodiment, SPF in a composition of the present disclosure have a polydispersity of about 3.2. In an embodiment, SPF in a composition of the present disclosure have a polydispersity of about 3.3. In an embodiment, SPF in a composition of the present disclosure have a polydispersity of about 3.4. In an embodiment, SPF in a composition of the present disclosure have a polydispersity of about 3.5. In an embodiment, SPF in a composition of the present disclosure have a polydispersity of about 3.6. In an embodiment, SPF in a composition of the present disclosure have a polydispersity of about 3.7. In an embodiment, SPF in a composition of the present disclosure have a polydispersity of about 3.8. In an embodiment, SPF in a composition of the present disclosure have a polydispersity of about 3.9. In an embodiment, SPF in a composition of the present disclosure have a polydispersity of about 4.0. In an embodiment, SPF in a composition of the present disclosure have a polydispersity of about 4.1. In an embodiment, SPF in a composition of the present disclosure have a polydispersity of about 4.2. In an embodiment, SPF in a composition of the present disclosure have a polydispersity of about 4.3. In an embodiment, SPF in a composition of the present disclosure have a polydispersity of about 4.4. In an embodiment, SPF in a composition of the present disclosure have a polydispersity of about 4.5. In an embodiment, SPF in a composition of the present disclosure have a polydispersity of about 4.6. In an embodiment, SPF in a composition of the present disclosure have a polydispersity of about 4.7. In an embodiment, SPF in a composition of the present disclosure have a polydispersity of about 4.8. In an embodiment, SPF in a composition of the present disclosure have a polydispersity of about 4.9. In an embodiment, SPF in a composition of the present disclosure have a polydispersity of about 5.0.

In some embodiments, in compositions described herein having combinations of low, medium, and/or high molecular weight SPF, such low, medium, and/or high molecular weight SPF may have the same or different polydispersities.

Silk Fibroin Fragments

Methods of making silk fibroin or silk fibroin protein fragments and their applications in various fields are known and are described for example in U.S. Pat. Nos. 9,187,538, 9,511,012, 9,517,191, 9,522,107, 9,522,108, 9,545,369, and 10,166,177, 10,287,728 and 10,301,768, all of which are incorporated herein in their entireties. Raw silk from silkworm *Bombyx mori* is composed of two primary proteins: silk fibroin (approximately 75%) and sericin (approximately 25%). Silk fibroin is a fibrous protein with a semi-crystalline structure that provides stiffness and strength. As used herein, the term "silk fibroin" means the fibers of the cocoon of *Bombyx mori* having a weight average molecular weight of about 370,000 Da. The crude silkworm fiber consists of a double thread of fibroin. The adhesive substance holding these double fibers together is sericin. The silk fibroin is composed of a heavy chain having a weight average molecular weight of about 350,000 Da (H chain), and a light chain having a weight average molecular weight about 25,000 Da (L chain). Silk fibroin is an amphiphilic polymer with large hydrophobic domains occupying the major component of the polymer, which has a high molecular weight. The hydrophobic regions are interrupted by small hydrophilic spacers, and the N- and C-termini of the chains are also highly hydrophilic. The hydrophobic domains of the H-chain contain a repetitive hexapeptide sequence of Gly-Ala-Gly-Ala-Gly-Ser and repeats of Gly-Ala/Ser/Tyr dipeptides, which can form stable anti-parallel-sheet crystallites. The amino acid sequence of the L-chain is non-repetitive, so the L-chain is more hydrophilic and relatively elastic. The hydrophilic (Tyr, Ser) and hydrophobic (Gly, Ala) chain segments in silk fibroin molecules are arranged alternatively such that allows self-assembling of silk fibroin molecules.

Provided herein are methods for producing pure and highly scalable silk fibroin-protein fragment mixture solutions that may be used across multiple industries for a variety of applications. Without wishing to be bound by any particular theory, it is believed that these methods are equally applicable to fragmentation of any SPF described herein, including without limitation recombinant silk proteins, and fragmentation of silk-like or fibroin-like proteins.

As used herein, the term "fibroin" includes silk worm fibroin and insect or spider silk protein. In an embodiment, fibroin is obtained from *Bombyx mori*. Raw silk from *Bombyx mori* is composed of two primary proteins: silk fibroin (approximately 75%) and sericin (approximately 25%). Silk fibroin is a fibrous protein with a semi-crystalline structure that provides stiffness and strength. As used herein, the term "silk fibroin" means the fibers of the cocoon of *Bombyx mori* having a weight average molecular weight of about 370,000 Da. Conversion of these insoluble silk fibroin fibrils into water-soluble silk fibroin protein fragments requires the addition of a concentrated neutral salt (e.g., 8-10 M lithium bromide), which interferes with inter- and intramolecular ionic and hydrogen bonding that would otherwise render the fibroin protein insoluble in water. Methods of making silk fibroin protein fragments, and/or compositions thereof, are known and are described for example in U.S. Pat. Nos. 9,187,538, 9,511,012, 9,517,191, 9,522,107, 9,522,108, 9,545,369, and 10,166,177.

The raw silk cocoons from the silkworm *Bombyx mori* was cut into pieces. The pieces silk cocoons were processed in an aqueous solution of $Na_2CO_3$ at about 100° C. for about 60 minutes to remove sericin (degumming). The volume of the water used equals about 0.4×raw silk weight and the amount of $Na_2CO_3$ is about 0.848×the weight of the raw silk cocoon pieces. The resulting degummed silk cocoon pieces were rinsed with deionized water three times at about 60° C. (20 minutes per rinse). The volume of rinse water for each cycle was 0.2 L×the weight of the raw silk cocoon pieces. The excess water from the degummed silk cocoon pieces was removed. After the DI water washing step, the wet degummed silk cocoon pieces were dried at room temperature. The degummed silk cocoon pieces were mixed with a LiBr solution, and the mixture was heated to about 100° C.

The warmed mixture was placed in a dry oven and was heated at about 100° C. for about 60 minutes to achieve complete dissolution of the native silk protein. The resulting silk fibroin solution was filtered and dialyzed using Tangential Flow Filtration (TFF) and a 10 kDa membrane against deionized water for 72 hours. The resulting silk fibroin aqueous solution has a concentration of about 8.5 wt. %. Then, 8.5% silk solution was diluted with water to result in a 1.0% w/v silk solution. TFF can then be used to further concentrate the pure silk solution to a concentration of 20.0% w/w silk to water.

Dialyzing the silk through a series of water changes is a manual and time intensive process, which could be accelerated by changing certain parameters, for example diluting the silk solution prior to dialysis. The dialysis process could be scaled for manufacturing by using semi-automated equipment, for example a tangential flow filtration system.

In some embodiments, the silk solutions are prepared under various preparation condition parameters such as: 90° C. 30 min, 90° C. 60 min, 100° C. 30 min, and 100° C. 60 min. Briefly, 9.3 M LiBr was prepared and allowed to sit at room temperature for at least 30 minutes. 5 mL of LiBr solution was added to 1.25 g of silk and placed in the 60° C. oven. Samples from each set were removed at 4, 6, 8, 12, 24, 168 and 192 hours.

In some embodiments, the silk solutions are prepared under various preparation condition parameters such as: 90° C. 30 min, 90° C. 60 min, 100° C. 30 min, and 100° C. 60 min. Briefly, 9.3 M LiBr solution was heated to one of four temperatures: 60° C., 80° C., 100° C. or boiling. 5 mL of hot LiBr solution was added to 1.25 g of silk and placed in the 60° C. oven. Samples from each set were removed at 1, 4 and 6 hours.

In some embodiments, the silk solutions are prepared under various preparation condition parameters such as: Four different silk extraction combinations were used: 90° C. 30 min, 90° C. 60 min, 100° C. 30 min, and 100° C. 60 min. Briefly, 9.3 M LiBr solution was heated to one of four temperatures: 60° C., 80° C., 100° C. or boiling. 5 mL of hot LiBr solution was added to 1.25 g of silk and placed in the oven at the same temperature of the LiBr. Samples from each set were removed at 1, 4 and 6 hours. 1 mL of each sample was added to 7.5 mL of 9.3 M LiBr and refrigerated for viscosity testing.

In some embodiments, SPF are obtained by dissolving raw unscoured, partially scoured, or scoured silkworm fibers with a neutral lithium bromide salt. The raw silkworm silks are processed under selected temperature and other conditions in order to remove any sericin and achieve the desired weight average molecular weight (Mw) and polydispersity (PD) of the fragment mixture. Selection of process parameters may be altered to achieve distinct final silk protein fragment characteristics depending upon the intended use. The resulting final fragment solution is silk fibroin protein fragments and water with parts per million (ppm) to non-detectable levels of process contaminants, levels acceptable in the pharmaceutical, medical and consumer eye care markets. The concentration, size and polydispersity of SPF may further be altered depending upon the desired use and performance requirements.

FIG. 1 is a flow chart showing various embodiments for producing pure silk fibroin protein fragments (SPFs) of the present disclosure. It should be understood that not all of the steps illustrated are necessarily required to fabricate all silk solutions of the present disclosure. As illustrated in FIG. 1, step A, cocoons (heat-treated or non-heat-treated), silk fibers, silk powder, spider silk or recombinant spider silk can be used as the silk source. If starting from raw silk cocoons from *Bombyx mori*, the cocoons can be cut into small pieces, for example pieces of approximately equal size, step B 1. The raw silk is then extracted and rinsed to remove any sericin, step C1a. This results in substantially sericin free raw silk. In an embodiment, water is heated to a temperature between 84° C. and 100° C. (ideally boiling) and then $Na_2CO_3$ (sodium carbonate) is added to the boiling water until the $Na_2CO_3$ is completely dissolved. The raw silk is added to the boiling water/$Na_2CO_3$ (100° C.) and submerged for approximately 15-90 minutes, where boiling for a longer time results in smaller silk protein fragments. In an embodiment, the water volume equals about 0.4×raw silk weight and the $Na_2CO_3$ volume equals about 0.848×raw silk weight. In an embodiment, the water volume equals 0.1×raw silk weight and the $Na_2CO_3$ volume is maintained at 2.12 g/L.

Subsequently, the water dissolved $Na_2CO_3$ solution is drained and excess water/$Na_2CO_3$ is removed from the silk fibroin fibers (e.g., ring out the fibroin extract by hand, spin cycle using a machine, etc.). The resulting silk fibroin extract is rinsed with warm to hot water to remove any remaining adsorbed sericin or contaminate, typically at a temperature range of about 40° C. to about 80° C., changing the volume of water at least once (repeated for as many times as required). The resulting silk fibroin extract is a substantially sericin-depleted silk fibroin. In an embodiment, the resulting silk fibroin extract is rinsed with water at a temperature of about 60° C. In an embodiment, the volume of rinse water for each cycle equals 0.1 L to 0.2 L×raw silk weight. It may be advantageous to agitate, turn or circulate the rinse water to maximize the rinse effect. After rinsing, excess water is removed from the extracted silk fibroin fibers (e.g., ring out fibroin extract by hand or using a machine). Alternatively, methods known to one skilled in the art such as pressure, temperature, or other reagents or combinations thereof may be used for the purpose of sericin extraction. Alternatively, the silk gland (100% sericin free silk protein) can be removed directly from a worm. This would result in liquid silk protein, without any alteration of the protein structure, free of sericin.

The extracted fibroin fibers are then allowed to dry completely. Once dry, the extracted silk fibroin is dissolved using a solvent added to the silk fibroin at a temperature between ambient and boiling, step C1b. In an embodiment, the solvent is a solution of Lithium bromide (LiBr) (boiling for LiBr is 140° C.). Alternatively, the extracted fibroin fibers are not dried but wet and placed in the solvent; solvent concentration can then be varied to achieve similar concentrations as to when adding dried silk to the solvent. The final concentration of LiBr solvent can range from 0.1 M to 9.3 M. Complete dissolution of the extracted fibroin fibers can be achieved by varying the treatment time and temperature along with the concentration of dissolving solvent. Other solvents may be used including, but not limited to, phosphate phosphoric acid, calcium nitrate, calcium chloride solution or other concentrated aqueous solutions of inorganic salts. To ensure complete dissolution, the silk fibers should be fully immersed within the already heated solvent solution and then maintained at a temperature ranging from about 60° C. to about 140° C. for 1-168 hrs. In an embodiment, the silk fibers should be fully immersed within the solvent solution and then placed into a dry oven at a temperature of about 100° C. for about 1 hour.

The temperature at which the silk fibroin extract is added to the LiBr solution (or vice versa) has an effect on the time required to completely dissolve the fibroin and on the resulting molecular weight and polydispersity of the final SPF mixture solution. In an embodiment, silk solvent solution concentration is less than or equal to 20% w/v. In addition, agitation during introduction or dissolution may be used to facilitate dissolution at varying temperatures and concentrations. The temperature of the LiBr solution will provide control over the silk protein fragment mixture molecular weight and polydispersity created. In an embodiment, a higher temperature will more quickly dissolve the silk offering enhanced process scalability and mass production of silk solution. In an embodiment, using a LiBr solution heated to a temperature from 80° C. to 140° C. reduces the time required in an oven in order to achieve full dissolution. Varying time and temperature at or above 60° C. of the dissolution solvent will alter and control the MW and polydispersity of the SPF mixture solutions formed from the original molecular weight of the native silk fibroin protein.

Alternatively, whole cocoons may be placed directly into a solvent, such as LiBr, bypassing extraction, step B2. This requires subsequent filtration of silk worm particles from the silk and solvent solution and sericin removal using methods know in the art for separating hydrophobic and hydrophilic proteins such as a column separation and/or chromatography, ion exchange, chemical precipitation with salt and/or pH, and or enzymatic digestion and filtration or extraction, all methods are common examples and without limitation for standard protein separation methods, step C2. Non-heat treated cocoons with the silkworm removed, may alternatively be placed into a solvent such as LiBr, bypassing extraction. The methods described above may be used for sericin separation, with the advantage that non-heat treated cocoons will contain significantly less worm debris.

Dialysis may be used to remove the dissolution solvent from the resulting dissolved fibroin protein fragment solution by dialyzing the solution against a volume of water, step E1. Pre-filtration prior to dialysis is helpful to remove any debris (i.e., silk worm remnants) from the silk and LiBr solution, step D. In one example, a 3 μm or 5 μm filter is used with a flow-rate of 200-300 mL/min to filter a 0.1% to 1.0% silk-LiBr solution prior to dialysis and potential concentration if desired. A method disclosed herein, as described above, is to use time and/or temperature to decrease the concentration from 9.3 M LiBr to a range from 0.1 M to 9.3 M to facilitate filtration and downstream dialysis, particularly when considering creating a scalable process method. Alternatively, without the use of additional time or temperate, a 9.3 M LiBr-silk protein fragment solution may be diluted with water to facilitate debris filtration and dialysis. The result of dissolution at the desired time and temperate filtration is a translucent particle-free room temperature shelf-stable silk protein fragment-LiBr solution of a known MW and polydispersity. It is advantageous to change the dialysis water regularly until the solvent has been removed (e.g., change water after 1 hour, 4 hours, and then every 12 hours for a total of 6 water changes). The total number of water volume changes may be varied based on the resulting concentration of solvent used for silk protein dissolution and fragmentation. After dialysis, the final silk solution maybe further filtered to remove any remaining debris (i.e., silk worm remnants).

Alternatively, Tangential Flow Filtration (TFF), which is a rapid and efficient method for the separation and purification of biomolecules, may be used to remove the solvent from the resulting dissolved fibroin solution, step E2. TFF offers a highly pure aqueous silk protein fragment solution and enables scalability of the process in order to produce large volumes of the solution in a controlled and repeatable manner. The silk and LiBr solution may be diluted prior to TFF (20% down to 0.1% silk in either water or LiBr). Pre-filtration as described above prior to TFF processing may maintain filter efficiency and potentially avoids the creation of silk gel boundary layers on the filter's surface as the result of the presence of debris particles. Pre-filtration prior to TFF is also helpful to remove any remaining debris (i.e., silk worm remnants) from the silk and LiBr solution that may cause spontaneous or long-term gelation of the resulting water only solution, step D. TFF, recirculating or single pass, may be used for the creation of water-silk protein fragment solutions ranging from 0.1% silk to 30.0% silk (more preferably, 0.1%-6.0% silk). Different cutoff size TFF membranes may be required based upon the desired concentration, molecular weight and polydispersity of the silk protein fragment mixture in solution. Membranes ranging from 1-100 kDa may be necessary for varying molecular weight silk solutions created for example by varying the length of extraction boil time or the time and temperate in dissolution solvent (e.g., LiBr). In an embodiment, a TFF 5 or 10 kDa membrane is used to purify the silk protein fragment mixture solution and to create the final desired silk-to-water ratio. As well, TFF single pass, TFF, and other methods known in the art, such as a falling film evaporator, may be used to concentrate the solution following removal of the dissolution solvent (e.g., LiBr) (with resulting desired concentration ranging from 0.1% to 30% silk). This can be used as an alternative to standard HFIP concentration methods known in the art to create a water-based solution. A larger pore membrane could also be utilized to filter out small silk protein fragments and to create a solution of higher molecular weight silk with and/or without tighter polydispersity values.

An assay for LiBr and $Na_2CO_3$ detection can be performed using an HPLC system equipped with evaporative light scattering detector (ELSD). The calculation was performed by linear regression of the resulting peak areas for the analyte plotted against concentration. More than one sample of a number of formulations of the present disclosure was used for sample preparation and analysis. Generally, four samples of different formulations were weighed directly in a 10 mL volumetric flask. The samples were suspended in 5 mL of 20 mM ammonium formate (pH 3.0) and kept at 2-8° C. for 2 hours with occasional shaking to extract analytes from the film. After 2 hours the solution was diluted with 20 mM ammonium formate (pH 3.0). The sample solution from the volumetric flask was transferred into HPLC vials and injected into the HPLC-ELSD system for the estimation of sodium carbonate and lithium bromide.

The analytical method developed for the quantitation of $Na_2CO_3$ and LiBr in silk protein formulations was found to be linear in the range 10-165 μg/mL, with RSD for injection precision as 2% and 1% for area and 0.38% and 0.19% for retention time for sodium carbonate and lithium bromide respectively. The analytical method can be applied for the quantitative determination of sodium carbonate and lithium bromide in silk protein formulations.

Figure 2:
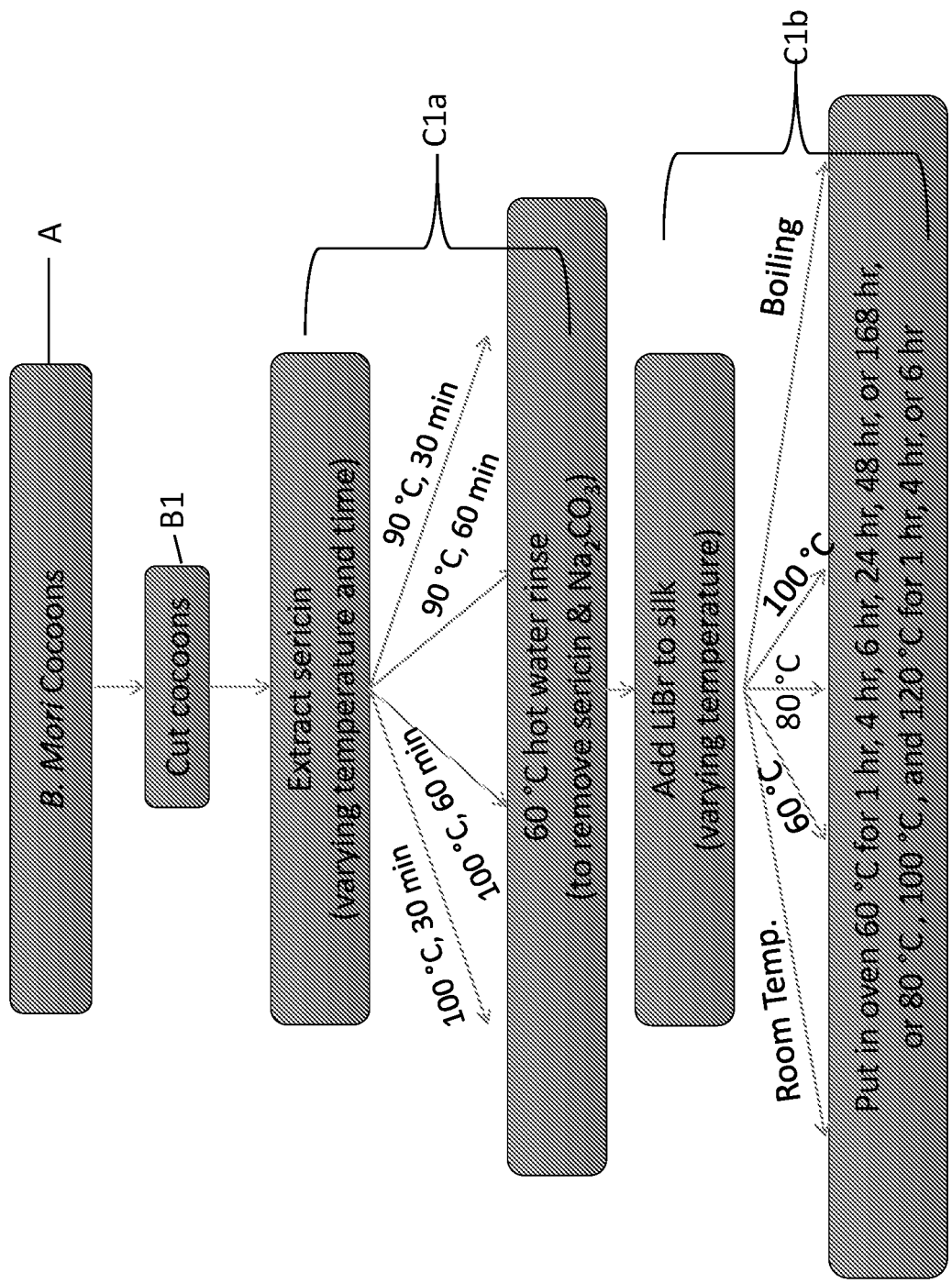
FIG. 2 is a flow chart showing various parameters that can be modified during the process of producing a silk protein fragment solution of the present disclosure during the extraction and the dissolution steps.

FIG. 2 is a flow chart showing various parameters that can be modified during the process of producing a silk protein fragment solution of the present disclosure during the extraction and the dissolution steps. Select method parameters may be altered to achieve distinct final solution characteristics depending upon the intended use, e.g., molecular weight and polydispersity. It should be understood that not all of the steps illustrated are necessarily required to fabricate all silk solutions of the present disclosure.

In an embodiment, silk protein fragment solutions useful for a wide variety of applications are prepared according to the following steps: forming pieces of silk cocoons from the *Bombyx mori* silkworm; extracting the pieces at about 100° C. in a $Na_2CO_3$ water solution for about 60 minutes, wherein a volume of the water equals about 0.4×raw silk weight and the amount of $Na_2CO_3$ is about 0.848×the weight of the pieces to form a silk fibroin extract; triple rinsing the silk fibroin extract at about 60° C. for about 20 minutes per rinse in a volume of rinse water, wherein the rinse water for each cycle equals about 0.2 L×the weight of the pieces; removing excess water from the silk fibroin extract; drying the silk fibroin extract; dissolving the dry silk fibroin extract in a LiBr solution, wherein the LiBr solution is first heated to about 100° C. to create a silk and LiBr solution and maintained; placing the silk and LiBr solution in a dry oven at about 100° C. for about 60 minutes to achieve complete dissolution and further fragmentation of the native silk protein structure into mixture with desired molecular weight and polydispersity; filtering the solution to remove any remaining debris from the silkworm; diluting the solution with water to result in a 1.0 wt. % silk solution; and removing solvent from the solution using Tangential Flow Filtration (TFF). In an embodiment, a 10 kDa membrane is utilized to purify the silk solution and create the final desired silk-to-water ratio. TFF can then be used to further concentrate the silk solution to a concentration of 2.0 wt. % silk in water.

Without wishing to be bound by any particular theory, varying extraction (i.e., time and temperature), LiBr (i.e., temperature of LiBr solution when added to silk fibroin extract or vice versa) and dissolution (i.e., time and temperature) parameters results in solvent and silk solutions with different viscosities, homogeneities, and colors. Also without wishing to be bound by any particular theory, increasing the temperature for extraction, lengthening the extraction time, using a higher temperature LiBr solution at emersion and over time when dissolving the silk and increasing the time at temperature (e.g., in an oven as shown here, or an alternative heat source) all resulted in less viscous and more homogeneous solvent and silk solutions.

The extraction step could be completed in a larger vessel, for example an industrial washing machine where temperatures at or in between 60° C. to 100° C. can be maintained. The rinsing step could also be completed in the industrial washing machine, eliminating the manual rinse cycles. Dissolution of the silk in LiBr solution could occur in a vessel other than a convection oven, for example a stirred tank reactor. Dialyzing the silk through a series of water changes is a manual and time intensive process, which could be accelerated by changing certain parameters, for example diluting the silk solution prior to dialysis. The dialysis process could be scaled for manufacturing by using semi-automated equipment, for example a tangential flow filtration system.

Varying extraction (i.e., time and temperature), LiBr (i.e., temperature of LiBr solution when added to silk fibroin extract or vice versa) and dissolution (i.e., time and temperature) parameters results in solvent and silk solutions with different viscosities, homogeneities, and colors. Increasing the temperature for extraction, lengthening the extraction time, using a higher temperature LiBr solution at emersion and over time when dissolving the silk and increasing the time at temperature (e.g., in an oven as shown here, or an alternative heat source) all resulted in less viscous and more homogeneous solvent and silk solutions. While almost all parameters resulted in a viable silk solution, methods that allow complete dissolution to be achieved in fewer than 4 to 6 hours are preferred for process scalability.

In an embodiment, solutions of silk fibroin protein fragments having a weight average selected from between about 6 kDa to about 17 kDa are prepared according to following steps: degumming a silk source by adding the silk source to a boiling (100° C.) aqueous solution of sodium carbonate for a treatment time of between about 30 minutes to about 60 minutes; removing sericin from the solution to produce a silk fibroin extract comprising non-detectable levels of sericin; draining the solution from the silk fibroin extract; dissolving the silk fibroin extract in a solution of lithium bromide having a starting temperature upon placement of the silk fibroin extract in the lithium bromide solution that ranges from about 60° C. to about 140° C.; maintaining the solution of silk fibroin-lithium bromide in an oven having a temperature of about 140° C. for a period of at most 1 hour; removing the lithium bromide from the silk fibroin extract; and producing an aqueous solution of silk protein fragments, the aqueous solution comprising: fragments having a weight average molecular weight selected from between about 6 kDa to about 17 kDa, and a polydispersity of between 1 and about 5, or between about 1.5 and about 3.0. The method may further comprise drying the silk fibroin extract prior to the dissolving step. The aqueous solution of silk fibroin protein fragments may comprise lithium bromide residuals of less than 300 ppm as measured using a high-performance liquid chromatography lithium bromide assay. The aqueous solution of silk fibroin protein fragments may comprise sodium carbonate residuals of less than 100 ppm as measured using a high-performance liquid chromatography sodium carbonate assay. The aqueous solution of silk fibroin protein fragments may be lyophilized. In some embodiments, the silk fibroin protein fragment solution may be further processed into various forms including gel, powder, and nanofiber.

In an embodiment, solutions of silk fibroin protein fragments having a weight average molecular weight selected from between about 17 kDa to about 39 kDa are prepared according to the following steps: adding a silk source to a boiling (100° C.) aqueous solution of sodium carbonate for a treatment time of between about 30 minutes to about 60 minutes so as to result in degumming; removing sericin from the solution to produce a silk fibroin extract comprising non-detectable levels of sericin; draining the solution from the silk fibroin extract; dissolving the silk fibroin extract in a solution of lithium bromide having a starting temperature upon placement of the silk fibroin extract in the lithium bromide solution that ranges from about 80° C. to about 140° C.; maintaining the solution of silk fibroin-lithium bromide in a dry oven having a temperature in the range between about 60° C. to about 100° C. for a period of at most 1 hour; removing the lithium bromide from the silk fibroin extract; and producing an aqueous solution of silk fibroin protein fragments, wherein the aqueous solution of silk fibroin protein fragments comprises lithium bromide residuals of between about 10 ppm and about 300 ppm, wherein the aqueous solution of silk protein fragments comprises sodium carbonate residuals of between about 10 ppm and about 100 ppm, wherein the aqueous solution of silk fibroin protein fragments comprises fragments having a weight average molecular weight selected from between about 17 kDa to about 39 kDa, and a polydispersity of between 1 and about 5, or between about 1.5 and about 3.0. The method may further comprise drying the silk fibroin extract prior to the dissolving step. The aqueous solution of silk fibroin protein fragments may comprise lithium bromide residuals of less than 300 ppm as measured using a high-performance liquid chromatography lithium bromide assay. The aqueous solution of silk fibroin protein fragments may comprise sodium carbonate residuals of less than 100 ppm as measured using a high-performance liquid chromatography sodium carbonate assay.

In some embodiments, a method for preparing an aqueous solution of silk fibroin protein fragments having an average weight average molecular weight selected from between about 6 kDa to about 17 kDa includes the steps of: degumming a silk source by adding the silk source to a boiling (100° C.) aqueous solution of sodium carbonate for a treatment time of between about 30 minutes to about 60 minutes; removing sericin from the solution to produce a silk fibroin extract comprising non-detectable levels of sericin; draining the solution from the silk fibroin extract; dissolving the silk fibroin extract in a solution of lithium bromide having a starting temperature upon placement of the silk fibroin extract in the lithium bromide solution that ranges from about 60° C. to about 140° C.; maintaining the solution of silk fibroin-lithium bromide in an oven having a temperature of about 140° C. for a period of at least 1 hour; removing the lithium bromide from the silk fibroin extract; and producing an aqueous solution of silk protein fragments, the aqueous solution comprising: fragments having an average weight average molecular weight selected from between about 6 kDa to about 17 kDa, and a polydispersity of between 1 and about 5, or between about 1.5 and about 3.0. The method may further comprise drying the silk fibroin extract prior to the dissolving step. The aqueous solution of pure silk fibroin protein fragments may comprise lithium bromide residuals of less than 300 ppm as measured using a high-performance liquid chromatography lithium bromide assay. The aqueous solution of pure silk fibroin protein fragments may comprise sodium carbonate residuals of less than 100 ppm as measured using a high-performance liquid chromatography sodium carbonate assay. The method may further comprise adding a therapeutic agent to the aqueous solution of pure silk fibroin protein fragments. The method may further comprise adding a molecule selected from one of an antioxidant or an enzyme to the aqueous solution of pure silk fibroin protein fragments. The method may further comprise adding a vitamin to the aqueous solution of pure silk fibroin protein fragments. The vitamin may be vitamin C or a derivative thereof. The aqueous solution of pure silk fibroin protein fragments may be lyophilized. The method may further comprise adding an alpha hydroxy acid to the aqueous solution of pure silk fibroin protein fragments. The alpha hydroxy acid may be selected from the group consisting of glycolic acid, lactic acid, tartaric acid and citric acid. The method may further comprise adding hyaluronic acid or its salt form at a concentration of about 0.5% to about 10.0% to the aqueous solution of pure silk fibroin protein fragments. The method may further comprise adding at least one of zinc oxide or titanium dioxide. A film may be fabricated from the aqueous solution of pure silk fibroin protein fragments produced by this method. The film may comprise from about 1.0 wt. % to about 50.0 wt. % of vitamin C or a derivative thereof. The film may have a water content ranging from about 2.0 wt. % to about 20.0 wt. %. The film may comprise from about 30.0 wt. % to about 99.5 wt. % of pure silk fibroin protein fragments. A gel may be fabricated from the aqueous solution of pure silk fibroin protein fragments produced by this method. The gel may comprise from about 0.5 wt. % to about 20.0 wt. % of vitamin C or a derivative thereof. The gel may have a silk content of at least 2% and a vitamin content of at least 20%.

In some embodiments, a method for preparing an aqueous solution of silk fibroin protein fragments having an average weight average molecular weight selected from between about 17 kDa to about 39 kDa includes the steps of: adding a silk source to a boiling (100° C.) aqueous solution of sodium carbonate for a treatment time of between about 30 minutes to about 60 minutes so as to result in degumming; removing sericin from the solution to produce a silk fibroin extract comprising non-detectable levels of sericin; draining the solution from the silk fibroin extract; dissolving the silk fibroin extract in a solution of lithium bromide having a starting temperature upon placement of the silk fibroin extract in the lithium bromide solution that ranges from about 80° C. to about 140° C.; maintaining the solution of silk fibroin-lithium bromide in a dry oven having a temperature in the range between about 60° C. to about 100° C. for a period of at least 1 hour; removing the lithium bromide from the silk fibroin extract; and producing an aqueous solution of pure silk fibroin protein fragments, wherein the aqueous solution of pure silk fibroin protein fragments comprises lithium bromide residuals of between about 10 ppm and about 300 ppm, wherein the aqueous solution of silk protein fragments comprises sodium carbonate residuals of between about 10 ppm and about 100 ppm, wherein the aqueous solution of pure silk fibroin protein fragments comprises fragments having an average weight average molecular weight selected from between about 17 kDa to about 39 kDa, and a polydispersity of between 1 and about 5, or between about 1.5 and about 3.0. The method may further comprise drying the silk fibroin extract prior to the dissolving step. The aqueous solution of pure silk fibroin protein fragments may comprise lithium bromide residuals of less than 300 ppm as measured using a high-performance liquid chromatography lithium bromide assay. The aqueous solution of pure silk fibroin protein fragments may comprise sodium carbonate residuals of less than 100 ppm as measured using a high-performance liquid chromatography sodium carbonate assay. The method may further comprise adding a therapeutic agent to the aqueous solution of pure silk fibroin protein fragments. The method may further comprise adding a molecule selected from one of an antioxidant or an enzyme to the aqueous solution of pure silk fibroin protein fragments. The method may further comprise adding a vitamin to the aqueous solution of pure silk fibroin protein fragments. The vitamin may be vitamin C or a derivative thereof. The aqueous solution of pure silk fibroin protein fragments may be lyophilized. The method may further comprise adding an alpha hydroxy acid to the aqueous solution of pure silk fibroin protein fragments. The alpha hydroxy acid may be selected from the group consisting of glycolic acid, lactic acid, tartaric acid and citric acid. The method may further comprise adding hyaluronic acid or its salt form at a concentration of about 0.5% to about 10.0% to the aqueous solution of pure silk fibroin protein fragments. The method may further comprise adding at least one of zinc oxide or titanium dioxide. A film may be fabricated from the aqueous solution of pure silk fibroin protein fragments produced by this method. The film may comprise from about 1,0 wt. % to about 50.0 wt. % of vitamin C or a derivative thereof. The film may have a water content ranging from about 2.0 wt. % to about 20.0 wt. %. The film may comprise from about 30.0 wt. % to about 99.5 wt. % of pure silk fibroin protein fragments. A gel may be fabricated from the aqueous solution of pure silk fibroin protein fragments produced by this method. The gel may comprise from about 0.5 wt. % to about 20.0 wt. % of vitamin C or a derivative thereof. The gel may have a silk content of at least 2% and a vitamin content of at least 20%.

In an embodiment, solutions of silk fibroin protein fragments having a weight average molecular weight selected from between about 39 kDa to about 80 kDa are prepared according to the following steps: adding a silk source to a boiling (100° C.) aqueous solution of sodium carbonate for a treatment time of about 30 minutes so as to result in degumming; removing sericin from the solution to produce a silk fibroin extract comprising non-detectable levels of sericin; draining the solution from the silk fibroin extract; dissolving the silk fibroin extract in a solution of lithium bromide having a starting temperature upon placement of the silk fibroin extract in the lithium bromide solution that ranges from about 80° C. to about 140° C.; maintaining the solution of silk fibroin-lithium bromide in a dry oven having a temperature in the range between about 60° C. to about 100° C. for a period of at most 1 hour; removing the lithium bromide from the silk fibroin extract; and producing an aqueous solution of silk fibroin protein fragments, wherein the aqueous solution of silk fibroin protein fragments comprises lithium bromide residuals of between about 10 ppm and about 300 ppm, sodium carbonate residuals of between about 10 ppm and about 100 ppm, fragments having a weight average molecular weight selected from between about 39 kDa to about 80 kDa, and a polydispersity of between 1 and about 5, or between about 1.5 and about 3.0. The method may further comprise drying the silk fibroin extract prior to the dissolving step. The aqueous solution of silk fibroin protein fragments may comprise lithium bromide residuals of less than 300 ppm as measured using a high-performance liquid chromatography lithium bromide assay. The aqueous solution of silk fibroin protein fragments may comprise sodium carbonate residuals of less than 100 ppm as measured using a high-performance liquid chromatography sodium carbonate assay. In some embodiments, the method may further comprise adding an active agent (e.g., therapeutic agent) to the aqueous solution of pure silk fibroin protein fragments. The method may further comprise adding an active agent selected from one of an antioxidant or an enzyme to the aqueous solution of pure silk fibroin protein fragments. The method may further comprise adding a vitamin to the aqueous solution of pure silk fibroin protein fragments. The vitamin may be vitamin C or a derivative thereof. The aqueous solution of pure silk fibroin protein fragments may be lyophilized. The method may further comprise adding an alpha-hydroxy acid to the aqueous solution of pure silk fibroin protein fragments. The alpha hydroxy acid may be selected from the group consisting of glycolic acid, lactic acid, tartaric acid and citric acid. The method may further comprise adding hyaluronic acid or its salt form at a concentration of about 0.5% to about 10.0% to the aqueous solution of pure silk fibroin protein fragments. A film may be fabricated from the aqueous solution of pure silk fibroin protein fragments produced by this method. The film may comprise from about 1.0 wt. % to about 50.0 wt. % of vitamin C or a derivative thereof. The film may have a water content ranging from about 2.0 wt. % to about 20.0 wt. %. The film may comprise from about 30.0 wt. % to about 99.5 wt. % of pure silk fibroin protein fragments. A gel may be fabricated from the aqueous solution of pure silk fibroin protein fragments produced by this method. The gel may comprise from about 0.5 wt. % to about 20.0 wt. % of vitamin C or a derivative thereof. The gel may have a silk content of at least 2 wt. % and a vitamin content of at least 20 wt. %.

Molecular weight of the silk protein fragments may be controlled based upon the specific parameters utilized during the extraction step, including extraction time and temperature; specific parameters utilized during the dissolution step, including the LiBr temperature at the time of submersion of the silk in to the lithium bromide and time that the solution is maintained at specific temperatures; and specific parameters utilized during the filtration step. By controlling process parameters using the disclosed methods, it is possible to create silk fibroin protein fragment solutions with polydispersity equal to or lower than 2.5 at a variety of different molecular weight selected from between 5 kDa to 200 kDa, or between 10 kDa and 80 kDa. By altering process parameters to achieve silk solutions with different molecular weights, a range of fragment mixture end products, with desired polydispersity of equal to or less than 2.5 may be targeted based upon the desired performance requirements. For example, a higher molecular weight silk film containing an ophthalmic drug may have a controlled slow release rate compared to a lower molecular weight film making it ideal for a delivery vehicle in eye care products. Additionally, the silk fibroin protein fragment solutions with a polydispersity of greater than 2.5 can be achieved. Further, two solutions with different average molecular weights and polydispersity can be mixed to create combination solutions. Alternatively, a liquid silk gland (100% sericin free silk protein) that has been removed directly from a worm could be used in combination with any of the silk fibroin protein fragment solutions of the present disclosure. Molecular weight of the pure silk fibroin protein fragment composition was determined using High Pressure Liquid Chromatography (HPLC) with a Refractive Index Detector (RID). Polydispersity was calculated using Cirrus GPC Online GPC/SEC Software Version 3.3 (Agilent).

Differences in the processing parameters can result in regenerated silk fibroins that vary in molecular weight, and peptide chain size distribution (polydispersity, PD). This, in turn, influences the regenerated silk fibroin performance, including mechanical strength, water solubility etc.

Parameters were varied during the processing of raw silk cocoons into the silk solution. Varying these parameters affected the MW of the resulting silk solution. Parameters manipulated included (i) time and temperature of extraction, (ii) temperature of LiBr, (iii) temperature of dissolution oven, and (iv) dissolution time. Experiments were carried out to determine the effect of varying the extraction time. Tables A-G summarize the results. Below is a summary:

- A sericin extraction time of 30 minutes resulted in larger molecular weight than a sericin extraction time of 60 minutes
- Molecular weight decreases with time in the oven
- 140° C. LiBr and oven resulted in the low end of the confidence interval to be below a molecular weight of 9500 Da
- 30 min extraction at the 1 hour and 4 hour time points have undigested silk
- 30 min extraction at the 1 hour time point resulted in a significantly high molecular weight with the low end of the confidence interval being 35,000 Da
- The range of molecular weight reached for the high end of the confidence interval was 18000 to 216000 Da (important for offering solutions with specified upper limit).

TABLE A

The effect of extraction time (30 min vs 60 min) on molecular weight of silk processed under the conditions of 100° C. Extraction Temperature, 100° C. Lithium Bromide (LiBr) and 100 ° C. Oven Dissolution (Oven/Dissolution Time was varied).

| Boil Time | Oven Time | Average Mw | Std dev | Confidence Interval | | PD |
|---|---|---|---|---|---|---|
| 30 | 1 | 57247 | 12780 | 35093 | 93387 | 1.63 |
| 60 | 1 | 31520 | 1387 | 11633 | 85407 | 2.71 |
| 30 | 4 | 40973 | 2632 | 14268 | 117658 | 2.87 |
| 60 | 4 | 25082 | 1248 | 10520 | 59803 | 2.38 |
| 30 | 6 | 25604 | 1405 | 10252 | 63943 | 2.50 |
| 60 | 6 | 20980 | 1262 | 10073 | 43695 | 2.08 |

TABLE B

The effect of extraction time (30 min vs 60 min) on molecular weight of silk processed under the conditions of 100° C. Extraction Temperature, boiling Lithium Bromide (LiBr) and 60° C. Oven Dissolution for 4 hr.

| Sample | Boil Time | Average Mw | Std dev | Confidence Interval | | PD |
|---|---|---|---|---|---|---|
| 30 min, 4 hr | 30 | 49656 | 4580 | 17306 | 142478 | 2.87 |
| 60 min, 4 hr | 60 | 30042 | 1536 | 11183 | 80705 | 2.69 |

TABLE C

The effect of extraction time (30 min vs 60 min) on molecular weight of silk processed under the conditions of 100° C. Extraction Temperature, 60° C. Lithium Bromide (LiBr) and 60° C. Oven Dissolution (Oven/Dissolution Time was varied).

| Sample | Boil Time | Oven Time | Average Mw | Std dev | Confidence Interval | | PD |
|---|---|---|---|---|---|---|---|
| 30 min, 1 hr | 30 | 1 | 58436 | | 22201 | 153809 | 2.63 |
| 60 min, 1 hr | 60 | 1 | 31700 | | 11931 | 84224 | 2.66 |
| 30 min, 4 hr | 30 | 4 | 61956.5 | 13337 | 21463 | 178847 | 2.89 |
| 60 min, 4 hr | 60 | 4 | 25578.5 | 2446 | 9979 | 65564 | 2.56 |

TABLE D

The effect of extraction time (30 min vs 60 min) on molecular weight of silk processed under the conditions of 100° C. Extraction Temperature, 80° C. Lithium Bromide (LiBr) and 80° C. Oven Dissolution for 6 hr.

| Sample | Boil Time | Average Mw | Std dev | Confidence Interval | | PD |
|---|---|---|---|---|---|---|
| 30 min, 6 hr | 30 | 63510 | | 18693 | 215775 | 3.40 |
| 60 min, 6 hr | 60 | 25164 | 238 | 9637 | 65706 | 2.61 |

TABLE E

The effect of extraction time (30 min vs 60 min) on molecular weight of silk processed under the conditions of 100° C. Extraction Temperature, 80° C. Lithium Bromide (LiBr) and 60° C. Oven Dissolution (Oven/Dissolution Time was varied).

| Sample | Boil Time | Oven Time | Average Mw | Std dev | Confidence Interval | | PD |
|---|---|---|---|---|---|---|---|
| 30 min, 4 hr | 30 | 4 | 59202 | 14028 | 19073 | 183760 | 3.10 |
| 60 min, 4 hr | 60 | 4 | 26312.5 | 637 | 10266 | 67442 | 2.56 |
| 30 min, 6 hr | 30 | 6 | 46824 | | 18076 | 121293 | 2.59 |
| 60 min, 6 hr | 60 | 6 | 26353 | | 10168 | 68302 | 2.59 |

TABLE F

The effect of extraction time (30 min vs 60 min) on molecular weight of silk processed under the conditions of 100° C. Extraction Temperature, 140° C. Lithium Bromide (LiBr) and 140° C. Oven Dissolution (Oven/Dissolution Time was varied).

| Sample | Boil Time | Oven Time | Average Mw | Std dev | Confidence Interval | | PD |
|---|---|---|---|---|---|---|---|
| 30 min, 4 hr | 30 | 4 | 9024.5 | 1102 | 4493 | 18127 | 2.00865 |
| 60 min, 4 hr | 60 | 4 | 15548 | 6954 | 34762 | | 2.2358 |
| 30 min, 6 hr | 30 | 6 | 13021 | 5987 | 28319 | | 2.1749 |
| 60 min, 6 hr | 60 | 6 | 10888 | 5364 | 22100 | | 2.0298 |

Experiments were carried out to determine the effect of varying the extraction temperature. Table G summarizes the results. Below is a summary:

- Sericin extraction at 90° C. resulted in higher MW than sericin extraction at 100° C. extraction
- Both 90° C. and 100° C. show decreasing MW over time in the oven.

TABLE G

The effect of extraction temperature (90° C. vs. 100° C.) on molecular weight of silk processed under the conditions of 60 min. Extraction Temperature, 100° C. Lithium Bromide (LiBr) and 100° C. Oven Dissolution (Oven/Dissolution Time was varied).

| Sample | Boil Time | Oven Time | Average Mw | Std dev | Confidence Interval | | PD |
|---|---|---|---|---|---|---|---|
| 90° C., 4 hr | 60 | 4 | 37308 | 4204 | 13368 | 104119 | 2.79 |
| 100° C., 4 hr | 60 | 4 | 25082 | 1248 | 10520 | 59804 | 2.38 |
| 90° C., 6 hr | 60 | 6 | 34224 | 1135 | 12717 | 92100 | 2.69 |
| 100° C., 6 hr | 60 | 6 | 20980 | 1262 | 10073 | 43694 | 2.08 |

Experiments were carried out to determine the effect of varying the Lithium Bromide (LiBr) temperature when added to silk. Tables H-I summarize the results. Below is a summary:

- No impact on molecular weight or confidence interval (all CI~10500-6500 Da)
- Studies illustrated that the temperature of LiBr-silk dissolution, as LiBr is added and begins dissolving, rapidly drops below the original LiBr temperature due to the majority of the mass being silk at room temperature

TABLE H

The effect of Lithium Bromide (LiBr) temperature on molecular weight of silk processed under the conditions of 60 min. Extraction Time., 100° C. Extraction Temperature and 60° C. Oven Dissolution (Oven/Dissolution Time was varied).

| Sample | LiBr Temp (° C.) | Oven Time | Average Mw | Std dev | Confidence Interval | | PD |
|---|---|---|---|---|---|---|---|
| 60° C. LiBr, 1 hr | 60 | 1 | 31700 | | 11931 | 84223 | 2.66 |
| 100° C. LiBr, 1 hr | 100 | 1 | 27907 | 200 | 10735 | 72552 | 2.60 |
| RT LiBr, 4 hr | RT | 4 | 29217 | 1082 | 10789 | 79119 | 2.71 |
| 60° C. LiBr, 4 hr | 60 | 4 | 25578 | 2445 | 9978 | 65564 | 2.56 |
| 80° C. LiBr, 4 hr | 80 | 4 | 26312 | 637 | 10265 | 67441 | 2.56 |
| 100° C. LiBr, 4 hr | 100 | 4 | 27681 | 1729 | 11279 | 67931 | 2.45 |
| Boil LiBr, 4 hr | Boil | 4 | 30042 | 1535 | 11183 | 80704 | 2.69 |
| RT LiBr, 6 hr | RT | 6 | 26543 | 1893 | 10783 | 65332 | 2.46 |
| 80° C. LiBr, 6 hr | 80 | 6 | 26353 | | 10167 | 68301 | 2.59 |
| 100° C. LiBr, 6 hr | 100 | 6 | 27150 | 916 | 11020 | 66889 | 2.46 |

TABLE I

The effect of Lithium Bromide (LiBr) temperature on molecular weight of silk processed under the conditions of 30 min. Extraction Time, 100° C. Extraction Temperature and 60° C. Oven Dissolution (Oven/Dissolution Time was varied).

| Sample | LiBr Temp (° C.) | Oven Time | Average Mw | Std dev | Confidence Interval | | PD |
|---|---|---|---|---|---|---|---|
| 60° C. LiBr, 4 hr | 60 | 4 | 61956 | 13336 | 21463 | 178847 | 2.89 |
| 80° C. LiBr, 4 hr | 80 | 4 | 59202 | 14027 | 19073 | 183760 | 3.10 |
| 100° C. LiBr, 4 hr | 100 | 4 | 47853 | | 19757 | 115899 | 2.42 |
| 80° C. LiBr, 6 hr | 80 | 6 | 46824 | | 18075 | 121292 | 2.59 |
| 100° C. LiBr, 6 hr | 100 | 6 | 55421 | 8991 | 19152 | 160366 | 2.89 |

Experiments were carried out to determine the effect of v oven/dissolution temperature. Tables J-N summarize the results. Below is a summary:

- Oven temperature has less of an effect on 60 min extracted silk than 30 min extracted silk. Without wishing to be bound by theory, it is believed that the 30 min silk is less degraded during extraction and therefore the oven temperature has more of an effect on the larger MW, less degraded portion of the silk.
- For 60° C. vs. 140° C. oven the 30 min extracted silk showed a very significant effect of lower MW at higher oven temp, while 60 min extracted silk had an effect but much less
- The 140° C. oven resulted in a low end in the confidence interval at ~6000 Da.

TABLE J

The effect of oven/dissolution temperature on molecular weight of silk processed under the conditions of 100° C. Extraction Temperature, 30 min. Extraction Time, and 100° C. Lithium Bromide (LiBr) (Oven/Dissolution Time was varied).

| Boil Time | Oven Temp (° C.) | Oven Time | Average Mw | Std dev | Confidence Interval | | PD |
|---|---|---|---|---|---|---|---|
| 30 | 60 | 4 | 47853 | | 19758 | 115900 | 2.42 |
| 30 | 100 | 4 | 40973 | 2632 | 14268 | 117658 | 2.87 |
| 30 | 60 | 6 | 55421 | 8992 | 19153 | 160366 | 2.89 |
| 30 | 100 | 6 | 25604 | 1405 | 10252 | 63943 | 2.50 |

TABLE K

The effect of oven/dissolution temperature on molecular weight of silk processed under the conditions of 100° C. Extraction Temperature, 60 min. Extraction Time, and 100° C. Lithium Bromide (LiBr) (Oven/Dissolution Time was varied).

| Boil Time (minutes) | Oven Temp | Oven Time | Average Mw | Std dev | Confidence Interval | | PD |
|---|---|---|---|---|---|---|---|
| 60 | 60  | 1 | 27908 | 200  | 10735 | 72552 | 2.60 |
| 60 | 100 | 1 | 31520 | 1387 | 11633 | 85407 | 2.71 |
| 60 | 60  | 4 | 27681 | 1730 | 11279 | 72552 | 2.62 |
| 60 | 100 | 4 | 25082 | 1248 | 10520 | 59803 | 2.38 |
| 60 | 60  | 6 | 27150 | 916  | 11020 | 66889 | 2.46 |
| 60 | 100 | 6 | 20980 | 1262 | 10073 | 43695 | 2.08 |

TABLE L

The effect of oven/dissolution temperature on molecular weight of silk processed under the conditions of 100° C. Extraction Temperature, 60 min. Extraction Time, and 140° C. Lithium Bromide (LiBr) (Oven/Dissolution Time was varied).

| Boil Time (minutes) | Oven Temp (° C.) | Oven Time | Average | Std dev | Confidence Interval | | PD |
|---|---|---|---|---|---|---|---|
| 60 | 60  | 4 | 30042 | 1536 | 11183 | 80705 | 2.69 |
| 60 | 140 | 4 | 15548 |      | 7255  | 33322 | 2.14 |

TABLE M

The effect of oven/dissolution temperature on molecular weight of silk processed under the conditions of 100° C. Extraction Temperature, 30 min. Extraction Time, and 140° C. Lithium Bromide (LiBr) (Oven/Dissolution Time was varied).

| Boil Time (minutes) | Oven Temp (° C.) | Oven Time | Average Mw | Std dev | Confidence Interval | | PD |
|---|---|---|---|---|---|---|---|
| 30 | 60  | 4 | 49656 | 4580  | 17306 | 142478 | 2.87 |
| 30 | 140 | 4 | 9025  | 1102  | 4493  | 18127  | 2.01 |
| 30 | 60  | 6 | 59383 | 11640 | 17641 | 199889 | 3.37 |
| 30 | 140 | 6 | 13021 |       | 5987  | 28319  | 2.17 |

TABLE N

The effect of oven/dissolution temperature on molecular weight of silk processed under the conditions of 100° C. Extraction Temperature, 60 min. Extraction Time, and 80° C. Lithium Bromide (LiBr) (Oven/Dissolution Time was varied).

| Boil Time (minutes) | Oven Temp (° C.) | Oven Time | Average Mw | Std dev | Confidence Interval | | PD |
|---|---|---|---|---|---|---|---|
| 60 | 60 | 4 | 26313 | 637  | 10266 | 67442 | 2.56 |
| 60 | 80 | 4 | 30308 | 4293 | 12279 | 74806 | 2.47 |
| 60 | 60 | 6 | 26353 |      | 10168 | 68302 | 2.59 |
| 60 | 80 | 6 | 25164 | 238  | 9637  | 65706 | 2.61 |

The raw silk cocoons from the silkworm *Bombyx mori* was cut into pieces. The pieces of raw silk cocoons were boiled in an aqueous solution of $Na_2CO_3$ (about 100° C.) for a period of time between about 30 minutes to about 60 minutes to remove sericin (degumming). The volume of the water used equals about 0.4×raw silk weight and the amount of $Na_2CO_3$ is about 0.848×the weight of the raw silk cocoon pieces. The resulting degummed silk cocoon pieces were rinsed with deionized water three times at about 60° C. (20 minutes per rinse). The volume of rinse water for each cycle was 0.2 L×the weight of the raw silk cocoon pieces. The excess water from the degummed silk cocoon pieces was removed. After the DI water washing step, the wet degummed silk cocoon pieces were dried at room temperature. The degummed silk cocoon pieces were mixed with a LiBr solution, and the mixture was heated to about 100° C. The warmed mixture was placed in a dry oven and was heated at a temperature ranging from about 60° C. to about 140° C. for about 60 minutes to achieve complete dissolution of the native silk protein. The resulting solution was allowed to cool to room temperature and then was dialyzed to remove LiBr salts using a 3,500 Da MWCO membrane. Multiple exchanges were performed in Di water until $Br^-$ ions were less than 1 ppm as determined in the hydrolyzed fibroin solution read on an Oakton Bromide ($Br^-$) double-junction ion-selective electrode.

The resulting silk fibroin aqueous solution has a concentration of about 8.0% w/v containing pure silk fibroin protein fragments having an average weight average molecular weight selected from between about 6 kDa to about 16 kDa, about 17 kDa to about 39 kDa, and about 39 kDa to about 80 kDa and a polydispersity of between about 1.5 and about 3.0. The 8.0% w/v was diluted with DI water to provide a 1.0% w/v, 2.0% w/v, 3.0% w/v, 4.0% w/v, 5.0% w/v by the coating solution.

A variety of % silk concentrations have been produced through the use of Tangential Flow Filtration (TFF). In all cases a 1% silk solution was used as the input feed. A range of 750-18,000 mL of 1% silk solution was used as the starting volume. Solution is diafiltered in the TFF to remove lithium bromide. Once below a specified level of residual LiBr, solution undergoes ultrafiltration to increase the concentration through removal of water. See examples below.

Six (6) silk solutions were utilized in standard silk structures with the following results:

Solution #1 is a silk concentration of 5.9 wt. %, average MW of 19.8 kDa and 2.2 PDI (made with a 60 min boil extraction, 100° C. LiBr dissolution for 1 hour).

Solution #2 is a silk concentration of 6.4 wt. % (made with a 30 min boil extraction, 60° C. LiBr dissolution for 4 hrs).

Solution #3 is a silk concentration of 6.17 wt. % (made with a 30 min boil extraction 100° C. LiBr dissolution for 1 hour).

Solution #4 is a silk concentration of 7.30 wt. %: A 7.30% silk solution was produced beginning with 30 minute extraction batches of 100 g silk cocoons per batch. Extracted silk fibers were then dissolved using 100° C. 9.3 M LiBr in a 100° C. oven for 1 hour. 100 g of silk fibers were dissolved per batch to create 20% silk in LiBr. Dissolved silk in LiBr was then diluted to 1% silk and filtered through a 5 μm filter to remove large debris. 15,500 mL of 1%, filtered silk solution was used as the starting volume/diafiltration volume for TFF. Once LiBr was removed, the solution was ultrafiltered to a volume around 1300 mL. 1262 mL of 7.30% silk was then collected. Water was added to the feed to help remove the remaining solution and 547 mL of 3.91% silk was then collected.

Solution #5 is a silk concentration of 6.44 wt. %: A 6.44 wt. % silk solution was produced beginning with 60 minute extraction batches of a mix of 25, 33, 50, 75 and 100 g silk cocoons per batch. Extracted silk fibers were then dissolved using 100° C. 9.3 M LiBr in a 100° C. oven for 1 hour. 35, 42, 50 and 71 g per batch of silk fibers were dissolved to create 20% silk in LiBr and combined. Dissolved silk in LiBr was then diluted to 1% silk and filtered through a 5 μm filter to remove large debris. 17,000 mL of 1%, filtered silk solution was used as the starting volume/diafiltration volume for TFF. Once LiBr was removed, the solution was ultrafiltered to a volume around 3000 mL. 1490 mL of 6.44% silk was then collected. Water was added to the feed to help remove the remaining solution and 1454 mL of 4.88% silk was then collected.

Solution #6 is a silk concentration of 2.70 wt. %: A 2.70% silk solution was produced beginning with 60-minute extraction batches of 25 g silk cocoons per batch. Extracted silk fibers were then dissolved using 100° C. 9.3 M LiBr in a 100° C. oven for 1 hour. 35.48 g of silk fibers were dissolved per batch to create 20% silk in LiBr. Dissolved silk in LiBr was then diluted to 1% silk and filtered through a 5 μm filter to remove large debris. 1000 mL of 1%, filtered silk solution was used as the starting volume/diafiltration volume for TFF. Once LiBr was removed, the solution was ultrafiltered to a volume around 300 mL. 312 mL of 2.7% silk was then collected.

The preparation of silk fibroin solutions with higher molecular weights is given in Table O.

TABLE O

Preparation and properties of silk fibroin solutions.

| Sample Name | Extraction Time (mins) | Extraction Temp (° C.) | LiBr Temp (° C.) | Oven/ Sol'n Temp | Average weight average molecular weight (kDa) | Average polydispersity |
|---|---|---|---|---|---|---|
| Group A TFF | 60 | 100 | 100 | 100° C. oven | 34.7 | 2.94 |
| Group A DIS | 60 | 100 | 100 | 100° C. oven | 44.7 | 3.17 |
| Group B TFF | 60 | 100 | 100 | 100° C. sol'n | 41.6 | 3.07 |
| Group B DIS | 60 | 100 | 100 | 100° C. sol'n | 44.0 | 3.12 |
| Group D DIS | 30 | 90 | 60 | 60° C. sol'n | 129.7 | 2.56 |
| Group D FIL | 30 | 90 | 60 | 60° C. sol'n | 144.2 | 2.73 |
| Group E DIS | 15 | 100 | RT | 60° C. sol'n | 108.8 | 2.78 |
| Group E FIL | 15 | 100 | RT | 60° C. sol'n | 94.8 | 2.62 |

Silk aqueous coating composition for application to fabrics are given in Tables P and Q below.

TABLE P

| | Silk Solution Characteristics | | | | |
|---|---|---|---|---|---|
| | Molecular Weight: | 57 kDa | | | |
| | Polydispersity: | 1.6 | | | |
| | % Silk | 5.0% | 3.0% | 1.0% | 0.5% |
| Process Parameters | | | | | |
| | Extraction | | | | |
| | Boil Time: | 30 minutes | | | |
| | Boil Temperature: | 100° C. | | | |
| | Rinse Temperature: | 60° C. | | | |
| | Dissolution | | | | |
| | LiBr Temperature: | 100 | | | |
| | Oven Temperature: | 100° C. | | | |
| | Oven Time: | 60 minutes | | | |

TABLE Q

| | Silk Solution Characteristics | | | | |
|---|---|---|---|---|---|
| | Molecular Weight: | 25 kDa | | | |
| | Polydispersity: | 2.4 | | | |
| | % Silk | 5.0% | 3.0% | 1.0% | 0.5% |
| Process Parameters | | | | | |
| | Extraction | | | | |
| | Boil Time: | 60 minutes | | | |
| | Boil Temperature: | 100° C. | | | |
| | Rinse Temperature: | 60° C. | | | |
| | Dissolution | | | | |
| | LiBr Temperature: | 100° C. | | | |
| | Oven Temperature: | 100° C. | | | |
| | Oven Time: | 60 minutes | | | |

Three (3) silk solutions were utilized in film making with the following results:

Solution #1 is a silk concentration of 5.9%, average MW of 19.8 kDa and 2.2 PD (made with a 60 min boil extraction, 100° C. LiBr dissolution for 1 hr).

Solution #2 is a silk concentration of 6.4% (made with a 30 min boil extraction, 60° C. LiBr dissolution for 4 hrs).

Solution #3 is a silk concentration of 6.17% (made with a 30 min boil extraction, 100° C. LiBr dissolution for 1 hour).

Films were made in accordance with Rockwood et al. (Nature Protocols; Vol. 6; No. 10; published on-line Sep. 22, 2011; doi:10.1038/nprot.2011.379). 4 mL of 1% or 2% (wt/vol) aqueous silk solution was added into 100 mm Petri dish (Volume of silk can be varied for thicker or thinner films and is not critical) and allowed to dry overnight uncovered. The bottom of a vacuum desiccator was filled with water. Dry films were placed in the desiccator and vacuum applied, allowing the films to water anneal for 4 hours prior to removal from the dish. Films cast from solution #1 did not result in a structurally continuous film; the film was cracked in several pieces. These pieces of film dissolved in water in spite of the water annealing treatment.

Silk solutions of various molecular weights and/or combinations of molecular weights can be optimized for gel applications. The following provides an example of this process but it not intended to be limiting in application or formulation. Three (3) silk solutions were utilized in gel making with the following results:

Solution #1 is a silk concentration of 5.9%, average MW of 19.8 kDa and 2.2 PD (made with a 60 min boil extraction, 100° C. LiBr dissolution for 1 hr).

Solution #2 is a silk concentration of 6.4% (made with a 30 min boil extraction, 60° C. LiBr dissolution for 4 hrs).

Solution #3 is a silk concentration of 6.17% (made with a 30 min boil extraction, 100° C. LiBr dissolution for 1 hour).

"Egel" is an electrogelation process as described in Rockwood of al. Briefly, 10 ml of aqueous silk solution is added to a 50 ml conical tube and a pair of platinum wire electrodes immersed into the silk solution. A 20 volt potential was applied to the platinum electrodes for 5 minutes, the power supply turned off and the gel collected. Solution #1 did not form an EGEL over the 5 minutes of applied electric current.

Solutions #2 and #3 were gelled in accordance with the published horseradish peroxidase (HRP) protocol. Behavior seemed typical of published solutions.

Materials and Methods: the following equipment and material are used in determination of Silk Molecular weight: Agilent 1100 with chemstation software ver. 10.01; Refractive Index Detector (RID); analytical balance; volumetric flasks (1000 mL, 10 mL and 5 mL); HPLC grade water; ACS grade sodium chloride; ACS grade sodium phosphate dibasic heptahydrate; phosphoric acid; dextran MW Standards-Nominal Molecular Weights of 5 kDa, 11.6 kDa, 23.8 kDa, 48.6 kDa, and 148 kDa; 50 mL PET or polypropylene disposable centrifuge tubes; graduated pipettes; amber glass HPLC vials with Teflon caps; Phenomenex PolySep GFC P-4000 column (size: 7.8 mm×300 mm).

Procedural Steps:

A) Preparation of 1 L Mobile Phase (0.1 M Sodium Chloride solution in 0.0125 M Sodium phosphate buffer)

Take a 250 mL clean and dry beaker, place it on the balance and tare the weight. Add about 3.3509 g of sodium phosphate dibasic heptahydrate to the beaker. Note down the exact weight of sodium phosphate dibasic weighed. Dissolve the weighed sodium phosphate by adding 100 mL of HPLC water into the beaker. Take care not to spill any of the content of the beaker. Transfer the solution carefully into a clean and dry 1000 mL volumetric flask. Rinse the beaker and transfer the rinse into the volumetric flask. Repeat the rinse 4-5 times. In a separate clean and dry 250 mL beaker weigh exactly about 5.8440 g of sodium chloride. Dissolve the weighed sodium chloride in 50 mL of water and transfer the solution to the sodium phosphate solution in the volumetric flask. Rinse the beaker and transfer the rinse into the volumetric flask. Adjust the pH of the solution to 7.0±0.2 with phosphoric acid. Make up the volume in volumetric flask with HPLC water to 1000 mL and shake it vigorously to homogeneously mix the solution. Filter the solution through 0.45 μm polyamide membrane filter. Transfer the solution to a clean and dry solvent bottle and label the bottle. The volume of the solution can be varied to the requirement by correspondingly varying the amount of sodium phosphate dibasic heptahydrate and sodium chloride.

B) Preparation of Dextran Molecular Weight Standard solutions

At least five different molecular weight standards are used for each batch of samples that are run so that the expected value of the sample to be tested is bracketed by the value of the standard used. Label six 20 mL scintillation glass vials respective to the molecular weight standards. Weigh accurately about 5 mg of each of dextran molecular weight standards and record the weights. Dissolve the dextran molecular weight standards in 5 mL of mobile phase to make a 1 mg/mL standard solution.

C) Preparation of Sample solutions

When preparing sample solutions, if there are limitations on how much sample is available, the preparations may be scaled as long as the ratios are maintained. Depending on sample type and silk protein content in sample weigh enough sample in a 50 mL disposable centrifuge tube on an analytical balance to make a 1 mg/mL sample solution for analysis. Dissolve the sample in equivalent volume of mobile phase make a 1 mg/mL solution. Tightly cap the tubes and mix the samples (in solution). Leave the sample solution for 30 minutes at room temperature. Gently mix the sample solution again for 1 minute and centrifuge at 4000 RPM for 10 minutes.

D) HPLC Analysis of the Samples

Transfer 1.0 mL of all the standards and sample solutions into individual HPLC vials. Inject the molecular weight standards (one injection each) and each sample in duplicate. Analyze all the standards and sample solutions using the following HPLC conditions:

| | |
|---|---|
| Column | PolySep GFC P-4000 (7.8 × 300 mm) |
| Column Temperature | 25° C. |
| Detector | Refractive Index Detector (Temperature @ 35° C.) |
| Injection Volume | 25.0 μL |
| Mobile Phase | 0.1M Sodium Chloride solution in 0.0125M sodium phosphate buffer |
| Flow Rate | 1.0 mL/min |
| Run Time | 20.0 min |

E) Data Analysis and Calculations—Calculation of Average Molecular Weight Using Cirrus Software Upload the chromatography data files of the standards and the analytical samples into Cirrus SEC data collection and molecular weight analysis software. Calculate the weight average molecular weight (Mw), number average molecular weight (Mn), peak average molecular weight (M e), and polydispersity for each injection of the sample.

Spider Silk Fragments

Spider silks are natural polymers that consist of three domains: a repetitive middle core domain that dominates the protein chain, and non-repetitive N-terminal and C-terminal domains. The large core domain is organized in a block copolymer-like arrangement, in which two basic sequences, crystalline [poly(A) or poly(GA)] and less crystalline (GGX or GPGXX) polypeptides alternate. Dragline silk is the protein complex composed of major ampullate dragline silk protein 1 (MaSp1) and major ampullate dragline silk protein 2 (MaSp2). Both silks are approximately 3500 amino acid long. MaSp1 can be found in the fibre core and the periphery, whereas MaSp2 forms clusters in certain core areas. The large central domains of MaSp1 and MaSp2 are organized in block copolymer-like arrangements, in which two basic sequences, crystalline [poly(A) or poly(GA)] and less crystalline (GGX or GPGXX) polypeptides alternate in core domain. Specific secondary structures have been assigned to poly(A)/(GA), GGX and GPGXX motifs including β-sheet, α-helix and β-spiral respectively. The primary sequence, composition and secondary structural elements of the repetitive core domain are responsible for mechanical properties of spider silks; whereas, non-repetitive N- and C-terminal domains are essential for the storage of liquid silk dope in a lumen and fibre formation in a spinning duct.

The main difference between MaSp1 and MaSp2 is the presence of proline (P) residues accounting for 15% of the total amino acid content in MaSp2, whereas MaSp1 is proline-free. By calculating the number of proline residues in *N. clavipes* dragline silk, it is possible to estimate the presence of the two proteins in fibres; 81% MaSp1 and 19% MaSp2. Different spiders have different ratios of MaSp1 and MaSp2. For example, a dragline silk fibre from the orb weaver *Argiope aurantia* contains 41% MaSp1 and 59% MaSp2. Such changes in the ratios of major ampullate silks can dictate the performance of the silk fibre.

At least seven different types of silk proteins are known for one orb-weaver species of spider. Silks differ in primary sequence, physical properties and functions. For example, dragline silks used to build frames, radii and lifelines are known for outstanding mechanical properties including strength, toughness and elasticity. On an equal weight basis, spider silk has a higher toughness than steel and Kevlar. Flageliform silk found in capture spirals has extensibility of up to 500%. Minor ampullate silk, which is found in auxiliary spirals of the orb-web and in prey wrapping, possesses high toughness and strength almost similar to major ampullate silks, but does not supercontract in water.

Spider silks are known for their high tensile strength and toughness. The recombinant silk proteins also confer advantageous properties to cosmetic or dermatological compositions, in particular to be able to improve the hydrating or softening action, good film forming property and low surface density. Diverse and unique biomechanical properties together with biocompatibility and a slow rate of degradation make spider silks excellent candidates as biomaterials for tissue engineering, guided tissue repair and drug delivery, for cosmetic products (e.g. nail and hair strengthener, skin care products), and industrial materials (e.g. nanowires, nanofibers, surface coatings).

In an embodiment, a silk protein may include a polypeptide derived from natural spider silk proteins. The polypeptide is not limited particularly as long as it is derived from natural spider silk proteins, and examples of the polypeptide include natural spider silk proteins and recombinant spider silk proteins such as variants, analogs, derivatives or the like of the natural spider silk proteins. In terms of excellent tenacity, the polypeptide may be derived from major dragline silk proteins produced in major ampullate glands of spiders. Examples of the major dragline silk proteins include major ampullate spidroin MaSp1 and MaSp2 from *Nephila clavipes*, and ADF3 and ADF4 from *Araneus diadematus*, etc. Examples of the polypeptide derived from major dragline silk proteins include variants, analogs, derivatives or the like of the major dragline silk proteins. Further, the polypeptide may be derived from flagelliform silk proteins produced in flagelliform glands of spiders. Examples of the flagelliform silk proteins include flagelliform silk proteins derived from *Nephila clavipes*, etc.

Examples of the polypeptide derived from major dragline silk proteins include a polypeptide containing two or more units of an amino acid sequence represented by the formula 1: REP1-REP2 (1), preferably a polypeptide containing five or more units thereof, and more preferably a polypeptide containing ten or more units thereof. Alternatively, the polypeptide derived from major dragline silk proteins may be a polypeptide that contains units of the amino acid sequence represented by the formula 1: REP1-REP2 (1) and that has, at a C-terminal, an amino acid sequence represented by any of SEQ ID NOS: 1 to 3 of U.S. Pat. No. 9,051,453 or an amino acid sequence having a homology of 90% or more with the amino acid sequence represented by any of SEQ ID NOS: 1 to 3 of U.S. Pat. No. 9,051,453. In the polypeptide derived from major dragline silk proteins, units of the amino acid sequence represented by the formula 1: REP1-REP2 (1) may be the same or may be different from each other. In the case of producing a recombinant protein using a microbe such as *Escherichia coli* as a host, the molecular weight of the polypeptide derived from major dragline silk proteins is 500 kDa or less, or 300 kDa or less, or 200 kDa or less, in terms of productivity.

In the formula (1), the REP1 indicates polyalanine. In the REP1, the number of alanine residues arranged in succession is preferably 2 or more, more preferably 3 or more, further preferably 4 or more, and particularly preferably 5 or more. Further, in the REP1, the number of alanine residues arranged in succession is preferably 20 or less, more preferably 16 or less, further preferably 12 or less, and particularly preferably 10 or less. In the formula (1), the REP2 is an amino acid sequence composed of 10 to 200 amino acid residues. The total number of glycine, serine, glutamine and alanine residues contained in the amino acid sequence is 40% or more, preferably 60% or more, and more preferably 70% or more with respect to the total number of amino acid residues contained therein.

In the major dragline silk, the REP1 corresponds to a crystal region in a fiber where a crystal β sheet is formed, and the REP2 corresponds to an amorphous region in a fiber where most of the parts lack regular configurations and that has more flexibility. Further, the [REP1-REP2] corresponds to a repetitious region (repetitive sequence) composed of the crystal region and the amorphous region, which is a characteristic sequence of dragline silk proteins.

Recombinant Silk Fragments

In some embodiments, the recombinant silk protein refers to recombinant spider silk polypeptides, recombinant insect silk polypeptides, or recombinant mussel silk polypeptides. In some embodiments, the recombinant silk protein fragment disclosed herein include recombinant spider silk polypeptides of *Araneidae* or *Araneoids*, or recombinant insect silk polypeptides of *Bombyx mori*. In some embodiments, the recombinant silk protein fragment disclosed herein include recombinant spider silk polypeptides of *Araneidae* or *Araneoids*. In some embodiments, the recombinant silk protein fragment disclosed herein include block copolymer having repetitive units derived from natural spider silk polypeptides of *Araneidae* or *Araneoids*. In some embodiments, the recombinant silk protein fragment disclosed herein include block copolymer having synthetic repetitive units derived from spider silk polypeptides of *Araneidae* or *Araneoids* and non-repetitive units derived from natural repetitive units of spider silk polypeptides of *Araneidae* or *Araneoids*.

Recent advances in genetic engineering have provided a route to produce various types of recombinant silk proteins. Recombinant DNA technology has been used to provide a more practical source of silk proteins. As used herein "recombinant silk protein" refers to synthetic proteins produced heterologously in prokaryotic or eukaryotic expression systems using genetic engineering methods.

Various methods for synthesizing recombinant silk peptides are known and have been described by Ausubel et al., Current Protocols in Molecular Biology § 8 (John Wiley & Sons 1987, (1990)), incorporated herein by reference. A gram-negative, rod-shaped bacterium *E. coli* is a well-established host for industrial scale production of proteins. Therefore, the majority of recombinant silks have been produced in *E. coli*. *E. coli* which is easy to manipulate, has a short generation time, is relatively low cost and can be scaled up for larger amounts protein production.

The recombinant silk proteins can be produced by transformed prokaryotic or eukaryotic systems containing the cDNA coding for a silk protein, for a fragment of this protein or for an analog of such a protein. The recombinant DNA approach enables the production of recombinant silks with programmed sequences, secondary structures, architectures and precise molecular weight. There are four main steps in the process: (i) design and assembly of synthetic silk-like genes into genetic 'cassettes', (ii) insertion of this segment into a DNA recombinant vector, (iii) transformation of this recombinant DNA molecule into a host cell and (iv) expression and purification of the selected clones.

The term "recombinant vectors", as used herein, includes any vectors known to the skilled person including plasmid vectors, cosmid vectors, phage vectors such as lambda phage, viral vectors such as adenoviral or baculoviral vectors, or artificial chromosome vectors such as bacterial artificial chromosomes (BAC), yeast artificial chromosomes (YAC), or P1 artificial chromosomes (PAC). Said vectors include expression as well as cloning vectors. Expression vectors comprise plasmids as well as viral vectors and generally contain a desired coding sequence and appropriate DNA sequences necessary for the expression of the operably linked coding sequence in a particular host organism (e.g., bacteria, yeast, or plant) or in in vitro expression systems. Cloning vectors are generally used to engineer and amplify a certain desired DNA fragment and may lack functional sequences needed for expression of the desired DNA fragments.

The prokaryotic systems include Gram-negative bacteria or Gram-positive bacteria. The prokaryotic expression vectors can include an origin of replication which can be recognized by the host organism, a homologous or heterologous promoter which is functional in the said host, the DNA sequence coding for the spider silk protein, for a fragment of this protein or for an analogous protein. Nonlimiting examples of prokaryotic expression organisms are *Escherichia coli*, *Bacillus subtilis*, *Bacillus megaterium*, *Corynebacterium glutamicum*, *Anabaena*, *Caulobacter*, *Gluconobacter*, *Rhodobacter*, *Pseudomonas*, *Para coccus*, *Bacillus* (e.g. *Bacillus subtilis*) *Brevibacterium*, *Corynebacterium*, *Rhizobium* (*Sinorhizobium*), *Flavobacterium*, *Klebsiella*, *Enterobacter*, *Lactobacillus*, *Lactococcus*, *Methylobacterium*, *Propionibacterium*, *Staphylococcus* or *Streptomyces* cells.

The eukaryotic systems include yeasts and insect, mammalian or plant cells. In this case, the expression vectors can include a yeast plasmid origin of replication or an autonomous replication sequence, a promoter, a DNA sequence coding for a spider silk protein, for a fragment or for an analogous protein, a polyadenylation sequence, a transcription termination site and, lastly, a selection gene. Nonlimiting examples of eukaryotic expression organisms include yeasts, such as *Saccharomyces cerevisiae*, *Pichia pastoris*, basidiosporogenous, ascosporogenous, filamentous fungi, such as *Aspergillus niger*, *Aspergillus oryzae*, *Aspergillus nidulans*, *Trichoderma reesei*, *Acremonium chrysogenum*, *Candida*, *Hansenula*, *Kluyveromyces*, *Saccharomyces* (e.g. *Saccharomyces cerevisiae*), *Schizosaccharomyces*, *Pichia* (e.g. *Pichia pastoris*) or *Yarrowia* cells etc., mammalian cells, such as HeLa cells, COS cells, CHO cells etc., insect cells, such as Sf9 cells, MEL cells, etc., "insect host cells" such as *Spodoptera frupperda* or *Trichoplusia ni* cells. SF9 cells, SF-21 cells or High-Five cells, wherein SF-9 and SF-21 are ovarian cells from *Spodoptera frugiperda*, and High-Five cells are egg cells from *Trichoplusia ni.*, "plant host cells", such as tobacco, potato or pea cells.

A variety of heterologous host systems have been explored to produce different types of recombinant silks. Recombinant partial spidroins as well as engineered silks have been cloned and expressed in bacteria (*Escherichia coli*), yeast (*Pichia pastoris*), insects (silkworm larvae), plants (tobacco, soybean, potato, Arabidopsis), mammalian cell lines (BHT/hamster) and transgenic animals (mice, goats). Most of the silk proteins are produced with an N- or C-terminal His-tags to make purification simple and produce enough amounts of the protein.

In some embodiments, the host suitable for expressing the recombinant spider silk protein using heterogeneous system may include transgenic animals and plants. In some embodiments, the host suitable for expressing the recombinant spider silk protein using heterogeneous system comprises bacteria, yeasts, mammalian cell lines. In some embodiments, the host suitable for expressing the recombinant spider silk protein using heterogeneous system comprises *E. coli*. In some embodiments, the host suitable for expressing the recombinant spider silk protein using heterogeneous system comprises transgenic *B. mori* silkworm generated using genome editing technologies (e.g. CRISPR).

The recombinant silk protein in this disclosure comprises synthetic proteins which are based on repeat units of natural silk proteins. Besides the synthetic repetitive silk protein sequences, these can additionally comprise one or more natural nonrepetitive silk protein sequences.

In some embodiments, "recombinant silk protein" refers to recombinant silkworm silk protein or fragments thereof. The recombinant production of silk fibroin and silk sericin has been reported. A variety of hosts are used for the production including *E. coli*, *Saccharomyces cerevisiae*, *Pseudomonas* sp., *Rhodopseudomonas* sp., *Bacillus* sp., and *Strepomyces*. See EP 0230702, which is incorporate by reference herein by its entirety.

Provided herein also include design and biological-synthesis of silk fibroin protein-like multiblock polymer comprising GAGAGX (SEQ ID NO:1) hexapeptide (X is A, Y, V or S) derived from the repetitive domain of *B. mori* silk heavy chain (H chain)

In some embodiments, this disclosure provides silk protein-like multiblock polymers derived from the repetitive domain of *B. mori* silk heavy chain (H chain) comprising the GAGAGS_(SEQ ID NO:2) hexapeptide repeating units. The GAGAGS (SEQ ID NO:2) hexapeptide is the core unit of H-chain and plays an important role in the formation of crystalline domains. The silk protein-like multiblock polymers containing the GAGAGS (SEQ ID NO:2) hexapeptide repeating units spontaneously aggregate into β-sheet structures, similar to natural silk fibroin protein, where in the silk protein-like multiblock polymers having any weight average molecular weight described herein.

In some embodiments, this disclosure provides silk-peptide like multiblock copolymers composed of the GAGAGS (SEQ ID NO:2) hexapeptide repetitive fragment derived from H chain of *B. mori* silk heavy chain and mammalian elastin VPGVG (SEQ ID NO:3) motif produced by *E. coli*. In some embodiments, this disclosure provides fusion silk fibroin proteins composed of the GAGAGS (SEQ ID NO:2) hexapeptide repetitive fragment derived from H chain of *B. mori* silk heavy chain and GVGVP (SEQ ID NO:4) produced by *E. coli*, where in the silk protein-like multiblock polymers having any weight average molecular weight described herein.

In some embodiments, this disclosure provides *B. mori* silkworm recombinant proteins composed of the (GAGAGS)$_{16}$ (SEQ ID NO:5) repetitive fragment. In some embodiments, this disclosure provides recombinant proteins composed of the (GAGAGS)$_{16}$ (SEQ ID NO:5) repetitive fragment and the non-repetitive (GAGAGS)$_{16}$—F—COOH, (GAGAGS)$_{16}$—F—F—COOH, (GAGAGS)$_{16}$—F—F—F—COOH, (GAGAGS)$_{16}$—F—F—F—F—COOH, (GAGAGS)$_{16}$—F—F—F—F—F—F—F—F—COOH, (GAGAGS)$_{16}$—F—F—F—F—F—F—F—F—F—F—F—COOH produced by *E. coli*, where F has the following amino acid sequence SGFGPVANGGSGEASS-ESDFGSSGFGPVANASSGEASSESDFAG (SEQ ID NO:6), and where in the silk protein-like multiblock polymers having any weight average molecular weight described herein.

In some embodiments, "recombinant silk protein" refers to recombinant spider silk protein or fragments thereof. The productions of recombinant spider silk proteins based on a partial cDNA clone have been reported. The recombinant spider silk proteins produced as such comprise a portion of the repetitive sequence derived from a dragline spider silk protein, Spidroin 1, from the spider *Nephila clavipes*. see Xu et al. (Proc. Natl. Acad. Sci. U.S.A., 87:7120-7124 (1990). cDNA clone encoding a portion of the repeating sequence of a second fibroin protein, Spidroin 2, from dragline silk of *Nephila clavipes* and the recombinant synthesis thereof is described in J. Biol. Chem., 1992, volume 267, pp. 19320-19324. The recombinant synthesis of spider silk proteins including protein fragments and variants of *Nephila clavipes* from transformed *E. coli* is described in U.S. Pat. Nos. 5,728,810 and 5,989,894. cDNA clones encoding minor ampullate spider silk proteins and the expression thereof is described in U.S. Pat. Nos. 5,733,771 and 5,756,677. cDNA clone encoding the flagelliform silk protein from an orb-web spinning spider is described in U.S. Pat. No. 5,994,099. U.S. Pat. No. 6,268,169 describes the recombinant synthesis of spider silk like proteins derived from the repeating peptide sequence found in the natural spider dragline of *Nephila clavipes* by *E. coli, Bacillus subtilis*, and *Pichia pastoris* recombinant expression systems. WO 03/020916 describes the cDNA clone encoding and recombinant production of spider spider silk proteins having repeative sequences derived from the major ampullate glands of *Nephila madagascariensis, Nephila senegalensis, Tetragnatha kauaiensis, Tetragnatha versicolor, Argiope aurantia, Argiope trifasciata, Gasteracantha mammosa*, and *Latrodectus geometricus*, the flagelliform glands of *Argiope trifasciata*, the ampullate glands of *Dolomedes tenebrosus*, two sets of silk glands from *Plectreurys tristis*, and the silk glands of the mygalomorph *Euagrus chisoseus*. Each of the above reference is incorporated herein by reference in its entirety.

In some embodiments, the recombinant spider silk protein is a hybrid protein of a spider silk protein and an insect silk protein, a spider silk protein and collagen, a spider silk protein and resilin, or a spider silk protein and keratin. The spider silk repetitive unit comprises or consists of an amino acid sequence of a region that comprises or consists of at least one peptide motif that repetitively occurs within a naturally occurring major ampullate gland polypeptide, such as a dragline spider silk polypeptide, a minor ampullate gland polypeptide, a flagelliform polypeptide, an aggregate spider silk polypeptide, an aciniform spider silk polypeptide or a pyriform spider silk polypeptide.

In some embodiments, the recombinant spider silk protein in this disclosure comprises synthetic spider silk proteins derived from repetitive units of natural spider silk proteins, consensus sequence, and optionally one or more natural non-repetitive spider silk protein sequences. The repeated units of natural spider silk polypeptide may include dragline spider silk polypeptides or flagelliform spider silk polypeptides of *Araneidae* or *Araneoids*.

As used herein, the spider silk "repetitive unit" comprises or consists of at least one peptide motif that repetitively occurs within a naturally occurring major ampullate gland polypeptide, such as a dragline spider silk polypeptide, a minor ampullate gland polypeptide, a flagelliform polypeptide, an aggregate spider silk polypeptide, an aciniform spider silk polypeptide or a pyriform spider silk polypeptide. A "repetitive unit" refers to a region which corresponds in amino acid sequence to a region that comprises or consists of at least one peptide motif (e.g. AAAAAA)_(SEQ ID NO:21) or GPGQQ (SEQ ID NO:16)) that repetitively occurs within a naturally occurring silk polypeptide (e.g. MaSpI, ADF-3, ADF-4, or Flag) (i.e. identical amino acid sequence) or to an amino acid sequence substantially similar thereto (i.e. variational amino acid sequence). A "repetitive unit" having an amino acid sequence which is "substantially similar" to a corresponding amino acid sequence within a naturally occurring silk polypeptide (i.e. wild-type repetitive unit) is also similar with respect to its properties, e.g. a silk protein comprising the "substantially similar repetitive unit" is still insoluble and retains its insolubility. A "repetitive unit" having an amino acid sequence which is "identical" to the amino acid sequence of a naturally occurring silk polypeptide, for example, can be a portion of a silk polypeptide corresponding to one or more peptide motifs of MaSpI, MaSpII, ADF-3 and/or ADF-4. A "repetitive unit" having an amino acid sequence which is "substantially similar" to the amino acid sequence of a naturally occurring silk polypeptide, for example, can be a portion of a silk polypeptide corresponding to one or more peptide motifs of MaSpI, MaSpII, ADF-3 and/or ADF-4, but having one or more amino acid substitution at specific amino acid positions.

As used herein, the term "consensus peptide sequence" refers to an amino acid sequence which contains amino acids which frequently occur in a certain position (e.g. "G") and wherein, other amino acids which are not further determined are replaced by the place holder "X". In some embodiments, the consensus sequence is at least one of (i) GPGXX (SEQ ID NO:7), wherein X is an amino acid selected from A, S, G, Y, P and Q; (ii) GGX, wherein X is an amino acid selected from Y, P, R, S, A, T, N and Q, preferably Y, P and Q; (iii) Ax, wherein x is an integer from 5 to 10.

The consensus peptide sequences GPGXX (SEQ ID NO:7) and GGX, i.e. glycine rich motifs, provide flexibility to the silk polypeptide and thus, to the thread formed from the silk protein containing said motifs. In detail, the iterated GPGXX (SEQ ID NO:7) motif forms turn spiral structures, which imparts elasticity to the silk polypeptide. Major ampullate and flagelliform silks both have a GPGXX (SEQ ID NO:7) motif. The iterated GGX motif is associated with a helical structure having three amino acids per turn and is found in most spider silks. The GGX motif may provide additional elastic properties to the silk. The iterated poly-alanine Ax (peptide) motif forms a crystalline β-sheet structure that provides strength to the silk polypeptide, as described for example in WO 03/057727.

In some embodiments, the recombinant spider silk protein in this disclosure comprises two identical repetitive units each comprising at least one, preferably one, amino acid sequence selected from the group consisting of: GGRPSDTYG (SEQ ID NO:8) and GGRPSSSYG (SEQ ID NO:9) derived from Resilin. Resilin is an elastomeric protein found in most arthropods that provides low stiffness and high strength.

As used herein, "non-repetitive units" refers to an amino acid sequence which is "substantially similar" to a corresponding non-repetitive (carboxy terminal) amino acid sequence within a naturally occurring dragline polypeptide (i.e. wild-type non-repetitive (carboxy terminal) unit), preferably within ADF-3 (SEQ ID NO:1), ADF-4 (SEQ ID NO:2), NR3 (SEQ ID NO:41), NR4 (SEQ ID NO:42), ADF-4 of the spider *Araneus diadematus* as described in U.S. Pat. No. 8,367,803, C16 peptide (spider silk protein eADF4, molecular weight of 47.7 kDa, AMSilk) comprising the 16 repeats of the sequence GSSAAAAAAAASGPG-GYGPENQGPSGPGGYGPGGP (SEQ ID NO:10), an amino acid sequence adapted from the natural sequence of ADF4 from *A. diadematus*. Non-repetitive ADF-4 and variants thereof display efficient assembly behavior.

Among the synthetic spider silk proteins, the recombinant silk protein in this disclosure comprises in some embodiments the C16-protein having the polypeptide sequence SEQ ID NO: 1 as described in U.S. Pat. No. 8,288,512. Besides the polypeptide sequence shown in SEQ ID NO:1, particularly functional equivalents, functional derivatives and salts of this sequence are also included.

As used herein, "functional equivalents" refers to mutant which, in at least one sequence position of the abovementioned amino acid sequences, have an amino acid other than that specifically mentioned.

In some embodiments, the recombinant spider silk protein in this disclosure comprises, in an effective amount, at least one natural or recombinant silk protein including spider silk protein, corresponding to Spidroin major 1 described by Xu et al., PNAS, USA, 87, 7120, (1990), Spidroin major 2 described by Hinman and Lewis, J. Biol. Chem., 267, 19320, (1922), recombinant spider silk protein as described in U.S. Patent Application No. 2016/0222174 and U.S. Pat. Nos. 9,051,453, 9,617,315, 9,689,089, 8,173,772, 8,642,734, 8,367,803 8,097,583, 8,030,024, 7,754,851, 7,148,039, 7,060,260, or alternatively the minor Spidroins described in patent application WO 95/25165. Each of the above-cited references is incorporated herein by reference in its entirety. Additional recombinant spider silk proteins suitable for the recombinant RSPF of this disclosure include ADF3 and ADF4 from the "Major Ampullate" gland of *Araneus diadematus*.

Recombinant silk is also described in other patents and patent applications, incorporated by reference herein: US 2004590196, U.S. Pat. No. 7,754,851, US 2007654470, U.S. Pat. No. 7,951,908, US 2010785960, U.S. Pat. No. 8,034, 897, US 20090263430, US 2008226854, US 20090123967, US 2005712095, US 2007991037, US 20090162896, US 200885266, U.S. Pat. No. 8,372,436, US 2007989907, US 2009267596, US 2010319542, US 2009265344, US 2012684607, US 2004583227, U.S. Pat. No. 8,030,024, US 2006643569, U.S. Pat. No. 7,868,146, US 2007991916, U.S. Pat. No. 8,097,583, US 2006643200, U.S. Pat. Nos. 8,729, 238, 8,877,903, US 20190062557, US 20160280960, US 20110201783, US 2008991916, US 2011986662, US 2012697729, US 20150328363, U.S. Pat. No. 9,034,816, US 20130172478, U.S. Pat. No. 9,217,017, US 20170202995, U.S. Pat. No. 8,721,991, US 2008227498, U.S. Pat. Nos. 9,233,067, 8,288,512, US 2008161364, U.S. Pat. No. 7,148, 039, U.S. Ser. No. 19/992,47806, US 2001861597, US 2004887100, U.S. Pat. Nos. 9,481,719, 8,765,688, US 200880705, US 2010809102, U.S. Pat. No. 8,367,803, US 2010664902, U.S. Pat. No. 7,569,660, U.S. Ser. No. 19/991, 38833, US 2000591632, US 20120065126, US 20100278882, US 2008161352, US 20100015070, US 2009513709, US 20090194317, US 2004559286, US 200589551, US 2008187824, US 20050266242, US 20050227322, and US 20044418.

Recombinant silk is also described in other patents and patent applications, incorporated by reference herein: US 20190062557, US 20150284565, US 20130225476, US 20130172478, US 20130136779, US 20130109762, US 20120252294, US 20110230911, US 20110201783, US 20100298877, U.S. Pat. Nos. 10,478,520, 10,253,213, 10,072,152, 9,233,067, 9,217,017, 9,034,816, 8,877,903, 8,729,238, 8,721,991, 8,097,583, 8,034,897, 8,030,024, 7,951,908, 7,868,146, and 7,754,851.

In some embodiments, the recombinant spider silk protein in this disclosure comprises or consists of 2 to 80 repetitive units, each independently selected from GPGXX, GGX and Ax as defined herein.

In some embodiments, the recombinant spider silk protein in this disclosure comprises or consists of repetitive units each independently selected from selected from the group consisting of (SEQ ID NO:11-SEQ ID NO:26) GPGAS, GPGSG, GPGGY, GPGGP, GPGGA, GPGQQ, GPGGG, GPGQG, GPGGS, GGY, GGP, GGA, GGR, GGS, GGT, GGN, GGQ, AAAAA, AAAAAA, AAAAAAA, AAAAAAAA, AAAAAAAAA, AAAAAAAAAA, GGRPSDTYG and GGRPSSSYG (SEQ ID NO:27), (i) GPYGPGASAAAAAAGGYGPGSGQQ (SEQ ID NO:28), (ii) GSSAAAAAAAASGPGGYGPENQGPSGPGGYGP-GGP (SEQ ID NO:29), (iii) GPGQQGPGQQGPGQ-QGPGQQ (SEQ ID NO:30) (iv) GPGGAGGPYGPG-GAGGPYGPGGAGGPY (SEQ ID NO:31), (v) GGT-TIIEDLDITIDGADGPITISEELTI (SEQ ID NO:32), (vi) PGSSAAAAAAAASGPGQGQGQGQGGRPSDTYG (SEQ ID NO:33), (vii) SAAAAAAAAGPGGGNG-GRPSDTYGAPGGGNGGRPSSSYG (SEQ ID NO:34), (viii) GGAGGAGGAGGSGGAGGS(SEQ ID NO:35), (ix) GPGGAGPGGYGPGGSGPGGYGPGGSGPGGY (SEQ ID NO:36), (x) GPYGPGASAAAAAAGGYGPGCGQQ (SEQ ID NO:37), (xi) GPYGPGASAAAAAAGGYGPGKGQQ (SEQ ID NO:38), (xii) GSSAAAAAAAASGPGGYG-PENQGPCGPGGYGPGGP (SEQ ID NO:39), (xiii)

GSSAAAAAAAASGPGGYGPKNQGPSGPGGYGPGGP (SEQ ID NO:40), (xiv) GSSAAAAAAAASGPGGYGPKNQGPSGPGGYGPGGP (SEQ ID NO:40), or variants thereof as described in U.S. Pat. No. 8,877,903, for example, a synthetic spider peptide having sequential order of GPGAS (SEQ ID NO:11), GGY, GPGSG (SEQ ID NO:12) in the peptide chain, or sequential order of AAAAAAAA (SEQ ID NO:23), GPGGY (SEQ ID NO:13), GPGGP (SEQ ID NO:14) in the peptide chain, sequential order of AAAAAAAA (SEQ ID NO:23), GPGQG (SEQ ID NO:18), GGR in the peptide chain. In some embodiments, this disclosure provides silk protein-like multiblock peptides that imitate the repeating units of amino acids derived from natural spider silk proteins such as Spidroin major 1 domain, Spidroin major 2 domain or Spidroin minor 1 domain and the profile of variation between the repeating units without modifying their three-dimensional conformation, wherein these silk protein-like multiblock peptides comprise a repeating unit of amino acids corresponding to one of the sequences (I), (II), (III) and/or (IV) below.

$[(XGG)_x(XGA)(GXG)_x(AGA)_y(G)_zAG]_p$ Formula (I) in which: X corresponds to tyrosine or to glutamine, w is an integer equal to 2 or 3, x is an integer from 1 to 3, y is an integer from 5 to 7, z is an integer equal to 1 or 2, and p is an integer and having any weight average molecular weight described herein, and/or $[(GPG_2YGPGQ_2)_a(X')_2S(A)_b]_p$ Formula (II) in which: X' corresponds to the amino acid sequence GPS or GPG, a is equal to 2 or 3, b is an integer from 7 to 10, and p is an integer and having any weight average molecular weight described herein, and/or $[(GR)(GA)_l(A)_m(GGX)_n(GA)_l(A)_m]_p$ Formula (III) and/or $[(GGX)_n(GA)_m(A)_l]_p$ Formula (IV) in which: X" corresponds to tyrosine, glutamine or alanine, l is an integer from 1 to 6, m is an integer from 0 to 4, n is an integer from 1 to 4, and p is an integer.

In some embodiments, the recombinant spider silk protein or an analog of a spider silk protein comprising an amino acid repeating unit of sequence (V):

$[(Xaa\ Gly\ Gly)_w(Xaa\ Gly\ Ala)(Gly\ Xaa\ Gly)_x(Ala\ Gly\ Ala)_y(Gly)_zAla\ Gly]_p$ Formula (V), wherein Xaa is tyrosine or glutamine, w is an integer equal to 2 or 3, x is an integer from 1 to 3, y is an integer from 5 to 7, z is an integer equal to 1 or 2, and p is an integer.

In some embodiments, the recombinant spider silk protein in this disclosure is selected from the group consisting of ADF-3 or variants thereof, ADF-4 or variants thereof, MaSpI (SEQ ID NO: 43) or variants thereof, MaSpII (SEQ ID NO: 44) or variants thereof as described in U.S. Pat. No. 8,367,803.

In some embodiments, this disclosure provides water soluble recombinant spider silk proteins produced in mammalian cells. The solubility of the spider silk proteins produced in mammalian cells was attributed to the presence of the COOH-terminus in these proteins, which makes them more hydrophilic. These COOH-terminal amino acids are absent in spider silk proteins expressed in microbial hosts.

In some embodiments, the recombinant spider silk protein in this disclosure comprises water soluble recombinant spider silk protein C16 modified with an amino or carboxyl terminal selected from the amino acid sequences consisting of: GCGGGGGG (SEQ ID NO: 41), GKGGGGGG (SEQ ID NO:42), GCGGSGGGGSGGGG (SEQ ID NO:43), GKGGGGGGSGGGG (SEQ ID NO:44), and GCGGGGGGSGGGG (SEQ ID NO:45). In some embodiments, the recombinant spider silk protein in this disclosure comprises $C_{16}NR4$, $C_{32}NR4$, C16, C32, $NR4C_{16}NR4$, $NR4C_{32}NR4$, $NR3C_{16}NR3$, or $NR3C_{32}NR3$ such that the molecular weight of the protein ranges as described herein.

In some embodiments, the recombinant spider silk protein in this disclosure comprises recombinant spider silk protein having a synthetic repetitive peptide segments and an amino acid sequence adapted from the natural sequence of ADF4 from *A. diadematus* as described in U.S. Pat. No. 8,877,903. In some embodiments, the RSPF in this disclosure comprises the recombinant spider silk proteins having repeating peptide units derived from natural spider silk proteins such as Spidroin major 1 domain, Spidroin major 2 domain or Spidroin minor 1 domain, wherein the repeating peptide sequence is GSSAAAAAAAASGPGQGQGQGQGQG-GRPSDTYG (SEQ ID NO: 46) or SAAAAAAAAGPGGG-NGGRPSDTYGAPGGGNGGRPSSSYG (SEQ ID NO:47), as described in U.S. Pat. No. 8,367,803.

In some embodiments, this disclosure provides recombinant spider proteins composed of the GPGGAGPG-GYGPGGSGPGGYGPGGSGPGGY (SEQ ID NO:48) repetitive fragment and having a molecular weight as described herein.

As used herein, the term "recombinant silk" refers to recombinant spider and/or silkworm silk protein or fragments thereof. In an embodiment, the spider silk protein is selected from the group consisting of swathing silk (Achniform gland silk), egg sac silk (Cylindriform gland silk), egg case silk (Tubuliform silk), non-sticky dragline silk (Ampullate gland silk), attaching thread silk (Pyriform gland silk), sticky silk core fibers (Flagelliform gland silk), and sticky silk outer fibers (Aggregate gland silk). For example, recombinant spider silk protein, as described herein, includes the proteins described in U.S. Patent Application No. 2016/0222174 and U.S. Pat. Nos. 9,051,453, 9,617,315, 9,689,089, 8,173,772, and 8,642,734.

Some organisms make multiple silk fibers with unique sequences, structural elements, and mechanical properties. For example, orb weaving spiders have six unique types of glands that produce different silk polypeptide sequences that are polymerized into fibers tailored to fit an environmental or lifecycle niche. The fibers are named for the gland they originate from and the polypeptides are labeled with the gland abbreviation (e.g. "Ma") and "Sp" for spidroin (short for spider fibroin). In orb weavers, these types include Major Ampullate (MaSp, also called dragline), Minor Ampullate (MiSp), Flagelliform (Flag), Aciniform (AcSp), Tubuliform (TuSp), and Pyriform (PySp). This combination of polypeptide sequences across fiber types, domains, and variation amongst different genus and species of organisms leads to a vast array of potential properties that can be harnessed by commercial production of the recombinant fibers. To date, the vast majority of the work with recombinant silks has focused on the Major Ampullate Spidroins (MaSp).

Aciniform (AcSp) silks tend to have high toughness, a result of moderately high strength coupled with moderately high extensibility. AcSp silks are characterized by large block ("ensemble repeat") sizes that often incorporate motifs of poly serine and GPX. Tubuliform (TuSp or Cylindrical) silks tend to have large diameters, with modest strength and high extensibility. TuSp silks are characterized by their poly serine and poly threonine content, and short tracts of poly alanine. Major Ampullate (MaSp) silks tend to have high strength and modest extensibility. MaSp silks can be one of two subtypes: MaSp1 and MaSp2. MaSp1 silks are generally less extensible than MaSp2 silks, and are characterized by poly alanine, GX, and GGX motifs. MaSp2 silks are characterized by poly alanine, GGX, and GPX motifs. Minor Ampullate (MiSp) silks tend to have modest strength and modest extensibility. MiSp silks are characterized by GGX, GA, and poly A motifs, and often contain spacer elements of approximately 100 amino acids. Flagelliform (Flag) silks tend to have very high extensibility and modest strength. Flag silks are usually characterized by GPG, GGX, and short spacer motifs.

Silk polypeptides are characteristically composed of a repeat domain (REP) flanked by non-repetitive regions (e.g., C-terminal and N-terminal domains). In an embodiment, both the C-terminal and N-terminal domains are between 75-350 amino acids in length. The repeat domain exhibits a hierarchical architecture. The repeat domain comprises a series of blocks (also called repeat units). The blocks are repeated, sometimes perfectly and sometimes imperfectly (making up a quasi-repeat domain), throughout the silk repeat domain. The length and composition of blocks varies among different silk types and across different species. Table 1 of U.S. Published Application No. 2016/0222174, the entirety of which is incorporated herein, lists examples of block sequences from selected species and silk types, with further examples presented in Rising, A. et al., Spider silk proteins: recent advances in recombinant production, structure-function relationships and biomedical applications, *Cell Mol. Life Sci.*, 68:2, µg 169-184 (2011); and Gatesy, J. et al., Extreme diversity, conservation, and convergence of spider silk fibroin sequences, Science, 291:5513, pg. 2603-2605 (2001). In some cases, blocks may be arranged in a regular pattern, forming larger macro-repeats that appear multiple times (usually 2-8) in the repeat domain of the silk sequence. Repeated blocks inside a repeat domain or macro-repeat, and repeated macro-repeats within the repeat domain, may be separated by spacing elements.

The construction of certain spider silk block copolymer polypeptides from the blocks and/or macro-repeat domains, according to certain embodiments of the disclosure, is illustrated in U.S. Published Patent Application No. 2016/0222174.

The recombinant block copolymer polypeptides based on spider silk sequences produced by gene expression in a recombinant prokaryotic or eukaryotic system can be purified according to methods known in the art. In a preferred embodiment, a commercially available expression/secretion system can be used, whereby the recombinant polypeptide is expressed and thereafter secreted from the host cell, to be easily purified from the surrounding medium. If expression/secretion vectors are not used, an alternative approach involves purifying the recombinant block copolymer polypeptide from cell lysates (remains of cells following disruption of cellular integrity) derived from prokaryotic or eukaryotic cells in which a polypeptide was expressed. Methods for generation of such cell lysates are known to those of skill in the art. In some embodiments, recombinant block copolymer polypeptides are isolated from cell culture supernatant.

Recombinant block copolymer polypeptide may be purified by affinity separation, such as by immunological interaction with antibodies that bind specifically to the recombinant polypeptide or nickel columns for isolation of recombinant polypeptides tagged with 6-8 histidine residues at their N-terminus or C-terminus Alternative tags may comprise the FLAG epitope or the hemagglutinin epitope. Such methods are commonly used by skilled practitioners.

A solution of such polypeptides (i.e., recombinant silk protein) may then be prepared and used as described herein.

In another embodiment, recombinant silk protein may be prepared according to the methods described in U.S. Pat. No. 8,642,734, the entirety of which is incorporated herein, and used as described herein.

In an embodiment, a recombinant spider silk protein is provided. The spider silk protein typically consists of from 170 to 760 amino acid residues, such as from 170 to 600 amino acid residues, preferably from 280 to 600 amino acid residues, such as from 300 to 400 amino acid residues, more preferably from 340 to 380 amino acid residues. The small size is advantageous because longer spider silk proteins tend to form amorphous aggregates, which require use of harsh solvents for solubilization and polymerization. The recombinant spider silk protein may contain more than 760 residues, in particular in cases where the spider silk protein contains more than two fragments derived from the N-terminal part of a spider silk protein, The spider silk protein comprises an N-terminal fragment consisting of at least one fragment (NT) derived from the corresponding part of a spider silk protein, and a repetitive fragment (REP) derived from the corresponding internal fragment of a spider silk protein. Optionally, the spider silk protein comprises a C-terminal fragment (CT) derived from the corresponding fragment of a spider silk protein. The spider silk protein comprises typically a single fragment (NT) derived from the N-terminal part of a spider silk protein, but in preferred embodiments, the N-terminal fragment include at least two, such as two fragments (NT) derived from the N-terminal part of a spider silk protein. Thus, the spidroin can schematically be represented by the formula $NT_m$-REP, and alternatively $NT_m$-REP-CT, where m is an integer that is 1 or higher, such as 2 or higher, preferably in the ranges of 1-2, 1-4, 1-6, 2-4 or 2-6. Preferred spidroins can schematically be represented by the formulas $NT_2$-REP or NT-REP, and alternatively $NT_2$-REP-CT or NT-REP-CT. The protein fragments are covalently coupled, typically via a peptide bond. In one embodiment, the spider silk protein consists of the NT fragment(s) coupled to the REP fragment, which REP fragment is optionally coupled to the CT fragment.

In one embodiment, the first step of the method of producing polymers of an isolated spider silk protein involves expression of a polynucleic acid molecule which encodes the spider silk protein in a suitable host, such as *Escherichia coli*. The thus obtained protein is isolated using standard procedures. Optionally, lipopolysaccharides and other pyrogens are actively removed at this stage.

In the second step of the method of producing polymers of an isolated spider silk protein, a solution of the spider silk protein in a liquid medium is provided. By the terms "soluble" and "in solution" is meant that the protein is not visibly aggregated and does not precipitate from the solvent at 60,000×g. The liquid medium can be any suitable medium, such as an aqueous medium, preferably a physiological medium, typically a buffered aqueous medium, such as a 10-50 mM Tris-HCl buffer or phosphate buffer. The liquid medium has a pH of 6.4 or higher and/or an ion composition that prevents polymerization of the spider silk protein. That is, the liquid medium has either a pH of 6.4 or higher or an ion composition that prevents polymerization of the spider silk protein, or both.

Ion compositions that prevent polymerization of the spider silk protein can readily be prepared by the skilled person utilizing the methods disclosed herein. A preferred ion composition that prevents polymerization of the spider silk protein has an ionic strength of more than 300 mM. Specific examples of ion compositions that prevent polymerization of the spider silk protein include above 300 mM NaCl, 100 mM phosphate and combinations of these ions having desired preventive effect on the polymerization of the spider silk protein, e.g. a combination of 10 mM phosphate and 300 mM NaCl.

The presence of an NT fragment improves the stability of the solution and prevents polymer formation under these conditions. This can be advantageous when immediate polymerization may be undesirable, e.g. during protein purification, in preparation of large batches, or when other conditions need to be optimized. It is preferred that the pH of the liquid medium is adjusted to 6.7 or higher, such as 7.0 or higher, or even 8.0 or higher, such as up to 10.5, to achieve high solubility of the spider silk protein. It can also be advantageous that the pH of the liquid medium is adjusted to the range of 6.4-6.8, which provides sufficient solubility of the spider silk protein but facilitates subsequent pH adjustment to 6.3 or lower.

In the third step, the properties of the liquid medium are adjusted to a pH of 6.3 or lower and ion composition that allows polymerization. That is, if the liquid medium wherein the spider silk protein is dissolved has a pH of 6.4 or higher, the pH is decreased to 6.3 or lower. The skilled person is well aware of various ways of achieving this, typically involving addition of a strong or weak acid. If the liquid medium wherein the spider silk protein is dissolved has an ion composition that prevents polymerization, the ion composition is changed so as to allow polymerization. The skilled person is well aware of various ways of achieving this, e.g. dilution, dialysis or gel filtration. If required, this step involves both decreasing the pH of the liquid medium to 6.3 or lower and changing the ion composition so as to allow polymerization. It is preferred that the pH of the liquid medium is adjusted to 6.2 or lower, such as 6.0 or lower. In particular, it may be advantageous from a practical point of view to limit the pH drop from 6.4 or 6.4-6.8 in the preceding step to 6.3 or 6.0-6.3, e.g. 6.2 in this step. In a preferred embodiment, the pH of the liquid medium of this step is 3 or higher, such as 4.2 or higher. The resulting pH range, e.g. 4.2-6.3 promotes rapid polymerization, In the fourth step, the spider silk protein is allowed to polymerize in the liquid medium having pH of 6.3 or lower and an ion composition that allows polymerization of the spider silk protein. Although the presence of the NT fragment improves solubility of the spider silk protein at a pH of 6.4 or higher and/or an ion composition that prevents polymerization of the spider silk protein, it accelerates polymer formation at a pH of 6.3 or lower when the ion composition allows polymerization of the spider silk protein. The resulting polymers are preferably solid and macroscopic, and they are formed in the liquid medium having a pH of 6.3 or lower and an ion composition that allows polymerization of the spider silk protein. In a preferred embodiment, the pH of the liquid medium of this step is 3 or higher, such as 4.2 or higher. The resulting pH range, e.g. 4.2-6.3 promotes rapid polymerization, Resulting polymer may be provided at the molecular weights described herein and prepared as a solution form that may be used as necessary for article coatings.

Ion compositions that allow polymerization of the spider silk protein can readily be prepared by the skilled person utilizing the methods disclosed herein. A preferred ion composition that allows polymerization of the spider silk protein has an ionic strength of less than 300 mM. Specific examples of ion compositions that allow polymerization of the spider silk protein include 150 mM NaCl, 10 mM phosphate, 20 mM phosphate and combinations of these ions lacking preventive effect on the polymerization of the spider silk protein, e.g. a combination of 10 mM phosphate or 20 mM phosphate and 150 mM NaCl. It is preferred that the ionic strength of this liquid medium is adjusted to the range of 1-250 mM.

Without desiring to be limited to any specific theory, it is envisaged that the NT fragments have oppositely charged poles, and that environmental changes in pH affects the charge balance on the surface of the protein followed by polymerization, whereas salt inhibits the same event.

At neutral pH, the energetic cost of burying the excess negative charge of the acidic pole may be expected to prevent polymerization. However, as the dimer approaches its isoelectric point at lower pH, attractive electrostatic forces will eventually become dominant, explaining the observed salt and pH-dependent polymerization behavior of NT and NT-containing minispidroins. It is proposed that, in some embodiments, pH-induced NT polymerization, and increased efficiency of fiber assembly of NT-minispidroins, are due to surface electrostatic potential changes, and that clustering of acidic residues at one pole of NT shifts its charge balance such that the polymerization transition occurs at pH values of 6.3 or lower.

In a fifth step, the resulting, preferably solid spider silk protein polymers are isolated from said liquid medium. Optionally, this step involves actively removing lipopolysaccharides and other pyrogens from the spidroin polymers.

Without desiring to be limited to any specific theory, it has been observed that formation of spidroin polymers progresses via formation of water-soluble spidroin dimers. The present disclosure thus also provides a method of producing dimers of an isolated spider silk protein, wherein the first two method steps are as described above. The spider silk proteins are present as dimers in a liquid medium at a pH of 6.4 or higher and/or an ion composition that prevents polymerization of said spider silk protein. The third step involves isolating the dimers obtained in the second step, and optionally removal of lipopolysaccharides and other pyrogens. In a preferred embodiment, the spider silk protein polymer of the disclosure consists of polymerized protein dimers. The present disclosure thus provides a novel use of a spider silk protein, preferably those disclosed herein, for producing dimers of the spider silk protein.

According to another aspect, the disclosure provides a polymer of a spider silk protein as disclosed herein. In an embodiment, the polymer of this protein is obtainable by any one of the methods therefor according to the disclosure. Thus, the disclosure provides various uses of recombinant spider silk protein, preferably those disclosed herein, for producing polymers of the spider silk protein as recombinant silk based coatings. According to one embodiment, the present disclosure provides a novel use of a dimer of a spider silk protein, preferably those disclosed herein, for producing polymers of the isolated spider silk protein as recombinant silk based coatings. In these uses, it is preferred that the polymers are produced in a liquid medium having a pH of 6.3 or lower and an ion composition that allows polymerization of said spider silk protein. In an embodiment, the pH of the liquid medium is 3 or higher, such as 4.2 or higher. The resulting pH range, e.g. 4.2-6.3 promotes rapid polymerization, Using the method(s) of the present disclosure, it is possible to control the polymerization process, and this allows for optimization of parameters for obtaining silk polymers with desirable properties and shapes.

In an embodiment, the recombinant silk proteins described herein, include those described in U.S. Pat. No. 8,642,734, the entirety of which is incorporated by reference.

In another embodiment, the recombinant silk proteins described herein may be prepared according to the methods described in U.S. Pat. No. 9,051,453, the entirety of which is incorporated herein by reference.

An amino acid sequence represented by SEQ ID NO: 1 of U.S. Pat. No. 9,051,453 is identical to an amino acid sequence that is composed of 50 amino acid residues of an amino acid sequence of ADF3 at the C-terminal (NCBI Accession No.: AAC47010, GI: 1263287). An amino acid sequence represented by SEQ ID NO: 2 of U.S. Pat. No. 9,051,453 is identical to an amino acid sequence represented by SEQ ID NO: 1 of U.S. Pat. No. 9,051,453 from which 20 residues have been removed from the C-terminal. An amino acid sequence represented by SEQ ID NO: 3 of U.S. Pat. No. 9,051,453 is identical to an amino acid sequence represented by SEQ ID NO: 1 from which 29 residues have been removed from the C-terminal.

An example of the polypeptide that contains units of the amino acid sequence represented by the formula 1: REP1-REP2 (1) and that has, at a C-terminal, an amino acid sequence represented by any of SEQ ID NOS: 1 to 3 or an amino acid sequence having a homology of 90% or more with the amino acid sequence represented by any of SEQ ID NOS: 1 to 3 of U.S. Pat. No. 9,051,453 is a polypeptide having an amino acid sequence represented by SEQ ID NO: 8 of U.S. Pat. No. 9,051,453. The polypeptide having the amino acid sequence represented by SEQ ID NO: 8 of U.S. Pat. No. 9,051,453 is obtained by the following mutation: in an amino acid sequence of ADF3 (NCBI Accession No.: AAC47010, GI: 1263287) to the N-terminal of which has been added an amino acid sequence (SEQ ID NO: 5 of U.S. Pat. No. 9,051,453) composed of a start codon, His 10 tags and an HRV3C Protease (Human rhinovirus 3C Protease) recognition site, $1^{st}$ to $13^{th}$ repetitive regions are about doubled and the translation ends at the $1154^{th}$ amino acid residue. In the polypeptide having the amino acid sequence represented by SEQ ID NO: 8 of U.S. Pat. No. 9,051,453, the C-terminal sequence is identical to the amino acid sequence represented by SEQ ID NO: 3.

Further, the polypeptide that contains units of the amino acid sequence represented by the formula 1: REP1-REP2 (1) and that has, at a C-terminal, an amino acid sequence represented by any of SEQ ID NOS: 1 to 3 of U.S. Pat. No. 9,051,453 or an amino acid sequence having a homology of 90% or more with the amino acid sequence represented by any of SEQ ID NOS: 1 to 3 of U.S. Pat. No. 9,051,453 may be a protein that has an amino acid sequence represented by SEQ ID NO: 8 of U.S. Pat. No. 9,051,453 in which one or a plurality of amino acids have been substituted, deleted, inserted and/or added and that has a repetitious region composed of a crystal region and an amorphous region.

Further, an example of the polypeptide containing two or more units of the amino acid sequence represented by the formula 1: REP1-REP2 (1) is a recombinant protein derived from ADF4 having an amino acid sequence represented by SEQ ID NO: 15 of U.S. Pat. No. 9,051,453. The amino acid sequence represented by SEQ ID NO: 15 of U.S. Pat. No. 9,051,453 is an amino acid sequence obtained by adding the amino acid sequence (SEQ ID NO: 5 of U.S. Pat. No. 9,051,453) composed of a start codon, His 10 tags and an HRV3C Protease (Human rhinovirus 3C Protease) recognition site, to the N-terminal of a partial amino acid sequence of ADF4 obtained from the NCBI database (NCBI Accession No.: AAC47011, GI: 1263289). Further, the polypeptide containing two or more units of the amino acid sequence represented by the formula 1: REP1-REP2 (1) may be a polypeptide that has an amino acid sequence represented by SEQ ID NO: 15 of U.S. Pat. No. 9,051,453 in which one or a plurality of amino acids have been substituted, deleted, inserted and/or added and that has a repetitious region composed of a crystal region and an amorphous region. Further, an example of the polypeptide containing two or more units of the amino acid sequence represented by the formula 1: REP1-REP2 (1) is a recombinant protein derived from MaSp2 that has an amino acid sequence represented by SEQ ID NO: 17 of U.S. Pat. No. 9,051,453. The amino acid sequence represented by SEQ ID NO: 17 of U.S. Pat. No. 9,051,453 is an amino acid sequence obtained by adding the amino acid sequence (SEQ ID NO: 5 of U.S. Pat. No. 9,051,453) composed of a start codon, His 10 tags and an HRV3C Protease (Human rhinovirus 3C Protease) recognition site, to the N-terminal of a partial sequence of MaSp2 obtained from the NCBI web database (NCBI Accession No.: AAT75313, GI: 50363147). Furthermore, the polypeptide containing two or more units of the amino acid sequence represented by the formula 1: REP1-REP2 (1) may be a polypeptide that has an amino acid sequence represented by SEQ ID NO: 17 of U.S. Pat. No. 9,051,453 in which one or a plurality of amino acids have been substituted, deleted, inserted and/or added and that has a repetitious region composed of a crystal region and an amorphous region.

Examples of the polypeptide derived from flagelliform silk proteins include a polypeptide containing 10 or more units of an amino acid sequence represented by the formula 2: REP3 (2), preferably a polypeptide containing 20 or more units thereof, and more preferably a polypeptide containing 30 or more units thereof. In the case of producing a recombinant protein using a microbe such as *Escherichia coli* as a host, the molecular weight of the polypeptide derived from flagelliform silk proteins is preferably 500 kDa or less, more preferably 300 kDa or less, and further preferably 200 kDa or less, in terms of productivity.

In the formula (2), the REP 3 indicates an amino acid sequence composed of Gly-Pro-Gly-Gly-X, where X indicates an amino acid selected from the group consisting of Ala, Ser, Tyr and Val.

A major characteristic of the spider silk is that the flagelliform silk does not have a crystal region, but has a repetitious region composed of an amorphous region. Since the major dragline silk and the like have a repetitious region composed of a crystal region and an amorphous region, they are expected to have both high stress and stretchability. Meanwhile, as to the flagelliform silk, although the stress is inferior to that of the major dragline silk, the stretchability is high. The reason for this is considered to be that most of the flagelliform silk is composed of amorphous regions.

An example of the polypeptide containing 10 or more units of the amino acid sequence represented by the formula 2: REP3 (2) is a recombinant protein derived from flagelliform silk proteins having an amino acid sequence represented by SEQ ID NO: 19 of U.S. Pat. No. 9,051,453. The amino acid sequence represented by SEQ ID NO: 19 of U.S. Pat. No. 9,051,453 is an amino acid sequence obtained by combining a partial sequence of flagelliform silk protein of *Nephila clavipes* obtained from the NCBI database (NCBI Accession No.: AAF36090, GI: 7106224), specifically, an amino acid sequence thereof from the $1220^{th}$ residue to the $1659^{th}$ residue from the N-terminal that corresponds to repetitive sections and motifs (referred to as a PR1 sequence), with a partial sequence of flagelliform silk protein of *Nephila clavipes* obtained from the NCBI database (NCBI Accession No.: AAC38847, GI: 2833649), specifically, a C-terminal amino acid sequence thereof from the $816^{th}$ residue to the $907^{th}$ residue from the C-terminal, and thereafter adding the amino acid sequence (SEQ ID NO: 5 of U.S. Pat. No. 9,051,453) composed of a start codon, His 10 tags and an HRV3C Protease recognition site, to the N-terminal of the combined sequence. Further, the polypeptide containing 10 or more units of the amino acid sequence represented by the formula 2: REP3 (2) may be a polypeptide that has an amino acid sequence represented by SEQ ID NO: 19 of U.S. Pat. No. 9,051,453 in which one or a plurality of amino acids have been substituted, deleted, inserted and/or added and that has a repetitious region composed of an amorphous region.

The polypeptide can be produced using a host that has been transformed by an expression vector containing a gene encoding a polypeptide. A method for producing a gene is not limited particularly, and it may be produced by amplifying a gene encoding a natural spider silk protein from a cell derived from spiders by a polymerase chain reaction (PCR), etc., and cloning it, or may be synthesized chemically. Also, a method for chemically synthesizing a gene is not limited particularly, and it can be synthesized as follows, for example: based on information of amino acid sequences of natural spider silk proteins obtained from the NCBI web database, etc., oligonucleotides that have been synthesized automatically with AKTA oligopilot plus 10/100 (GE Healthcare Japan Corporation) are linked by PCR, etc. At this time, in order to facilitate the purification and observation of protein, it is possible to synthesize a gene that encodes a protein having an amino acid sequence of the above-described amino acid sequence to the N-terminal of which has been added an amino acid sequence composed of a start codon and His 10 tags.

Examples of the expression vector include a plasmid, a phage, a virus, and the like that can express protein based on a DNA sequence. The plasmid-type expression vector is not limited particularly as long as it allows a target gene to be expressed in a host cell and it can amplify itself. For example, in the case of using *Escherichia coli* Rosetta (DE3) as a host, a pET22b(+) plasmid vector, a pCold plasmid vector, and the like can be used. Among these, in terms of productivity of protein, it is preferable to use the pET22b(+) plasmid vector. Examples of the host include animal cells, plant cells, microbes, etc.

The polypeptide used in the present disclosure is preferably a polypeptide derived from ADF3, which is one of two principal dragline silk proteins of *Araneus diadematus*. This polypeptide has advantages of basically having high strength-elongation and toughness and of being synthesized easily.

Accordingly, the recombinant silk protein (e.g., the recombinant spider silk-based protein) used in accordance with the embodiments, articles, and/or methods described herein, may include one or more recombinant silk proteins described above or recited in U.S. Pat. Nos. 8,173,772, 8,278,416, 8,618,255, 8,642,734, 8,691,581, 8,729,235, 9,115,204, 9,157,070, 9,309,299, 9,644,012, 9,708,376, 9,051,453, 9,617,315, 9,968,682, 9,689,089, 9,732,125, 9,856,308, 9,926,348, 10,065,997, 10,316,069, and 10,329,332; and U.S. Patent Publication Nos. 2009/0226969, 2011/0281273, 2012/0041177, 2013/0065278, 2013/0115698, 2013/0316376, 2014/0058066, 2014/0079674, 2014/0245923, 2015/0087046, 2015/0119554, 2015/0141618, 2015/0291673, 2015/0291674, 2015/0239587, 2015/0344542, 2015/0361144, 2015/0374833, 2015/0376247, 2016/0024464, 2017/0066804, 2017/0066805, 2015/0293076, 2016/0222174, 2017/0283474, 2017/0088675, 2019/0135880, 2015/0329587, 2019/0040109, 2019/0135881, 2019/0177363, 2019/0225646, 2019/0233481, 2019/0031842, 2018/0355120, 2019/0186050, 2019/0002644, 2020/0031887, 2018/0273590, 20191/094403, 2019/0031843, 2018/0251501, 2017/0066805, 2018/0127553, 2019/0329526, 2020/0031886, 2018/0080147, 2019/0352349, 2020/0043085, 2019/0144819, 2019/0228449, 2019/0340666, 2020/0000091, 2019/0194710, 2019/0151505, 2018/0265555, 2019/0352330, 2019/0248847, and 2019/0378191, the entirety of which are incorporated herein by reference.

Silk Fibroin-like Protein Fragments

The recombinant silk protein in this disclosure comprises synthetic proteins which are based on repeat units of natural silk proteins. Besides the synthetic repetitive silk protein sequences, these can additionally comprise one or more natural nonrepetitive silk protein sequences. As used herein, "silk fibroin-like protein fragments" refer to protein fragments having a molecular weight and polydispersity as defined herein, and a certain degree of homology to a protein selected from native silk protein, fibroin heavy chain, fibroin light chain, or any protein comprising one or more GAGAGS hexa amino acid repeating units. In some embodiments, a degree of homology is selected from about 99%, about 98%, about 97%, about 96%, about 95%, about 94%, about 93%, about 92%, about 91%, about 90%, about 89%, about 88%, about 87%, about 86%, about 85%, about 84%, about 83%, about 82%, about 81%, about 80%, about 79%, about 78%, about 77%, about 76%, about 75%, or less than 75%.

As described herein, a protein such as native silk protein, fibroin heavy chain, fibroin light chain, or any protein comprising one or more GAGAGS hexa amino acid repeating units includes between about 9% and about 45% glycine, or about 9% glycine, or about 10% glycine, about 43% glycine, about 44% glycine, about 45% glycine, or about 46% glycine. As described herein, a protein such as native silk protein, fibroin heavy chain, fibroin light chain, or any protein comprising one or more GAGAGS hexa amino acid repeating units includes between about 13% and about 30% alanine, or about 13% alanine, or about 28% alanine, or about 29% alanine, or about 30% alanine, or about 31% alanine. As described herein, a protein such as native silk protein, fibroin heavy chain, fibroin light chain, or any protein comprising one or more GAGAGS hexa amino acid repeating units includes between 9% and about 12% serine, or about 9% serine, or about 10% serine, or about 11% serine, or about 12% serine.

In some embodiments, a silk fibroin-like protein described herein includes about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, or about 55% glycine. In some embodiments, a silk fibroin-like protein described herein includes about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, or about 39% alanine. In some embodiments, a silk fibroin-like protein described herein includes about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, or about 22% serine. In some embodiments, a silk fibroin-like protein described herein may include independently any amino acid known to be included in natural fibroin. In some embodiments, a silk fibroin-like protein described herein may exclude independently any amino acid known to be included in natural fibroin. In some embodiments, on average 2 out of 6 amino acids, 3 out of 6 amino acids, or 4 out of 6 amino acids in a silk fibroin-like protein described herein is glycine. In some embodiments, on average 1 out of 6 amino acids, 2 out of 6 amino acids, or 3 out of 6 amino acids in a silk fibroin-like protein described herein is alanine. In some embodiments, on average none out of 6 amino acids, 1 out of 6 amino acids, or 2 out of 6 amino acids in a silk fibroin-like protein described herein is serine.

Sericin or Sericin Fragments

The main body of the raw silk is silk fibroin fiber, and the silk fibroin fiber is coated with an adhesive substance silk sericin. Sericin is a colloidal silk protein that covers the surface of the silk thread and is composed of bulky amino acids rich in chemical reactivity such as serine, threonine, and aspartic acid, in addition to glycine and alanine. In the various processes of producing silk from raw silk, sericin is important in controlling the solubility of silk and producing high quality silk. Moreover, it plays an extremely important role as an adhesion functional protein. When silk fiber is used as a clothing material, most of the silk sericin covering the silk thread is removed and discarded, so sericin is a valuable unused resource.

In some embodiments, the silk protein fragments described herein include sericin or sericin fragments. Methods of preparing sericin or sericin fragments and their applications in various fields are known and are described herein, and are also described, for example, in U.S. Pat. Nos. 7,115,388, 7,157,273, and 9,187,538, all of which are incorporated by reference herein in their entireties.

In some embodiments, sericin removed from the raw silk cocoons, such as in a degumming step, can be collected and used in the methods described herein. Sericin can also be reconstituted from a powder, and used within the compositions and methods of the disclosure.

Other Properties of SPF

Compositions of the present disclosure are "biocompatible" or otherwise exhibit "biocompatibility" meaning that the compositions are compatible with living tissue or a living system by not being toxic, injurious, or physiologically reactive and not causing immunological rejection or an inflammatory response. Such biocompatibility can be evidenced by participants topically applying compositions of the present disclosure on their skin for an extended period of time. In an embodiment, the extended period of time is about 3 days. In an embodiment, the extended period of time is about 7 days. In an embodiment, the extended period of time is about 14 days. In an embodiment, the extended period of time is about 21 days. In an embodiment, the extended period of time is about 30 days. In an embodiment, the extended period of time is selected from the group consisting of about 1 month, about 2 months, about 3 months, about 4 months, about 5 months, about 6 months, about 7 months, about 8 months, about 9 months, about 10 months, about 11 months, about 12 months, and indefinitely. For example, in some embodiments, the coatings described herein are biocompatible coatings.

In some embodiments, compositions described herein, which may be biocompatible compositions (e.g., biocompatible coatings that include silk), may be evaluated and comply with International Standard ISO 10993-1, titled the "Biological evaluation of medical devices—Part 1: Evaluation and testing within a risk management process." In some embodiments, compositions described herein, which may be biocompatible compositions, may be evaluated under ISO 106993-1 for one or more of cytotoxicity, sensitization, hemocompatibility, pyrogenicity, implantation, genotoxicity, carcinogenicity, reproductive and developmental toxicity, and degradation.

Compositions of the present disclosure are "hypoallergenic" meaning that they are relatively unlikely to cause an allergic reaction. Such hypoallergenicity can be evidenced by participants topically applying compositions of the present disclosure on their skin for an extended period of time. In an embodiment, the extended period of time is about 3 days. In an embodiment, the extended period of time is about 7 days. In an embodiment, the extended period of time is about 14 days. In an embodiment, the extended period of time is about 21 days. In an embodiment, the extended period of time is about 30 days. In an embodiment, the extended period of time is selected from the group consisting of about 1 month, about 2 months, about 3 months, about 4 months, about 5 months, about 6 months, about 7 months, about 8 months, about 9 months, about 10 months, about 11 months, about 12 months, and indefinitely.

In an embodiment, the stability of a composition of the present disclosure is about 1 day. In an embodiment, the stability of a composition of the present disclosure is about 2 days. In an embodiment, the stability of a composition of the present disclosure is about 3 days. In an embodiment, the stability of a composition of the present disclosure is about 4 days. In an embodiment, the stability of a composition of the present disclosure is about 5 days. In an embodiment, the stability of a composition of the present disclosure is about 6 days. In an embodiment, the stability of a composition of the present disclosure is about 7 days. In an embodiment, the stability of a composition of the present disclosure is about 8 days. In an embodiment, the stability of a composition of the present disclosure is about 9 days. In an embodiment, the stability of a composition of the present disclosure is about 10 days.

In an embodiment, the stability of a composition of the present disclosure is about 11 days, about 12 days, about 13 days, about 14 days, about 15 days, about 16 days, about 17 days, about 18 days, about 19 days, about 20 days, about 21 days, about 22 days, about 23 days, about 24 days, about 25 days, about 26 days, about 27 days, about 28 days, about 29 days, or about 30 days.

In an embodiment, the stability of a composition of the present disclosure is 10 days to 6 months. In an embodiment, the stability of a composition of the present disclosure is 6 months to 12 months. In an embodiment, the stability of a composition of the present disclosure is 12 months to 18 months. In an embodiment, the stability of a composition of the present disclosure is 18 months to 24 months. In an embodiment, the stability of a composition of the present disclosure is 24 months to 30 months. In an embodiment, the stability of a composition of the present disclosure is 30 months to 36 months. In an embodiment, the stability of a composition of the present disclosure is 36 months to 48 months. In an embodiment, the stability of a composition of the present disclosure is 48 months to 60 months.

In an embodiment, a SPF composition of the present disclosure is not soluble in an aqueous solution due to the crystallinity of the protein. In an embodiment, a SPF composition of the present disclosure is soluble in an aqueous solution. In an embodiment, the SPF of a composition of the present disclosure include a crystalline portion of about two-thirds and an amorphous region of about one-third. In an embodiment, the SPF of a composition of the present disclosure include a crystalline portion of about one-half and an amorphous region of about one-half. In an embodiment, the SPF of a composition of the present disclosure include a 99% crystalline portion and a 1% amorphous region. In an embodiment, the SPF of a composition of the present disclosure include a 95% crystalline portion and a 5% amorphous region. In an embodiment, the SPF of a composition of the present disclosure include a 90% crystalline portion and a 10% amorphous region. In an embodiment, the SPF of a composition of the present disclosure include a 85% crystalline portion and a 15% amorphous region. In an embodiment, the SPF of a composition of the present disclosure include a 80% crystalline portion and a 20% amorphous region. In an embodiment, the SPF of a composition of the present disclosure include a 75% crystalline portion and a 25% amorphous region. In an embodiment, the SPF of a composition of the present disclosure include a 70% crystalline portion and a 30% amorphous region. In an embodiment, the SPF of a composition of the present disclosure include a 65% crystalline portion and a 35% amorphous region. In an embodiment, the SPF of a composition of the present disclosure include a 60% crystalline portion and a 40% amorphous region. In an embodiment, the SPF of a composition of the present disclosure include a 50% crystalline portion and a 50% amorphous region. In an embodiment, the SPF of a composition of the present disclosure include a 40% crystalline portion and a 60% amorphous region. In an embodiment, the SPF of a composition of the present disclosure include a 35% crystalline portion and a 65% amorphous region. In an embodiment, the SPF of a composition of the present disclosure include a 30% crystalline portion and a 70% amorphous region. In an embodiment, the SPF of a composition of the present disclosure include a 25% crystalline portion and a 75% amorphous region. In an embodiment, the SPF of a composition of the present disclosure include a 20% crystalline portion and a 80% amorphous region. In an embodiment, the SPF of a composition of the present disclosure include a 15% crystalline portion and a 85% amorphous region. In an embodiment, the SPF of a composition of the present disclosure include a 10% crystalline portion and a 90% amorphous region. In an embodiment, the SPF of a composition of the present disclosure include a 5% crystalline portion and a 90% amorphous region. In an embodiment, the SPF of a composition of the present disclosure include a 1% crystalline portion and a 99% amorphous region.

As used herein, the term "substantially free of inorganic residuals" means that the composition exhibits residuals of 0.1% (w/w) or less. In an embodiment, substantially free of inorganic residuals refers to a composition that exhibits residuals of 0.05% (w/w) or less. In an embodiment, substantially free of inorganic residuals refers to a composition that exhibits residuals of 0.01% (w/w) or less. In an embodiment, the amount of inorganic residuals is between 0 ppm ("non-detectable" or "ND") and 1000 ppm. In an embodiment, the amount of inorganic residuals is ND to about 500 ppm. In an embodiment, the amount of inorganic residuals is ND to about 400 ppm. In an embodiment, the amount of inorganic residuals is ND to about 300 ppm. In an embodiment, the amount of inorganic residuals is ND to about 200 ppm. In an embodiment, the amount of inorganic residuals is ND to about 100 ppm. In an embodiment, the amount of inorganic residuals is between 10 ppm and 1000 ppm.

As used herein, the term "substantially free of organic residuals" means that the composition exhibits residuals of 0.1% (w/w) or less, in an embodiment, substantially free of organic residuals refers to a composition that exhibits residuals of 0.05% (w/w) or less. In an embodiment, substantially free of organic residuals refers to a composition that exhibits residuals of 0.01% (w/w) or less. In an embodiment, the amount of organic residuals is between 0 ppm ("non-detectable" or "ND") and 1000 ppm. In an embodiment, the amount of organic residuals is ND to about 500 ppm. In an embodiment, the amount of organic residuals is ND to about 400 ppm. In an embodiment, the amount of organic residuals is ND to about 300 ppm. In an embodiment, the amount of organic residuals is ND to about 200 ppm. In an embodiment, the amount of organic residuals is ND to about 100 ppm. In an embodiment, the amount of organic residuals is between 10 ppm and 1000 ppm.

Compositions of the present disclosure exhibit "biocompatibility" meaning that the compositions are compatible with living tissue or a living system by not being toxic, injurious, or physiologically reactive and not causing immunological rejection. Such biocompatibility can be evidenced by participants topically applying compositions of the present disclosure on their skin for an extended period of time. In an embodiment, the extended period of time is about 3 days. In an embodiment, the extended period of time is about 7 days, in an embodiment, the extended period of time is about 14 days, in an embodiment, the extended period of time is about 21 days. In an embodiment, the extended period of time is about 30 days. In an embodiment, the extended period of time is selected from the group consisting of about l month, about 2 months, about 3 months, about 4 months, about 5 months, about 6 months, about 7 months, about 8 months, about 9 months, about 10 months, about 11 months, about 12 months, and indefinitely.

Compositions of the present disclosure are "hypoallergenic" meaning that they are relatively unlikely to cause an allergic reaction. Such hypoallergenicity can be evidenced by participants topically applying compositions of the present disclosure on their skin for an extended period of time. In an embodiment, the extended period of time is about 3 days. In an embodiment, the extended period of time is about 7 days. In an embodiment, the extended period of time is about 14 days. In an embodiment, the extended period of time is about 21 days. In an embodiment, the extended period of time is about 30 days. In an embodiment, the extended period of time is selected from the group consisting of about 1 month, about 2 months, about 3 months, about 4 months, about 5 months, about 6 months, about 7 months, about 8 months, about 9 months, about 10 months, about 11 months, about 12 months, and indefinitely.

Following are non-limiting examples of suitable ranges for various parameters in and for preparation of the silk solutions of the present disclosure. The silk solutions of the present disclosure may include one or more, but not necessarily all, of these parameters and may be prepared using various combinations of ranges of such parameters.

In an embodiment, the percent SPF in the solution is less than 30.0 wt. %. In an embodiment, the percent SPF in the solution is less than 25.0 wt. %. In an embodiment, the percent SPF in the solution is less than 20.0 wt. %. In an embodiment, the percent SPF in the solution is less than 19.0 wt. %. In an embodiment, the percent SPF in the solution is less than 18.0 wt. %. In an embodiment, the percent SPF in the solution is less than 17.0 wt. %. In an embodiment, the percent SPF in the solution is less than 16.0 wt. %. In an embodiment, the percent SPF in the solution is less than 15.0 wt. %. In an embodiment, the percent SPF in the solution is less than 14.0 wt. %. In an embodiment, the percent SPF in the solution is less than 13.0 wt. %. In an embodiment, the percent SPF in the solution is less than 12.0 wt. %. In an embodiment, the percent SPF in the solution is less than 11.0 wt. %. In an embodiment, the percent SPF in the solution is less than 10.0 wt. %. In an embodiment, the percent SPF in the solution is less than 9.0 wt. %. In an embodiment, the percent SPF in the solution is less than 8.0 wt. %. In an embodiment, the percent SPF in the solution is less than 7.0 wt. %. In an embodiment, the percent SPF in the solution is less than 6.0 wt. %. In an embodiment, the percent SPF in the solution is less than 5.0 wt. %. In an embodiment, the percent SPF in the solution is less than 4.0 wt. %. In an embodiment, the percent SPF in the solution is less than 3.0 wt. %. In an embodiment, the percent SPF in the solution is less than 2.0 wt. %. In an embodiment, the percent SPF in the solution is less than 1.0 wt. %. In an embodiment, the percent SPF in the solution is less than 0.9 wt. %. In an embodiment, the percent SPF in the solution is less than 0.8 wt. %. In an embodiment, the percent SPF in the solution is less than 0.7 wt. %. In an embodiment, the percent SPF in the solution is less than 0.6 wt. %. In an embodiment, the percent SPF in the solution is less than 0.5 wt. %. In an embodiment, the percent SPF in the solution is less than 0.4 wt. %. In an embodiment, the percent SPF in the solution is less than 0.3 wt. %. In an embodiment, the percent SPF in the solution is less than 0.2 wt. %. In an embodiment, the percent SPF in the solution is less than 0.1 wt. %.

In an embodiment, the percent SPF in the solution is greater than 0.1 wt. %. In an embodiment, the percent SPF in the solution is greater than 0.2 wt. %. In an embodiment, the percent SPF in the solution is greater than 0.3 wt. %. In an embodiment, the percent SPF in the solution is greater than 0.4 wt. %. In an embodiment, the percent SPF in the solution is greater than 0.5 wt. %. In an embodiment, the percent SPF in the solution is greater than 0.6 wt. %. In an embodiment, the percent SPF in the solution is greater than 0.7 wt. %. In an embodiment, the percent SPF in the solution is greater than 0.8 wt. %. In an embodiment, the percent SPF in the solution is greater than 0.9 wt. %. In an embodiment, the percent SPF in the solution is greater than 1.0 wt. %. In an embodiment, the percent SPF in the solution is greater than 2.0 wt. %. In an embodiment, the percent SPF in the solution is greater than 3.0 wt. %. In an embodiment, the percent SPF in the solution is greater than 4.0 wt. %. In an embodiment, the percent SPF in the solution is greater than 5.0 wt. %. In an embodiment, the percent SPF in the solution is greater than 6.0 wt. %. In an embodiment, the percent SPF in the solution is greater than 7.0 wt. %. In an embodiment, the percent SPF in the solution is greater than 8.0 wt. %. In an embodiment, the percent SPF in the solution is greater than 9.0 wt. %. In an embodiment, the percent SPF in the solution is greater than 10.0 wt. %. In an embodiment, the percent SPF in the solution is greater than 11.0 wt. %. In an embodiment, the percent SPF in the solution is greater than 12.0 wt. %. In an embodiment, the percent SPF in the solution is greater than 13.0 wt. %. In an embodiment, the percent SPF in the solution is greater than 14.0 wt. %. In an embodiment, the percent SPF in the solution is greater than 15.0 wt. %. In an embodiment, the percent SPF in the solution is greater than 16.0 wt. %. In an embodiment, the percent SPF in the solution is greater than 17.0 wt. %. In an embodiment, the percent SPF in the solution is greater than 18.0 wt. %. In an embodiment, the percent SPF in the solution is greater than 19.0 wt. %. In an embodiment, the percent SPF in the solution is greater than 20.0 wt. %. In an embodiment, the percent SPF in the solution is greater than 25.0 wt. %.

In an embodiment, the percent SPF in the solution ranges from about 0.1 wt. % to about 30.0 wt. %. In an embodiment, the percent SPF in the solution ranges from about 0.1 wt. % to about 25.0 wt. %. In an embodiment, the percent SPF in the solution ranges from about 0.1 wt. % to about 20.0 wt. %. In an embodiment, the percent SPF in the solution ranges from about 0.1 wt. % to about 15.0 wt. %. In an embodiment, the percent SPF in the solution ranges from about 0.1 wt. % to about 10.0 wt. %. In an embodiment, the percent SPF in the solution ranges from about 0.1 wt. % to about 9.0 wt. %. In an embodiment, the percent SPF in the solution ranges from about 0.1 wt. % to about 8.0 wt. %. In an embodiment, the percent SPF in the solution ranges from about 0.1 wt. % to about 7.0 wt. %. In an embodiment, the percent SPF in the solution ranges from about 0.1 wt. % to about 6.5 wt. %. In an embodiment, the percent SPF in the solution ranges from about 0.1 wt. % to about 6.0 wt. %. In an embodiment, the percent SPF in the solution ranges from about 0.1 wt. % to about 5.5 wt. %. In an embodiment, the percent SPF in the solution ranges from about 0.1 wt. % to about 5.0 wt. %. In an embodiment, the percent SPF in the solution ranges from about 0.1 wt. % to about 4.5 wt. %. In an embodiment, the percent SPF in the solution ranges from about 0.1 wt. % to about 4.0 wt. %. In an embodiment, the percent SPF in the solution ranges from about 0.1 wt. % to about 3.5 wt. %. In an embodiment, the percent SPF in the solution ranges from about 0.1 wt. % to about 3.0 wt. %. In an embodiment, the percent SPF in the solution ranges from about 0.1 wt. % to about 2.5 wt. %. In an embodiment, the percent SPF in the solution ranges from about 0.1 wt. % to about 2.0 wt. %. In an embodiment, the percent SPF in the solution ranges from about 0.1 wt. % to about 2.4 wt. %. In an embodiment, the percent SPF in the solution ranges from about 0.5 wt. % to about 5.0 wt. %. In an embodiment, the percent SPF in the solution ranges from about 0.5 wt. % to about 4.5 wt. %. In an embodiment, the percent SPF in the solution ranges from about 0.5 wt. % to about 4.0 wt. %. In an embodiment, the percent SPF in the solution ranges from about 0.5 wt. % to about 3.5 wt. %. In an embodiment, the percent SPF in the solution ranges from about 0.5 wt. % to about 3.0 wt. %. In an embodiment, the percent SPF in the solution ranges from about 0.5 wt. % to about 2.5 wt. %. In an embodiment, the percent SPF in the solution ranges from about 1.0 wt. % to about 4.0 wt. %. In an embodiment, the percent SPF in the solution ranges from about 1.0 wt. % to about 3.5 wt. %. In an embodiment, the percent SPF in the solution ranges from about 1.0 wt. % to about 3.0 wt. %. In an embodiment, the percent SPF in the solution ranges from about 1.0 wt. % to about 2.5 wt. %. In an embodiment, the percent SPF in the solution ranges from about 1.0 wt. % to about 2.4 wt. %. In an embodiment, the percent SPF in the solution ranges from about 1.0 wt. % to about 2.0 wt. %.

In an embodiment, the percent SPF in the solution ranges from about 20.0 wt. % to about 30.0 wt. %. In an embodiment, the percent SPF in the solution ranges from about 0.1 wt. % to about 10.0 wt. %. In an embodiment, the percent SPF in the solution ranges from about 1.0 wt. % to about 10.0 wt. %. In an embodiment, the percent SPF in the solution ranges from about 2 wt. % to about 10.0 wt. %. In an embodiment, the percent SPF in the solution ranges from about 0.1 wt. % to about 6.0 wt. %. In an embodiment, the percent SPF in the solution ranges from about 6.0 wt. % to about 10.0 wt. %. In an embodiment, the percent SPF in the solution ranges from about 6.0 wt. % to about 8.0 wt. %. In an embodiment, the percent SPF in the solution ranges from about 6.0 wt. % to about 9.0 wt. %. In an embodiment, the percent SPF in the solution ranges from about 10.0 wt. % to about 20.0 wt. %. In an embodiment, the percent SPF in the solution ranges from about 11.0 wt. % to about 19.0 wt. %. In an embodiment, the percent SPF in the solution ranges from about 12.0 wt. % to about 18.0 wt. %. In an embodiment, the percent SPF in the solution ranges from about 13.0 wt. % to about 17.0 wt. %. In an embodiment, the percent SPF in the solution ranges from about 14.0 wt. % to about 16.0 wt. %. In an embodiment, the percent SPF in the solution is about 1.0 wt. %. In an embodiment, the percent SPF in the solution is about 1.5 wt. %. In an embodiment, the percent SPF in the solution is about 2.0 wt. %. In an embodiment, the percent SPF in the solution is about 2.4 wt. %. In an embodiment, the percent SPF in the solution is 3.0 wt. %. In an embodiment, the percent SPF in the solution is 3.5 wt. %. In an embodiment, the percent SPF in the solution is about 4.0 wt. %. In an embodiment, the percent SPF in the solution is about 4.5 wt. %. In an embodiment, the percent SPF in the solution is about 5.0 wt. %. In an embodiment, the percent SPF in the solution is about 5.5 wt. %. In an embodiment the percent SPF in the solution is about 6.0 wt. %. In an embodiment, the percent SPF in the solution is about 6.5 wt. %. In an embodiment, the percent SPF in the solution is about 7.0 wt. %. In an embodiment, the percent SPF in the solution is about 7.5 wt. %. In an embodiment, the percent SPF in the solution is about 8.0 wt. %. In an embodiment, the percent SPF in the solution is about 8.5 wt. %. In an embodiment, the percent SPF in the solution is about 9.0 wt. %. In an embodiment, the percent SPF in the solution is about 9.5 wt. %. In an embodiment, the percent SPF in the solution is about 10.0 wt. %.

In an embodiment, the percent sericin in the solution is non-detectable to 25.0 wt. %. In an embodiment, the percent sericin in the solution is non-detectable to 5.0 wt. %. In an embodiment, the percent sericin in the solution is 1.0 wt. %. In an embodiment, the percent sericin in the solution is 2.0 wt. %. In an embodiment, the percent sericin in the solution is 3.0 wt. %. In an embodiment, the percent sericin in the solution is 4.0 wt. %. In an embodiment, the percent sericin in the solution is 5.0 wt. %. In an embodiment, the percent sericin in the solution is 10.0 wt. %. In an embodiment, the percent sericin in the solution is 25.0 wt. %.

In some embodiments, the silk fibroin protein fragments of the present disclosure are shelf stable (they will not slowly or spontaneously gel when stored in an aqueous solution and there is no aggregation of fragments and therefore no increase in molecular weight over time), from 10 days to 3 years depending on storage conditions, percent SPF, and number of shipments and shipment conditions. Additionally, pH may be altered to extend shelf life and/or support shipping conditions by preventing premature folding and aggregation of the silk. In an embodiment, the stability of the LiBr-silk fragment solution is 0 to 1 year. In an embodiment, the stability of the LiBr-silk fragment solution is 0 to 2 years. In an embodiment, the stability of the LiBr-silk fragment solution is 0 to 3 years. In an embodiment, the stability of the LiBr-silk fragment solution is 0 to 4 years. In an embodiment, the stability of the LiBr-silk fragment solution is 0 to 5 years. In an embodiment, the stability of the LiBr-silk fragment solution is 1 to 2 years. In an embodiment, the stability of the LiBr-silk fragment solution is 1 to 3 years. In an embodiment, the stability of the LiBr-silk fragment solution is 1 to 4 years. In an embodiment, the stability of the LiBr-silk fragment solution is 1 to 5 years. In an embodiment, the stability of the LiBr-silk fragment solution is 2 to 3 years. In an embodiment, the stability of the LiBr-silk fragment solution is 2 to 4 years. In an embodiment, the stability of the LiBr-silk fragment solution is 2 to 5 years. In an embodiment, the stability of the LiBr-silk fragment solution is 3 to 4 years. In an embodiment, the stability of the LiBr-silk fragment solution is 3 to 5 years. In an embodiment, the stability of the LiBr-silk fragment solution is 4 to 5 years.

In an embodiment, the stability of a composition of the present disclosure is 10 days to 6 months. In an embodiment, the stability of a composition of the present disclosure is 6 months to 12 months. In an embodiment, the stability of a composition of the present disclosure is 12 months to 18 months. In an embodiment, the stability of a composition of the present disclosure is 18 months to 24 months. In an embodiment, the stability of a composition of the present disclosure is 24 months to 30 months. In an embodiment, the stability of a composition of the present disclosure is 30 months to 36 months. In an embodiment, the stability of a composition of the present disclosure is 36 months to 48 months. In an embodiment, the stability of a composition of the present disclosure is 48 months to 60 months.

In an embodiment, a composition of the present disclosure having SPF has non-detectable levels of LiBr residuals. In an embodiment, the amount of the LiBr residuals in a composition of the present disclosure is between 10 ppm and 1000 ppm. In an embodiment, the amount of the LiBr residuals in a composition of the present disclosure is between 10 ppm and 300 ppm. In an embodiment, the amount of the LiBr residuals in a composition of the present disclosure is less than 25 ppm. In an embodiment, the amount of the Li Br residuals in a composition of the present disclosure is less than 50 ppm. In an embodiment, the amount of the LiBr residuals in a composition of the present disclosure is less than 75 ppm. In an embodiment, the amount of the LiBr residuals in a composition of the present disclosure is less than 100 ppm. In an embodiment, the amount of the LiBr residuals in a composition of the present disclosure is less than 200 ppm. In an embodiment, the amount of the LiBr residuals in a composition of the present disclosure is less than 300 ppm. In an embodiment, the amount of the LiBr residuals in a composition of the present disclosure is less than 400 ppm. In an embodiment, the amount of the LiBr residuals in a composition of the present disclosure is less than 500 ppm. In an embodiment, the amount of the LiBr residuals in a composition of the present disclosure is less than 600 ppm. In an embodiment, the amount of the LiBr residuals in a composition of the present disclosure is less than 700 ppm. In an embodiment, the amount of the LiBr residuals in a composition of the present disclosure is less than 800 ppm. In an embodiment, the amount of the LiBr residuals in a composition of the present disclosure is less than 900 ppm. In an embodiment, the amount of the LiBr residuals in a composition of the present disclosure is less than 1000 ppm. In an embodiment, the amount of the LiBr residuals in a composition of the present disclosure is non-detectable to 500 ppm. In an embodiment, the amount of the LiBr residuals in a composition of the present disclosure is non-detectable to 450 ppm. In an embodiment, the amount of the LiBr residue in a composition of the present disclosure is non-detectable to 400 ppm. In an embodiment, the amount of the LiBr residuals in a composition of the present disclosure is non-detectable to 350 ppm. In an embodiment, the amount of the LiBr residuals in a composition of the present disclosure is non-detectable to 300 ppm. In an embodiment, the amount of the LiBr residuals in a composition of the present disclosure is non-detectable to 250 ppm. In an embodiment, the amount of the LiBr residuals in a composition of the present disclosure is non-detectable to 200 ppm. In an embodiment, the amount of the LiBr residuals in a composition of the present disclosure is non-detectable to 150 ppm. In an embodiment, the amount of the LiBr residuals in a composition of the present disclosure is non-detectable to 100 ppm. In an embodiment, the amount of the LiBr residuals in a composition of the present disclosure is 100 ppm to 200 ppm. In an embodiment, the amount of the LiBr residuals in a composition of the present disclosure is 200 ppm to 300 ppm. In an embodiment, the amount of the LiBr residuals in a composition of the present disclosure is 300 ppm to 400 ppm. In an embodiment, the amount of the LiBr residuals in a composition of the present disclosure is 400 ppm to 500 ppm.

In an embodiment, a composition of the present disclosure having SPF, has non-detectable levels of $Na_2CO_3$ residuals. In an embodiment, the amount of the $Na_2CO_3$ residuals in a composition of the present disclosure is less than 100 ppm. In an embodiment, the amount of the $Na_2CO_3$ residuals in a composition of the present disclosure is less than 200 ppm. In an embodiment, the amount of the $Na_2CO_3$ residuals in a composition of the present disclosure is less than 300 ppm. In an embodiment, the amount of the $Na_2CO_3$ residuals in a composition of the present disclosure is less than 400 ppm. In an embodiment, the amount of the $Na_2CO_3$ residuals in a composition of the present disclosure is less than 500 ppm. In an embodiment, the amount of the $Na_2CO_3$ residuals in a composition of the present disclosure is less than 600 ppm. In an embodiment, the amount of the $Na_2CO_3$ residuals in a composition of the present disclosure is less than 700 ppm. In an embodiment, the amount of the $Na_2CO_3$ residuals in a composition of the present disclosure is less than 800 ppm. In an embodiment, the amount of the $Na_2CO_3$ residuals in a composition of the present disclosure is less than 900 ppm. In an embodiment, the amount of the $Na_2CO_3$ residuals in a composition of the present disclosure is less than 1000 ppm. In an embodiment, the amount of the $Na_2CO_3$ residuals in a composition of the present disclosure is non-detectable to 500 ppm. In an embodiment, the amount of the $Na_2CO_3$ residuals in a composition of the present disclosure is non-detectable to 450 ppm. In an embodiment, the amount of the $Na_2CO_3$ residuals in a composition of the present disclosure is non-detectable to 400 ppm. In an embodiment, the amount of the $Na_2CO_3$ residuals in a composition of the present disclosure is non-detectable to 350 ppm. In an embodiment, the amount of the $Na_2CO_3$ residuals in a composition of the present disclosure is non-detectable to 300 ppm. In an embodiment, the amount of the $Na_2CO_3$ residuals in a composition of the present disclosure is non-detectable to 250 ppm. In an embodiment, the amount of the $Na_2CO_3$ residuals in a composition of the present disclosure is non-detectable to 200 ppm. In an embodiment, the amount of the $Na_2CO_3$ residuals in a composition of the present disclosure is non-detectable to 150 ppm. In an embodiment, the amount of the $Na_2CO_3$ residuals in a composition of the present disclosure is non-detectable to 100 ppm. In an embodiment, the amount of the $Na_2CO_3$ residuals in a composition of the present disclosure is 100 ppm to 200 ppm. In an embodiment, the amount of the $Na_2CO_3$ residuals in a composition of the present disclosure is 200 ppm to 300 ppm. In an embodiment, the amount of the $Na_2CO_3$ residuals in a composition of the present disclosure is 300 ppm to 400 ppm. In an embodiment, the amount of the $Na_2CO_3$ residuals in a composition of the present disclosure is 400 ppm to 500 ppm.

A unique feature of the SPF compositions of the present disclosure are shelf stability (they will not slowly or spontaneously gel when stored in an aqueous solution and there is no aggregation of fragments and therefore no increase in molecular weight over time), from 10 days to 3 years depending on storage conditions, percent silk, and number of shipments and shipment conditions. Additionally pH may be altered to extend shelf-life and/or support shipping conditions by preventing premature folding and aggregation of the silk. In an embodiment, a SPF solution composition of the present disclosure has a shelf stability for up to 2 weeks at room temperature (RT). In an embodiment, a SPF solution composition of the present disclosure has a shelf stability for up to 4 weeks at RT. In an embodiment, a SPF solution composition of the present disclosure has a shelf stability for up to 6 weeks at RT. In an embodiment, a SPF solution composition of the present disclosure has a shelf stability for up to 8 weeks at RT. In an embodiment, a SPF solution composition of the present disclosure has a shelf stability for up to 10 weeks at RT. In an embodiment, a SPF solution composition of the present disclosure has a shelf stability for up to 12 weeks at RT. In an embodiment, a SPF solution composition of the present disclosure has a shelf stability ranging from about 4 weeks to about 52 weeks at RT.

Table R below shows shelf stability test results for embodiments of SPF compositions of the present disclosure.

TABLE R

Shelf Stability of SPF Compositions of the Present Disclosure

| % Silk | Temperature | Time to Gelation |
|---|---|---|
| 2 | RT | 4 weeks |
| 2 | 4° C. | >9 weeks |
| 4 | RT | 4 weeks |
| 4 | 4° C. | >9 weeks |
| 6 | RT | 2 weeks |
| 6 | 4° C. | >9 weeks |

In some embodiments, the water solubility of the silk film derived from silk fibroin protein fragments as described herein can be modified by solvent annealing (water annealing or methanol annealing), chemical crosslinking, enzyme crosslinking and heat treatment.

In some embodiments, the process of annealing may involve inducing beta-sheet formation in the silk fibroin protein fragment solutions used as a coating material. Techniques of annealing (e.g., increase crystallinity) or otherwise promoting "molecular packing" of silk fibroin-protein based fragments have been described. In some embodiments, the amorphous silk film is annealed to introduce beta-sheet in the presence of a solvent selected from the group of water or organic solvent. In some embodiments, the amorphous silk film is annealed to introduce beta-sheet in the presence of water (water annealing process). In some embodiments, the amorphous silk fibroin protein fragment film is annealed to introduce beta-sheet in the presence of methanol. In some embodiments, annealing (e.g., the beta sheet formation) is induced by addition of an organic solvent. Suitable organic solvents include, but are not limited to methanol, ethanol, acetone, isopropanol, or combination thereof.

In some embodiments, annealing is carried out by so-called "water-annealing" or "water vapor annealing" in which water vapor is used as an intermediate plasticizing agent or catalyst to promote the packing of beta-sheets. In some embodiments, the process of water annealing may be performed under vacuum. Suitable such methods have been described in Jin H-J et al. (2005), Water-stable Silk Films with Reduced Beta-Sheet Content, Advanced Functional Materials, 15: 1241-1247; Xiao H. et al. (2011), Regulation of Silk Material Structure by Temperature-Controlled Water Vapor Annealing, Biomacromolecules, 12(5): 1686-1696.

The important feature of the water annealing process is to drive the formation of crystalline beta-sheet in the silk fibroin protein fragment peptide chain to allow the silk fibroin self-assembling into a continuous film. In some embodiments, the crystallinity of the silk fibroin protein fragment film is controlled by controlling the temperature of water vapor and duration of the annealing. In some embodiments, the annealing is performed at a temperature ranging from about 65° C. to about 110° C. In some embodiments, the temperature of the water is maintained at about 80° C. In some embodiments, annealing is performed at a temperature selected from the group of about 65° C., about 70° C., about 75° C., about 80° C., about 85° C., about 90° C., about 95° C., about 100° C., about 105° C., and about 110° C.

In some embodiments, the annealing process lasts a period of time selected from the group of about 1 minute to about 40 minutes, about 1 minute to about 50 minutes, about 1 minute to about 60 minutes, about 1 minute to about 70 minutes, about 1 minute to about 80 minutes, about 1 minute to about 90 minutes, about 1 minute to about 100 minutes, about 1 minute to about 110 minutes, about 1 minute to about 120 minutes, about 1 minute to about 130 minutes, about 5 minutes to about 40 minutes, about 5 minutes to about 50 minutes, about 5 minutes to about 60 minutes, about 5 minutes to about 70 minutes, about 5 minutes to about 80 minutes, about 5 minutes to about 90 minutes, about 5 minutes to about 100 minutes, about 5 minutes to about 110 minutes, about 5 minutes to about 120 minutes, about 5 minutes to about 130 minutes, about 10 minutes to about 40 minutes, about 10 minutes to about 50 minutes, about 10 minutes to about 60 minutes, about 10 minutes to about 70 minutes, about 10 minutes to about 80 minutes, about 10 minutes to about 90 minutes, about 10 minutes to about 100 minutes, about 10 minutes to about 110 minutes, about 10 minutes to about 120 minutes, about 10 minutes to about 130 minutes, about 15 minutes to about 40 minutes, about 15 minutes to about 50 minutes, about 15 minutes to about 60 minutes, about 15 minutes to about 70 minutes, about 15 minutes to about 80 minutes, about 15 minutes to about 90 minutes, about 15 minutes to about 100 minutes, about 15 minutes to about 110 minutes, about 15 minutes to about 120 minutes, about 15 minutes to about 130 minutes, about 20 minutes to about 40 minutes, about 20 minutes to about 50 minutes, about 20 minutes to about 60 minutes, about 20 minutes to about 70 minutes, about 20 minutes to about 80 minutes, about 20 minutes to about 90 minutes, about 20 minutes to about 100 minutes, about 20 minutes to about 110 minutes, about 20 minutes to about 120 minutes, about 20 minutes to about 130 minutes, about 25 minutes to about 40 minutes, about 25 minutes to about 50 minutes, about 25 minutes to about 60 minutes, about 25 minutes to about 70 minutes, about 25 minutes to about 80 minutes, about 25 minutes to about 90 minutes, about 25 minutes to about 100 minutes, about 25 minutes to about 110 minutes, about 25 minutes to about 120 minutes, about 25 minutes to about 130 minutes, about 30 minutes to about 40 minutes, about 30 minutes to about 50 minutes, about 30 minutes to about 60 minutes, about 30 minutes to about 70 minutes, about 30 minutes to about 80 minutes, about 30 minutes to about 90 minutes, about 30 minutes to about 100 minutes, about 30 minutes to about 110 minutes, about 30 minutes to about 120 minutes, about 30 minutes to about 130 minutes, about 35 minutes to about 40 minutes, about 35 minutes to about 50 minutes, about 35 minutes to about 60 minutes, about 35 minutes to about 70 minutes, about 35 minutes to about 80 minutes, about 35 minutes to about 90 minutes, about 35 minutes to about 100 minutes, about 35 minutes to about 110 minutes, about 35 minutes to about 120 minutes, about 35 minutes to about 130 minutes, about 40 minutes to about 50 minutes, about 40 minutes to about 60 minutes, about 40 minutes to about 70 minutes, about 40 minutes to about 80 minutes, about 40 minutes to about 90 minutes, about 40 minutes to about 100 minutes, about 40 minutes to about 110 minutes, about 40 minutes to about 120 minutes, about 40 minutes to about 130 minutes, about 45 minutes to about 50 minutes, about 45 minutes to about 60 minutes, about 45 minutes to about 70 minutes, about 45 minutes to about 80 minutes, about 45 minutes to about 90 minutes, about 45 minutes to about 100 minutes, about 45 minutes to about 110 minutes, about 45 minutes to about 120 minutes, and about 45 minutes to about 130 minutes. In some embodiments, the annealing process lasts a period of time ranging from about 1 minute to about 60 minutes. In some embodiments, the annealing process lasts a period of time ranging from about 45 minutes to about 60 minutes. The longer water annealing post-processing corresponded an increased crystallinity of silk fibroin protein fragments.

In some embodiments, the annealed silk fibroin protein fragment film is immersing the wet silk fibroin protein fragment film in 100% methanol for 60 minutes at room temperature. The methanol annealing changed the composition of silk fibroin protein fragment film from predominantly amorphous random coil to crystalline antiparallel beta-sheet structure.

In some embodiments, the SPF as described herein can be used to prepare SPF microparticles by precipitation with methanol. Alternative flash drying, fluid-bed drying, spray drying or vacuum drying can be applied to remove water from the silk solution. The SPF powder can then be stored and handled without refrigeration or other special handling procedures. In some embodiments, the SPF powders comprise low molecular weight silk fibroin protein fragments. In some embodiments, the SPF powders comprise mid-molecular weight silk fibroin protein fragments. In some embodiments, the SPF powders comprise a mixture of low molecular weight silk fibroin protein fragments and mid-molecular weight silk fibroin protein fragment.

Silk Fibroin-Based Protein Fragments and Solutions Thereof

Provided herein are methods for producing pure and highly scalable silk protein fragment (SPF) mixture solutions that may be used to process, make, and/or coat at least a portion of faux or bonded leather and/or faux or bonded leather articles, or to repair at least one defect in a portion of faux or bonded leather and/or faux or bonded leather article. In some embodiments, SPF mixture solutions may also refer to silk fibroin solutions (SFS), and vice versa. The solutions are generated from raw pure intact silk protein material and processed in order to remove any sericin and achieve the desired average weight average molecular weight (MW) and polydispersity of the fragment mixture. Select method parameters may be altered to achieve distinct final silk protein fragment characteristics depending upon the intended use. The resulting final fragment solution is pure silk protein fragments and water with PPM to non-detectable levels of process contaminants. The concentration, size and polydispersity of silk protein fragments in the solution may further be altered depending upon the desired use and performance requirements. In an embodiment, the pure silk fibroin-based protein fragments in the solution are substantially devoid of sericin, have an average weight average molecular weight selected from between about 6 kDa to about 17 kDa, and have a polydispersity ranging from about 1.5 and about 3.0. In an embodiment, the pure silk fibroin-based protein fragments in the solution are substantially devoid of sericin, have an average weight average molecular weight selected from between about 17 kDa to about 39 kDa, and have a polydispersity ranging from about 1.5 and about 3.0. In an embodiment, the pure silk fibroin-based protein fragments in the solution are substantially devoid of sericin, have an average weight average molecular weight selected from between about 39 kDa to about 80 kDa, and have a polydispersity ranging from about 1.5 and about 3.0. As used herein, the term "silk solution" may refer to solutions of silk proteins, including solutions of silk fibroin-based protein fragments.

Without wishing to be bound by any particular theory, any and all solutions described herein can be further used or processed to obtain a variety of silk and/or SPF compositions, including, but not limited to, silk non-Newtonian fluids, silk materials that can sustain a shear stress network spanning the system, silk solutions containing water or another solvent trapped inside a loose silk polymer network, silk materials that transition from a liquid form via bond percolation transition such as gels, silk immobile network entrapping a mobile solvent, silk materials forming reversible or irreversible crosslinks, silk materials that exhibit a shear modulus, silk elastomers or silk materials exhibiting thermoplastic behavior, silk materials formed by the processes of either glass formation, gelation, or colloidal aggregation, silk crystals, and/or silk crystals polish, glues, gels, pastes, putties, and/or waxes.

As used herein, "silk based proteins or fragments thereof" includes silk fibroin-based proteins or fragments thereof, natural silk based proteins or fragments thereof, recombinant silk based proteins or fragments thereof, and combinations thereof. Natural silk based proteins or fragments thereof include spider silk based proteins or fragments thereof, silkworm silk based proteins or fragments thereof, and combinations thereof. Silkworm based proteins or fragments thereof may include *Bombyx mori* silk based proteins or fragments thereof. The SPF mixture solutions described herein may include silk based proteins or fragments thereof. Moreover, SFS, as described herein, may be replaced with SPF mixture solutions. The silk based proteins or fragments thereof, silk solutions or mixtures (e.g., SPF or SFS solutions or mixture), and the like, may be prepared according to the methods described in U.S. Pat. Nos. 9,187,538, 9,522,107, 9,522,108, 9,511,012, 9,517,191, and 9,545,369, and U.S. Patent Publication Nos. 2016/0222579 and 2016/0281294, and International Patent Publication Nos. WO 2016/090055 and WO 2017/011679, the entirety of which are incorporated herein by reference. In some embodiments, the silk based proteins or fragments thereof may be provided as a silk composition, which may be an aqueous solution or mixture of silk, a silk gel, and/or a silk wax as described herein.

As used herein, the term "substantially homogeneous" may refer to pure silk fibroin-based protein fragments that are distributed in a normal distribution about an identified molecular weight. As used herein, the term "substantially homogeneous" may refer to an even distribution of an additive, for example a pigment, throughout a composition of the present disclosure.

As used herein, "residuals" refer to materials related to one or more process steps in the manufacturing of silk fibroin solutions, silk fibroin fragments solutions, or concentrates thereof.

In some embodiments, compositions described herein, which in some embodiments may be biocompatible compositions (e.g., biocompatible coatings that include silk), may be evaluated and comply with International Standard ISO 10993-1, titled the "Biological evaluation of medical devices—Part 1: Evaluation and testing within a risk management process." In some embodiments, compositions described herein, which may be biocompatible compositions, may be evaluated under ISO-106993-1 for one or more of cytotoxicity, sensitization, hemocompatibility, pyrogenicity, implantation, genotoxicity, carcinogenicity, reproductive and developmental toxicity, and degradation. In some embodiments, the coatings described herein are biocompatible coatings.

In some embodiments, compositions and articles described herein, and methods of preparing the same, include silk coated bonded leather or faux leather, or faux leather or bonded leather article.

The faux or bonded leather, or faux or bonded leather article may be a polymeric material such as those described elsewhere herein. The terms "infused" and/or "partially dissolved" includes mixing to form a dispersion of, e.g., a portion of faux or bonded leather, or faux or bonded leather article with a portion of the silk based coating. In some embodiments, the dispersion may be a solid suspension (i.e., a dispersion comprising domains on the order of 10 nm) or a solid solution (i.e., a molecular dispersion) of silk. In some embodiments, the dispersion may be localized at the surface interface between the silk coating and the faux or bonded leather, or faux or bonded leather article, and may have a depth of 1 nm, 2 nm, 5 nm, 10 nm, 25 nm, 50 nm, 75 nm, 100 nm, or greater than 100 nm, depending on the method of preparation. In some embodiments, the dispersion may be a layer sandwiched between the faux or bonded leather, or faux or bonded leather article and the silk coating. In some embodiments, the dispersion may be prepared by coating silk, including silk fibroin with the characteristics described herein, onto the faux or bonded leather, or faux or bonded leather article, and then performing an additional process to form the dispersion, including heating at a temperature of 100° C., 125° C., 150° C., 175° C., 200° C., 225° C., or 250° C. for a time period selected from the group consisting of 1 minute, 2 minutes, 5 minutes, 10 minutes, 15 minutes, 20 minutes, 30 minutes, 1 hour, 2 hours, 4 hours, 8 hours, 16 hours, or 24 hours. In some embodiments, heating may be performed at or above the glass transition temperature (Tg) of silk and/or the polymeric fabric or textile, which may be assessed by methods known in the art. In some embodiments, the dispersion may be formed by coating silk, including silk fibroin with the characteristics described herein, onto the faux or bonded leather, or faux or bonded leather article, and then performing an additional process to impregnate the silk coating into the faux or bonded leather, or faux or bonded leather article, including treatment with an organic solvent. Methods for characterizing the properties of polymers dissolved in one another are well known in the art and include differential scanning calorimetry and surface analysis methods capable of depth profiling, including spectroscopic methods.

In some embodiments, compositions of the present disclosure are "hypoallergenic" meaning that they are relatively unlikely to cause an allergic reaction. Such hypoallergenicity can be evidenced by participants topically applying compositions of the present disclosure on their skin for an extended period of time. In an embodiment, the extended period of time is about 3 days. In an embodiment, the extended period of time is about 7 days. In an embodiment, the extended period of time is about 14 days. In an embodiment, the extended period of time is about 21 days. In an embodiment, the extended period of time is about 30 days. In an embodiment, the extended period of time is selected from the group consisting of about 1 month, about 2 months, about 3 months, about 4 months, about 5 months, about 6 months, about 7 months, about 8 months, about 9 months, about 10 months, about 11 months, about 12 months, and indefinitely.

In some embodiments, where aqueous solutions are used to prepare SPF compositions or SPF containing coatings, the aqueous solutions are prepared using any type of water. In some embodiments, water may be DI water, tap water, or naturally available water. As used herein, "tap water" refers to potable water provided by public utilities and water of comparable quality, regardless of the source, without further refinement such as by reverse osmosis, distillation, and/or deionization. Therefore, the use of "DI water," "RODI water," or "water," as set forth herein, may be understood to be interchangeable with "tap water" according to the processes described herein without deleterious effects to such processes.

Single or Multilayered Material with a Silk Derived Protein

The disclosure provides a single or multilayered material comprising a plurality of fibers, filaments, powders, particles, or yarns, and a silk derived protein. In some embodiments, the material is a bonded leather or a faux leather.

In some embodiments, the plurality of fibers, filaments, powders, particles, or yarns can include both natural and/or synthetic components. Non-limiting examples of the plurality of fibers, filaments, powders, particles, or yarns comprise one or more of natural fibers, filaments, powders, particles, or yarns; synthetic fibers, filaments, powders, particles, or yarns; natural leather; recycled leather; one or more of fibrillated leather or grounded leather; one or more of bovine wet blue shaving, bovine post-industrial waste, or sheep post-industrial waste; synthetic leather; one or more of silk, cotton, alpaca fleece, alpaca wool, lama fleece, *lama* wool, cashmere, sheep fleece, and sheep wool; one or more of alpaca fiber, alpaca fleece, alpaca wool, lama fiber, lama fleece, lama wool, cotton, cashmere and sheep fiber, sheep fleece, sheep wool, byssus, chiengora, quiviut, yak, rabbit, lambswool, mohair wool, camel hair, angora wool, spider silk, silkworm silk, abaca fiber, coir fiber, flax fiber, jute fiber, kapok fiber, kenaf fiber, raffia fiber, bamboo fiber, hemp, modal fiber, pina, ramie, sisal, and soy protein fiber; one or more of polyester, nylon, and polyester-polyurethane copolymer; one or more of Lyocell and/or cellulose; one or more of acrylic, anidex, aramid, fluorocarbon, modacrylic, novoloid, nylon, nytril, olefin, PBI, polycarbonate, polyester, rubber, saran, spandex, vinal vinvon; and one or more of non-woven or woven fibers or filaments, non-woven or woven mat or fabric, a woven, knitted, or crochet fabric, or any combination thereof. In some embodiments, the plurality of fibers, filaments, powders, particles, or yarns comprises natural leather; recycled leather; one or more of fibrillated leather or grounded leather; one or more of bovine wet blue shaving, bovine post-industrial waste, sheep post-industrial waste; and/or synthetic leather.

In some embodiments, the plurality of fibers, filaments, powders, particles, or yarns comprises a leather filament. In some embodiments, the leather filament is a continuous filament.

In some embodiments, the silk derived protein comprises sericin. In some embodiments, the silk derived protein comprises silk fibroin proteins or fragments thereof. In some embodiments, the silk derived protein comprises sericin and silk fibroin proteins or fragments.

In some embodiments, the silk derived protein comprises silk fibroin proteins or fragments thereof having an average weight average molecular weight selected from between about 1 kDa and about 5 kDa, between about 5 kDa and about 10 kDa, between about 6 kDa and about 17 kDa, between about 10 kDa and about 15 kDa, between about 15 kDa and about 20 kDa, between about 17 kDa and about 39 kDa, between about 20 kDa and about 25 kDa, between about 25 kDa and about 30 kDa, between about 30 kDa and about 35 kDa, between about 35 kDa and about 40 kDa, between about 39 kDa and about 80 kDa, between about 40 kDa and about 45 kDa, between about 45 kDa and about 50 kDa, between about 60 kDa and about 100 kDa, and between about 80 kDa, and a polydispersity between 1 and about 5.

In some embodiments, the silk derived protein comprises one or more of low molecular weight silk fibroin proteins or fragments thereof, medium molecular weight silk fibroin proteins or fragments thereof, or high molecular weight silk fibroin proteins or fragments thereof. In some embodiments, the silk derived protein comprises one or more of low molecular weight SPF, medium molecular weight SPF, or high molecular weight SPF.

In some embodiments, the material further comprises a resin. Any resin is contemplated by the present disclosure. In a non-limiting example, the resin is selected from HX-200 and Hystretch 95™. In some embodiments, the material further comprises a flocculant. Any flocculant is contemplated by the present disclosure. A non-limiting example of a flocculant is Percol. As described herein, a resin, flocculant, or other ingredients, are incorporated in the material by way of using various formulations during a process of making a material or article described herein. As one skilled in the art would understand, in some embodiments such processes include heating steps, and thus parts of any formulation used may be lost during processes, for example, and without limitation, by evaporation. One skilled in the art can calculate the solid equivalent of an amount of any formulation described herein.

In some embodiments, the silk fibroin proteins or fragments thereof do not spontaneously or gradually gelate and do not visibly change in color or turbidity when in an aqueous solution for at least 10 days prior to being formulated into the material.

In some embodiments, the amount by weight of the plurality of fibers, filaments, powders, particles, or yarns in the material is between about 40% and about 95%. In some embodiments, the amount by weight of the plurality of fibers, filaments, powders, particles, or yarns in the material is between about 40% and about 90%. In some embodiments, the amount by weight of the plurality of fibers, filaments, powders, particles, or yarns in the material is between about 45% and about 95%. In some embodiments, the amount by weight of the plurality of fibers, filaments, powders, particles, or yarns in the material is between about 60% and about 95%. In some embodiments, the amount by weight of the plurality of fibers, filaments, powders, particles, or yarns in the material is between about 60% and about 95%. In some embodiments, the amount by weight of the plurality of fibers, filaments, powders, particles, or yarns in the material is between about 40% and about 45%. In some embodiments, the amount by weight of the plurality of fibers, filaments, powders, particles, or yarns in the material is between about 45% and about 50%. In some embodiments, the amount by weight of the plurality of fibers, filaments, powders, particles, or yarns in the material is between about 50% and about 55%. In some embodiments, the amount by weight of the plurality of fibers, filaments, powders, particles, or yarns in the material is between about 55% and about 60%. In some embodiments, the amount by weight of the plurality of fibers, filaments, powders, particles, or yarns in the material is between about 60% and about 65%. In some embodiments, the amount by weight of the plurality of fibers, filaments, powders, particles, or yarns in the material is between about 65% and about 70%. In some embodiments, the amount by weight of the plurality of fibers, filaments, powders, particles, or yarns in the material is between about 70% and about 75%. In some embodiments, the amount by weight of the plurality of fibers, filaments, powders, particles, or yarns in the material is between about 75% and about 80%. In some embodiments, the amount by weight of the plurality of fibers, filaments, powders, particles, or yarns in the material is between about 80% and about 85%. In some embodiments, the amount by weight of the plurality of fibers, filaments, powders, particles, or yarns in the material is between about 85% and about 90%. In some embodiments, the amount by weight of the plurality of fibers, filaments, powders, particles, or yarns in the material is between about 90% and about 95%.

In some embodiments, the amount by weight of the plurality of fibers, filaments, powders, particles, or yarns in the material is about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, or about 90%.

In some embodiments, the amount by weight of the silk derived protein in the material is between about 0.01% and about 50%. In some embodiments, the amount by weight of the silk derived protein in the material is between about 0.01% and about 25%. In some embodiments, the amount by weight of the silk derived protein in the material is between about 1% and about 10%. In some embodiments, the amount by weight of the silk derived protein in the material is between about 5% and about 25%. In some embodiments, the amount by weight of the silk derived protein in the material is between about 1% and about 5%, between about 5% and about 10%, between about 10% and about 15%, between about 15% and about 20%, between about 20% and about 25%, between about 25% and about 30%, between about 30% and about 35%, between about 35% and about 40%; between about 40% and about 45%, or between about 45% and about 50%.

In some embodiments, the amount by weight of the silk derived protein in the material is between about 0.01% and about 1%; between about 1% and about 2%; between about 2% and about 3%; between about 3% and about 4%; between about 4% and about 5%; between about 5% and about 6%; between about 6% and about 7%; between about 7% and about 8%; between about 8% and about 9%; between about 9% and about 10%; between about 10% and about 11%; between about 11% and about 12%; between about 12% and about 13%; between about 13% and about 14%; between about 14% and about 15%; between about 15% and about 16%; between about 16% and about 17%; between about 17% and about 18%; between about 18% and about 19%; between about 19% and about 20%; between about 20% and about 21%, between about 21% and about 22%; between about 22% and about 23%; between about 23% and about 24%; between about 24% and about 25%; between about 25% and about 26%; between about 26% and about 27%; between about 27% and about 28%; between about 28% and about 29%; between about 29% and about 30%; between about 30% and about 31%; between about 31% and about 32%; between about 32% and about 33%; between about 33% and about 34%; between about 34% and about 35%; between about 35% and about 36%; between about 36% and about 37%; between about 37% and about 38%; between about 38% and about 39%; between about 39% and about 40%; between about 40% and 41%, between about 41% and about 42%; between about 42% and about 43%; between about 43% and about 44%; between about 44% and about 45%; between about 45% and about 46%; between about 46% and about 47%; between about 47% and about 48%; between about 48% and about 49%; or between about 49% and about 50%.

In some embodiments, the amount by weight of the silk derived protein in the material is about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, or about 50%.

In some embodiments, the amount by weight of the resin in the material is between about 0.01% and about 50%. In some embodiments, the amount by weight of resin in the material is between about 15% and about 30%. In some embodiments, the amount by weight of the resin the material is between about 1% and about 10%. In some embodiments, the amount by weight of the resin in the material is between about 1% and about 5%. In some embodiments, the amount by weight of the resin in the material is between about 5% and about 10%. In some embodiments, the amount by weight of the resin in the material is between about 10% and about 15%. In some embodiments, the amount by weight of the resin in the material is between about 15% and about 25%. In some embodiments, the amount by weight of the resin in the material is between about 20% and about 25%. In some embodiments, the amount by weight of the resin in the material is between about 25% and about 30%. In some embodiments, the amount by weight of the resin in the material is between about 30% and about 35%. In some embodiments, the amount by weight of the resin in the material is between about 35% and about 40%. In some embodiments, the amount by weight of the resin in the material is between about 40% and about 45%. In some embodiments, the amount by weight of the resin in the material is between about 45% and about 50%.

In some embodiments, the amount by weight of the resin in the material is between about 0.01% and about 1%; between about 1% and about 2%; between about 2% and about 3%; between about 3% and about 4%; between about 4% and about 5%; between about 5% and about 6%; between about 6% and about 7%; between about 7% and about 8%; between about 8% and about 9%; between about 9% and about 10%; between about 10% and about 11%; between about 11% and about 12%; between about 12% and about 13%; between about 13% and about 14%; between about 14% and about 15%; between about 15% and about 16%; between about 16% and about 17%; between about 17% and about 18%; between about 18% and about 19%; between about 19% and about 20%; between about 20% and about 21%, between about 21% and about 22%; between about 22% and about 23%; between about 23% and about 24%; between about 24% and about 25%; between about 25% and about 26%; between about 26% and about 27%; between about 27% and about 28%; between about 28% and about 29%; between about 29% and about 30%; between about 30% and about 31%; between about 31% and about 32%; between about 32% and about 33%; between about 33% and about 34%; between about 34% and about 35%; between about 35% and about 36%; between about 36% and about 37%; between about 37% and about 38%; between about 38% and about 39%; between about 39% and about 40%; between about 40% and 41%, between about 41% and about 42%; between about 42% and about 43%; between about 43% and about 44%; between about 44% and about 45%; between about 45% and about 46%; between about 46% and about 47%; between about 47% and about 48%; between about 48% and about 49%; or between about 49% and about 50%.

In some embodiments, the amount by weight of the resin in the material is about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, or about 50%.

In some embodiments, the amount by weight of the flocculant in the material is between about 0.01% and about 10%. In some embodiments, the amount by weight of the flocculant in the material is between about 0.01% and about 5%. In some embodiments, the amount by weight of the flocculant in the material is between about 0.01% and about 0.1%. In some embodiments, the amount by weight of the flocculant the material is between about 0.01% and about 1%. In some embodiments, the amount by weight of the flocculant the material is between about 0.1% and about 1%.

In some embodiments, the amount by weight of the flocculant in the material is between about 0.1% and about 0.2%, between about 0.2% and about 0.3%, between about 0.3% and about 0.4%, between about 0.4% and about 0.5%, between about 0.5% and about 0.6%, between about 0.6% and about 0.7%, between about 0.7% and about 0.8%, between about 0.8% and about 0.9%, or between about 0.9% and about 1%, between about 1% and about 2%, between about 2% and about 3%, between about 3% and about 4%, between about 4% and about 5%, between about 5% and about 6%, between about 6% and about 7%, between about 7% and about 8%, between about 8% and about 9%, or between about 9% and about 10%.

In some embodiments, the amount by weight of the flocculant in the material is about 0.1%, about 0.2%, about 0.3%, about 0.4%, about 0.5%, about 0.6%, about 0.7%, about 0.8%, about 0.9%, about 1%, about 2%, about 3%, about 4%, about 5%, about 6%, about 7%, about 8%, about 9%, or about 10%.

In some embodiments, the material comprises an amount of the plurality of fibers, filaments, powders, particles, or yarns, and an amount of the combined total amount of silk derived protein, resin (if present), and flocculant (if present) in a ratio of about 99.9 to about 0.01; about 99 to about 1; about 98 to about 2; about 97 to about 3; about 96 to about 4; about 95 to about 5; about 94 to about 6; about 93 to about 7; about 92 to about 8; about 91 to about 9; about 90 to about 10; about 89 to about 11; about 88 to about 12; about 87 to about 13; about 86 to about 14; about 85 to about 15; about 84 to about 16; about 83 to about 17; about 82 to about 18; about 81 to about 19; about 80 to about 20; about 79 to about 21; about 78 to about 22; about 77 to about 23; 7 about 6 to about 24; about 75 to about 25; about 74 to about 26; about 73 to about 27; about 72 to about 28; about 71 to about 29; about 70 to about 30; about 69 to about 31; about 68 to about 32; about 67 to about 33; about 66 to about 34; about 65 to about 35; about 64 to about 36; about 63 to about 37; about 62 to about 38; about 61 to about 39; about 60 to about 40; 5 about 9 to about 41; about 58 to about 42; about 57 to about 43; about 56 to about 44; about 55 to about 45; about 54 to about 46; about 53 to about 47; about 52 to about 48; about 51 to about 49; about 50 to about 50; about 49 to about 51; about 48 to about 52; about 47 to about 53; about 46 to about 54; about 45 to about 55; about 44 to about 56; about 43 to about 57; about 42 to about 58; about 41 to about 59; or about 40 to about 60.

In some embodiments, the material comprises, consists of, or consists essentially of: 40%-95% by weight of a plurality of fibers, filaments, powders, particles, or yarns; 5%-50% by weight of a silk derived protein; 0%-40% by weight of a resin; and 0%-2% by weight of a flocculant. In some embodiments, the material comprises, consists of, or consists essentially of a plurality of fibers, filaments, powders, particles, or yarns in the material in an amount of about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, or about 90%, with the balance comprising one or more of a silk derived protein, a resin, and/or a flocculant, as described herein. In some embodiments, the material comprises, consists of, or consists essentially of a plurality of fibers, filaments, powders, particles, or yarns in the material in an amount of about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, or about 49%, with the balance comprising one or more of a silk derived protein, a resin, and/or a flocculant, as described herein.

In some embodiments, the material comprises, consists of, or consists essentially of: 50%-60% by weight of a plurality of fibers, filaments, powders, particles, or yarns; and 40%-50% by weight of a silk derived protein.

In some embodiments, the material comprises, consists of, or consists essentially of: 85%-95% by weight of a plurality of fibers, filaments, powders, particles, or yarns; and 5%-15% by weight of a silk derived protein.

In some embodiments, the material comprises, consists of, or consists essentially of: 85%-95% by weight of a plurality of fibers, filaments, powders, particles, or yarns; and 5%-15% by weight of a silk derived protein.

In some embodiments, the material comprises, consists of, or consists essentially of: 50%-60% by weight of a plurality of fibers, filaments, powders, particles, or yarns; 10%-20% by weight of a silk derived protein; and 20%-30% by weight of a resin.

In some embodiments, the material comprises, consists of, or consists essentially of: 40%-50% by weight of a plurality of fibers, filaments, powders, particles, or yarns; 5%-15% by weight of a silk derived protein; and 25%-35% by weight of a resin.

In some embodiments, the material comprises, consists of, or consists essentially of: 85%-94.5% by weight of a plurality of fibers, filaments, powders, particles, or yarns; 5%-15% by weight of a silk derived protein; and 0.5%-2% by weight of a flocculant.

In some embodiments, the material comprises, consists of, or consists essentially of: 60%-70.5% by weight of a plurality of fibers, filaments, powders, particles, or yarns; 3%-7% by weight of a silk derived protein; 20%-26% by weight of a resin; and 0.5%-2% by weight of a flocculant.

In some embodiments, the material further comprises one or more of a polymer, a pigment, a dye, or any combinations thereof. In some embodiments, the material further comprises one or more of a silicone, a dye, a pigment, and a polyurethane.

The present disclosure provides an article comprising a material disclosed herein. In some embodiments, the material is injected or entangled into the article. For additional examples, see U.S. Pat. Nos. 7,731,814, 8,225,469, and US 2014/0113520, all of which are incorporated by reference herein in their entireties. In some embodiments, the article comprises a flat substrate, and the material is deposited onto the substrate in order to produce a layer. Any method of deposition is contemplated by the present disclosure, as would be understood by one of ordinary skill in the art. Non-limiting examples of substrates include woven and non-woven fabrics.

In some embodiments, the article comprising a layer of material having a thickness of about 1 mm, about 2 mm, about 3 mm, about 4 mm, about 5 mm, about 6, mm, about 7 mm, about 8 mm, about 9 mm, or about 10 mm.

In some embodiments, the article further comprises one or more of a coating, a laminated film, or a combination thereof. In some embodiments, the coating or the laminated film comprises one or more polymers selected from polyglycolide (PGA), polyethylene glycols, copolymers of glycolide, glycolide/L-lactide copolymers (PGA/PLLA), glycolide/trimethylene carbonate copolymers (PGA/TMC), polylactides (PLA), stereocopolymers of PLA, poly-L-lactide (PLLA), poly-DL-lactide (PDLLA), L-lactide/DL-lactide copolymers, co-polymers of PLA, lactide/tetramethylglycolide copolymers, lactide/trimethylene carbonate copolymers, lactide/δ-valerolactone copolymers, lactide/ε-caprolactone copolymers, polydepsipeptides, PLA/polyethylene oxide copolymers, unsymmetrically 3,6-substituted poly-1,4-dioxane-2,5-diones, poly-β-hydroxybutyrate (PHBA), PHBA/β-hydroxyvalerate copolymers (PHBA/HVA), poly-β-hydroxypropionate (PHPA), poly-p-dioxanone (PDS), poly-δ-valerolactone, poly-ε-caprolactone, methylmethacrylate-N-vinyl pyrrolidine copolymers, polyesteramides, polyesters of oxalic acid, polydihydropyrans, polyalkyl-2-cyanoacrylates, polyurethanes (PU), polyvinylalcohols (PVA), polypeptides, poly-β-malic acid (PMLA), poly-β-alkanoic acids, polyvinylalcohol (PVA), polyethyleneoxide (PEO), chitine polymers, polyethylene, polypropylene, polyasetal, polyamides, polyesters, polysulphone, polyether ether ketone, polyethylene terephthalate, polycarbonate, polyaryl ether ketone, and polyether ketone ketone.

In some embodiments, the coating or the laminated film comprises silk fibroin proteins or fragments thereof having an average weight average molecular weight in a range selected from between about 1 kDa and about 5 kDa, between about 5 kDa and about 10 kDa, between about 6 kDa and about 17 kDa, between about 10 kDa and about 15 kDa, between about 15 kDa and about 20 kDa, between about 17 kDa and about 39 kDa, between about 20 kDa and about 25 kDa, between about 25 kDa and about 30 kDa, between about 30 kDa and about 35 kDa, between about 35 kDa and about 40 kDa, between about 39 kDa and about 80 kDa, between about 40 kDa and about 45 kDa, between about 45 kDa and about 50 kDa, between about 60 kDa and about 100 kDa, and between about 80 kDa and about 144 kDa, and a polydispersity between 1 and about 5.

In some embodiments, the coating or the laminated film comprises silk fibroin proteins or fragments thereof having one or more of low molecular weight silk fibroin proteins or fragments thereof, medium molecular weight silk fibroin proteins or fragments thereof, or high molecular weight silk fibroin proteins or fragments thereof.

In some embodiments, the silk fibroin proteins or fragments thereof do not spontaneously or gradually gelate and do not visibly change in color or turbidity when in an aqueous solution for at least 10 days prior to being formulated into the coating or the laminated film.

The disclosure provides a method of making a material of the disclosure or an article of the disclosure. In some embodiments, the method comprising providing or obtaining the plurality of fibers, filaments, powders, particles, or yarns, and formulating with a silk derived protein composition.

In some embodiments, the concentration of silk derived protein in the silk derived protein composition is between about 0.1% w/v and about 15% w/v.

In some embodiments, the concentration of silk derived protein in the silk derived protein composition is about 0.1% w/v, about 0.2% w/v, about 0.3% w/v, about 0.4% w/v, about 0.5% w/v, about 0.6% w/v, about 0.7% w/v, about 0.8% w/v, about 0.9% w/v, about 1% w/v, about 2% w/v, about 3% w/v, about 4% w/v, about 5% w/v, about 6% w/v, about 7% w/v, about 8% w/v, about 9% w/v, about 10% w/v, about 11% w/v, about 12% w/v, about 13% w/v, about 14% w/v, or about 15% w/v. In some embodiments, the concentration of silk derived protein in the silk derived protein composition is about 6% w/v.

In some embodiments, the concentration of silk derived protein in the silk derived protein composition is between about 5 mg/mL and about 125 mg/mL.

In some embodiments, the concentration of silk derived protein in the silk derived protein composition is about 5 mg/mL, about 10 mg/mL, 15 mg/mL, about 20 mg/mL, about 25 mg/mL, about 30 mg/mL, 35 mg/mL, about 40 mg/mL, 45 mg/mL, about 50 mg/mL, 55 mg/mL, about 60 mg/mL, about 65 mg/mL, about 70 mg/mL, 75 mg/mL, about 80 mg/mL, 85 mg/mL, about 90 mg/mL, 95 mg/mL, about 1000 mg/mL, about 105 mg/mL, about 110 mg/mL, 115 mg/mL, about 120 mg/mL, or 125 mg/mL.

In some embodiments, the silk derived protein composition further comprises a pH adjusting agent. Non-limiting examples of a pH adjusting agent include ammonium hydroxide, citric acid, and hydrochloric acid.

In some embodiments, the silk derived protein composition has a pH of about 2, about 3, about 4, about 5, about 6, about 7, about 8, about 9, about 10, about 11, or about 12.

In some embodiments, the method further comprising one or more additional steps selected from grinding, fibrillating, dyeing, drying, water annealing, mechanical stretching, trimming, performing one or more polishing steps, applying a pigment, applying a colorant, applying an acrylic formulation, chemical fixing, stamping, applying a silicone finish, providing a Uniflex treatment, and/or providing a Finiflex treatment.

The disclosure provides an article comprising a plurality of fibers or yarns and a silk derived protein or fragments thereof, wherein a portion of the silk derived protein or fragments thereof are coated onto a plurality of fibers.

In some embodiments, the plurality of fibers, filaments, powders, particles, or yarns can include both natural and/or synthetic components. Non-limiting examples of the plurality of fibers, filaments, powders, particles, or yarns comprise one or more of natural fibers, filaments, powders, particles, or yarns; synthetic fibers, filaments, powders, particles, or yarns; natural leather; recycled leather; one or more of fibrillated leather or grounded leather; one or more of bovine wet blue shaving, bovine post-industrial waste, or sheep post-industrial waste; synthetic leather; one or more of silk, cotton, alpaca fleece, alpaca wool, lama fleece, *lama* wool, cashmere, sheep fleece, and sheep wool; one or more of alpaca fiber, alpaca fleece, alpaca wool, lama fiber, lama fleece, lama wool, cotton, cashmere and sheep fiber, sheep fleece, sheep wool, byssus, chiengora, quiviut, yak, rabbit, lambswool, mohair wool, camel hair, angora wool, spider silk, silkworm silk, abaca fiber, coir fiber, flax fiber, jute fiber, kapok fiber, kenaf fiber, raffia fiber, bamboo fiber, hemp, modal fiber, pina, ramie, sisal, and soy protein fiber; one or more of polyester, nylon, and polyester-polyurethane copolymer; one or more of Lyocell and/or cellulose; one or more of acrylic, anidex, aramid, fluorocarbon, modacrylic, novoloid, nylon, nytril, olefin, PBI, polycarbonate, polyester, rubber, saran, spandex, vinal vinvon; and one or more of non-woven or woven fibers or filaments, non-woven or woven mat or fabric, a woven, knitted, or crochet fabric, or any combination thereof. In some embodiments, the plurality of fibers, filaments, powders, particles, or yarns comprises natural leather; recycled leather; one or more of fibrillated leather or grounded leather; one or more of bovine wet blue shaving, bovine post-industrial waste, sheep post-industrial waste; and/or synthetic leather.

In some embodiments, the silk derived protein comprises sericin. In some embodiments, the silk derived protein comprises silk fibroin proteins or fragments thereof. In some embodiments, the silk derived protein comprises sericin and silk fibroin proteins or fragments.

In some embodiments, the silk derived protein comprises silk fibroin proteins or fragments thereof having an average weight average molecular weight selected from between about 1 kDa and about 5 kDa, between about 5 kDa and about 10 kDa, between about 6 kDa and about 17 kDa, between about 10 kDa and about 15 kDa, between about 15 kDa and about 20 kDa, between about 17 kDa and about 39 kDa, between about 20 kDa and about 25 kDa, between about 25 kDa and about 30 kDa, between about 30 kDa and about 35 kDa, between about 35 kDa and about 40 kDa, between about 39 kDa and about 80 kDa, between about 40 kDa and about 45 kDa, between about 45 kDa and about 50 kDa, between about 60 kDa and about 100 kDa, and between about 80 kDa, and a polydispersity between 1 and about 5.

In some embodiments, the silk derived protein includes silk fibroin proteins or fragments thereof having one or more of low molecular weight silk fibroin proteins or fragments thereof, medium molecular weight silk fibroin proteins or fragments thereof, or high molecular weight silk fibroin proteins or fragments thereof.

In some embodiments, the silk fibroin proteins or fragments thereof do not spontaneously or gradually gelate and do not visibly change in color or turbidity when in an aqueous solution for at least 10 days prior to being formulated into the coating or the laminated film.

In some embodiments, the article is a spun yarn. In some embodiments, the spun yarn comprises one or more slivers comprising the plurality of fibers or yarns. In some embodiments, the spun yarn is further coated with a wax.

Faux or Bonded Leather and Faux or Bonded Leather Articles Processed, Coated, and/or Repaired with Silk Fibroin-BasedProteinFragments The disclosure provides a faux or bonded leather including silk fibroin proteins or fragments thereof having an average weight average molecular weight in a range selected from between about 1 kDa and about 5 kDa, between about 5 kDa and about 10 kDa, between about 6 kDa and about 17 kDa, between about 10 kDa and about 15 kDa, between about 15 kDa and about 20 kDa, between about 17 kDa and about 39 kDa, between about 20 kDa and about 25 kDa, between about 25 kDa and about 30 kDa, between about 30 kDa and about 35 kDa, between about 35 kDa and about 40 kDa, between about 39 kDa and about 80 kDa, between about 40 kDa and about 45 kDa, between about 45 kDa and about 50 kDa, between about 60 kDa and about 100 kDa, and between about 80 kDa and about 144 kDa, and a polydispersity between 1 and about 5. In some embodiments, the silk fibroin proteins or fragments thereof have any average weight average molecular weight described herein. In some embodiments, the silk fibroin proteins or fragments thereof have a polydispersity between 1 and about 1.5. In some embodiments, the silk fibroin proteins or fragments thereof have a polydispersity between about 1.5 and about 2. In some embodiments, the silk fibroin proteins or fragments thereof have a polydispersity between about 2 and about 2.5. In some embodiments, the silk fibroin proteins or fragments thereof have a polydispersity between about 2.5 and about 3. In some embodiments, the silk fibroin proteins or fragments thereof have a polydispersity between about 3 and about 3.5. In some embodiments, the silk fibroin proteins or fragments thereof have a polydispersity between about 3.5 and about 4. In some embodiments, of claim 1, wherein the silk fibroin proteins or fragments thereof have a polydispersity between about 4 and about 4.5. In some embodiments, the silk fibroin proteins or fragments thereof have a polydispersity between about 4.5 and about 5. Some methods for adding a protein to a substrate, are described in U.S. Pat. No. 8,993,065, incorporated herein by reference in its entirety.

The disclosure also provides a faux or bonded leather article including silk fibroin proteins or fragments thereof having any average weight average molecular weight and polydispersity described herein, and optionally any other limitations described herein, and about 0.001% (w/w) to about 10% (w/w) sericin relative to the silk fibroin proteins or fragments thereof. In some embodiments, the w/w ratio between silk fibroin proteins or fragments thereof and sericin is about 99:1, about 98:2, about 97:3, about 96:4, about 95:5, about 94:6, about 93:7, about 92:8, about 91:9, about 90:10, about 89:11, about 88:12, about 87:13, about 86:14, about 85:15, about 84:16, about 83:17, about 82:18, about 81:19, about 80:20, about 79:21, about 78:22, about 77:23, about 76:24, or about 75:25. In some embodiments, the relative w/w amount of sericin to the silk fibroin proteins or fragments thereof is about 10%, about 9%, about 8%, about 7%, about 6%, about 5%, about 4%, about 3%, about 2%, about 1%, about 0.9%, about 0.8%, about 0.7%, about 0.6%, about 0.5%, 0.4%, about 0.3%, about 0.2%, about 0.1%, about 0.01%, or about 0.001%.

The disclosure also provides a faux or bonded leather article including silk fibroin proteins or fragments thereof having any average weight average molecular weight and polydispersity described herein, and optionally any other limitations described herein, wherein the silk fibroin proteins or fragments thereof do not spontaneously or gradually gelate and do not visibly change in color or turbidity when in an aqueous solution for at least 10 days prior to being added to the faux or bonded leather substrate. In some embodiments, the silk fibroin proteins or fragments thereof do not spontaneously or gradually gelate and do not visibly change in color or turbidity when in an aqueous solution for at least 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 4 weeks, or 1 month prior to being added to the faux or bonded leather substrate.

The disclosure also provides a faux or bonded leather article including silk fibroin proteins or fragments thereof having any average weight average molecular weight and polydispersity described herein, and optionally any other limitations described herein, wherein: 1) a portion of the silk fibroin proteins or fragments thereof is coated on a surface of the faux or bonded leather substrate; or 2) a portion of the silk fibroin proteins or fragments thereof is infused into a layer of the faux or bonded leather substrate, in some embodiments, such layers having a thickness as described herein; or 3) a portion of the silk fibroin proteins or fragments thereof is in a recessed portion of the faux or bonded leather substrate selected from an opening, a crevice, and a defect in the faux or bonded leather substrate; or 4) any combination of the above.

In some embodiments, a portion of the silk fibroin proteins or fragments thereof, which is coated on a surface of the faux or bonded leather substrate can have a thickness of about 1 μm, about 2 μm, about 3 μm, about 4 μm, about 5 μm, about 6 μm, about 7 μm, about 8 μm, about 9 μm, about 10 μm, about 1 μm, about 2 μm, about 3 μm, about 4 μm, about 5 μm, about 6 μm, about 7 μm, about 8 μm, about 9 μm, about 10 μm, about 11 μm, about 12 μm, about 13 μm, about 14 μm, about 15 μm, about 16 μm, about 17 μm, about 18 μm, about 19 μm, about 20 μm, about 21 μm, about 22 μm, about 23 μm, about 24 μm, about 25 μm, about 26 μm, about 27 μm, about 28 μm, about 29 μm, or about 30 μm. In some embodiments, a coating including silk fibroin proteins or fragments thereof, and optionally rheology modifiers and/or plasticizer, which is coated on a surface of the faux or bonded leather substrate, can have a thickness of about 1 μm, about 2 μm, about 3 μm, about 4 μm, about 5 μm, about 6 μm, about 7 μm, about 8 μm, about 9 μm, about 10 μm, about 1 μm, about 2 μm, about 3 μm, about 4 μm, about 5 μm, about 6 μm, about 7 μm, about 8 μm, about 9 μm, about 10 μm, about 11 μm, about 12 μm, about 13 μm, about 14 μm, about 15 μm, about 16 μm, about 17 μm, about 18 μm, about 19 μm, about 20 μm, about 21 μm, about 22 μm, about 23 μm, about 24 μm, about 25 μm, about 26 μm, about 27 μm, about 28 μm, about 29 μm, or about 30 μm. In some embodiments, a coating including silk fibroin proteins or fragments thereof, and optionally rheology modifiers and/or plasticizer, which is coated on a surface of the faux orbonded leather substrate, can have a thickness of less than about 1 μm, less than about 2 μm, less than about 3 μm, less than about 4 μm, less than about 5 μm, less than about 6 μm, less than about 7 μm, less than about 8 μm, less than about 9 μm, less than about 10 μm, less than about 1 μm, less than about 2 μm, less than about 3 μm, less than about 4 μm, less than about 5 μm, less than about 6 μm, less than about 7 μm, less than about 8 μm, less than about 9 μm, less than about 10 μm, less than about 11 μm, less than about 12 μm, less than about 13 μm, less than about 14 μm, less than about 15 μm, less than about 16 μm, less than about 17 μm, less than about 18 μm, less than about 19 μm, less than about 20 μm, less than about 21 μm, less than about 22 μm, less than about 23 μm, less than about 24 μm, less than about 25 μm, less than about 26 μm, less than about 27 μm, less than about 28 μm, less than about 29 μm, or less than about 30 μm. In some embodiments, a coating including silk fibroin proteins or fragments thereof, and optionally rheology modifiers and/or plasticizer, which is coated on a surface of the faux or bonded leather substrate, can have a thickness of greater than about 1 μm, greater than about 2 μm, greater than about 3 μm, greater than about 4 μm, greater than about 5 μm, greater than about 6 μm, greater than about 7 μm, greater than about 8 μm, greater than about 9 μm, greater than about 10 μm, greater than about 1 μm, greater than about 2 μm, greater than about 3 μm, greater than about 4 μm, greater than about 5 μm, greater than about 6 μm, greater than about 7 μm, greater than about 8 μm, greater than about 9 μm, greater than about 10 μm, greater than about 11 μm, greater than about 12 μm, greater than about 13 μm, greater than about 14 μm, greater than about 15 μm, greater than about 16 μm, greater than about 17 μm, greater than about 18 μm, greater than about 19 μm, greater than about 20 μm, greater than about 21 μm, greater than about 22 μm, greater than about 23 μm, greater than about 24 μm, greater than about 25 μm, greater than about 26 μm, greater than about 27 μm, greater than about 28 μm, greater than about 29 μm, or greater than about 30 μm.

As described herein, silk fibroin proteins or fragments thereof can be coated, embedded, infused on and/or into any surface or layer of the faux leather or bonded leather substrate, or included in a recessed portion of the faux leather or bonded leather substrate. A recessed portion of the faux leather or bonded leather substrate can have various depths, including, without limitation, between about 1 μm and about 15 μm, between about 5 μm and about 25 μm, between about 10 μm and about 50 μm, between about 25 μm and about 75 μm, between about 50 μm and about 150 μm, between about 75 μm and about 500 μm, and between about 100 μm and about 1000 μm. In some embodiments, a recessed portion of the faux leather or bonded leather substrate can have a depth of about 1 μm, about 2 μm, about 3 μm, about 4 μm, about 5 μm, about 6 μm, about 7 μm, about 8 μm, about 9 μm, about 10 μm, about 11 μm, about 12 μm, about 13 μm, 15 about 14 μm, about 15 μm, about 16 μm, about 17 μm, about 18 μm, about 19 μm, about 20 μm, about 21 μm, about 22 μm, about 23 μm, about 24 μm, about 25 μm, about 26 μm, about 27 μm, about 28 μm, about 29 μm, about 30 μm, about 31 μm, about 32 μm, about 33 μm, about 34 μm, about 35 μm, about 36 μm, about 37 μm, about 38 μm, about 39 μm, about 40 μm, about 41 μm, about 42 μm, about 43 μm, about 44 μm, about 45 μm, about 46 μm, about 47 μm, about 48 μm, about 49 μm, about 50 μm, about 51 μm, about 52 μm, about 53 μm, about 54 μm, about 55

μm, about 56 μm, about 57 μm, about 58 μm, about 59 μm, about 60 μm, about 61 μm, about 62 μm, about 63 μm, about 64 μm, about 65 μm, about 66 μm, about 67 μm, about 68 μm, about 69 μm, about 70 μm, about 71 μm, about 72 μm, about 73 μm, about 74 μm, about 75 μm, about 76 μm, about 77 μm, about 78 μm, about 79 μm, about 80 μm, about 81 μm, about 82 μm, about 83 μm, about 84 μm, about 85 μm, about 86 μm, about 87 μm, about 88 μm, about 89 μm, about 90 μm, about 91 μm, about 92 μm, about 93 μm, about 94 μm, about 95 μm, about 96 μm, about 97 μm, about 98 μm, about 99 μm, about 100 μm, about 101 μm, about 102 μm, about 103 μm, about 104 μm, about 105 μm, about 106 μm, about 107 μm, about 108 μm, about 109 μm, about 110 μm, about 111 μm, about 112 μm, about 113 μm, about 114 μm, about 115 μm, about 116 μm, about 117 μm, about 118 μm, about 119 μm, about 120 μm, about 121 μm, about 122 μm, about 123 μm, about 124 μm, about 125 μm, about 126 μm, about 127 μm, about 128 μm, about 129 μm, about 130 μm, about 131 μm, about 132 μm, about 133 μm, about 134 μm, about 135 μm, about 136 μm, about 137 μm, about 138 μm, about 139 μm, about 140 μm, about 141 μm, about 142 μm, about 143 μm, about 144 μm, about 145 μm, about 146 μm, about 147 μm, about 148 μm, about 149 μm, about 150 μm, about 151 μm, about 152 μm, about 153 μm, about 154 μm, about 155 μm, about 156 μm, about 157 μm, about 158 μm, about 159 μm, about 160 μm, about 161 μm, about 162 μm, about 163 μm, about 164 μm, about 165 μm, about 166 μm, about 167 μm, about 168 μm, about 169 μm, about 170 μm, about 171 μm, about 172 μm, about 173 μm, about 174 μm, about 175 μm, about 176 μm, about 177 μm, about 178 μm, about 179 μm, about 180 μm, about 181 μm, about 182 μm, about 183 μm, about 184 μm, about 185 μm, about 186 μm, about 187 μm, about 188 μm, about 189 μm, about 190 μm, about 191 μm, about 192 μm, about 193 μm, about 194 μm, about 195 μm, about 196 μm, about 197 μm, about 198 μm, about 199 μm, or about 200 μm. In some embodiments, a recessed portion of the faux leather or bonded leather substrate can have a depth of about 132 μm, about 151 μm, about 126 μm, about 132 μm, and/or about 63 μm of the depth of the recessed portion.

In some embodiments, a portion of the silk fibroin proteins or fragments thereof is in a recessed portion of the faux leather or bonded leather substrate selected from an opening, a crevice, and a defect in the faux leather or bonded leather substrate, the recessed portion having a depth as described herein, wherein the portion of the silk fibroin proteins or fragments thereof fill at least between about 50% and about 75% of the depth of the recessed portion, at least between about 45% and about 80% of the depth of the recessed portion, at least between about 65% and about 85% of the depth of the recessed portion, at least between about 75% and about 95% of the depth of the recessed portion. In some embodiments, a portion of the silk fibroin proteins or fragments thereof is in a recessed portion of the faux leather or bonded leather substrate selected from an opening, a crevice, and a defect in the faux leather or bonded leather substrate, the recessed portion having a depth as described herein, wherein the portion of the silk fibroin proteins or fragments thereof fill at least 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 69%, 68%, 67%, 66%, 65%, 64%, 63%, 62%, 61%, 60%, 59%, 58%, 57%, 56%, 55%, 53%, 52%, 51%, or 50% of the depth of the recessed portion. In some embodiments, a portion of the silk fibroin proteins or fragments thereof is in a recessed portion of the faux leather or bonded leather substrate selected from an opening, a crevice, and a defect in the faux leather or bonded leather substrate, the recessed portion having a depth as described herein, wherein the portion of the silk fibroin proteins or fragments thereof fill at least between about 5% and about 25% of the depth of the recessed portion, at least between about 10% and about 35% of the depth of the recessed portion, at least between about 15% and about 50% of the depth of the recessed portion, at least between about 25% and about 75% of the depth of the recessed portion.

In some embodiments, a portion of the silk fibroin proteins or fragments thereof is in a recessed portion of the faux leather or bonded leather substrate selected from an opening, a crevice, and a defect in the faux leather or bonded leather substrate, the recessed portion having a depth as described herein, wherein the portion of the silk fibroin proteins or fragments thereof fill less than about 1 μm, less than about 2 μm, less than about 3 μm, less than about 4 μm, less than about 5 μm, less than about 6 μm, less than about 7 μm, less than about 8 μm, less than about 9 μm, less than about 10 μm, less than about 1 μm, less than about 2 μm, less than about 3 μm, less than about 4 μm, less than about 5 μm, less than about 6 μm, less than about 7 μm, less than about 8 μm, less than about 9 μm, less than about 10 μm, less than about 11 μm, less than about 12 μm, less than about 13 μm, less than about 14 μm, less than about 15 μm, less than about 16 μm, less than about 17 μm, less than about 18 μm, less than about 19 μm, less than about 20 μm, less than about 21 μm, less than about 22 μm, less than about 23 μm, less than about 24 μm, less than about 25 μm, less than about 26 μm, less than about 27 μm, less than about 28 μm, less than about 29 μm, less than about 30 μm, less than about 31 μm, less than about 32 μm, less than about 33 μm, less than about 34 μm, less than about 35 μm, less than about 36 μm, less than about 37 μm, less than about 38 μm, less than about 39 μm, less than about 40 μm, less than about 41 μm, less than about 42 μm, less than about 43 μm, less than about 44 μm, less than about 45 μm, less than about 46 μm, less than about 47 μm, less than about 48 μm, less than about 49 μm, less than about 50 μm, less than about 51 μm, less than about 52 μm, less than about 53 μm, less than about 54 μm, less than about 55 μm, less than about 56 μm, less than about 57 μm, less than about 58 μm, less than about 59 μm, less than about 60 μm, less than about 61 μm, less than about 62 μm, less than about 63 μm, less than about 64 μm, less than about 65 μm, less than about 66 μm, less than about 67 μm, less than about 68 μm, less than about 69 μm, less than about 70 μm, less than about 71 μm, less than about 72 μm, less than about 73 μm, less than about 74 μm, less than about 75 μm, less than about 76 μm, less than about 77 μm, less than about 78 μm, less than about 79 μm, less than about 80 μm, less than about 81 μm, less than about 82 μm, less than about 83 μm, less than about 84 μm, less than about 85 μm, less than about 86 μm, less than about 87 μm, less than about 88 μm, less than about 89 μm, less than about 90 μm, less than about 91 μm, less than about 92 μm, less than about 93 μm, less than about 94 μm, less than about 95 μm, less than about 96 μm, less than about 97 μm, less than about 98 μm, less than about 99 μm, less than about 100 μm, less than about 101 μm, less than about 102 μm, less than about 103 μm, less than about 104 μm, less than about 105 μm, less than about 106 μm, less than about 107 μm, less than about 108 μm, less than about 109 μm, less than about 110 μm, less than about 111 μm, less than about 112 μm, less than about 113 μm, less than about 114 μm, less than about 115 μm, less than about 116 μm, less than about 117 μm, less than about 118 μm, less than about 119 μm, less than about 120 μm, less than about 121 μm, less than about 122 μm, less than about 123 μm, less than about 124 µm, less than about 125 µm, less than about 126 µm, less than about 127 µm, less than about 128 µm, less than about 129 µm, less than about 130 µm, less than about 131 µm, less than about 132 µm, less than about 133 µm, less than about 134 µm, less than about 135 µm, less than about 136 µm, less than about 137 µm, less than about 138 µm, less than about 139 µm, less than about 140 µm, less than about 141 µm, less than about 142 µm, less than about 143 µm, less than about 144 µm, less than about 145 µm, less than about 146 µm, less than about 147 µm, less than about 148 µm, less than about 149 µm, less than about 150 µm, less than about 151 µm, less than about 152 µm, less than about 153 µm, less than about 154 µm, less than about 155 µm, less than about 156 µm, less than about 157 µm, less than about 158 µm, less than about 159 µm, less than about 160 µm, less than about 161 µm, less than about 162 µm, less than about 163 µm, less than about 164 µm, less than about 165 µm, less than about 166 µm, less than about 167 µm, less than about 168 µm, less than about 169 µm, less than about 170 µm, less than about 171 µm, less than about 172 µm, less than about 173 µm, less than about 174 µm, less than about 175 µm, less than about 176 µm, less than about 177 µm, less than about 178 µm, less than about 179 µm, less than about 180 µm, less than about 181 µm, less than about 182 µm, less than about 183 µm, less than about 184 µm, less than about 185 µm, less than about 186 µm, less than about 187 µm, less than about 188 µm, less than about 189 µm, less than about 190 µm, less than about 191 µm, less than about 192 µm, less than about 193 µm, less than about 194 µm, less than about 195 µm, less than about 196 µm, less than about 197 µm, less than about 198 µm, less than about 199 µm, or less than about 200 µm of the depth. In some embodiments, a portion of the silk fibroin proteins or fragments thereof is in a recessed portion of the faux leather or bonded leather substrate selected from an opening, a crevice, and a defect in the faux leather or bonded leather substrate, the recessed portion having a depth as described herein, wherein the portion of the silk fibroin proteins or fragments thereof fill less than about 132 µm, less than about 151 µm, less than about 126 µm, less than about 132 µm, and/or less than about 63 µm of the depth of the recessed portion.

In some embodiments, a portion of the silk fibroin proteins or fragments thereof is in a recessed portion of the faux leather or bonded leather substrate selected from an opening, a crevice, and a defect in the faux leather or bonded leather substrate, the recessed portion having a depth as described herein, wherein the portion of the silk fibroin proteins or fragments thereof fill greater than about 1 µm, greater than about 2 µm, greater than about 3 µm, greater than about 4 µm, greater than about 5 µm, greater than about 6 µm, greater than about 7 µm, greater than about 8 µm, greater than about 9 µm, greater than about 10 µm, greater than about 1 µm, greater than about 2 µm, greater than about 3 µm, greater than about 4 µm, greater than about 5 µm, greater than about 6 µm, greater than about 7 µm, greater than about 8 µm, greater than about 9 µm, greater than about 10 µm, greater than about 11 µm, greater than about 12 µm, greater than about 13 µm, greater than about 14 µm, greater than about 15 µm, greater than about 16 µm, greater than about 17 µm, greater than about 18 µm, greater than about 19 µm, greater than about 20 µm, greater than about 21 µm, greater than about 22 µm, greater than about 23 µm, greater than about 24 µm, greater than about 25 µm, greater than about 26 µm, greater than about 27 µm, greater than about 28 µm, greater than about 29 µm, greater than about 30 µm, greater than about 31 µm, greater than about 32 µm, greater than about 33 µm, greater than about 34 µm, greater than about 35 µm, greater than about 36 µm, greater than about 37 µm, greater than about 38 µm, greater than about 39 µm, greater than about 40 µm, greater than about 41 µm, greater than about 42 µm, greater than about 43 µm, greater than about 44 µm, greater than about 45 µm, greater than about 46 µm, greater than about 47 µm, greater than about 48 µm, greater than about 49 µm, greater than about 50 µm, greater than about 51 µm, greater than about 52 µm, greater than about 53 µm, greater than about 54 µm, greater than about 55 µm, greater than about 56 µm, greater than about 57 µm, greater than about 58 µm, greater than about 59 µm, greater than about 60 µm, greater than about 61 µm, greater than about 62 µm, greater than about 63 µm, greater than about 64 µm, greater than about 65 µm, greater than about 66 µm, greater than about 67 µm, greater than about 68 µm, greater than about 69 µm, greater than about 70 µm, greater than about 71 µm, greater than about 72 µm, greater than about 73 µm, greater than about 74 µm, greater than about 75 µm, greater than about 76 µm, greater than about 77 µm, greater than about 78 µm, greater than about 79 µm, greater than about 80 µm, greater than about 81 µm, greater than about 82 µm, greater than about 83 µm, greater than about 84 µm, greater than about 85 µm, greater than about 86 µm, greater than about 87 µm, greater than about 88 µm, greater than about 89 µm, greater than about 90 µm, greater than about 91 µm, greater than about 92 µm, greater than about 93 µm, greater than about 94 µm, greater than about 95 µm, greater than about 96 µm, greater than about 97 µm, greater than about 98 µm, greater than about 99 µm, greater than about 100 µm, greater than about 101 µm, greater than about 102 µm, greater than about 103 µm, greater than about 104 µm, greater than about 105 µm, greater than about 106 µm, greater than about 107 µm, greater than about 108 µm, greater than about 109 µm, greater than about 110 µm, greater than about 111 µm, greater than about 112 µm, greater than about 113 µm, greater than about 114 µm, greater than about 115 µm, greater than about 116 µm, greater than about 117 µm, greater than about 118 µm, greater than about 119 µm, greater than about 120 µm, greater than about 121 µm, greater than about 122 µm, greater than about 123 µm, greater than about 124 µm, greater than about 125 µm, greater than about 126 µm, greater than about 127 µm, greater than about 128 µm, greater than about 129 µm, greater than about 130 µm, greater than about 131 µm, greater than about 132 µm, greater than about 133 µm, greater than about 134 µm, greater than about 135 µm, greater than about 136 µm, greater than about 137 µm, greater than about 138 µm, greater than about 139 µm, greater than about 140 µm, greater than about 141 µm, greater than about 142 µm, greater than about 143 µm, greater than about 144 µm, greater than about 145 µm, greater than about 146 µm, greater than about 147 µm, greater than about 148 µm, greater than about 149 µm, greater than about 150 µm, greater than about 151 µm, greater than about 152 µm, greater than about 153 µm, greater than about 154 µm, greater than about 155 µm, greater than about 156 µm, greater than about 157 µm, greater than about 158 µm, greater than about 159 µm, greater than about 160 µm, greater than about 161 µm, greater than about 162 µm, greater than about 163 µm, greater than about 164 µm, greater than about 165 µm, greater than about 166 µm, greater than about 167 µm, greater than about 168 µm, greater than about 169 µm, greater than about 170 µm, greater than about 171 µm, greater than about 172 µm, greater than about 173 µm, greater than about 174 µm, greater than about 175 µm, greater than about 176 µm, greater than about 177 µm, greater than about 178 µm, greater than about 179 µm, greater than about 180 µm, greater than about 181 µm, greater than about 182 µm, greater than about 183 µm, greater than about 184 µm, greater than about 185 µm, greater than about 186 µm, greater than about 187 µm, greater than about 188 µm, greater than about 189 µm, greater than about 190 µm, greater than about 191 µm, greater than about 192 µm, greater than about 193 µm, greater than about 194 µm, greater than about 195 µm, greater than about 196 µm, greater than about 197 µm, greater than about 198 µm, greater than about 199 µm, or greater than about 200 µm of the depth. In some embodiments, a portion of the silk fibroin proteins or fragments thereof is in a recessed portion of the faux leather or bonded leather substrate selected from an opening, a crevice, and a defect in the faux leather or bonded leather substrate, the recessed portion having a depth as described herein, wherein the portion of the silk fibroin proteins or fragments thereof fill greater than about 132 µm, greater than about 151 µm, greater than about 126 µm, greater than about 132 µm, and/or greater than about 63 µm of the depth of the recessed portion.

The disclosure also provides a faux leather or bonded leather article including silk fibroin proteins or fragments thereof having any average weight average molecular weight and polydispersity described herein, and optionally any other limitations described herein, the article further including one or more polysaccharides selected from starch, cellulose, gum arabic, guar gum, xanthan gum, alginate, pectin, chitin, chitosan, carrageenan, inulin, and gellan gum. In some embodiments, the polysaccharide is gellan gum. In some embodiments, the gellan gum comprises low-acyl content gellan gum. In some embodiments, the w/w ratio between the silk fibroin proteins or fragments thereof and the polysaccharide is about 25:1, about 24:1. about 23:1, about 22:1, about 21:1, about 20:1, about 19:1, about 18:1, about 17:1, about 16:1, about 15:1, about 14:1, about 13:1, about 12:1, about 11:1, abut 10:1, about 9:1, about 8:1, about 7:1, about 6:1, about 5:1, about 4:1, about 3:1, about 2:1, about 1:1, about 1:2, about 1:3, about 1:4, or about 1:5. In some embodiments, the w/w ratio between the silk fibroin proteins or fragments thereof and the polysaccharide is about 12:1, about 11.9:1, about 11.8:1, about 11.7:1, about 11.6:1, about 11.5:1, about 11.4:1, about 11.3:1, about 11.2:1, about 11.1:1, about 11:1, abut 10.9:1, abut 10.8:1, abut 10.7:1, abut 10.6:1, abut 10.5:1, abut 10.4:1, abut 10.3:1, abut 10.2:1, abut 10.1:1, abut 10:1, about 9.9:1, about 9.8:1, about 9.7:1, about 9.6:1, about 9.5:1, about 9.4:1, about 9.3:1, about 9.2:1, about 9.1:1, about 9:1, about 8.9:1, about 8.8:1, about 8.7:1, about 8.6:1, about 8.5:1, about 8.4:1, about 8.3:1, about 8.2:1, about 8.1:1, about 8:1, about 7.9:1, about 7.8:1, about 7.7:1, about 7.6:1, about 7.5:1, about 7.4:1, about 7.3:1, about 7.2:1, about 7.1:1, about 7:1, about 6.9:1, about 6.8:1, about 6.7:1, about 6.6:1, about 6.5:1, about 6.4:1, about 6.3:1, about 6.2:1, about 6.1:1, about 6:1, about 5.9:1, about 5.8:1, about 5.7:1, about 5.6:1, about 5.5:1, about 5.4:1, about 5.3:1, about 5.2:1, about 5.1:1, about 5:1, about 4.9:1, about 4.8:1, about 4.7:1, about 4.6:1, about 4.5:1, about 4.4:1, about 4.3:1, about 4.2:1, about 4.1:1, about 4:1, about 3.9:1, about 3.8:1, about 3.7:1, about 3.6:1, about 3.5:1, about 3.4:1, about 3.3:1, about 3.2:1, about 3.1:1, about 3:1, about 2.9:1, about 2.8:1, about 2.7:1, about 2.6:1, about 2.5:1, about 2.4:1, about 2.3:1, about 2.2:1, about 2.1:1, about 2:1, about 1.9:1, about 1.8:1, about 1.7:1, about 1.6:1, about 1.5:1, about 1.4:1, about 1.3:1, about 1.2:1, about 1.1:1, about 1:1, about 0.9:1, about 0.8:1, about 0.7:1, about 0.6:1, about 0.5:1, about 0.4:1, about 0.3:1, about 0.2:1, or about 0.1:1. In some embodiments, the w/w ratio between the silk fibroin proteins or fragments thereof and the polysaccharide is about 99:1, about 98:2, about 97:3, about 96:4, about 95:5, about 94:6, about 93:7, about 92:8, about 91:9, about 90:10, about 89:11, about 88:12, about 87:13, about 86:14, about 85:15, about 84:16, about 83:17, about 82:18, about 81:19, about 80:20, about 79:21, about 78:22, about 77:23, about 76:24, about 75:25, about 74:26, about 73:27, about 72:28, about 71:29, about 70:30, about 69:31, about 68:32, about 67:33, about 66:34, about 65:35, about 64:36, about 63:37, about 62:38, about 61:39, about 60:40, about 59:41, about 58:42, about 57:43, about 56:44, about 55:45, about 54:46, about 53:47, about 52:48, about 51:49, about 50:50, about 49:51, about 48:52, about 47:53, about 46:54, about 45:55, about 44:56, about 43:57, about 42:58, about 41:59, about 40:60, about 39:61, about 38:62, about 37:63, about 36:64, about 35:65, about 34:66, about 33:67, about 32:68, about 31:69, about 30:70, about 29:71, about 28:72, about 27:73, about 26:74, about 25:75, about 24:76, about 23:77, about 22:78, about 21:79, about 20:80, about 19:81, about 18:82, about 17:83, about 16:84, about 15:85, about 14:86, about 13:87, about 12:88, about 11:89, about 10:90, about 9:91, about 8:92, about 7:93, about 6:94, about 5:95, about 4:96, about 3:97, about 2:98, or about 1:99. The ratio between the silk fibroin proteins or fragments thereof and the polysaccharide, or any other ingredient described herein, can be determined by any method known in the art, for example a mass spectrometry method, a spectroscopic method such as IR or NMR, a surface analysis method, or the like.

The disclosure also provides a faux leather or bonded leather article including silk fibroin proteins or fragments thereof having an average weight average molecular weight between about 1 kDa and about 5 kDa, and a polydispersity between 1 and about 5, or 1 and about 3, or any other range described herein; the article optionally including about 0.001% (w/w) to about 10% (w/w) sericin relative to the silk fibroin proteins or fragments thereof; wherein optionally the silk fibroin proteins or fragments thereof do not spontaneously or gradually gelate and do not visibly change in color or turbidity when in an aqueous solution for at least 10 days prior to being added to the faux leather or bonded leather substrate; wherein optionally a portion of the silk fibroin proteins or fragments thereof is a layer coated on a surface of the faux leather or bonded leather substrate, or a portion of the silk fibroin proteins or fragments thereof is infused into a layer of the faux leather or bonded leather substrate, in some embodiments, such layers having a thickness as described herein, or a portion of the silk fibroin proteins or fragments thereof is in a recessed portion of the faux leather or bonded leather substrate selected from an opening, a crevice, and a defect in the faux leather or bonded leather substrate; the article optionally including one or more polysaccharides selected from starch, cellulose, gum arabic, guar gum, xanthan gum, alginate, pectin, chitin, chitosan, carrageenan, inulin, and gellan gum, wherein the w/w ratio between the silk fibroin proteins or fragments thereof and the polysaccharide is about 25:1, about 24:1. about 23:1, about 22:1, about 21:1, about 20:1, about 19:1, about 18:1, about 17:1, about 16:1, about 15:1, about 14:1, about 13:1, about 12:1, about 11:1, abut 10:1, about 9:1, about 8:1, about 7:1, about 6:1, about 5:1, about 4:1, about 3:1, about 2:1, or about 1:1.

The disclosure also provides a faux leather or bonded leather article including silk fibroin proteins or fragments thereof having an average weight average molecular weight between about 5 kDa and about 10 kDa, and a polydispersity between 1 and about 5, or 1 and about 3, or any other range described herein; the article optionally including about 0.001% (w/w) to about 10% (w/w) sericin relative to the silk fibroin proteins or fragments thereof; wherein optionally the silk fibroin proteins or fragments thereof do not spontaneously or gradually gelate and do not visibly change in color or turbidity when in an aqueous solution for at least 10 days prior to being added to the faux leather or bonded leather substrate; wherein optionally a portion of the silk fibroin proteins or fragments thereof is a layer coated on a surface of the faux leather or bonded leather substrate, or a portion of the silk fibroin proteins or fragments thereof is infused into a layer of the faux leather or bonded leather substrate, in some embodiments, such layers having a thickness as described herein, or a portion of the silk fibroin proteins or fragments thereof is in a recessed portion of the faux leather or bonded leather substrate selected from an opening, a crevice, and a defect in the faux leather or bonded leather substrate; the article optionally including one or more polysaccharides selected from starch, cellulose, gum arabic, guar gum, xanthan gum, alginate, pectin, chitin, chitosan, carrageenan, inulin, and gellan gum, wherein the w/w ratio between the silk fibroin proteins or fragments thereof and the polysaccharide is about 25:1, about 24:1. about 23:1, about 22:1, about 21:1, about 20:1, about 19:1, about 18:1, about 17:1, about 16:1, about 15:1, about 14:1, about 13:1, about 12:1, about 11:1, abut 10:1, about 9:1, about 8:1, about 7:1, about 6:1, about 5:1, about 4:1, about 3:1, about 2:1, or about 1:1.

The disclosure also provides a faux leather or bonded leather article including silk fibroin proteins or fragments thereof having an average weight average molecular weight between about 6 kDa and about 17 kDa, and a polydispersity between 1 and about 5, or 1 and about 3, or any other range described herein; the article optionally including about 0.001% (w/w) to about 10% (w/w) sericin relative to the silk fibroin proteins or fragments thereof; wherein optionally the silk fibroin proteins or fragments thereof do not spontaneously or gradually gelate and do not visibly change in color or turbidity when in an aqueous solution for at least 10 days prior to being added to the faux leather or bonded leather substrate; wherein optionally a portion of the silk fibroin proteins or fragments thereof is a layer coated on a surface of the faux leather or bonded leather substrate, or a portion of the silk fibroin proteins or fragments thereof is infused into a layer of the faux leather or bonded leather substrate, in some embodiments, such layers having a thickness as described herein, or a portion of the silk fibroin proteins or fragments thereof is in a recessed portion of the faux leather or bonded leather substrate selected from an opening, a crevice, and a defect in the faux leather or bonded leather substrate; the article optionally including one or more polysaccharides selected from starch, cellulose, gum arabic, guar gum, xanthan gum, alginate, pectin, chitin, chitosan, carrageenan, inulin, and gellan gum, wherein the w/w ratio between the silk fibroin proteins or fragments thereof and the polysaccharide is about 25:1, about 24:1. about 23:1, about 22:1, about 21:1, about 20:1, about 19:1, about 18:1, about 17:1, about 16:1, about 15:1, about 14:1, about 13:1, about 12:1, about 11:1, abut 10:1, about 9:1, about 8:1, about 7:1, about 6:1, about 5:1, about 4:1, about 3:1, about 2:1, or about 1:1.

The disclosure also provides a faux leather or bonded leather article including silk fibroin proteins or fragments thereof having an average weight average molecular weight between about 10 kDa and about 15 kDa, and a polydispersity between 1 and about 5, or 1 and about 3, or any other range described herein; the article optionally including about 0.001% (w/w) to about 10% (w/w) sericin relative to the silk fibroin proteins or fragments thereof; wherein optionally the silk fibroin proteins or fragments thereof do not spontaneously or gradually gelate and do not visibly change in color or turbidity when in an aqueous solution for at least 10 days prior to being added to the faux leather or bonded leather substrate; wherein optionally a portion of the silk fibroin proteins or fragments thereof is a layer coated on a surface of the faux leather or bonded leather substrate, or a portion of the silk fibroin proteins or fragments thereof is infused into a layer of the faux leather or bonded leather substrate, in some embodiments, such layers having a thickness as described herein, or a portion of the silk fibroin proteins or fragments thereof is in a recessed portion of the faux leather or bonded leather substrate selected from an opening, a crevice, and a defect in the faux leather or bonded leather substrate; the article optionally including one or more polysaccharides selected from starch, cellulose, gum arabic, guar gum, xanthan gum, alginate, pectin, chitin, chitosan, carrageenan, inulin, and gellan gum, wherein the w/w ratio between the silk fibroin proteins or fragments thereof and the polysaccharide is about 25:1, about 24:1. about 23:1, about 22:1, about 21:1, about 20:1, about 19:1, about 18:1, about 17:1, about 16:1, about 15:1, about 14:1, about 13:1, about 12:1, about 11:1, abut 10:1, about 9:1, about 8:1, about 7:1, about 6:1, about 5:1, about 4:1, about 3:1, about 2:1, or about 1:1.

The disclosure also provides a faux leather or bonded leather article including silk fibroin proteins or fragments thereof having an average weight average molecular weight between about 15 kDa and about 20 kDa, and a polydispersity between 1 and about 5, or 1 and about 3, or any other range described herein; the article optionally including about 0.001% (w/w) to about 10% (w/w) sericin relative to the silk fibroin proteins or fragments thereof; wherein optionally the silk fibroin proteins or fragments thereof do not spontaneously or gradually gelate and do not visibly change in color or turbidity when in an aqueous solution for at least 10 days prior to being added to the faux leather or bonded leather substrate; wherein optionally a portion of the silk fibroin proteins or fragments thereof is a layer coated on a surface of the faux leather or bonded leather substrate, or a portion of the silk fibroin proteins or fragments thereof is infused into a layer of the faux leather or bonded leather substrate, in some embodiments, such layers having a thickness as described herein, or a portion of the silk fibroin proteins or fragments thereof is in a recessed portion of the faux leather or bonded leather substrate selected from an opening, a crevice, and a defect in the faux leather or bonded leather substrate; the article optionally including one or more polysaccharides selected from starch, cellulose, gum arabic, guar gum, xanthan gum, alginate, pectin, chitin, chitosan, carrageenan, inulin, and gellan gum, wherein the w/w ratio between the silk fibroin proteins or fragments thereof and the polysaccharide is about 25:1, about 24:1. about 23:1, about 22:1, about 21:1, about 20:1, about 19:1, about 18:1, about 17:1, about 16:1, about 15:1, about 14:1, about 13:1, about 12:1, about 11:1, abut 10:1, about 9:1, about 8:1, about 7:1, about 6:1, about 5:1, about 4:1, about 3:1, about 2:1, or about 1:1.

The disclosure also provides a faux leather or bonded leather article including silk fibroin proteins or fragments thereof having an average weight average molecular weight between about 17 kDa and about 39 kDa, and a polydispersity between 1 and about 5, or 1 and about 3, or any other range described herein; the article optionally including about 0.001% (w/w) to about 10% (w/w) sericin relative to the silk fibroin proteins or fragments thereof; wherein optionally the silk fibroin proteins or fragments thereof do not spontaneously or gradually gelate and do not visibly change in color or turbidity when in an aqueous solution for at least 10 days prior to being added to the faux leather or bonded leather substrate; wherein optionally a portion of the silk fibroin proteins or fragments thereof is a layer coated on a surface of the faux leather or bonded leather substrate, or a portion of the silk fibroin proteins or fragments thereof is infused into a layer of the faux leather or bonded leather substrate, in some embodiments, such layers having a thickness as described herein, or a portion of the silk fibroin proteins or fragments thereof is in a recessed portion of the faux leather or bonded leather substrate selected from an opening, a crevice, and a defect in the faux leather or bonded leather substrate; the article optionally including one or more polysaccharides selected from starch, cellulose, gum arabic, guar gum, xanthan gum, alginate, pectin, chitin, chitosan, carrageenan, inulin, and gellan gum, wherein the w/w ratio between the silk fibroin proteins or fragments thereof and the polysaccharide is about 25:1, about 24:1. about 23:1, about 22:1, about 21:1, about 20:1, about 19:1, about 18:1, about 17:1, about 16:1, about 15:1, about 14:1, about 13:1, about 12:1, about 11:1, abut 10:1, about 9:1, about 8:1, about 7:1, about 6:1, about 5:1, about 4:1, about 3:1, about 2:1, or about 1:1.

The disclosure also provides a faux leather or bonded leather article including silk fibroin proteins or fragments thereof having an average weight average molecular weight between about 20 kDa and about 25 kDa, and a polydispersity between 1 and about 5, or 1 and about 3, or any other range described herein; the article optionally including about 0.001% (w/w) to about 10% (w/w) sericin relative to the silk fibroin proteins or fragments thereof; wherein optionally the silk fibroin proteins or fragments thereof do not spontaneously or gradually gelate and do not visibly change in color or turbidity when in an aqueous solution for at least 10 days prior to being added to the faux leather or bonded leather substrate; wherein optionally a portion of the silk fibroin proteins or fragments thereof is a layer coated on a surface of the faux leather or bonded leather substrate, or a portion of the silk fibroin proteins or fragments thereof is infused into a layer of the faux leather or bonded leather substrate, in some embodiments, such layers having a thickness as described herein, or a portion of the silk fibroin proteins or fragments thereof is in a recessed portion of the faux leather or bonded leather substrate selected from an opening, a crevice, and a defect in the faux leather or bonded leather substrate; the article optionally including one or more polysaccharides selected from starch, cellulose, gum arabic, guar gum, xanthan gum, alginate, pectin, chitin, chitosan, carrageenan, inulin, and gellan gum, wherein the w/w ratio between the silk fibroin proteins or fragments thereof and the polysaccharide is about 25:1, about 24:1. about 23:1, about 22:1, about 21:1, about 20:1, about 19:1, about 18:1, about 17:1, about 16:1, about 15:1, about 14:1, about 13:1, about 12:1, about 11:1, abut 10:1, about 9:1, about 8:1, about 7:1, about 6:1, about 5:1, about 4:1, about 3:1, about 2:1, or about 1:1.

The disclosure also provides a faux leather or bonded leather article including silk fibroin proteins or fragments thereof having an average weight average molecular weight between about 25 kDa and about 30 kDa, and a polydispersity between 1 and about 5, or 1 and about 3, or any other range described herein; the article optionally including about 0.001% (w/w) to about 10% (w/w) sericin relative to the silk fibroin proteins or fragments thereof; wherein optionally the silk fibroin proteins or fragments thereof do not spontaneously or gradually gelate and do not visibly change in color or turbidity when in an aqueous solution for at least 10 days prior to being added to the faux leather or bonded leather substrate; wherein optionally a portion of the silk fibroin proteins or fragments thereof is a layer coated on a surface of the faux leather or bonded leather substrate, or a portion of the silk fibroin proteins or fragments thereof is infused into a layer of the faux leather or bonded leather substrate, in some embodiments, such layers having a thickness as described herein, or a portion of the silk fibroin proteins or fragments thereof is in a recessed portion of the faux leather or bonded leather substrate selected from an opening, a crevice, and a defect in the faux leather or bonded leather substrate; the article optionally including one or more polysaccharides selected from starch, cellulose, gum arabic, guar gum, xanthan gum, alginate, pectin, chitin, chitosan, carrageenan, inulin, and gellan gum, wherein the w/w ratio between the silk fibroin proteins or fragments thereof and the polysaccharide is about 25:1, about 24:1. about 23:1, about 22:1, about 21:1, about 20:1, about 19:1, about 18:1, about 17:1, about 16:1, about 15:1, about 14:1, about 13:1, about 12:1, about 11:1, abut 10:1, about 9:1, about 8:1, about 7:1, about 6:1, about 5:1, about 4:1, about 3:1, about 2:1, or about 1:1.

The disclosure also provides a faux leather or bonded leather article including silk fibroin proteins or fragments thereof having an average weight average molecular weight between about 30 kDa and about 35 kDa, and a polydispersity between 1 and about 5, or 1 and about 3, or any other range described herein; the article optionally including about 0.001% (w/w) to about 10% (w/w) sericin relative to the silk fibroin proteins or fragments thereof; wherein optionally the silk fibroin proteins or fragments thereof do not spontaneously or gradually gelate and do not visibly change in color or turbidity when in an aqueous solution for at least 10 days prior to being added to the faux leather or bonded leather substrate; wherein optionally a portion of the silk fibroin proteins or fragments thereof is a layer coated on a surface of the faux leather or bonded leather substrate, or a portion of the silk fibroin proteins or fragments thereof is infused into a layer of the faux leather or bonded leather substrate, in some embodiments, such layers having a thickness as described herein, or a portion of the silk fibroin proteins or fragments thereof is in a recessed portion of the faux leather or bonded leather substrate selected from an opening, a crevice, and a defect in the faux leather or bonded leather substrate; the article optionally including one or more polysaccharides selected from starch, cellulose, gum arabic, guar gum, xanthan gum, alginate, pectin, chitin, chitosan, carrageenan, inulin, and gellan gum, wherein the w/w ratio between the silk fibroin proteins or fragments thereof and the polysaccharide is about 25:1, about 24:1. about 23:1, about 22:1, about 21:1, about 20:1, about 19:1, about 18:1, about 17:1, about 16:1, about 15:1, about 14:1, about 13:1, about 12:1, about 11:1, abut 10:1, about 9:1, about 8:1, about 7:1, about 6:1, about 5:1, about 4:1, about 3:1, about 2:1, or about 1:1.

The disclosure also provides a faux leather or bonded leather article including silk fibroin proteins or fragments thereof having an average weight average molecular weight between about 35 kDa and about 40 kDa, and a polydispersity between 1 and about 5, or 1 and about 3, or any other range described herein; the article optionally including about 0.001% (w/w) to about 10% (w/w) sericin relative to the silk fibroin proteins or fragments thereof; wherein optionally the silk fibroin proteins or fragments thereof do not spontaneously or gradually gelate and do not visibly change in color or turbidity when in an aqueous solution for at least 10 days prior to being added to the faux leather or bonded leather substrate; wherein optionally a portion of the silk fibroin proteins or fragments thereof is a layer coated on a surface of the faux leather or bonded leather substrate, or a portion of the silk fibroin proteins or fragments thereof is infused into a layer of the faux leather or bonded leather substrate, in some embodiments, such layers having a thickness as described herein, or a portion of the silk fibroin proteins or fragments thereof is in a recessed portion of the faux leather or bonded leather substrate selected from an opening, a crevice, and a defect in the faux leather or bonded leather substrate; the article optionally including one or more polysaccharides selected from starch, cellulose, gum arabic, guar gum, xanthan gum, alginate, pectin, chitin, chitosan, carrageenan, inulin, and gellan gum, wherein the w/w ratio between the silk fibroin proteins or fragments thereof and the polysaccharide is about 25:1, about 24:1. about 23:1, about 22:1, about 21:1, about 20:1, about 19:1, about 18:1, about 17:1, about 16:1, about 15:1, about 14:1, about 13:1, about 12:1, about 11:1, abut 10:1, about 9:1, about 8:1, about 7:1, about 6:1, about 5:1, about 4:1, about 3:1, about 2:1, or about 1:1.

The disclosure also provides a faux leather or bonded leather article including silk fibroin proteins or fragments thereof having an average weight average molecular weight between about 39 kDa and about 80 kDa, and a polydispersity between 1 and about 5, or 1 and about 3, or any other range described herein; the article optionally including about 0.001% (w/w) to about 10% (w/w) sericin relative to the silk fibroin proteins or fragments thereof; wherein optionally the silk fibroin proteins or fragments thereof do not spontaneously or gradually gelate and do not visibly change in color or turbidity when in an aqueous solution for at least 10 days prior to being added to the faux leather or bonded leather substrate; wherein optionally a portion of the silk fibroin proteins or fragments thereof is a layer coated on a surface of the faux leather or bonded leather substrate, or a portion of the silk fibroin proteins or fragments thereof is infused into a layer of the faux leather or bonded leather substrate, in some embodiments, such layers having a thickness as described herein, or a portion of the silk fibroin proteins or fragments thereof is in a recessed portion of the faux leather or bonded leather substrate selected from an opening, a crevice, and a defect in the faux leather or bonded leather substrate; the article optionally including one or more polysaccharides selected from starch, cellulose, gum arabic, guar gum, xanthan gum, alginate, pectin, chitin, chitosan, carrageenan, inulin, and gellan gum, wherein the w/w ratio between the silk fibroin proteins or fragments thereof and the polysaccharide is about 25:1, about 24:1. about 23:1, about 22:1, about 21:1, about 20:1, about 19:1, about 18:1, about 17:1, about 16:1, about 15:1, about 14:1, about 13:1, about 12:1, about 11:1, abut 10:1, about 9:1, about 8:1, about 7:1, about 6:1, about 5:1, about 4:1, about 3:1, about 2:1, or about 1:1.

The disclosure also provides a faux leather or bonded leather article including silk fibroin proteins or fragments thereof having an average weight average molecular weight between about 40 kDa and about 45 kDa, and a polydispersity between 1 and about 5, or 1 and about 3, or any other range described herein; the article optionally including about 0.001% (w/w) to about 10% (w/w) sericin relative to the silk fibroin proteins or fragments thereof; wherein optionally the silk fibroin proteins or fragments thereof do not spontaneously or gradually gelate and do not visibly change in color or turbidity when in an aqueous solution for at least 10 days prior to being added to the faux leather or bonded leather substrate; wherein optionally a portion of the silk fibroin proteins or fragments thereof is a layer coated on a surface of the faux leather or bonded leather substrate, or a portion of the silk fibroin proteins or fragments thereof is infused into a layer of the faux leather or bonded leather substrate, in some embodiments, such layers having a thickness as described herein, or a portion of the silk fibroin proteins or fragments thereof is in a recessed portion of the faux leather or bonded leather substrate selected from an opening, a crevice, and a defect in the faux leather or bonded leather substrate; the article optionally including one or more polysaccharides selected from starch, cellulose, gum arabic, guar gum, xanthan gum, alginate, pectin, chitin, chitosan, carrageenan, inulin, and gellan gum, wherein the w/w ratio between the silk fibroin proteins or fragments thereof and the polysaccharide is about 25:1, about 24:1. about 23:1, about 22:1, about 21:1, about 20:1, about 19:1, about 18:1, about 17:1, about 16:1, about 15:1, about 14:1, about 13:1, about 12:1, about 11:1, abut 10:1, about 9:1, about 8:1, about 7:1, about 6:1, about 5:1, about 4:1, about 3:1, about 2:1, or about 1:1.

The disclosure also provides a faux leather or bonded leather article including silk fibroin proteins or fragments thereof having an average weight average molecular weight between about 45 kDa and about 50 kDa, and a polydispersity between 1 and about 5, or 1 and about 3, or any other range described herein; the article optionally including about 0.001% (w/w) to about 10% (w/w) sericin relative to the silk fibroin proteins or fragments thereof; wherein optionally the silk fibroin proteins or fragments thereof do not spontaneously or gradually gelate and do not visibly change in color or turbidity when in an aqueous solution for at least 10 days prior to being added to the faux leather or bonded leather substrate; wherein optionally a portion of the silk fibroin proteins or fragments thereof is a layer coated on a surface of the faux leather or bonded leather substrate, or a portion of the silk fibroin proteins or fragments thereof is infused into a layer of the faux leather or bonded leather substrate, in some embodiments, such layers having a thickness as described herein, or a portion of the silk fibroin proteins or fragments thereof is in a recessed portion of the faux leather or bonded leather substrate selected from an opening, a crevice, and a defect in the faux leather or bonded leather substrate; the article optionally including one or more polysaccharides selected from starch, cellulose, gum arabic, guar gum, xanthan gum, alginate, pectin, chitin, chitosan, carrageenan, inulin, and gellan gum, wherein the w/w ratio between the silk fibroin proteins or fragments thereof and the polysaccharide is about 25:1, about 24:1. about 23:1, about 22:1, about 21:1, about 20:1, about 19:1, about 18:1, about 17:1, about 16:1, about 15:1, about 14:1, about 13:1, about 12:1, about 11:1, abut 10:1, about 9:1, about 8:1, about 7:1, about 6:1, about 5:1, about 4:1, about 3:1, about 2:1, or about 1:1.

The disclosure also provides a faux leather or bonded leather article including silk fibroin proteins or fragments thereof having an average weight average molecular weight between about 60 kDa and about 100 kDa, and a polydispersity between 1 and about 5, or 1 and about 3, or any other range described herein; the article optionally including about 0.001% (w/w) to about 10% (w/w) sericin relative to the silk fibroin proteins or fragments thereof; wherein optionally the silk fibroin proteins or fragments thereof do not spontaneously or gradually gelate and do not visibly change in color or turbidity when in an aqueous solution for at least 10 days prior to being added to the faux leather or bonded leather substrate; wherein optionally a portion of the silk fibroin proteins or fragments thereof is a layer coated on a surface of the faux leather or bonded leather substrate, or a portion of the silk fibroin proteins or fragments thereof is infused into a layer of the faux leather or bonded leather substrate, in some embodiments, such layers having a thickness as described herein, or a portion of the silk fibroin proteins or fragments thereof is in a recessed portion of the faux leather or bonded leather substrate selected from an opening, a crevice, and a defect in the faux leather or bonded leather substrate; the article optionally including one or more polysaccharides selected from starch, cellulose, gum arabic, guar gum, xanthan gum, alginate, pectin, chitin, chitosan, carrageenan, inulin, and gellan gum, wherein the w/w ratio between the silk fibroin proteins or fragments thereof and the polysaccharide is about 25:1, about 24:1. about 23:1, about 22:1, about 21:1, about 20:1, about 19:1, about 18:1, about 17:1, about 16:1, about 15:1, about 14:1, about 13:1, about 12:1, about 11:1, abut 10:1, about 9:1, about 8:1, about 7:1, about 6:1, about 5:1, about 4:1, about 3:1, about 2:1, or about 1:1.

The disclosure also provides a faux leather or bonded leather article including silk fibroin proteins or fragments thereof having an average weight average molecular weight between about 80 kDa and about 144 kDa, and a polydispersity between 1 and about 5, or 1 and about 3, or any other range described herein; the article optionally including about 0.001% (w/w) to about 10% (w/w) sericin relative to the silk fibroin proteins or fragments thereof; wherein optionally the silk fibroin proteins or fragments thereof do not spontaneously or gradually gelate and do not visibly change in color or turbidity when in an aqueous solution for at least 10 days prior to being added to the faux leather or bonded leather substrate; wherein optionally a portion of the silk fibroin proteins or fragments thereof is a layer coated on a surface of the faux leather or bonded leather substrate, or a portion of the silk fibroin proteins or fragments thereof is infused into a layer of the faux leather or bonded leather substrate, in some embodiments, such layers having a thickness as described herein, or a portion of the silk fibroin proteins or fragments thereof is in a recessed portion of the faux leather or bonded leather substrate selected from an opening, a crevice, and a defect in the faux leather or bonded leather substrate; the article optionally including one or more polysaccharides selected from starch, cellulose, gum arabic, guar gum, xanthan gum, alginate, pectin, chitin, chitosan, carrageenan, inulin, and gellan gum, wherein the w/w ratio between the silk fibroin proteins or fragments thereof and the polysaccharide is about 25:1, about 24:1. about 23:1, about 22:1, about 21:1, about 20:1, about 19:1, about 18:1, about 17:1, about 16:1, about 15:1, about 14:1, about 13:1, about 12:1, about 11:1, abut 10:1, about 9:1, about 8:1, about 7:1, about 6:1, about 5:1, about 4:1, about 3:1, about 2:1, or about 1:1.

The disclosure also provides a faux leather or bonded leather article including and silk fibroin proteins or fragments thereof having any average weight average molecular weight and polydispersity described herein, and optionally any other limitations described herein, the article further including one or more polyols, and/or one or more polyethers. In some embodiments, the polyols include one or more of glycol, glycerol, sorbitol, glucose, sucrose, and dextrose. In some embodiments, the polyethers include one or more polyethyleneglycols (PEGs). In some embodiments, the w/w ratio between the silk fibroin proteins or fragments thereof and the one or more polyols and/or one or more polyethers is about 5:1, about 4.9:1, about 4.8:1, about 4.7:1, about 4.6:1, about 4.5:1, about 4.4:1, about 4.3:1, about 4.2:1, about 4.1:1, about 4:1, about 3.9:1, about 3.8:1, about 3.7:1, about 3.6:1, about 3.5:1, about 3.4:1, about 3.3:1, about 3.2:1, about 3.1:1, about 3:1, about 2.9:1, about 2.8:1, about 2.7:1, about 2.6:1, about 2.5:1, about 2.4:1, about 2.3:1, about 2.2:1, about 2.1:1, about 2:1, about 1.9:1, about 1.8:1, about 1.7:1, about 1.6:1, about 1.5:1, about 1.4:1, about 1.3:1, about 1.2:1, about 1.1:1, about 1:1, about 0.9:1, about 0.8:1, about 0.7:1, about 0.6:1, about 0.5:1, about 0.4:1, about 0.3:1, about 0.2:1, about 0.1:1, about 1:0.1, about 1:0.2, about 1:0.3, about 1:0.4, about 1:0.5, about 1:0.6, about 1:0.7, about 1:0.8, about 1:0.9, about 1:1.1, about 1:1.2, about 1:1.3, about 1:1.4, about 1:1.5, about 1:1.6, about 1:1.7, about 1:1.8, about 1:1.9, about 1:2, about 1:2.1, about 1:2.2, about 1:2.3, about 1:2.4, about 1:2.5, about 1:2.6, about 1:2.7, about 1:2.8, about 1:2.9, about 1:3, about 1:3.1, about 1:3.2, about 1:3.3, about 1:3.4, about 1:3.5, about 1:3.6, about 1:3.7, about 1:3.8, about 1:3.9, about 1:4, about 1:4.1, about 1:4.2, about 1:4.3, about 1:4.4, about 1:4.5, about 1:4.6, about 1:4.7, about 1:4.8, about 1:4.9, or about 1:5. In some embodiments, the w/w ratio between the silk fibroin proteins or fragments thereof and the one or more polyols and/or one or more polyethers is about 99:1, about 98:2, about 97:3, about 96:4, about 95:5, about 94:6, about 93:7, about 92:8, about 91:9, about 90:10, about 89:11, about 88:12, about 87:13, about 86:14, about 85:15, about 84:16, about 83:17, about 82:18, about 81:19, about 80:20, about 79:21, about 78:22, about 77:23, about 76:24, about 75:25, about 74:26, about 73:27, about 72:28, about 71:29, about 70:30, about 69:31, about 68:32, about 67:33, about 66:34, about 65:35, about 64:36, about 63:37, about 62:38, about 61:39, about 60:40, about 59:41, about 58:42, about 57:43, about 56:44, about 55:45, about 54:46, about 53:47, about 52:48, about 51:49, about 50:50, about 49:51, about 48:52, about 47:53, about 46:54, about 45:55, about 44:56, about 43:57, about 42:58, about 41:59, about 40:60, about 39:61, about 38:62, about 37:63, about 36:64, about 35:65, about 34:66, about 33:67, about 32:68, about 31:69, about 30:70, about 29:71, about 28:72, about 27:73, about 26:74, about 25:75, about 24:76, about 23:77, about 22:78, about 21:79, about 20:80, about 19:81, about 18:82, about 17:83, about 16:84, about 15:85, about 14:86, about 13:87, about 12:88, about 11:89, about 10:90, about 9:91, about 8:92, about 7:93, about 6:94, about 5:95, about 4:96, about 3:97, about 2:98, or about 1:99 The disclosure also provides a faux leather or bonded leather article including and silk fibroin proteins or fragments thereof having any average weight average molecular weight and polydispersity described herein, and optionally any other limitations described herein, the article further including one or more of a silicone, a dye, a pigment, and a polyurethane as described herein.

In an embodiment, the disclosure described herein includes faux leather or bonded leather and faux leather or bonded leather articles processed with a silk composition described herein. In an embodiment, the disclosure described herein includes faux leather or bonded leather and faux leather or bonded leather articles coated with a silk composition described herein. In an embodiment, the disclosure described herein includes faux leather or bonded leather and faux leather or bonded leather articles repaired with a silk composition described herein, for example by filling, masking, or hiding a defect in the surface or structure of the faux leather.

As used herein, the term "hand" refers to the feel of a material, which may be further described as the feeling of softness, crispness, dryness, silkiness, smoothness, and combinations thereof. Material hand is also referred to as "drape." A material with a hard hand is coarse, rough, and generally less comfortable for the wearer. A material with a soft hand is fluid and smooth and generally more comfortable for the wearer. Material hand can be determined by comparison to collections of material samples, or by use of methods such as the Kawabata Evaluation System (KES) or the Fabric Assurance by Simple Testing (FAST) methods. Behera and Hari, *Ind. J Fibre & Textile Res.,* 1994, 19, 168-71. In some embodiments, and as described herein, silk can change the hand of faux leather, as may be evaluated by SynTouch Touch-Scale methodology or another methodology as described herein.

As used herein, a "coating" refers to a material, or combination of materials, that form a substantially continuous layer or film on an exterior surface of a substrate, such as faux leather or bonded leather or faux leather or bonded leather article. In some embodiments, a portion of the coating may penetrate at least partially into the substrate. In some embodiments, the coating may penetrate at least partially into the interstices of a substrate. In some embodiments, the coating may be infused into a surface of the substrate such that the application of the coating, or coating process, may include infusing (at the melting temperature of the substrate) at least one coating component at least partially into a surface of the substrate. A coating may be applied to a substrate by one or more of the processes described herein.

In embodiments described where the coating may be infused into a surface of the substrate, the coating may be codissolved in a surface of the substrate such that a component of the coating may be intermixed in the surface of the substrate to a depth of at least about 1 nm, or at least about 2 nm, or at least about 3 nm, or at least about 4 nm, or at least about 5 nm, or at least about 6 nm, or at least about 7 nm, or at least about 8 nm, or at least about 9 nm, or at least about 10 nm, or at least about 20 nm, or at least about 30 nm, or at least about 40 nm, or at least about 50 nm, or at least about 60 nm, or at least about 70 nm, or at least about 80 nm, or at least about 90 nm, or at least about 100 nm. In some embodiments, the coating may be infused into a surface of the substrate where the substrate includes faux leather or bonded leather or a faux leather or bonded leather article.

As used herein, the term "bath coating" encompasses coating a material in a bath, immersing a material in a bath, and submerging a material in a bath. Concepts of bath coating are set forth in U.S. Pat. No. 4,521,458, the entirety of which is incorporated by reference.

As used herein, and unless more specifically described, the term "drying" may refer to drying a coated material as described herein at a temperature greater than room temperature (i.e., 20° C.).

In an embodiment, the disclosure provides a faux leather or bonded leather or faux leather or bonded leather article processed, coated, and/or repaired with silk fibroin-based proteins or fragments thereof. In an embodiment, the disclosure provides a faux leather or bonded leather, or faux leather or bonded leather article processed, coated, or repaired with silk fibroin-based proteins or fragments thereof, wherein the faux leather or bonded leather, or faux leather or bonded leather article is a faux leather or bonded leather, or faux leather or bonded leather article used for human apparel, including apparel. In an embodiment, the disclosure provides a faux leather or bonded leather, or faux leather or bonded leather article processed, coated, or repaired with silk fibroin-based proteins or fragments thereof, wherein the faux leather or bonded leather, or faux leather or bonded leather article is used for automobile upholstery. In an embodiment, the disclosure provides a faux leather or bonded leather, or faux leather or bonded leather article processed, coated, or repaired with silk fibroin-based proteins or fragments thereof, wherein the faux leather or bonded leather, or faux leather or bonded leather article is used for aircraft upholstery. In an embodiment, the disclosure provides a faux leather or bonded leather, or faux leather or bonded leather article processed, coated, or repaired with silk fibroin-based proteins or fragments thereof, wherein the faux leather or bonded leather, or faux leather or bonded leather article is used for upholstery in transportation vehicles for public, commercial, military, or other use, including buses and trains. In an embodiment, the disclosure provides a faux leather or bonded leather, or faux leather or bonded leather article processed, coated, or repaired with silk fibroin-based proteins or fragments thereof, wherein the faux leather or bonded leather, or faux leather or bonded leather article is used for upholstery of a product that requires a high degree of resistance to wear as compared to normal upholstery.

In an embodiment, a faux leather or bonded leather, or faux leather or bonded leather article is treated with a polymer, such as polyglycolide (PGA), polyethylene glycols, copolymers of glycolide, glycolide/L-lactide copolymers (PGA/PLLA), glycolide/trimethylene carbonate copolymers (PGA/TMC), polylactides (PLA), stereocopolymers of PLA, poly-L-lactide (PLLA), poly-DL-lactide (PDLLA), L-lactide/DL-lactide copolymers, co-polymers of PLA, lactide/tetramethylglycolide copolymers, lactide/trimethylene carbonate copolymers, lactide/δ-valerolactone copolymers, lactide/ε-caprolactone copolymers, polydepsipeptides, PLA/polyethylene oxide copolymers, unsymmetrically 3,6-substituted poly-1,4-dioxane-2,5-diones, poly-β-hydroxybutyrate (PHBA), PHBA/β-hydroxyvalerate copolymers (PHBA/HVA), poly-β-hydroxypropionate (PHPA), poly-p-dioxanone (PDS), poly-δ-valerolactone, poly-ε-caprolactone, methylmethacrylate-N-vinyl pyrrolidine copolymers, polyesteramides, polyesters of oxalic acid, polydihydropyrans, polyalkyl-2-cyanoacrylates, polyurethanes (PU), polyvinylalcohols (PVA), polypeptides, poly-β-malic acid (PMLA), poly-β-alkanoic acids, polyvinylalcohol (PVA), polyethyleneoxide (PEO), chitine polymers, polyethylene, polypropylene, polyasetal, polyamides, polyesters, polysulphone, polyether ether ketone, polyethylene terephthalate, polycarbonate, polyaryl ether ketone, and polyether ketone ketone.

In an embodiment, an aqueous solution of pure silk fibroin-based protein fragments of the present disclosure is used to process and/or coat a faux or bonded leather, or faux or bonded leather article. In an embodiment, the concentration of silk in the solution ranges from about 0.1% to about 20.0%. In an embodiment, the concentration of silk in the solution ranges from about 0.1% to about 15.0%. In an embodiment, the concentration of silk in the solution ranges from about 0.5% to about 10.0%. In an embodiment, the concentration of silk in the solution ranges from about 1.0% to about 5.0%. In an embodiment, an aqueous solution of pure silk fibroin-based protein fragments of the present disclosure is applied directly to a faux or bonded leather, or faux or bonded leather article. Alternatively, silk microsphere and any additives may be used for processing and/or coating a faux or bonded leather, or faux or bonded leather article. In an embodiment, additives can be added to an aqueous solution of pure silk fibroin-based protein fragments of the present disclosure before coating (e.g., alcohols) to further enhance material properties. In an embodiment, a silk coating of the present disclosure can have a pattern to optimize properties of the silk on the faux or bonded leather, or faux or bonded leather article. In an embodiment, a coating is applied to a faux or bonded leather, or faux or bonded leather article under tension and/or lax to vary penetration in to the faux or bonded leather, or faux or bonded leather article.

In an embodiment, a composition of pure silk fibroin-based protein fragments of the present disclosure is used to repair a faux or bonded leather, or faux or bonded leather article. In some embodiments, the composition is viscous. In some embodiments, the composition is thixotropic. In some embodiments, the composition is a gel, a putty, a wax, a paste, or the like. In some embodiments, the composition is shaped as a repairing bar, for example a repairing crayon. In some embodiments, the composition is delivered from a syringe, a delivery gun, a brush-type applicator, a roller-type applicator, a pen or marker-type applicator, or the like. In some embodiments, the composition is co-delivered from a multiple syringe, for example a double syringe, or a double delivery gun, along a different composition designed to harden, initiate curing of, or otherwise modify the SPF composition. In an embodiment, the concentration of silk in the composition ranges from about 0.1% to about 50.0%. In an embodiment, the concentration of silk in the solution ranges from about 0.1% to about 35.0%. In an embodiment, the concentration of silk in the solution ranges from about 0.5% to about 30.0%. In an embodiment, the concentration of silk in the solution ranges from about 1.0% to about 25.0%. In an embodiment, a composition of pure silk fibroin-based protein fragments of the present disclosure is applied directly to a faux or bonded leather, or faux or bonded leather article, for example to a faux leather defect. Alternatively, silk microsphere and any additives may be used for repairing a faux or bonded leather, or faux or bonded leather article. In an embodiment, additives can be added to the composition of pure silk fibroin-based protein fragments of the present disclosure before coating (e.g., alcohols) to further enhance material properties. In an embodiment, a composition is applied to a faux or bonded leather, or faux or bonded leather article under tension and/or lax to vary penetration in to the faux leather, faux leather article, or faux leather defect.

Chemical Agents for Use with Faux Leather and Faux Leather Articles Coated with Silk Fibroin-Based Protein Fragments In certain embodiments, chemical agents may be used to pretreat, treat, and/or post-treat a faux or bonded leather, or faux or bonded leather article described herein. In some embodiments, the silk and/or SPF solutions (e.g., SFS), or compositions, described herein, may include one or more of the chemical agents described herein. In some embodiments, the silk and/or SPF solutions or compositions described herein, may replace one or more of the chemical agents described herein. In some embodiments, the chemical agents may be selected from the group consisting of silicone, casein, an acidic agent, a dyeing agent, a pigment dye, a traditional finishing agent, and a technical finishing agent. In some embodiments, chemical agents may include one or more agents recited in Table 2. In some embodiments, the chemical agent may be selected from the group consisting of aqueous lacquers, waxes, oils, binders (protein or other), fillers, hand-modifiers, levelling agents, solvent lacquers, water-based lacquers, penetrators, acrylic resins, butadiene resins, compact resins, hybrid resins, impregnation resins, rheology modifiers, solvent dullers, solvent urethanes, water-based dullers, water-based topcoats, chromes, acidic dyes, basic dyes, dyes (chromium-based or other), colorants, and combinations thereof.

In an embodiment, the disclosure provides a faux or bonded leather, or faux or bonded leather article processed with a composition comprising silk based proteins or fragments thereof having an average weight average molecular weight range of about 5 kDa to about 144 kDa, wherein the faux or bonded leather, or faux or bonded leather article is pretreated with a wetting agent. In an embodiment, the disclosure provides a faux or bonded leather, or faux or bonded leather article having a coating, wherein the coating comprises silk based proteins or fragments thereof having an average weight average molecular weight range of about 5 kDa to about 144 kDa, wherein the faux or bonded leather, or faux or bonded leather article is pretreated with a wetting agent. In an embodiment, the disclosure provides a faux or bonded leather, or faux or bonded leather article including a defect repairing filling, wherein the filling comprises silk based proteins or fragments thereof having an average weight average molecular weight range of about 5 kDa to about 144 kDa, wherein the faux or bonded leather, or faux or bonded leather article is pretreated with a wetting agent. In an embodiment, the wetting agent improves one or more coating properties. Suitable wetting agents are known to those of skill in the art. Exemplary, non-limiting examples of wetting agents from a representative supplier, Lamberti SPA, are given in the following table.

| | |
|---|---|
| Imbitex NDT | Non silicone low foaming with high wetting in both hot or cold conditions, with good detergency and good stability to alkalis. |
| Imbitex TBL | Wetting and de-aerating agent. |
| Imbitex MRC | Wetting and penetrating agent for mercerizing of |
| Tensolam Na liq. | Low foam, special wetting and dispersing agent for non- woven wet treatments. |
| Imbitex NRW3 | Wetting agent for water-and oil repellent finishing. |

In an embodiment, the disclosure provides a faux or bonded leather, or faux or bonded leather article processed with a composition comprising silk based proteins or fragments thereof having an average weight average molecular weight range of about 5 kDa to about 144 kDa, wherein the faux or bonded leather, or faux or bonded leather article is pretreated with a detergent. In an embodiment, the disclosure provides a faux or bonded leather, or faux or bonded leather article having a coating, wherein the coating comprises silk based proteins or fragments thereof having an average weight average molecular weight range of about 5 kDa to about 144 kDa, wherein the faux or bonded leather, or faux or bonded leather article is pretreated with a detergent.

In an embodiment, the disclosure provides a faux or bonded leather, or faux or bonded leather article including a defect repairing filling, wherein the filling comprises silk based proteins or fragments thereof having an average weight average molecular weight range of about 5 kDa to about 144 kDa, wherein the faux or bonded leather, or faux or bonded leather article is pretreated with a detergent. In an embodiment, the detergent improves one or more coating properties. Suitable detergents are known to those of skill in the art. Exemplary, non-limiting examples of detergents from a representative supplier, Lamberti SPA, are given in the following table.

| | |
|---|---|
| Biorol CPNN | Wetting and detergent agent with alkaline stability in NaOH up to 10° C. Recommended for continuous scouring, bleaching, and Jigger applications. |
| Biorol JK new | Wetting and detergent agent with extremely low foam properties, recommended for high bath turbulence machine (e.g., jet, overflow, etc.). |
| Biorol OW 60 | General-purpose wetting and detergent agent suitable for desizing, scouring, and bleaching processes. |
| Biorol OWK | Detergent/wetting agent, low foaming, high concentration, recommended for over-flow. Useful for removal of silicone oil on Lycra blends. |
| Cesapon Silk liq. | Specific scouring, de-gumming agent for silk. |
| Cesapon Extra | High detergent power product containing solvent. |

In an embodiment, the disclosure provides a faux or bonded leather, or faux or bonded leather article processed with a composition comprising silk based proteins or fragments thereof having an average weight average molecular weight range of about 5 kDa to about 144 kDa, wherein the faux or bonded leather, or faux or bonded leather article is pretreated with a sequestering or dispersing agent. In an embodiment, the disclosure provides a faux or bonded leather, or faux or bonded leather article having a coating, wherein the coating comprises silk based proteins or fragments thereof having an average weight average molecular weight range of about 5 kDa to about 144 kDa, wherein the faux or bonded leather, or faux or bonded leather article is pretreated with a sequestering or dispersing agent. In an embodiment, the disclosure provides a faux or bonded leather, or faux or bonded leather article including a defect repairing filling, wherein the filling comprises silk based proteins or fragments thereof having an average weight average molecular weight range of about 5 kDa to about 144 kDa, wherein the faux or bonded leather, or faux or bonded leather article is pretreated with a sequestering or dispersing agent. Suitable sequestering or dispersing agents are known to those of skill in the art. Exemplary, non-limiting examples of sequestering or dispersing agents from a representative supplier, Lamberti SPA, are given in the following table.

| | |
|---|---|
| Lamegal DSP | Dispersing and anti-redepositing agent useful for preparation dyeing and after soaping of dyed and printed materials with reactive and vat dyes. This product is also useful as an anti- oligomer agent in reduction clearing of polyester, dyed or printed with disperse dyes. |
| Chelam TLW/T | Multi-purpose sequestering and dispersing agent for a wide variety of textile processes. No shade variation on dyestuff containing metals. |
| Lamegal TL5 | Multi-purpose sequestering and dispersing agent for a wide variety of textile processes. |

In an embodiment, the disclosure provides a faux or bonded leather, or faux or bonded leather article processed with a composition comprising silk based proteins or fragments thereof having an average weight average molecular weight range of about 5 kDa to about 144 kDa, wherein the faux or bonded leather, or faux or bonded leather article is pretreated with an enzyme. In an embodiment, the disclosure provides a faux or bonded leather, or faux or bonded leather article having a coating, wherein the coating comprises silk based proteins or fragments thereof having an average weight average molecular weight range of about 5 kDa to about 144 kDa, wherein the faux or bonded leather, or faux or bonded leather article is pretreated with an enzyme. In an embodiment, the disclosure provides a faux or bonded leather, or faux or bonded leather article including a defect repairing filling, wherein the filling comprises silk based proteins or fragments thereof having an average weight average molecular weight range of about 5 kDa to about 144 kDa, wherein the faux or bonded leather, or faux or bonded leather article is pretreated with an enzyme. Suitable enzymes are known to those of skill in the art. Exemplary, non-limiting examples of enzymes from a representative supplier, Lamberti SPA, are given in the following table.

| | |
|---|---|
| Lazim HT | Thermo-stable amylase for rapid high temperature desizing. |
| Lazim PE | Specific enzyme for bioscouring; provides optimal wettability, it improves dyeing and color fastness without causing depolymerization and fabric strength loss. |

In an embodiment, the disclosure provides a faux or bonded leather, or faux or bonded leather article processed with a composition comprising silk based proteins or fragments thereof having an average weight average molecular weight range of about 5 kDa to about 144 kDa, wherein the faux or bonded leather, or faux or bonded leather article is pretreated with a bleaching agent. In an embodiment, the disclosure provides a faux or bonded leather, or faux or bonded leather article having a coating, wherein the coating comprises silk based proteins or fragments thereof having an average weight average molecular weight range of about 5 kDa to about 144 kDa, wherein the faux or bonded leather, or faux or bonded leather article is pretreated with a bleaching agent. In an embodiment, the disclosure provides a faux or bonded leather, or faux or bonded leather article including a defect repairing filling, wherein the filling comprises silk based proteins or fragments thereof having an average weight average molecular weight range of about 5 kDa to about 144 kDa, wherein the faux or bonded leather, or faux or bonded leather article is pretreated with a bleaching agent. Suitable bleaching agents are known to those of skill in the art. Exemplary, non-limiting examples of bleaching agents from a representative supplier, Lamberti SPA, are given in the following table.

| | |
|---|---|
| Stabilox OTN conc. | Highly concentrated stabilizer for alkaline bleaching with hydrogen peroxide. Suitable for a wide variety of |

In an embodiment, the disclosure provides a faux or bonded leather, or faux or bonded leather article processed with a composition comprising silk based proteins or fragments thereof having an average weight average molecular weight range of about 5 kDa to about 144 kDa, wherein the faux or bonded leather, or faux or bonded leather article is pretreated with an antifoaming agent. In an embodiment, the disclosure provides a faux or bonded leather, or faux or bonded leather article having a coating, wherein the coating comprises silk based proteins or fragments thereof having an average weight average molecular weight range of about 5 kDa to about 144 kDa, wherein the faux or bonded leather, or faux or bonded leather article is pretreated with an antifoaming agent. In an embodiment, the disclosure provides a faux or bonded leather, or faux or bonded leather article including a defect repairing filling, wherein the filling comprises silk based proteins or fragments thereof having an average weight average molecular weight range of about 5 kDa to about 144 kDa, wherein the faux or bonded leather, or faux or bonded leather article is pretreated with an antifoaming agent. Suitable antifoaming agents are known to those of skill in the art. Exemplary, non-limiting examples of antifoaming agents from a representative supplier, Lamberti SPA, are given in the following table.

| | |
|---|---|
| Antifoam SE | General purpose defoaming agent. |
| Defomex JET | Silicone defoamer effective up to 130° C. Recommended for HT and JET dyeing systems. |
| Defomex 2033 | Non-silicone defoamer. |

In an embodiment, the disclosure provides a faux or bonded leather, or faux or bonded leather article processed with a composition comprising silk based proteins or fragments thereof having an average weight average molecular weight range of about 5 kDa to about 144 kDa, wherein the faux or bonded leather, or faux or bonded leather article is pretreated with an anti-creasing agent. In an embodiment, the disclosure provides a faux or bonded leather, or faux or bonded leather article having a coating, wherein the coating comprises silk based proteins or fragments thereof having an average weight average molecular weight range of about 5 kDa to about 144 kDa, wherein the faux or bonded leather, or faux or bonded leather article is pretreated with an anti-creasing agent. In an embodiment, the disclosure provides a faux or bonded leather, or faux or bonded leather article including a defect repairing filling, wherein the filling comprises silk based proteins or fragments thereof having an average weight average molecular weight range of about 5 kDa to about 144 kDa, wherein the faux or bonded leather, or faux or bonded leather article is pretreated with an anti-creasing agent. Suitable anti-creasing agents are known to those of skill in the art. Exemplary, non-limiting examples of anti-creasing agents from a representative supplier, Lamberti SPA, are given in the following table.

| | |
|---|---|
| Lubisol AM | Lubricating and anti-creasing agent for rope wet operation on all kind of fibers and machines. |

In an embodiment, the disclosure provides a faux or bonded leather, or faux or bonded leather article processed with a composition comprising silk based proteins or fragments thereof having an average weight average molecular weight range of about 5 kDa to about 144 kDa, wherein the faux or bonded leather, or faux or bonded leather article is treated with a dye dispersing agent. In an embodiment, the disclosure provides a faux or bonded leather, or faux or bonded leather article having a coating, wherein the coating comprises silk based proteins or fragments thereof having an average weight average molecular weight range of about 5 kDa to about 144 kDa, wherein the faux or bonded leather, or faux or bonded leather article is treated with a dye dispersing agent. In an embodiment, the disclosure provides a faux or bonded leather, or faux or bonded leather article including a defect repairing filling, wherein the filling comprises silk based proteins or fragments thereof having an average weight average molecular weight range of about 5 kDa to about 144 kDa, wherein the faux or bonded leather, or faux or bonded leather article is treated with a dye dispersing agent. Suitable dye dispersing agents are known to those of skill in the art. Exemplary, non-limiting examples of dye dispersing agents from a representative supplier, Lamberti SPA, are given in the following table.

| | |
|---|---|
| Lamegal BO | Liquid dispersing agent (non-ionic), suitable for direct, reactive, disperse dyeing and PES stripping. |
| Lamegal DSP | Dispersing and anti back-staining agent in preparation, dyeing and soaping of dyed and printed materials. Antioligomer agent. |
| Lamegal 619 | Effective low foam dispersing leveling agent for dyeing of PES. |
| Lamegal TL5 | Multi-purpose sequestering and dispersing agent for a variety of textile processes. |

In an embodiment, the disclosure provides a faux or bonded leather, or faux or bonded leather article processed with a composition comprising silk based proteins or fragments thereof having an average weight average molecular weight range of about 5 kDa to about 144 kDa, wherein the faux or bonded leather, or faux or bonded leather article is treated with a dye leveling agent. In an embodiment, the disclosure provides a faux or bonded leather, or faux or bonded leather article having a coating, wherein the coating comprises silk based proteins or fragments thereof having an average weight average molecular weight range of about 5 kDa to about 144 kDa, wherein the faux or bonded leather, or faux or bonded leather article is treated with a dye leveling agent. In an embodiment, the disclosure provides a faux or bonded leather, or faux or bonded leather article including a defect repairing filling, wherein the filling comprises silk based proteins or fragments thereof having an average weight average molecular weight range of about 5 article is treated with a dye leveling agent. Suitable dye leveling agents are known to those of skill in the art. Exemplary, non-limiting examples of dye leveling agents from a representative supplier, Lamberti SPA, are given in the following table.

| | |
|---|---|
| Lamegal A 12 | Leveling agent for dyeing on wool, polyamide and its blends with acid or metal |

In an embodiment, the disclosure provides a faux or bonded leather, or faux or bonded leather article processed with a composition comprising silk based proteins or fragments thereof having an average weight average molecular weight range of about 5 kDa to about 144 kDa, wherein the faux or bonded leather, or faux or bonded leather article is treated with a dye fixing agent. In an embodiment, the disclosure provides a faux or bonded leather, or faux or bonded leather article having a coating, wherein the coating comprises silk based proteins or fragments thereof having an average weight average molecular weight range of about 5 kDa to about 144 kDa, wherein the faux or bonded leather, or faux or bonded leather article is treated with a dye fixing agent. In an embodiment, the disclosure provides a faux or bonded leather, or faux or bonded leather article including a defect repairing filling, wherein the filling comprises silk based proteins or fragments thereof having an average weight average molecular weight range of about 5 kDa to about 144 kDa, wherein the faux or bonded leather, or faux or bonded leather article is treated with a dye fixing agent. Suitable dye fixing agents are known to those of skill in the art. Exemplary, non-limiting examples of dye fixing agents from a representative supplier, Lamberti SPA, are given in the following table.

| | |
|---|---|
| Lamfix L | Fixing agent for direct and reactive dyestuffs, containing formaldehyde. |

| | |
|---|---|
| Lamfix LU conc. | Formaldehyde free cationic fixing agent for direct and reactive dyes. It does not affect the shade and light fastness. |
| Lamfix PA/TR | Fixing agent to improve the wet fastness of acid dyes on polyamide fabrics, dyed or printed and polyamide yarns. Retarding agent in dyeing of Polyamide/cellulosic blends with direct dyes. |

In an embodiment, the disclosure provides a faux or bonded leather, or faux or bonded leather article processed with a composition comprising silk based proteins or fragments thereof having an average weight average molecular weight range of about 5 kDa to about 144 kDa, wherein the faux or bonded leather, or faux or bonded leather article is treated with a dye special resin agent. In an embodiment, the disclosure provides a faux or bonded leather, or faux or bonded leather article having a coating, wherein the coating comprises silk based proteins or fragments thereof having an average weight average molecular weight range of about 5 kDa to about 144 kDa, wherein the faux or bonded leather, or faux or bonded leather article is treated with a dye special resin agent. In an embodiment, the disclosure provides a faux or bonded leather, or faux or bonded leather article including a defect repairing filling, wherein the filling comprises silk based proteins or fragments thereof having an average weight average molecular weight range of about 5 kDa to about 144 kDa, wherein the faux or bonded leather, or faux or bonded leather article is treated with a dye special resin agent. Suitable dye special resin agents are known to those of skill in the art. Exemplary, non-limiting examples of dye special resin agents from a representative supplier, Lamberti SPA, are given in the following table.

| | |
|---|---|
| Denifast TC | Special resin for cationization of cellulose fibers to obtain special effects ("DENIFAST system" and "DENISOL system"). |
| Cobral DD/50 | Special resin for cationization of cellulose fibers to obtain special effect ("DENIFAST system" and "DENISOL system"). |

In an embodiment, the disclosure provides a faux or bonded leather, or faux or bonded leather article processed with a composition comprising silk based proteins or fragments thereof having an average weight average molecular weight range of about 5 article is treated with a dye anti-reducing agent. In an embodiment, the disclosure provides a faux or bonded leather, or faux or bonded leather article having a coating, wherein the coating comprises silk based proteins or fragments thereof having an average weight average molecular weight range of about 5 kDa to about 144 kDa, wherein the faux or bonded leather, or faux or bonded leather article is treated with a dye anti-reducing agent. In an embodiment, the disclosure provides a faux or bonded leather, or faux or bonded leather article including a defect repairing filling, wherein the filling comprises silk based proteins or fragments thereof having an average weight average molecular weight range of about 5 kDa to about 144 kDa, wherein the faux or bonded leather, or faux or bonded leather article is treated with a dye anti-reducing agent. Suitable dye anti-reducing agents are known to those of skill in the art. Exemplary, non-limiting examples of dye anti-reducing agents from a representative supplier, Lamberti SPA, are given in the following table.

| | |
|---|---|
| Lamberti Redox L2S gra | Anti-reducing agent in grain form. 100% active content. |
| Lamberti Redox L2S liq. | Anti-reducing agent in liquid form for automatic dosage. |

In an embodiment, the disclosure provides a faux or bonded leather, or faux or bonded leather article processed with a composition comprising silk based proteins or fragments thereof having an average weight average molecular weight range of about 5 kDa to about 144 kDa, wherein the faux or bonded leather, or faux or bonded leather article is treated with a pigment dye system anti-migrating agent. In an embodiment, the disclosure provides a faux or bonded leather, or faux or bonded leather article having a coating, wherein the coating comprises silk based proteins or fragments thereof having an average weight average molecular weight range of about 5 kDa to about 144 kDa, wherein the faux leather or faux leather article is treated with a pigment dye system anti-migrating agent. In an embodiment, the disclosure provides a faux or bonded leather, or faux or bonded leather article including a defect repairing filling, wherein the filling comprises silk based proteins or fragments thereof having an average weight average molecular weight range of about 5 kDa to about 144 kDa, wherein the faux or bonded leather, or faux or bonded leather article is treated with a pigment dye system anti-migrating agent. Suitable pigment dye system anti-migrating agents are known to those of skill in the art. Exemplary, non-limiting examples of pigment dye system anti-migrating agents from a representative supplier, Lamberti SPA, are given in the following table.

| | |
|---|---|
| Neopat Compound 96/m conc. | Compound, developed as migration inhibitor for continuous dyeing process with pigments (pad-dryprocess). |

In an embodiment, the disclosure provides a faux or bonded leather, or faux or bonded leather article processed with a composition comprising silk based proteins or fragments thereof having an average weight average molecular weight range of about 5 kDa to about 144 kDa, wherein the faux or bonded leather, or faux or bonded leather article is treated with a pigment dye system binder. In an embodiment, the disclosure provides a faux or bonded leather, or faux or bonded leather article having a coating, wherein the coating comprises silk based proteins or fragments thereof having an average weight average molecular weight range of about 5 kDa to about 144 kDa, wherein the faux or bonded leather, or faux or bonded leather article is treated with a pigment dye system binder. In an embodiment, the disclosure provides a faux or bonded leather, or faux or bonded leather article including a defect repairing filling, wherein the filling comprises silk based proteins or fragments thereof having an average weight average molecular weight range of about 5 kDa to about 144 kDa, wherein the faux or bonded leather, or faux or bonded leather article is treated with a pigment dye system binder. Suitable pigment dye system binders are known to those of skill in the art. Exemplary, non-limiting examples of pigment dye system binders from a representative supplier, Lamberti SPA, are given in the following table.

| | |
|---|---|
| Neopat Binder PM/S conc. | Concentrated version of a specific binder used to prepare pad-liquor for dyeing with pigments (pad-dry process). |
| Neopat compound FTN | Highly concentrated compound of surfactants and polymers specifically developed for pigment dyeing and pigment-reactive dyeing process; especially for medium/dark shades for wash off effect. |

In an embodiment, the disclosure provides a faux or bonded leather, or faux or bonded leather article processed with a composition comprising silk based proteins or fragments thereof having an average weight average molecular weight range of about 5 kDa to about 144 kDa, wherein the faux or bonded leather, or faux or bonded leather article is treated with a pigment dye system binder and anti-migrating agent combination. In an embodiment, the disclosure provides a faux or bonded leather, or faux or bonded leather article having a coating, wherein the coating comprises silk based proteins or fragments thereof having an average weight average molecular weight range of about 5 kDa to about 144 kDa, wherein the faux or bonded leather, or faux or bonded leather article is treated with a pigment dye system binder and anti-migrating agent combination. In an embodiment, the disclosure provides a faux or bonded leather, or faux or bonded leather article including a defect repairing filling, wherein the filling comprises silk based proteins or fragments thereof having an average weight average molecular weight range of about 5 kDa to about 144 kDa, wherein the faux or bonded leather, or faux or bonded leather article is treated with pigment dye system binder and anti-migrating agent combination. Suitable pigment dye system binder and anti-migrating agent combinations are known to those of skill in the art. Exemplary, non-limiting examples of pigment dye system binder and anti-migrating agent combinations from a representative supplier, Lamberti SPA, are given in the following table.

| | |
|---|---|
| Neopat Compound PK1 | Highly concentrated all-in-one product specifically developed as migration inhibitor with specific binder for continuous dyeing process with pigments (pad-dry process). |

In an embodiment, the disclosure provides a faux or bonded leather, or faux or bonded leather article processed with a composition comprising silk based proteins or fragments thereof having an average weight average molecular weight range of about 5 article is treated with a delave agent.

In an embodiment, the disclosure provides a faux or bonded leather, or faux or bonded leather article having a coating, wherein the coating comprises silk based proteins or fragments thereof having an average weight average molecular weight range of about 5 kDa to about 144 kDa, wherein the faux or bonded leather, or faux or bonded leather article is treated with a delave agent. In an embodiment, the disclosure provides a faux or bonded leather, or faux or bonded leather article including a defect repairing filling, wherein the filling comprises silk based proteins or fragments thereof having an average weight average molecular weight range of about 5 kDa to about 144 kDa, wherein the faux or bonded leather, or faux or bonded leather article is treated with a delave agent. Suitable delave agents are known to those of skill in the art. Exemplary, non-limiting examples of delave agents from a representative supplier, Lamberti SPA, are given in the following table.

In an embodiment, the disclosure provides a faux or bonded leather, or faux or bonded leather article processed with a composition comprising silk based proteins or fragments thereof having an average weight average molecular weight range of about 5 kDa to about 144 kDa, wherein the faux or bonded leather, or faux or bonded leather article is traditionally finished with a wrinkle free treatment. In an embodiment, the disclosure provides a faux or bonded leather, or faux or bonded leather article having a coating, wherein the coating comprises silk based proteins or fragments thereof having an average weight average molecular weight range of about 5 kDa to about 144 kDa, wherein the faux or bonded leather, or faux or bonded leather article is traditionally finished with a wrinkle free treatment. In an embodiment, the disclosure provides a faux or bonded leather, or faux or bonded leather article including a defect repairing filling, wherein the filling comprises silk based proteins or fragments thereof having an average weight average molecular weight range of about 5 kDa to about 144 kDa, wherein the faux or bonded leather, or faux or bonded leather article is traditionally finished with a wrinkle free treatment. Suitable wrinkle free treatments are known to those of skill in the art. Exemplary, non-limiting examples of wrinkle free treatments from a representative supplier, Lamberti SPA, are given in the following table.

| | |
|---|---|
| Cellofix ULF conc. | Anti-crease modified glyoxalic resin for finishing of cottons, cellulosics and blends with synthetics fibers. |
| Poliflex PO 40 | Polyethilenic resin for waxy, full and slippy handle by foulard applications. |
| Rolflex WF | Aliphatic waterborne Nano-PU dispersion used as extender for wrinkle free treatments. |

In an embodiment, the disclosure provides a faux or bonded leather, or faux or bonded leather article processed with a composition comprising silk based proteins or fragments thereof having an average weight average molecular weight range of about 5 kDa to about 144 kDa, wherein the faux or bonded leather, or faux or bonded leather article is traditionally finished with a softener. In an embodiment, the disclosure provides a faux or bonded leather, or faux or bonded leather article having a coating, wherein the coating comprises silk based proteins or fragments thereof having an average weight average molecular weight range of about 5 kDa to about 144 kDa, wherein the faux or bonded leather, or faux or bonded leather article is traditionally finished with a softener. In an embodiment, the disclosure provides a faux or bonded leather, or faux or bonded leather article including a defect repairing filling, wherein the filling comprises silk based proteins or fragments thereof having an average weight average molecular weight range of about 5 kDa to about 144 kDa, wherein the faux or bonded leather, or faux or bonded leather article is traditionally finished with a softener. Suitable softeners are known to those of skill in the art. Exemplary, non-limiting examples of softeners from a representative supplier, Lamberti SPA, are given in the following table.

| | |
|---|---|
| Texamina C/FPN | Cationic softening agent with a very soft handle particularly recommended for application by exhaustion for all kind of fabrics. Suitable also for cone application. |
| Texamina C SAL flakes | 100% cationic softening agent in flakes form for all type of fabrics. Dispersible at room temperature. |
| Texamina CL LIQ. | Anphoteric softening agent for all types of fabrics. Not yellowing. |
| Texamina HVO | Anphoteric softening agent for woven and knitted fabrics of cotton, other cellulosics and blends. Provides a soft, smooth and dry handle. Applied by padding. |
| Texamina SIL | Nonionic silicon dispersion in water. Excellent softening, lubricating and anti-static properties for all fibre types by padding. |
| Texamina SILK | Special cationic softener with silk protein inside. Provides a "swollen touch" particularly suitable for cellulosic, wool, silk. |
| Lamfinish LW | All-in compound based on special polymeric hydrophilic softeners; by coating, foulard, and exhaustion. |
| Elastolam E50 | General purpose mono-component silicone elastomeric softener for textile finishing. |
| Elastolam EC 100 | Modified polysiloxane micro-emulsion which gives a permanent finishing, with extremely soft and silky handle. |

In an embodiment, the disclosure provides a faux or bonded leather, or faux or bonded leather article processed with a composition comprising silk based proteins or fragments thereof having an average weight average molecular weight range of about 5 kDa to about 144 kDa, wherein the faux or bonded leather, or faux or bonded leather article is traditionally finished with a handle modifier. In an embodiment, the disclosure provides a faux or bonded leather, or faux or bonded leather article having a coating, wherein the coating comprises silk based proteins or fragments thereof having an average weight average molecular weight range of about 5 kDa to about 144 kDa, wherein the faux or bonded leather, or faux or bonded leather article is traditionally finished with a handle modifier. In an embodiment, the disclosure provides a faux or bonded leather, or faux or bonded leather article including a defect repairing filling, wherein the filling comprises silk based proteins or fragments thereof having an average weight average molecular weight range of about 5 kDa to about 144 kDa, wherein the faux or bonded leather, or faux or bonded leather article is traditionally finished with a handle modifier. Suitable handle modifiers are known to those of skill in the art. Exemplary, non-limiting examples of handle modifiers from a representative supplier, Lamberti SPA, are given in the following table.

| | |
|---|---|
| Poliflex CSW | Cationic anti-slipping agent. |
| Poliflex R 75 | Parafine finishing agent to give waxy handle. |
| Poliflex s | Compound specifically developed for special writing |
| Poliflex m | Compound for special dry-waxy handle. |
| Lamsoft SW 24 | Compound for special slippy handle specifically developed for coating application. |
| Lamfinish SLIPPY | All-in-one compound to get a slippy touch; by coating. |
| Lamfinish GUMMY | All-in-one compound to get a gummy touch; by coating. |
| Lamfinish OLDRY | All-in-one compound to get dry-sandy touch especially suitable for vintage effects; by coating. |

In an embodiment, the disclosure provides a faux or bonded leather, or faux or bonded leather article processed with a composition comprising silk based proteins or fragments thereof having an average weight average molecular weight range of about 5 kDa to about 144 kDa, wherein the faux or bonded leather, or faux or bonded leather article is traditionally finished with a waterborne polyurethane (PU) dispersion. In an embodiment, the disclosure provides a faux or bonded leather, or faux or bonded leather article having a coating, wherein the coating comprises silk based proteins or fragments thereof having an average weight average molecular weight range of about 5 kDa to about 144 kDa, wherein the faux or bonded leather, or faux or bonded leather article is traditionally finished with a waterborne polyurethane (PU) dispersion. In an embodiment, the disclosure provides a faux or bonded leather, or faux or bonded leather article including a defect repairing filling, wherein the filling comprises silk based proteins or fragments thereof having an average weight average molecular weight range of about 5 kDa to about 144 kDa, wherein the faux or bonded leather, or faux or bonded leather article is traditionally finished with a waterborne polyurethane (PU) dispersion. Suitable waterborne polyurethane dispersions for traditional finishing are known to those of skill in the art. Exemplary, non-limiting examples of waterborne polyurethane dispersions for traditional finishing from a representative supplier, Lamberti SPA, are given in the following table.

| | |
|---|---|
| Rolflex LB 2 | Aliphatic waterborne PU dispersion particularly suggested for the formulation of textile coatings where bright and rigid top finish is required. It is particularly suitable as a finishing agent for organza touch on silk fabrics. Transparent and shiny. |
| Rolflex HP 51 | Aliphatic waterborne PU dispersion particularly suggested for the formulation of textile coatings for outwear, luggage, technical articles especially where hard and flexible touch is required. Transparent and shiny. |
| Rolflex PU 879 | Aliphatic waterborne PU dispersion particularly suggested for the formulation of textile coatings for outwear, luggage, technical articles where a medium-hard and flexible touch is required. |
| Rolflex ALM | Aliphatic waterborne PU dispersion particularly suggested for the formulation of textile coatings for outwear, luggage, technical articles where a soft and flexible touch is required. Can be also suitable for printing application. |
| Rolflex AP | Aliphatic waterborne PU dispersion particularly suggested for the formulation of textile coatings for outwear, fashion where a soft and gummy touch is required. |
| Rolflex W4 | Aliphatic waterborne PU dispersion particularly suggested for the formulation of textile coatings for clothing, outwear where a full, soft and non sticky touch is required. |
| Rolflex ZB7 | Aliphatic waterborne PU dispersion particularly suggested for the formulation of textile coatings for clothing, outwear, sportswear, fashion and technical articles for industrial applications. The product has a very high charge digestion properties, electrolytes stability and excellent mechanical and tear resistance. Can be also suitable for foam coating and printing application. |
| Rolflex BZ 78 | Aliphatic waterborne PU dispersion particularly suggested for the formulation of textile coatings for clothing, outwear, sportswear, fashion and technical articles for industrial applications. The product has an excellent hydrolysis resistance, a very high charge digestion and electrolytes stability and an excellent mechanical and tear resistance. Can be also suitable for foam coating and printing application. |
| Rolflex K 110 | Gives to the coated fabric a full, soft, and slightly sticky handle with excellent fastness on all types of fabrics. |
| Rolflex OP 80 | Aliphatic waterborne PU dispersion particularly suggested for the formulation of textile coatings for outwear, luggage and fashion finishes where an opaque non writing effect is desired. |

| | |
|---|---|
| Rolflex NBC | Aliphatic waterborne PU dispersion generally used by padding application as a filling and zero formaldehyde sizing agent. Can be used for outwear and fashion finishing where a full, elastic and non-sticky touch is required. |
| Rolflex PAD | Aliphatic waterborne PU dispersion specifically designed for padding application for outwear, sportswear and fashion applications where a full, elastic and non sticky touch is required. Excellent washing and dry cleaning fastness as well as good bath stability. |
| Rolflex PN | Aliphatic waterborne PU dispersion generally applied by padding application for outerwear and fashion high quality applications where strong, elastic non sticky finishes are required. |
| Elafix PV 4 | Aliphatic blocked isocyanate nano-dispersion used in order to give anti-felting and anti-pilling properties to pure wool fabrics and his blend. |
| Rolflex SW3 | Aliphatic waterborne PU dispersion particularly suggested to be used by padding application for the finishing of outwear, sportswear and fashion where a slippery and elastic touch is required. It is also a good anti-pilling agent. Excellent in wool application. |
| Rolflex C 86 | Aliphatic cationic waterborne PU dispersion particularly suggested for the formulation of textile coatings for clothing, outwear, fashion where medium-soft and pleasant full touch is required. Fabrics treated with the product can be dyed with a selection of dyes, to get double-color effects of different intensity. |
| Rolflex CN 29 | Aliphatic cationic waterborne PU dispersion particularly suggested for the formulation of textile coatings for clothing, outwear, fashion where soft and pleasant full touch is required. Fabrics treated with the product can be dyed with a selection of dyes, to get double-color effects of different intensity. |

In an embodiment, the disclosure provides a faux or bonded leather, or faux or bonded leather article processed with a composition comprising silk based proteins or fragments thereof having an average weight average molecular weight range of about 5 kDa to about 144 kDa, wherein the faux or bonded leather, or faux or bonded leather article is traditionally finished with a finishing resin. In an embodiment, the disclosure provides a faux or bonded leather, or faux or bonded leather article having a coating, wherein the coating comprises silk based proteins or fragments thereof having an average weight average molecular weight range of about 5 kDa to about 144 kDa, wherein the faux or bonded leather, or faux or bonded leather article is traditionally finished with a finishing resin. In an embodiment, the disclosure provides a faux or bonded leather, or faux or bonded leather article including a defect repairing filling, wherein the filling comprises silk based proteins or fragments thereof having an average weight average molecular weight range of about 5 kDa to about 144 kDa, wherein the faux or bonded leather, or faux or bonded leather article is traditionally finished with a finishing resin. Suitable finishing resins are known to those of skill in the art. Exemplary, non-limiting examples of finishing resins from a representative supplier, Lamberti SPA, are given in the following table.

| | |
|---|---|
| Textol 110 | Handle modifier with very soft handle for coating |
| Textol RGD | Water emulsion of acrylic copolymer for textile coating, with very rigid handle. |
| Textol SB 21 Appretto PV/CC | Butadienic resin for finishing and binder for textile Vinylacetate water dispersion for rigid stiffening |
| Amisolo B | CMS water dispersion for textile finishing as stiffening |
| Lamovil RP | PVOH stabilized solution as stiffening agent |

In an embodiment, the disclosure provides a faux or bonded leather, or faux or bonded leather article processed with a composition comprising silk based proteins or fragments thereof having an average weight average molecular weight range of about 5 kDa to about 144 kDa, wherein the faux or bonded leather, or faux or bonded leather article is technically finished with a waterborne polyurethane dispersion. In an embodiment, the disclosure provides a faux or bonded leather, or faux or bonded leather article having a coating, wherein the coating comprises silk based proteins or fragments thereof having an average weight average molecular weight range of about 5 kDa to about 144 kDa, wherein the faux or bonded leather, or faux or bonded leather article is technically finished with a waterborne polyurethane dispersion. In an embodiment, the disclosure provides a faux or bonded leather, or faux or bonded leather article including a defect repairing filling, wherein the filling comprises silk based proteins or fragments thereof having an average weight average molecular weight range of about 5 kDa to about 144 kDa, wherein the faux or bonded leather, or faux or bonded leather article is technically finished with a waterborne polyurethane dispersion. Suitable waterborne polyurethane dispersions for technical finishing are known to those of skill in the art. Exemplary, non-limiting examples of waterborne polyurethane dispersions for technical finishing from a representative supplier, Lamb erti SPA, are given in the following table.

| | |
|---|---|
| Rolflex AFP | Aliphatic polyether polyurethane dispersion in water. The product has high hydrolysis resistance, good breaking load resistance and excellent tear resistance. |
| Rolflex ACF | Aliphatic polycarbonate polyurethane dispersion in water. The product shows good PU and PVC bonding properties, excellent abrasion resistance as well as chemical resistance, included alcohol. |
| Rolflex V 13 | Aliphatic polyether/acrylic copolymer polyurethane dispersion in water. The product has good thermoadhesive properties and good adhesion properties on PVC. |
| Rolflex K 80 | Aliphaticpolyether/acrylic copolymer polyurethane dispersion in water. ROLFLEX K 80 is specifically designed as a high performing adhesive for textile lamination. The product has excellent perchloroethylene and water fastness. |
| Rolflex ABC | Aliphatic polyether polyurethane dispersion in water. Particularly, the product presents very high water column, excellent electrolyte resistance, high LOI index, high resistance to multiple bending. |
| Rolflex ADH | Aliphatic polyether polyurethane dispersion in water. The product has a very high water column resistance. |
| Rolflex W4 | Aliphatic waterborne PU dispersion particularly suggested for the formulation of textile coatings for clothing, outwear where a full, soft and non-sticky touch is required. |
| Rolflex ZB7 | Aliphatic waterborne PU dispersion particularly suggested for the formulation of textile coatings for clothing, outwear, sportswear, fashion and technical articles for industrial applications. The product has a very high charge digestion properties, electrolytes stability and excellent mechanical and tear resistance. Can be also suitable for foam coating and printing application. |

| | |
|---|---|
| Rolflex BZ 78 | Aliphatic waterborne PU dispersion particularly suggested for the formulation of textile coatings for clothing, outwear, sportswear, fashion and technical articles for industrial applications. The product has an excellent hydrolysis resistance, a very high charge digestion and electrolytes stability and an excellent mechanical and tear resistance. Can be also suitable for |
| Rolflex PU 147 | Aliphatic polyether polyurethane dispersion in water. This product shows good film forming properties at room temperature. It has high fastness to light and ultraviolet radiation and good resistance to water, solvent and chemical agents, as well as mechanical resistance. |
| Rolflex SG | Aliphatic polyether polyurethane dispersion in water. Due to its thermoplastic properties it is suggested to formulate heat activated adhesives at low temperatures. |
| Elafix PV 4 | Aliphatic blocked isocyanate nano-dispersion used in order to give antifelting and antipilling properties to pure wool fabrics and his blend. |
| Rolflex C 86 | Aliphatic cationic waterborne PU dispersion particularly suggested for the formulation of textile coatings for clothing, outwear, fashion where medium-soft and pleasant full touch is required. Fabrics treated with the product can be dyed with a selection of dyes, to get double-color effects of different intensity. |
| Rolflex CN 29 | Aliphatic cationic waterborne PU dispersion particularly suggested for the formulation of textile coatings for clothing, outwear, fashion where soft and pleasant full touch is required. Fabrics treated with the product can be dyed with a selection of dyes, to get double-color effects of different intensity. |

In an embodiment, the disclosure provides a faux or bonded leather, or faux or bonded leather article processed with a composition comprising silk based proteins or fragments thereof having an average weight average molecular weight range of about 5 kDa to about 144 kDa, wherein the faux or bonded leather, or faux or bonded leather article is technically finished with an oil or water repellant. In an embodiment, the disclosure provides a faux or bonded leather, or faux or bonded leather article having a coating, wherein the coating comprises silk based proteins or fragments thereof having an average weight average molecular weight range of about 5 kDa to about 144 kDa, wherein the faux or bonded leather, or faux or bonded leather article is technically finished with an oil or water repellant. In an embodiment, the disclosure provides a faux or bonded leather, or faux or bonded leather article including a defect repairing filling, wherein the filling comprises silk based proteins or fragments thereof having an average weight average molecular weight range of about 5 kDa to about 144 kDa, wherein the faux or bonded leather, or faux or bonded leather article is technically finished with an oil or water repellant. Suitable oil or water repellants for technical finishing are known to those of skill in the art. Exemplary, non-limiting examples of oil or water repellants for technical finishing from a representative supplier, Lamberti SPA, are given in the followingtable.

| | |
|---|---|
| Lamgard FT 60 | General purpose fluorocarbon resin for water and oil repellency; by padding application. |
| Lamgard 48 | High performance fluorocarbon resin for water and oil repellency; by padding application. High rubbing |
| Imbitex NRW3 | Wetting agent for water-and oil repellent finishing. |
| Lamgard EXT | Crosslinker for fluorocarbon resins to improve washing fastness. |

In an embodiment, the disclosure provides a faux or bonded leather, or faux or bonded leather article processed with a composition comprising silk based proteins or fragments thereof having an average weight average molecular weight range of about 5 kDa to about 144 kDa, wherein the faux or bonded leather, or faux or bonded leather article is technically finished with a flame retardant. In an embodiment, the disclosure provides a faux or bonded leather, or faux or bonded leather article having a coating, wherein the coating comprises silk based proteins or fragments thereof having an average weight average molecular weight range of about 5 kDa to about 144 kDa, wherein the faux or bonded leather, or faux or bonded leather article is technically finished with a flame retardant. In an embodiment, the disclosure provides a faux or bonded leather, or faux or bonded leather article including a defect repairing filling, wherein the filling comprises silk based proteins or fragments thereof having an average weight average molecular weight range of about 5 kDa to about 144 kDa, wherein the faux or bonded leather, or faux or bonded leather article is technically finished with a flame retardant. Suitable flame retardants for technical finishing are known to those of skill in the art. Exemplary, non-limiting examples of flame retardants for technical finishing from a representative supplier, Lamberti SPA, are given in the following table.

| | |
|---|---|
| Piroflam 712 | Non-permanent flame retardant compound for padding and spray application. |
| Piroflam ECO | Alogen free flame retardant compound for back coating application for all kind of fibers. |
| Piroflam UBC | Flame retardant compound for back coating application for all kind offibers. |

In an embodiment, the disclosure provides a faux or bonded leather, or faux or bonded leather article processed with a composition comprising silk based proteins or fragments thereof having an average weight average molecular weight range of about 5 kDa to about 144 kDa, wherein the faux or bonded leather, or faux or bonded leather article is technically finished with a crosslinker. In an embodiment, the disclosure provides a faux or bonded leather, or faux or bonded leather article having a coating, wherein the coating comprises silk based proteins or fragments thereof having an average weight average molecular weight range of about 5 kDa to about 144 kDa, wherein the faux or bonded leather, or faux or bonded leather article is technically finished with a crosslinker. In an embodiment, the disclosure provides a faux or bonded leather, or faux or bonded leather article including a defect repairing filling, wherein the filling comprises silk based proteins or fragments thereof having an average weight average molecular weight range of about 5 kDa to about 144 kDa, wherein the faux or bonded leather, or faux or bonded leather article is technically finished with a crosslinker. Suitable crosslinkers for technical finishing are known to those of skill in the art. Exemplary, non-limiting examples of crosslinkers for technical finishing from a representative supplier, Lamberti SPA, are given in the following table.

| | |
|---|---|
| Rolflex BK8 | Aromatic blocked polyisocyanate in water dispersion. It is suggested as a cross-linking agent in coating pastes based of polyurethane resins to improve washing fastness. |
| Fissativo 05 | Water dispersible aliphatic polyisocyanate suitable as crosslinking agent for acrylic and polyurethane dispersions to improve adhesion and wet and dry scrub |
| Resina MEL | Melammine-formaldheyde resin. |
| Cellofix VLF | Low formaldheyde malammine resin. |

In an embodiment, the disclosure provides a faux or bonded leather, or faux or bonded leather article processed with a composition comprising silk based proteins or fragments thereof having an average weight average molecular weight range of about 5 kDa to about 144 kDa, wherein the faux or bonded leather, or faux or bonded leather article is technically finished with a thickener for technical finishing. In an embodiment, the disclosure provides a faux or bonded leather, or faux or bonded leather article having a coating, wherein the coating comprises silk based proteins or fragments thereof having an average weight average molecular weight range of about 5 kDa to about 144 kDa, wherein the faux or bonded leather, or faux or bonded leather article is technically finished with a thickener for technical finishing. In an embodiment, the disclosure provides a faux or bonded leather, or faux or bonded leather article including a defect repairing filling, wherein the filling comprises silk based proteins or fragments thereof having an average weight average molecular weight range of about 5 kDa to about 144 kDa, wherein the faux or bonded leather, or faux or bonded leather article is technically finished with a thickener for technical finishing. Suitable thickeners for technical finishing are known to those of skill in the art. Exemplary, non-limiting examples of thickeners for technical finishing from a representative supplier, Lamberti SPA, are given in the followingtable.

| | |
|---|---|
| Lambicol CL 60 | Fully neutralized synthetic thickener for pigment printing in oil/water emulsion; medium viscosity type |
| Viscolam PU conc. | Nonionic polyurethane based thickener with pseudoplastic behavior. |
| Viscolam 115 new | Acrylic thickener; not neutralized. |
| Viscolam PS 202 | Nonionic polyurethane based thickener with newtonian behavior. |
| Viscolam 1022 | Nonionic polyurethane based thickener with moderate pseudoplastic behavior. |

In an embodiment, the disclosure provides a faux or bonded leather, or faux or bonded leather article processed with a composition comprising silk based proteins or fragments thereof having an average weight average molecular weight range of about 5 kDa to about 144 kDa, wherein the faux or bonded leather, or faux or bonded leather article is finished with one or more of Silky Top 7425 NF, Uniseal 9049, Unithane 351 NF, and Unithane 2132 NF (Union Specialties, Inc.). In an embodiment, the disclosure provides a faux or bonded leather, or faux or bonded leather article having a coating, wherein the coating comprises silk based proteins or fragments thereof having an average weight average molecular weight range of about 5 kDa to about 144 kDa, wherein the faux or bonded leather, or faux or bonded leather article is finished with one or more of Silky Top 7425 NF, Uniseal 9049, Unithane 351 NF, and Unithane 2132 NF (Union Specialties, Inc.). In an embodiment, the disclosure provides a faux or bonded leather, or faux or bonded leather article including a defect repairing filling, wherein the filling comprises silk based proteins or fragments thereof having an average weight average molecular weight range of about 5 kDa to about 144 kDa, wherein the faux or bonded leather, or faux or bonded leather article is finished with one or more of Silky Top 7425 NF, Uniseal 9049, Unithane 351 NF, and Unithane 2132 NF (Union Specialties, Inc.). Other suitable Union Specialties products such as finishes, additive, and/or oils and waxes are known to those of skill in the art. Exemplary, non-limiting examples of Union Specialties products are given in the following table:

| | |
|---|---|
| Silky Top 7425 NF | NMP-free water-based spray wax top; can be used on any faux leather, e.g., sheepskin for garment and nappa; can be sprayed and then iron on a Finiflex to give desired gloss and feel; can be sprayed undiluted (for maximum effect) or diluted with water 1:1 or 1:2. |
| Uniseal 9049 | Slightly cationic pre-bottom for corrected grain faux leathers to give uniformity and filling properties; pigment can be added to UNISEAL 9049 up to 10% for added coverage; can be sprayed and then plate the faux leather prior to finishing; can be diluted and applied by spray method as follows; can be mixed for 30 minutes |
| Unithane 351 NF | Medium/soft, lightfast, NMP-free waterborne polyurethane, designed for use as a resin binder for basecoats where it has superior elasticity and recovery abrasion resistance; has good filling properties on porous substrates and very good compatibility with waterborne pigments and other additives that are commonly used in waterborne applications. |
| Unithane 2132 NF | NMP-free diamond clear, bright medium-hard topcoat that gives a feel similar to a nitrocellulose lacquer; when a light coat is sprayed at a ratio of 1:1 with water onto full grain faux leather, the UNITHANE 2132 NF has abrasion resistance and creates a clear film on faux leather. |

In any of the foregoing faux or bonded leather, or faux or bonded leather article embodiments, the processing composition comprises silk based proteins or fragments thereof having an average weight average molecular weight range of about 5 kDa to about 144 kDa. In any of the foregoing faux or bonded leather, or faux or bonded leather article embodiments, the processing composition comprises silk based proteins or fragments thereof having an average weight average molecular weight range of about 6 kDa to about 17 kDa. In any of the foregoing faux or bonded leather, or faux or bonded leather article embodiments, the processing composition comprises silk based proteins or fragments thereof having an average weight average molecular weight range of about 17 kDa to about 39 kDa. In any of the foregoing faux or bonded leather, or faux or bonded leather article embodiments, the processing composition comprises silk based proteins or fragments thereof having an average weight average molecular weight range of about 39 kDa to about 80 kDa. In any of the foregoing faux or bonded leather, or faux or bonded leather article embodiments, the coating comprises silk based proteins or fragments thereof having an average weight average molecular weight range of about 5 kDa to about 144 kDa. In any of the foregoing faux or bonded leather, or faux or bonded leather article embodiments, the coating comprises silk based proteins or fragments thereof having an average weight average molecular weight range of about 6 kDa to about 17 kDa. In any of the foregoing faux or bonded leather, or faux or bonded leather article embodiments, the coating comprises silk based proteins or fragments thereof having an average weight average molecular weight range of about 17 kDa to about 39 kDa. In any of the foregoing faux or bonded leather, or faux or bonded leather article embodiments, the coating comprises silk based proteins or fragments thereof having an average weight average molecular weight range of about 39 kDa to about 80 kDa.

In any of the foregoing faux or bonded leather, or faux or bonded leather article embodiments, the defect repairing filling comprises silk based proteins or fragments thereof having an average weight average molecular weight range of about 5 kDa to about 144 kDa. In any of the foregoing faux or bonded leather, or faux or bonded leather article embodiments, the defect repairing filling comprises silk based proteins or fragments thereof having an average weight average molecular weight range of about 6 kDa to about 17 kDa. In any of the foregoing faux or bonded leather, or faux or bonded leather article embodiments, the defect repairing filling comprises silk based proteins or fragments thereof having an average weight average molecular weight range of about 17 kDa to about 39 kDa. In any of the foregoing faux or bonded leather, or faux or bonded leather article embodiments, the defect repairing filling comprises silk based proteins or fragments thereof having an average weight average molecular weight range of about 39 kDa to about 80 kDa.

In any of the foregoing faux or bonded leather, or faux or bonded leather article embodiments, the processing composition comprises silk based proteins or fragments thereof a low molecular weight silk. In any of the foregoing faux or bonded leather, or faux or bonded leather article embodiments, the processing composition comprises a medium molecular weight silk. In any of the foregoing faux or bonded leather, or faux or bonded leather article embodiments, the processing composition comprises a heavy molecular weight silk. In any of the foregoing faux or bonded leather, or faux or bonded leather article embodiments, the processing composition comprises silk based proteins or fragments thereof that comprise one or more of low, medium, and high molecular weight silk.

In any of the foregoing faux or bonded leather, or faux or bonded leather article embodiments, the coating comprises silk based proteins or fragments thereof a low molecular weight silk. In any of the foregoing faux or bonded leather, or faux or bonded leather article embodiments, the coating comprises a medium molecular weight silk. In any of the foregoing faux or bonded leather, or faux or bonded leather article embodiments, the coating comprises a heavy molecular weight silk. In any of the foregoing faux or bonded leather, or faux or bonded leather article embodiments, the coating comprises silk based proteins or fragments thereof that comprise one or more of low, medium, and high molecular weight silk.

In any of the foregoing faux or bonded leather, or faux or bonded leather article embodiments, the defect repairing filling comprises silk based proteins or fragments thereof a low molecular weight silk. In any of the foregoing faux or bonded leather, or faux or bonded leather article embodiments, the defect repairing filling comprises a medium molecular weight silk. In any of the foregoing faux or bonded leather, or faux or bonded leather article embodiments, the defect repairing filling comprises a heavy molecular weight silk. In any of the foregoing faux or bonded leather, or faux or bonded leather article embodiments, the defect repairing filling comprises silk based proteins or fragments thereof that comprise one or more of low, medium, and high molecular weight silk.

In any of the foregoing faux or bonded leather, or faux or bonded leather article embodiments, the silk based proteins or protein fragments thereof have an average weight average molecular weight range selected from the group consisting of about 5 to about 10 kDa, about 6 kDa to about 17 kDa, about 17 kDa to about 39 kDa, about 39 kDa to about 80 kDa, about 60 to about 100 kDa, and about 80 kDa to about 144 kDa, wherein the silk based proteins or fragments thereof have a polydispersity of between about 1.5 and about 3.0, and optionally wherein the proteins or protein fragments, prior to processing, coating, and/or repairing the faux or bonded leather, or faux or bonded leather article, do not spontaneously or gradually gelate and do not visibly change in color or turbidity when in a solution for at least 10 days.

Processes for Production of Silk Fibroin-Based Protein Fragments and Solutions Thereof As used herein, the term "fibroin" includes silkworm fibroin and insect or spider silk protein. In an embodiment, fibroin is obtained from *Bombyx mori*. In an embodiment, the spider silk protein is selected from the group consisting of swathing silk (Achniform gland silk), egg sac silk (Cylindriform gland silk), egg case silk (Tubuliform silk), non-sticky dragline silk (Ampullate gland silk), attaching thread silk (Pyriform gland silk), sticky silk core fibers (Flagelliform gland silk), and sticky silk outer fibers (Aggregate gland silk).

The silk based proteins or fragments thereof, silk solutions or mixtures (e.g., SPF or SFS solutions or mixture), and the like, may be prepared according to the methods described in U.S. Pat. Nos. 9,187,538, 9,522,107, 9,522,108, 9,511,012, 9,517,191, 9,545,369, and 10,166,177, and U.S. Patent Publication Nos. 2016/0222579 and 2016/0281294, and International Patent Publication Nos. WO 2016/090055 and WO 2017/011679, the entirety of which are incorporated herein by reference. In some embodiments, the silk based proteins or fragments thereof may be provided as a silk composition, which may be an aqueous solution or mixture of silk, a silk gel, and/or a silk wax as described herein. Methods of using silk fibroin or silk fibroin fragments in coating applications are known and are described for example in U.S. Pat. Nos. 10,287,728 and 10,301,768.

Following are non-limiting examples of suitable ranges for various parameters in and for preparation of the silk solutions and/or compositions of the present disclosure. The silk solutions of the present disclosure may include one or more, but not necessarily all, of these parameters and may be prepared using various combinations of ranges of such parameters.

In an embodiment, the percent silk in the solution or composition is less than 50%. In an embodiment, the percent silk in the solution or composition is less than 45%. In an embodiment, the percent silk in the solution or composition is less than 40%. In an embodiment, the percent silk in the solution or composition is less than 35%. In an embodiment, the percent silk in the solution or composition is less than 30%. In an embodiment, the percent silk in the solution or composition is less than 25%. In an embodiment, the percent silk in the solution or composition is less than 20%. In an embodiment, the percent silk in the solution or composition is less than 19%. In an embodiment, the percent silk in the solution or composition is less than 18%. In an embodiment, the percent silk in the solution or composition is less than 17%. In an embodiment, the percent silk in the solution or composition is less than 16%. In an embodiment, the percent silk in the solution or composition is less than 15%. In an embodiment, the percent silk in the solution or composition is less than 14%. In an embodiment, the percent silk in the solution or composition is less than 13%. In an embodiment, the percent silk in the solution or composition is less than 12%. In an embodiment, the percent silk in the solution or composition is less than 11%. In an embodiment, the percent silk in the solution or composition is less than 10%. In an embodiment, the percent silk in the solution or composition is less than 9%. In an embodiment, the percent silk in the solution or composition is less than 8%. In an embodiment, the percent silk in the solution or composition is less than 7%. In an embodiment, the percent silk in the solution or composition is less than 6%. In an embodiment, the percent silk in the solution or composition is less than 5%. In an embodiment, the percent silk in the solution or composition is less than 4%. In an embodiment, the percent silk in the solution or composition is less than 3%. In an embodiment, the percent silk in the solution or composition is less than 2%. In an embodiment, the percent silk in the solution or composition is less than 1%. In an embodiment, the percent silk in the solution or composition is less than 0.9%. In an embodiment, the percent silk in the solution or composition is less than 0.8%. In an embodiment, the percent silk in the solution or composition is less than 0.7%. In an embodiment, the percent silk in the solution or composition is less than 0.6%. In an embodiment, the percent silk in the solution or composition is less than 0.5%. In an embodiment, the percent silk in the solution or composition is less than 0.4%. In an embodiment, the percent silk in the solution or composition is less than 0.3%. In an embodiment, the percent silk in the solution or composition is less than 0.2%. In an embodiment, the percent silk in the solution or composition is less than 0.1%. In an embodiment, the percent silk in the solution or composition is less than 0.01%. In an embodiment, the percent silk in the solution or composition is less than 0.001%.

In an embodiment, the percent silk in the solution or composition is greater than 0.001%. In an embodiment, the percent silk in the solution or composition is greater than 0.01%. In an embodiment, the percent silk in the solution or composition is greater than 0.1%. In an embodiment, the percent silk in the solution or composition is greater than 0.2%. In an embodiment, the percent silk in the solution or composition is greater than 0.3%. In an embodiment, the percent silk in the solution or composition is greater than 0.4%. In an embodiment, the percent silk in the solution or composition is greater than 0.5%. In an embodiment, the percent silk in the solution or composition is greater than 0.6%. In an embodiment, the percent silk in the solution or composition is greater than 0.7%. In an embodiment, the percent silk in the solution or composition is greater than 0.8%. In an embodiment, the percent silk in the solution or composition is greater than 0.9%. In an embodiment, the percent silk in the solution or composition is greater than 1%. In an embodiment, the percent silk in the solution or composition is greater than 2%. In an embodiment, the percent silk in the solution or composition is greater than 3%. In an embodiment, the percent silk in the solution or composition is greater than 4%. In an embodiment, the percent silk in the solution or composition is greater than 5%. In an embodiment, the percent silk in the solution or composition is greater than 6%. In an embodiment, the percent silk in the solution or composition is greater than 7%. In an embodiment, the percent silk in the solution or composition is greater than 8%. In an embodiment, the percent silk in the solution or composition is greater than 9%. In an embodiment, the percent silk in the solution or composition is greater than 10%. In an embodiment, the percent silk in the solution or composition is greater than 11%. In an embodiment, the percent silk in the solution or composition is greater than 12%. In an embodiment, the percent silk in the solution or composition is greater than 13%. In an embodiment, the percent silk in the solution or composition is greater than 14%. In an embodiment, the percent silk in the solution or composition is greater than 15%. In an embodiment, the percent silk in the solution or composition is greater than 16%. In an embodiment, the percent silk in the solution or composition is greater than 17%. In an embodiment, the percent silk in the solution or composition is greater than 18%. In an embodiment, the percent silk in the solution or composition is greater than 19%. In an embodiment, the percent silk in the solution or composition is greater than 20%. In an embodiment, the percent silk in the solution or composition is greater than 25%. In an embodiment, the percent silk in the solution or composition is greater than 30%. In an embodiment, the percent silk in the solution or composition is greater than 35%. In an embodiment, the percent silk in the solution or composition is greater than 40%. In an embodiment, the percent silk in the solution or composition is greater than 45%. In an embodiment, the percent silk in the solution or composition is greater than 50%.

In an embodiment, the percent silk in the solution or composition is between 0.1% and 50%. In an embodiment, the percent silk in the solution or composition is between 0.1% and 45%. In an embodiment, the percent silk in the solution or composition is between 0.1% and 40%. In an embodiment, the percent silk in the solution or composition is between 0.1% and 35%. In an embodiment, the percent silk in the solution or composition is between 0.1% and 30%. In an embodiment, the percent silk in the solution or composition is between 0.1% and 25%. In an embodiment, the percent silk in the solution or composition is between 0.1% and 20%. In an embodiment, the percent silk in the solution or composition is between 0.1% and 15%. In an embodiment, the percent silk in the solution or composition is between 0.1% and 10%. In an embodiment, the percent silk in the solution or composition is between 0.1% and 9%. In an embodiment, the percent silk in the solution or composition is between 0.1% and 8%. In an embodiment, the percent silk in the solution or composition is between 0.1% and 7%. In an embodiment, the percent silk in the solution or composition is between 0.1% and 6.5%. In an embodiment, the percent silk in the solution or composition is between 0.1% and 6%. In an embodiment, the percent silk in the solution or composition is between 0.1% and 5.5%. In an embodiment, the percent silk in the solution or composition is between 0.1% and 5%. In an embodiment, the percent silk in the solution or composition is between 0.1% and 4.5%. In an embodiment, the percent silk in the solution or composition is between 0.1% and 4%. In an embodiment, the percent silk in the solution or composition is between 0.1% and 3.5%. In an embodiment, the percent silk in the solution or composition is between 0.1% and 3%. In an embodiment, the percent silk in the solution or composition is between 0.1% and 2.5%. In an embodiment, the percent silk in the solution or composition is between 0.1% and 2.0%. In an embodiment, the percent silk in the solution or composition is between 0.1% and 2.4%. In an embodiment, the percent silk in the solution or composition is between 0.5% and 5%. In an embodiment, the percent silk in the solution or composition is between 0.5% and 4.5%. In an embodiment, the percent silk in the solution or composition is between 0.5% and 4%. In an embodiment, the percent silk in the solution or composition is between 0.5% and 3.5%. In an embodiment, the percent silk in the solution or composition is between 0.5% and 3%. In an embodiment, the percent silk in the solution or composition is between 0.5% and 2.5%. In an embodiment, the percent silk in the solution or composition is between 1 and 4%. In an embodiment, the percent silk in the solution or composition is between 1 and 3.5%. In an embodiment, the percent silk in the solution or composition is between 1 and 3%. In an embodiment, the percent silk in the solution or composition is between 1 and 2.5%. In an embodiment, the percent silk in the solution or composition is between 1 and 2.4%. In an embodiment, the percent silk in the solution or composition is between 1 and 2%. In an embodiment, the percent silk in the solution or composition is between 20% and 30%. In an embodiment, the percent silk in the solution or composition is between 0.1% and 6%. In an embodiment, the percent silk in the solution or composition is between 6% and 10%. In an embodiment, the percent silk in the solution or composition is between 6% and 8%. In an embodiment, the percent silk in the solution or composition is between 6% and 9%. In an embodiment, the percent silk in the solution or composition is between 10% and 20%. In an embodiment, the percent silk in the solution or composition is between 11% and 19%. In an embodiment, the percent silk in the solution or composition is between 12% and 18%. In an embodiment, the percent silk in the solution or composition is between 13% and 17%. In an embodiment, the percent silk in the solution or composition is between 14% and 16%. In an embodiment, the percent silk in the solution or composition is 2.4%. In an embodiment, the percent silk in the solution or composition is 2.0%.

In an embodiment, the percent sericin in the solution or composition is non-detectable to 30%. In an embodiment, the percent sericin in the solution or composition is non-detectable to 5%. In an embodiment, the percent sericin in the solution or composition is 1%. In an embodiment, the percent sericin in the solution or composition is 2%. In an embodiment, the percent sericin in the solution or composition is 3%. In an embodiment, the percent sericin in the solution or composition is 4%. In an embodiment, the percent sericin in the solution or composition is 5%. In an embodiment, the percent sericin in the solution or composition is 10%. In an embodiment, the percent sericin in the solution or composition is 30%.

In an embodiment, a solution or composition of the present disclosure includes pure silk fibroin-based protein fragments having an average weight average molecular weight selected from between 6 kDa to 17 kDa. In an embodiment, a solution or composition of the present disclosure includes pure silk fibroin-based protein fragments having an average weight average molecular weight selected from between 17 kDa to 39 kDa. In an embodiment, a solution or composition of the present disclosure includes pure silk fibroin-based protein fragments having an average weight average molecular weight selected from between 39 kDa to 80 kDa.

In an embodiment, a composition of the present disclosure includes pure silk fibroin-based protein fragments having an average weight average molecular weight selected from between 1 to 5 kDa. In an embodiment, a composition of the present disclosure includes pure silk fibroin-based protein fragments having an average weight average molecular weight selected from between 5 to 10 kDa. In an embodiment, a composition of the present disclosure includes pure silk fibroin-based protein fragments having an average weight average molecular weight selected from between 10 to 15 kDa. In an embodiment, a composition of the present disclosure includes pure silk fibroin-based protein fragments having an average weight average molecular weight selected from between 15 to 20 kDa. In an embodiment, a composition of the present disclosure includes pure silk fibroin-based protein fragments having an average weight average molecular weight selected from between 20 to 25 kDa. In an embodiment, a composition of the present disclosure includes pure silk fibroin-based protein fragments having an average weight average molecular weight selected from between 25 to 30 kDa. In an embodiment, a composition of the present disclosure includes pure silk fibroin-based protein fragments having an average weight average molecular weight selected from between 30 to 35 kDa. In an embodiment, a composition of the present disclosure includes pure silk fibroin-based protein fragments having an average weight average molecular weight selected from between 35 to 40 kDa. In an embodiment, a composition of the present disclosure includes pure silk fibroin-based protein fragments having an average weight average molecular weight selected from between 40 to 45 kDa. In an embodiment, a composition of the present disclosure includes pure silk fibroin-based protein fragments having an average weight average molecular weight selected from between 45 to 50 kDa. In an embodiment, a composition of the present disclosure includes pure silk fibroin-based protein fragments having an average weight average molecular weight selected from between 50 to 55 kDa. In an embodiment, a composition of the present disclosure includes pure silk fibroin-based protein fragments having an average weight average molecular weight selected from between 55 to 60 kDa. In an embodiment, a composition of the present disclosure includes pure silk fibroin-based protein fragments having an average weight average molecular weight selected from between 60 to 65 kDa. In an embodiment, a composition of the present disclosure includes pure silk fibroin-based protein fragments having an average weight average molecular weight selected from between 65 to 70 kDa. In an embodiment, a composition of the present disclosure includes pure silk fibroin-based protein fragments having an average weight average molecular weight selected from between 70 to 75 kDa. In an embodiment, a composition of the present disclosure includes pure silk fibroin-based protein fragments having an average weight average molecular weight selected from 75 to 80 kDa. In an embodiment, a composition of the present disclosure includes pure silk fibroin-based protein fragments having an average weight average molecular weight selected from between 80 to 85 kDa. In an embodiment, a composition of the present disclosure includes pure silk fibroin-based protein fragments having an average weight average molecular weight selected from between 85 to 90 kDa. In an embodiment, a composition of the present disclosure includes pure silk fibroin-based protein fragments having an average weight average molecular weight selected from between 90 to 95 kDa. In an embodiment, a composition of the present disclosure includes pure silk fibroin-based protein fragments having an average weight average molecular weight selected from between 95 to 100 kDa. In an embodiment, a composition of the present disclosure includes pure silk fibroin-based protein fragments having an average weight average molecular weight selected from between 100 to 105 kDa. In an embodiment, a composition of the present disclosure includes pure silk fibroin-based protein fragments having an average weight average molecular weight selected from between 105 to 110 kDa. In an embodiment, a composition of the present disclosure includes pure silk fibroin-based protein fragments having an average weight average molecular weight selected from between 110 to 115 kDa. In an embodiment, a composition of the present disclosure includes pure silk fibroin-based protein fragments having an average weight average molecular weight selected from between 115 to 120 kDa. In an embodiment, a composition of the present disclosure includes pure silk fibroin-based protein fragments having an average weight average molecular weight selected from between 120 to 125 kDa. In an embodiment, a composition of the present disclosure includes pure silk fibroin-based protein fragments having an average weight average molecular weight selected from between 125 to 130 kDa. In an embodiment, a composition of the present disclosure includes pure silk fibroin-based protein fragments having an average weight average molecular weight selected from between 130 to 135 kDa. In an embodiment, a composition of the present disclosure includes pure silk fibroin-based protein fragments having an average weight average molecular weight selected from between 135 to 140 kDa. In an embodiment, a composition of the present disclosure includes pure silk fibroin-based protein fragments having an average weight average molecular weight selected from between 140 to 145 kDa. In an embodiment, a composition of the present disclosure includes pure silk fibroin-based protein fragments having an average weight average molecular weight selected from between 145 to 150 kDa. In an embodiment, a composition of the present disclosure includes pure silk fibroin-based protein fragments having an average weight average molecular weight selected from between 150 to 155 kDa. In an embodiment, a composition of the present disclosure includes pure silk fibroin-based protein fragments having an average weight average molecular weight selected from between 155 to 160 kDa. In an embodiment, a composition of the present disclosure includes pure silk fibroin-based protein fragments having an average weight average molecular weight selected from between 160 to 165 kDa. I In an embodiment, a composition of the present disclosure includes pure silk fibroin-based protein fragments having an average weight average molecular weight selected from between 165 to 170 kDa. In an embodiment, a composition of the present disclosure includes pure silk fibroin-based protein fragments having an average weight average molecular weight selected from between 170 to 175 kDa. In an embodiment, a composition of the present disclosure includes pure silk fibroin-based protein fragments having an average weight average molecular weight selected from between 175 to 180 kDa. In an embodiment, a composition of the present disclosure includes pure silk fibroin-based protein fragments having an average weight average molecular weight selected from between 180 to 185 kDa. In an embodiment, a composition of the present disclosure includes pure silk fibroin-based protein fragments having an average weight average molecular weight selected from between 185 to 190 kDa. In an embodiment, a composition of the present disclosure includes pure silk fibroin-based protein fragments having an average weight average molecular weight selected from between 190 to 195 kDa. In an embodiment, a composition of the present disclosure includes pure silk fibroin-based protein fragments having an average weight average molecular weight selected from between 195 to 200 kDa. In an embodiment, a composition of the present disclosure includes pure silk fibroin-based protein fragments having an average weight average molecular weight selected from between 200 to 205 kDa. In an embodiment, a composition of the present disclosure includes pure silk fibroin-based protein fragments having an average weight average molecular weight selected from between 205 to 210 kDa. In an embodiment, a composition of the present disclosure includes pure silk fibroin-based protein fragments having an average weight average molecular weight selected from between 210 to 215 kDa. In an embodiment, a composition of the present disclosure includes pure silk fibroin-based protein fragments having an average weight average molecular weight selected from between 215 to 220 kDa. In an embodiment, a composition of the present disclosure includes pure silk fibroin-based protein fragments having an average weight average molecular weight selected from between 220 to 225 kDa. In an embodiment, a composition of the present disclosure includes pure silk fibroin-based protein fragments having an average weight average molecular weight selected from between 225 to 230 kDa. In an embodiment, a composition of the present disclosure includes pure silk fibroin-based protein fragments having an average weight average molecular weight selected from between 230 to 235 kDa. In an embodiment, a composition of the present disclosure includes pure silk fibroin-based protein fragments having an average weight average molecular weight selected from between 235 to 240 kDa. In an embodiment, a composition of the present disclosure includes pure silk fibroin-based protein fragments having an average weight average molecular weight selected from between 240 to 245 kDa. In an embodiment, a composition of the present disclosure includes pure silk fibroin-based protein fragments having an average weight average molecular weight selected from between 245 to 250 kDa. In an embodiment, a composition of the present disclosure includes pure silk fibroin-based protein fragments having an average weight average molecular weight selected from between 250 to 255 kDa. In an embodiment, a composition of the present disclosure includes pure silk fibroin-based protein fragments having an average weight average molecular weight selected from between 255 to 260 kDa. In an embodiment, a composition of the present disclosure includes pure silk fibroin-based protein fragments having an average weight average molecular weight selected from between 260 to 265 kDa. In an embodiment, a composition of the present disclosure includes pure silk fibroin-based protein fragments having an average weight average molecular weight selected from between 265 to 270 kDa. In an embodiment, a composition of the present disclosure includes pure silk fibroin-based protein fragments having an average weight average molecular weight selected from between 270 to 275 kDa. In an embodiment, a composition of the present disclosure includes pure silk fibroin-based protein fragments having an average weight average molecular weight selected from between 275 to 280 kDa. In an embodiment, a composition of the present disclosure includes pure silk fibroin-based protein fragments having an average weight average molecular weight selected from between 280 to 285 kDa. In an embodiment, a composition of the present disclosure includes pure silk fibroin-based protein fragments having an average weight average molecular weight selected from between 285 to 290 kDa. In an embodiment, a composition of the present disclosure includes pure silk fibroin-based protein fragments having an average weight average molecular weight selected from between 290 to 295 kDa. In an embodiment, a composition of the present disclosure includes pure silk fibroin-based protein fragments having an average weight average molecular weight selected from between 295 to 300 kDa. In an embodiment, a composition of the present disclosure includes pure silk fibroin-based protein fragments having an average weight average molecular weight selected from between 300 to 305 kDa. In an embodiment, a composition of the present disclosure includes pure silk fibroin-based protein fragments having an average weight average molecular weight selected from between 305 to 310 kDa. In an embodiment, a composition of the present disclosure includes pure silk fibroin-based protein fragments having an average weight average molecular weight selected from between 310 to 315 kDa. In an embodiment, a composition of the present disclosure includes pure silk fibroin-based protein fragments having an average weight average molecular weight selected from between 315 to 320 kDa. In an embodiment, a composition of the present disclosure includes pure silk fibroin-based protein fragments having an average weight average molecular weight selected from between 320 to 325 kDa. In an embodiment, a composition of the present disclosure includes pure silk fibroin-based protein fragments having an average weight average molecular weight selected from between 325 to 330 kDa. In an embodiment, a composition of the present disclosure includes pure silk fibroin-based protein fragments having an average weight average molecular weight selected from between 330 to 335 kDa. In an embodiment, a composition of the present disclosure includes pure silk fibroin-based protein fragments having an average weight average molecular weight selected from between 35 to 340 kDa. In an embodiment, a composition of the present disclosure includes pure silk fibroin-based protein fragments having an average weight average molecular weight selected from between 340 to 345 kDa. In an embodiment, a composition of the present disclosure includes pure silk fibroin-based protein fragments having an average weight average molecular weight selected from between 345 to 350 kDa.

In an embodiment, a composition of the present disclosure includes silk protein fragments having an average weight average molecular weight selected from between 6 kDa to 17 kDa. In an embodiment, a composition of the present disclosure includes silk protein fragments having an average weight average molecular weight selected from between 17 kDa to 39 kDa. In an embodiment, a composition of the present disclosure includes silk protein fragments having an average weight average molecular weight selected from between 39 kDa to 80 kDa.

In an embodiment, a composition of the present disclosure includes silk protein fragments having an average weight average molecular weight of about 1 kDa to about 350 kDa, or about 1 kDa to about 300 kDa, or about 1 kDa to about 250 kDa, or about 1 kDa to about 200 kDa, or about 1 kDa to about 150 kDa, or about 1 kDa to about 100 kDa, or about 1 kDa to about 50 kDa, or about 1 kDa to about 25 kDa.

In an embodiment, silk fibroin-based protein fragments incorporated into the silk compositions described herein have having an average weight average molecular weight selected from between 1 kDa to 6 kDa. In an embodiment, silk fibroin-based protein fragments incorporated into the silk compositions described herein have an average weight average molecular weight selected from between 6 kDa to 16 kDa. In an embodiment, silk fibroin-based protein fragments incorporated into the silk compositions described herein have an average weight average molecular weight selected from between 16 kDa to 38 kDa. In an embodiment, silk fibroin-based protein fragments incorporated into the silk compositions described herein have an average weight average molecular weight selected from between 38 kDa to 80 kDa. In an embodiment, silk fibroin-based protein fragments incorporated into the silk compositions described herein have an average weight average molecular weight selected from between 80 kDa to 150 kDa.

In an embodiment, silk fibroin-based protein fragments incorporated into the silk compositions described herein have an average weight average molecular weight selected from between 1 kDa to 250 kDa. In an embodiment, silk fibroin-based protein fragments incorporated into the silk compositions described herein have an average weight average molecular weight selected from between 1 kDa to 240 kDa. In an embodiment, silk fibroin-based protein fragments incorporated into the silk compositions described herein have an average weight average molecular weight selected from between 1 kDa to 230 kDa. In an embodiment, silk fibroin-based protein fragments incorporated into the silk compositions described herein have an average weight average molecular weight selected from between 1 kDa to 220 kDa. In an embodiment, silk fibroin-based protein fragments incorporated into the silk compositions described herein have an average weight average molecular weight selected from between 1 kDa to 210 kDa. In an embodiment, silk fibroin-based protein fragments incorporated into the silk compositions described herein have an average weight average molecular weight selected from between 1 kDa to 200 kDa. In an embodiment, silk fibroin-based protein fragments incorporated into the silk compositions described herein have an average weight average molecular weight selected from between 1 kDa to 190 kDa. In an embodiment, silk fibroin-based protein fragments incorporated into the silk compositions described herein have an average weight average molecular weight selected from between 1 kDa to 180 kDa. In an embodiment, silk fibroin-based protein fragments incorporated into the silk compositions described herein have an average weight average molecular weight selected from between 1 kDa to 170 kDa. In an embodiment, silk fibroin-based protein fragments incorporated into the silk compositions described herein have an average weight average molecular weight selected from between 1 kDa to 160 kDa. In an embodiment, silk fibroin-based protein fragments incorporated into the silk compositions described herein have an average weight average molecular weight selected from between 1 kDa to 150 kDa. In an embodiment, silk fibroin-based protein fragments incorporated into the silk compositions described herein have an average weight average molecular weight selected from between 1 kDa to 140 kDa. In an embodiment, silk fibroin-based protein fragments incorporated into the silk compositions described herein have an average weight average molecular weight selected from between 1 kDa to 130 kDa. In an embodiment, silk fibroin-based protein fragments incorporated into the silk compositions described herein have an average weight average molecular weight selected from between 1 kDa to 120 kDa. In an embodiment, silk fibroin-based protein fragments incorporated into the silk compositions described herein have an average weight average molecular weight selected from between 1 kDa to 110 kDa. In an embodiment, silk fibroin-based protein fragments incorporated into the silk compositions described herein have an average weight average molecular weight selected from between 1 kDa to 100 kDa. In an embodiment, silk fibroin-based protein fragments incorporated into the silk compositions described herein have an average weight average molecular weight selected from between 1 kDa to 90 kDa. In an embodiment, silk fibroin-based protein fragments incorporated into the silk compositions described herein have an average weight average molecular weight selected from between 1 kDa to 80 kDa. In an embodiment, silk fibroin-based protein fragments incorporated into the silk compositions described herein have an average weight average molecular weight selected from between 1 kDa to 70 kDa. In an embodiment, silk fibroin-based protein fragments incorporated into the silk compositions described herein have an average weight average molecular weight selected from between 1 kDa to 60 kDa. In an embodiment, silk fibroin-based protein fragments incorporated into the silk compositions described herein have an average weight average molecular weight selected from between 1 kDa to 50 kDa. In an embodiment, silk fibroin-based protein fragments incorporated into the silk compositions described herein have an average weight average molecular weight selected from between 1 kDa to 40 kDa. In an embodiment, silk fibroin-based protein fragments incorporated into the silk compositions described herein have an average weight average molecular weight selected from between 1 kDa to 30 kDa. In an embodiment, silk fibroin-based protein fragments incorporated into the silk compositions described herein have an average weight average molecular weight selected from between 1 kDa to 20 kDa. In an embodiment, silk fibroin-based protein fragments incorporated into the silk compositions described herein have an average weight average molecular weight selected from between 1 kDa to 10 kDa.

In an embodiment, a composition of the present disclosure includes silk protein fragments having an average weight average molecular weight selected from between 1 to 5 kDa. In an embodiment, a composition of the present disclosure includes silk protein fragments having an average weight average molecular weight selected from between 5 to 10 kDa. In an embodiment, a composition of the present disclosure includes silk protein fragments having an average weight average molecular weight selected from between 10 to 15 kDa. In an embodiment, a composition of the present disclosure includes silk protein fragments having an average weight average molecular weight selected from between 15 to 20 kDa. In an embodiment, a composition of the present disclosure includes silk protein fragments having an average weight average molecular weight selected from between 20 to 25 kDa. In an embodiment, a composition of the present disclosure includes silk protein fragments having an average weight average molecular weight selected from between 25 to 30 kDa. In an embodiment, a composition of the present disclosure includes silk protein fragments having an average weight average molecular weight selected from between 30 to 35 kDa. In an embodiment, a composition of the present disclosure includes silk protein fragments having an average weight average molecular weight selected from between 35 to 40 kDa. In an embodiment, a composition of the present disclosure includes silk protein fragments having an average weight average molecular weight selected from between 40 to 45 kDa. In an embodiment, a composition of the present disclosure includes silk protein fragments having an average weight average molecular weight selected from between 45 to 50 kDa. In an embodiment, a composition of the present disclosure includes silk protein fragments having an average weight average molecular weight selected from between 50 to 55 kDa. In an embodiment, a composition of the present disclosure includes silk protein fragments having an average weight average molecular weight selected from between 55 to 60 kDa. In an embodiment, a composition of the present disclosure includes silk protein fragments having an average weight average molecular weight selected from between 60 to 65 kDa. In an embodiment, a composition of the present disclosure includes silk protein fragments having an average weight average molecular weight selected from between 65 to 70 kDa. In an embodiment, a composition of the present disclosure includes silk protein fragments having an average weight average molecular weight selected from between 70 to 75 kDa. In an embodiment, a composition of the present disclosure includes silk protein fragments having an average weight average molecular weight selected from between 75 to 80 kDa. In an embodiment, a composition of the present disclosure includes silk protein fragments having an average weight average molecular weight selected from between 80 to 85 kDa. In an embodiment, a composition of the present disclosure includes silk protein fragments having an average weight average molecular weight selected from between 85 to 90 kDa. In an embodiment, a composition of the present disclosure includes silk protein fragments having an average weight average molecular weight selected from between 90 to 95 kDa. In an embodiment, a composition of the present disclosure includes silk protein fragments having an average weight average molecular weight selected from between 95 to 100 kDa. In an embodiment, a composition of the present disclosure includes silk protein fragments having an average weight average molecular weight selected from between 100 to 105 kDa. In an embodiment, a composition of the present disclosure includes silk protein fragments having an average weight average molecular weight selected from between 105 to 110 kDa. In an embodiment, a composition of the present disclosure includes silk protein fragments having an average weight average molecular weight selected from between 110 to 115 kDa. In an embodiment, a composition of the present disclosure includes silk protein fragments having an average weight average molecular weight selected from between 115 to 120 kDa. In an embodiment, a composition of the present disclosure includes silk protein fragments having an average weight average molecular weight selected from between 120 to 125 kDa. In an embodiment, a composition of the present disclosure includes silk protein fragments having an average weight average molecular weight selected from between 125 to 130 kDa. In an embodiment, a composition of the present disclosure includes silk protein fragments having an average weight average molecular weight selected from between 130 to 135 kDa. In an embodiment, a composition of the present disclosure includes silk protein fragments having an average weight average molecular weight selected from between 135 to 140 kDa. In an embodiment, a composition of the present disclosure includes silk protein fragments having an average weight average molecular weight selected from between 140 to 145 kDa. In an embodiment, a composition of the present disclosure includes silk protein fragments having an average weight average molecular weight selected from between 145 to 150 kDa. In an embodiment, a composition of the present disclosure includes silk protein fragments having an average weight average molecular weight selected from between 150 to 155 kDa. In an embodiment, a composition of the present disclosure includes silk protein fragments having an average weight average molecular weight selected from between 155 to 160 kDa. In an embodiment, a composition of the present disclosure includes silk protein fragments having an average weight average molecular weight selected from between 160 to 165 kDa. In an embodiment, a composition of the present disclosure includes silk protein fragments having an average weight average molecular weight selected from between 165 to 170 kDa. In an embodiment, a composition of the present disclosure includes silk protein fragments having an average weight average molecular weight selected from between 170 to 175 kDa. In an embodiment, a composition of the present disclosure includes silk protein fragments having an average weight average molecular weight selected from between 175 to 180 kDa. In an embodiment, a composition of the present disclosure includes silk protein fragments having an average weight average molecular weight selected from between 180 to 185 kDa. In an embodiment, a composition of the present disclosure includes silk protein fragments having an average weight average molecular weight selected from between 185 to 190 kDa. In an embodiment, a composition of the present disclosure includes silk protein fragments having an average weight average molecular weight selected from between 190 to 195 kDa. In an embodiment, a composition of the present disclosure includes silk protein fragments having an average weight average molecular weight selected from between 195 to 200 kDa. In an embodiment, a composition of the present disclosure includes silk protein fragments having an average weight average molecular weight selected from between 200 to 205 kDa. In an embodiment, a composition of the present disclosure includes silk protein fragments having an average weight average molecular weight selected from between 205 to 210 kDa. In an embodiment, a composition of the present disclosure includes silk protein fragments having an average weight average molecular weight selected from between 210 to 215 kDa. In an embodiment, a composition of the present disclosure includes silk protein fragments having an average weight average molecular weight selected from between 215 to 220 kDa. In an embodiment, a composition of the present disclosure includes silk protein fragments having an average weight average molecular weight selected from between 220 to 225 kDa. In an embodiment, a composition of the present disclosure includes silk protein fragments having an average weight average molecular weight selected from between 225 to 230 kDa. In an embodiment, a composition of the present disclosure includes silk protein fragments having an average weight average molecular weight selected from between 230 to 235 kDa. In an embodiment, a composition of the present disclosure includes silk protein fragments having an average weight average molecular weight selected from between 235 to 240 kDa. In an embodiment, a composition of the present disclosure includes silk protein fragments having an average weight average molecular weight selected from between 240 to 245 kDa. In an embodiment, a composition of the present disclosure includes silk protein fragments having an average weight average molecular weight selected from between 245 to 250 kDa. In an embodiment, a composition of the present disclosure includes silk protein fragments having an average weight average molecular weight selected from between 250 to 255 kDa. In an embodiment, a composition of the present disclosure includes silk protein fragments having an average weight average molecular weight selected from between 255 to 260 kDa. In an embodiment, a composition of the present disclosure includes silk protein fragments having an average weight average molecular weight selected from between 260 to 265 kDa. In an embodiment, a composition of the present disclosure includes silk protein fragments having an average weight average molecular weight selected from between 265 to 270 kDa. In an embodiment, a composition of the present disclosure includes silk protein fragments having an average weight average molecular weight selected from between 270 to 275 kDa. In an embodiment, a composition of the present disclosure includes silk protein fragments having an average weight average molecular weight selected from between 275 to 280 kDa. In an embodiment, a composition of the present disclosure includes silk protein fragments having an average weight average molecular weight selected from between 280 to 285 kDa. In an embodiment, a composition of the present disclosure includes silk protein fragments having an average weight average molecular weight selected from between 285 to 290 kDa. In an embodiment, a composition of the present disclosure includes silk protein fragments having an average weight average molecular weight selected from between 290 to 295 kDa. In an embodiment, a composition of the present disclosure includes silk protein fragments having an average weight average molecular weight selected from between 295 to 300 kDa. In an embodiment, a composition of the present disclosure includes silk protein fragments having an average weight average molecular weight selected from between 300 to 305 kDa. In an embodiment, a composition of the present disclosure includes silk protein fragments having an average weight average molecular weight selected from between 305 to 310 kDa. In an embodiment, a composition of the present disclosure includes silk protein fragments having an average weight average molecular weight selected from between 310 to 315 kDa. In an embodiment, a composition of the present disclosure includes silk protein fragments having an average weight average molecular weight selected from between 315 to 320 kDa. In an embodiment, a composition of the present disclosure includes silk protein fragments having an average weight average molecular weight selected from between 320 to 325 kDa. In an embodiment, a composition of the present disclosure includes silk protein fragments having an average weight average molecular weight selected from between 325 to 330 kDa. In an embodiment, a composition of the present disclosure includes silk protein fragments having an average weight average molecular weight selected from between 330 to 335 kDa. In an embodiment, a composition of the present disclosure includes silk protein fragments having an average weight average molecular weight selected from between 35 to 340 kDa. In an embodiment, a composition of the present disclosure includes silk protein fragments having an average weight average molecular weight selected from between 340 to 345 kDa. In an embodiment, a composition of the present disclosure includes silk protein fragments having an average weight average molecular weight selected from between 345 to 350 kDa.

In an embodiment, a composition of the present disclosure includes silk protein fragments having an average weight average molecular weight of about 5 kDa. In an embodiment, a composition of the present disclosure includes silk protein fragments having an average weight average molecular weight of about 6 kDa. In an embodiment, a composition of the present disclosure includes silk protein fragments having an average weight average molecular weight of about 7 kDa. In an embodiment, a composition of the present disclosure includes silk protein fragments having an average weight average molecular weight of about 8 kDa. In an embodiment, a composition of the present disclosure includes silk protein fragments having an average weight average molecular weight of about 9 kDa. In an embodiment, a composition of the present disclosure includes silk protein fragments having an average weight average molecular weight of about 10 kDa.

In an embodiment, a composition of the present disclosure includes silk protein fragments having an average weight average molecular weight of about 11 kDa. In an embodiment, a composition of the present disclosure includes silk protein fragments having an average weight average molecular weight of about 12 kDa. In an embodiment, a composition of the present disclosure includes silk protein fragments having an average weight average molecular weight of about 13 kDa. In an embodiment, a composition of the present disclosure includes silk protein fragments having an average weight average molecular weight of about 14 kDa. In an embodiment, a composition of the present disclosure includes silk protein fragments having an average weight average molecular weight of about 15 kDa. In an embodiment, a composition of the present disclosure includes silk protein fragments having an average weight average molecular weight of about 16 kDa. In an embodiment, a composition of the present disclosure includes silk protein fragments having an average weight average molecular weight of about 17 kDa. In an embodiment, a composition of the present disclosure includes silk protein fragments having an average weight average molecular weight of about 18 kDa. In an embodiment, a composition of the present disclosure includes silk protein fragments having an average weight average molecular weight of about 19 kDa. In an embodiment, a composition of the present disclosure includes silk protein fragments having an average weight average molecular weight of about 20 kDa.

In an embodiment, a composition of the present disclosure includes silk protein fragments having an average weight average molecular weight of about 21 kDa. In an embodiment, a composition of the present disclosure includes silk protein fragments having an average weight average molecular weight of about 22 kDa. In an embodiment, a composition of the present disclosure includes silk protein fragments having an average weight average molecular weight of about 23 kDa. In an embodiment, a composition of the present disclosure includes silk protein fragments having an average weight average molecular weight of about 24 kDa. In an embodiment, a composition of the present disclosure includes silk protein fragments having an average weight average molecular weight of about 25 kDa. In an embodiment, a composition of the present disclosure includes silk protein fragments having an average weight average molecular weight of about 26 kDa. In an embodiment, a composition of the present disclosure includes silk protein fragments having an average weight average molecular weight of about 27 kDa. In an embodiment, a composition of the present disclosure includes silk protein fragments having an average weight average molecular weight of about 28 kDa. In an embodiment, a composition of the present disclosure includes silk protein fragments having an average weight average molecular weight of about 29 kDa. In an embodiment, a composition of the present disclosure includes silk protein fragments having an average weight average molecular weight of about 30 kDa.

In an embodiment, a composition of the present disclosure includes silk protein fragments having an average weight average molecular weight of about 31 kDa. In an embodiment, a composition of the present disclosure includes silk protein fragments having an average weight average molecular weight of about 32 kDa. In an embodiment, a composition of the present disclosure includes silk protein fragments having an average weight average molecular weight of about 33 kDa. In an embodiment, a composition of the present disclosure includes silk protein fragments having an average weight average molecular weight of about 34 kDa. In an embodiment, a composition of the present disclosure includes silk protein fragments having an average weight average molecular weight of about 35 kDa. In an embodiment, a composition of the present disclosure includes silk protein fragments having an average weight average molecular weight of about 36 kDa. In an embodiment, a composition of the present disclosure includes silk protein fragments having an average weight average molecular weight of about 37 kDa. In an embodiment, a composition of the present disclosure includes silk protein fragments having an average weight average molecular weight of about 38 kDa. In an embodiment, a composition of the present disclosure includes silk protein fragments having an average weight average molecular weight of about 39 kDa. In an embodiment, a composition of the present disclosure includes silk protein fragments having an average weight average molecular weight of about 40 kDa.

In an embodiment, a composition of the present disclosure includes silk protein fragments having an average weight average molecular weight of about 41 kDa. In an embodiment, a composition of the present disclosure includes silk protein fragments having an average weight average molecular weight of about 42 kDa. In an embodiment, a composition of the present disclosure includes silk protein fragments having an average weight average molecular weight of about 43 kDa. In an embodiment, a composition of the present disclosure includes silk protein fragments having an average weight average molecular weight of about 44 kDa. In an embodiment, a composition of the present disclosure includes silk protein fragments having an average weight average molecular weight of about 45 kDa. In an embodiment, a composition of the present disclosure includes silk protein fragments having an average weight average molecular weight of about 46 kDa. In an embodiment, a composition of the present disclosure includes silk protein fragments having an average weight average molecular weight of about 47 kDa. In an embodiment, a composition of the present disclosure includes silk protein fragments having an average weight average molecular weight of about 48 kDa. In an embodiment, a composition of the present disclosure includes silk protein fragments having an average weight average molecular weight of about 49 kDa. In an embodiment, a composition of the present disclosure includes silk protein fragments having an average weight average molecular weight of about 50 kDa.

In an embodiment, a composition of the present disclosure includes silk protein fragments having an average weight average molecular weight of about 51 kDa. In an embodiment, a composition of the present disclosure includes silk protein fragments having an average weight average molecular weight of about 52 kDa. In an embodiment, a composition of the present disclosure includes silk protein fragments having an average weight average molecular weight of about 53 kDa. In an embodiment, a composition of the present disclosure includes silk protein fragments having an average weight average molecular weight of about 54 kDa. In an embodiment, a composition of the present disclosure includes silk protein fragments having an average weight average molecular weight of about 55 kDa. In an embodiment, a composition of the present disclosure includes silk protein fragments having an average weight average molecular weight of about 56 kDa. In an embodiment, a composition of the present disclosure includes silk protein fragments having an average weight average molecular weight of about 57 kDa. In an embodiment, a composition of the present disclosure includes silk protein fragments having an average weight average molecular weight of about 58 kDa. In an embodiment, a composition of the present disclosure includes silk protein fragments having an average weight average molecular weight of about 59 kDa. In an embodiment, a composition of the present disclosure includes silk protein fragments having an average weight average molecular weight of about 60 kDa.

In an embodiment, a composition of the present disclosure includes silk protein fragments having an average weight average molecular weight of about 61 kDa. In an embodiment, a composition of the present disclosure includes silk protein fragments having an average weight average molecular weight of about 62 kDa. In an embodiment, a composition of the present disclosure includes silk protein fragments having an average weight average molecular weight of about 63 kDa. In an embodiment, a composition of the present disclosure includes silk protein fragments having an average weight average molecular weight of about 64 kDa. In an embodiment, a composition of the present disclosure includes silk protein fragments having an average weight average molecular weight of about 65 kDa. In an embodiment, a composition of the present disclosure includes silk protein fragments having an average weight average molecular weight of about 66 kDa. In an embodiment, a composition of the present disclosure includes silk protein fragments having an average weight average molecular weight of about 67 kDa. In an embodiment, a composition of the present disclosure includes silk protein fragments having an average weight average molecular weight of about 68 kDa. In an embodiment, a composition of the present disclosure includes silk protein fragments having an average weight average molecular weight of about 69 kDa. In an embodiment, a composition of the present disclosure includes silk protein fragments having an average weight average molecular weight of about 70 kDa.

In an embodiment, a composition of the present disclosure includes silk protein fragments having an average weight average molecular weight of about 71 kDa. In an embodiment, a composition of the present disclosure includes silk protein fragments having an average weight average molecular weight of about 72 kDa. In an embodiment, a composition of the present disclosure includes silk protein fragments having an average weight average molecular weight of about 73 kDa. In an embodiment, a composition of the present disclosure includes silk protein fragments having an average weight average molecular weight of about 74 kDa. In an embodiment, a composition of the present disclosure includes silk protein fragments having an average weight average molecular weight of about 75 kDa. In an embodiment, a composition of the present disclosure includes silk protein fragments having an average weight average molecular weight of about 76 kDa. In an embodiment, a composition of the present disclosure includes silk protein fragments having an average weight average molecular weight of about 77 kDa. In an embodiment, a composition of the present disclosure includes silk protein fragments having an average weight average molecular weight of about 78 kDa. In an embodiment, a composition of the present disclosure includes silk protein fragments having an average weight average molecular weight of about 79 kDa. In an embodiment, a composition of the present disclosure includes silk protein fragments having an average weight average molecular weight of about 80 kDa.

In an embodiment, a composition of the present disclosure includes silk protein fragments having an average weight average molecular weight of about 81 kDa. In an embodiment, a composition of the present disclosure includes silk protein fragments having an average weight average molecular weight of about 82 kDa. In an embodiment, a composition of the present disclosure includes silk protein fragments having an average weight average molecular weight of about 83 kDa. In an embodiment, a composition of the present disclosure includes silk protein fragments having an average weight average molecular weight of about 84 kDa. In an embodiment, a composition of the present disclosure includes silk protein fragments having an average weight average molecular weight of about 85 kDa. In an embodiment, a composition of the present disclosure includes silk protein fragments having an average weight average molecular weight of about 86 kDa. In an embodiment, a composition of the present disclosure includes silk protein fragments having an average weight average molecular weight of about 87 kDa. In an embodiment, a composition of the present disclosure includes silk protein fragments having an average weight average molecular weight of about 88 kDa. In an embodiment, a composition of the present disclosure includes silk protein fragments having an average weight average molecular weight of about 89 kDa. In an embodiment, a composition of the present disclosure includes silk protein fragments having an average weight average molecular weight of about 90 kDa.

In an embodiment, a composition of the present disclosure includes silk protein fragments having an average weight average molecular weight of about 91 kDa. In an embodiment, a composition of the present disclosure includes silk protein fragments having an average weight average molecular weight of about 92 kDa. In an embodiment, a composition of the present disclosure includes silk protein fragments having an average weight average molecular weight of about 93 kDa. In an embodiment, a composition of the present disclosure includes silk protein fragments having an average weight average molecular weight of about 94 kDa. In an embodiment, a composition of the present disclosure includes silk protein fragments having an average weight average molecular weight of about 95 kDa. In an embodiment, a composition of the present disclosure includes silk protein fragments having an average weight average molecular weight of about 96 kDa. In an embodiment, a composition of the present disclosure includes silk protein fragments having an average weight average molecular weight of about 97 kDa. In an embodiment, a composition of the present disclosure includes silk protein fragments having an average weight average molecular weight of about 98 kDa. In an embodiment, a composition of the present disclosure includes silk protein fragments having an average weight average molecular weight of about 99 kDa. In an embodiment, a composition of the present disclosure includes silk protein fragments having an average weight average molecular weight of about 100 kDa.

In an embodiment, a composition of the present disclosure includes silk protein fragments having an average weight average molecular weight of about 101 kDa. In an embodiment, a composition of the present disclosure includes silk protein fragments having an average weight average molecular weight of about 102 kDa. In an embodiment, a composition of the present disclosure includes silk protein fragments having an average weight average molecular weight of about 103 kDa. In an embodiment, a composition of the present disclosure includes silk protein fragments having an average weight average molecular weight of about 104 kDa. In an embodiment, a composition of the present disclosure includes silk protein fragments having an average weight average molecular weight of about 105 kDa. In an embodiment, a composition of the present disclosure includes silk protein fragments having an average weight average molecular weight of about 106 kDa. In an embodiment, a composition of the present disclosure includes silk protein fragments having an average weight average molecular weight of about 107 kDa. In an embodiment, a composition of the present disclosure includes silk protein fragments having an average weight average molecular weight of about 108 kDa. In an embodiment, a composition of the present disclosure includes silk protein fragments having an average weight average molecular weight of about 109 kDa. In an embodiment, a composition of the present disclosure includes silk protein fragments having an average weight average molecular weight of about 110 kDa.

In an embodiment, a composition of the present disclosure includes silk protein fragments having an average weight average molecular weight of about 111 kDa. In an embodiment, a composition of the present disclosure includes silk protein fragments having an average weight average molecular weight of about 112 kDa. In an embodiment, a composition of the present disclosure includes silk protein fragments having an average weight average molecular weight of about 113 kDa. In an embodiment, a composition of the present disclosure includes silk protein fragments having an average weight average molecular weight of about 114 kDa. In an embodiment, a composition of the present disclosure includes silk protein fragments having an average weight average molecular weight of about 115 kDa. In an embodiment, a composition of the present disclosure includes silk protein fragments having an average weight average molecular weight of about 116 kDa. In an embodiment, a composition of the present disclosure includes silk protein fragments having an average weight average molecular weight of about 117 kDa. In an embodiment, a composition of the present disclosure includes silk protein fragments having an average weight average molecular weight of about 118 kDa. In an embodiment, a composition of the present disclosure includes silk protein fragments having an average weight average molecular weight of about 119 kDa. In an embodiment, a composition of the present disclosure includes silk protein fragments having an average weight average molecular weight of about 120 kDa.

In an embodiment, a composition of the present disclosure includes silk protein fragments having an average weight average molecular weight of about 121 kDa. In an embodiment, a composition of the present disclosure includes silk protein fragments having an average weight average molecular weight of about 122 kDa. In an embodiment, a composition of the present disclosure includes silk protein fragments having an average weight average molecular weight of about 123 kDa. In an embodiment, a composition of the present disclosure includes silk protein fragments having an average weight average molecular weight of about 124 kDa. In an embodiment, a composition of the present disclosure includes silk protein fragments having an average weight average molecular weight of about 125 kDa. In an embodiment, a composition of the present disclosure includes silk protein fragments having an average weight average molecular weight of about 126 kDa. In an embodiment, a composition of the present disclosure includes silk protein fragments having an average weight average molecular weight of about 127 kDa. In an embodiment, a composition of the present disclosure includes silk protein fragments having an average weight average molecular weight of about 128 kDa. In an embodiment, a composition of the present disclosure includes silk protein fragments having an average weight average molecular weight of about 129 kDa. In an embodiment, a composition of the present disclosure includes silk protein fragments having an average weight average molecular weight of about 130 kDa.

In an embodiment, a composition of the present disclosure includes silk protein fragments having an average weight average molecular weight of about 131 kDa. In an embodiment, a composition of the present disclosure includes silk protein fragments having an average weight average molecular weight of about 132 kDa. In an embodiment, a composition of the present disclosure includes silk protein fragments having an average weight average molecular weight of about 133 kDa. In an embodiment, a composition of the present disclosure includes silk protein fragments having an average weight average molecular weight of about 134 kDa. In an embodiment, a composition of the present disclosure includes silk protein fragments having an average weight average molecular weight of about 135 kDa. In an embodiment, a composition of the present disclosure includes silk protein fragments having an average weight average molecular weight of about 136 kDa. In an embodiment, a composition of the present disclosure includes silk protein fragments having an average weight average molecular weight of about 137 kDa. In an embodiment, a composition of the present disclosure includes silk protein fragments having an average weight average molecular weight of about 138 kDa. In an embodiment, a composition of the present disclosure includes silk protein fragments having an average weight average molecular weight of about 139 kDa. In an embodiment, a composition of the present disclosure includes silk protein fragments having an average weight average molecular weight of about 140 kDa.

In an embodiment, a composition of the present disclosure includes silk protein fragments having an average weight average molecular weight of about 141 kDa. In an embodiment, a composition of the present disclosure includes silk protein fragments having an average weight average molecular weight of about 142 kDa. In an embodiment, a composition of the present disclosure includes silk protein fragments having an average weight average molecular weight of about 143 kDa. In an embodiment, a composition of the present disclosure includes silk protein fragments having an average weight average molecular weight of about 144 kDa.

In an embodiment, a composition of the present disclosure includes silk fibroin-based protein fragments having one or more of low molecular weight, medium molecular weight, and high molecular weight. In an embodiment, a composition of the present disclosure includes silk fibroin-based protein fragments having low molecular weight and silk fibroin-based protein fragments having medium molecular weight. In an embodiment, a composition of the present disclosure includes silk fibroin-based protein fragments having low molecular weight and silk fibroin-based protein fragments having high molecular weight. In an embodiment, a composition of the present disclosure includes silk fibroin-based protein fragments having medium molecular weight and silk fibroin-based protein fragments having high molecular weight. In an embodiment, a composition of the present disclosure includes silk fibroin-based protein fragments having low molecular weight, silk fibroin-based protein fragments having medium molecular weight, and silk fibroin-based protein fragments having high molecular weight.

In an embodiment, a composition of the present disclosure includes silk fibroin-based protein fragments having low molecular weight and silk fibroin-based protein fragments having medium molecular weight. In some embodiments, the w/w ratio between low molecular weight silk fibroin-based protein fragments and medium molecular weight silk fibroin-based protein fragments is between about 99:1 to about 1:99, between about 95:5 to about 5:95, between about 90:10 to about 10:90, between about 75:25 to about 25:75, between about 65:35 to about 35:65, or between about 55:45 to about 45:55. In some embodiments, the w/w ratio between low molecular weight silk fibroin-based protein fragments and medium molecular weight silk fibroin-based protein fragments is between about 99:1 to about 55:45, between about 95:5 to about 45:55, between about 90:10 to about 35:65, between about 75:25 to about 15:85, between about 65:35 to about 10:90, or between about 55:45 to about 1:99. In an embodiment, the w/w ratio between low molecular weight silk fibroin-based protein fragments and medium molecular weight silk fibroin-based protein fragments is about 99:1, about 98:2, about 97:3, about 96:4, about 95:5, about 94:6, about 93:7, about 92:8, about 91:9, about 90:10, about 89:11, about 88:12, about 87:13, about 86:14, about 85:15, about 84:16, about 83:17, about 82:18, about 81:19, about 80:20, about 79:21, about 78:22, about 77:23, about 76:24, about 75:25, about 74:26, about 73:27, about 72:28, about 71:29, about 70:30, about 69:31, about 68:32, about 67:33, about 66:34, about 65:35, about 64:36, about 63:37, about 62:38, about 61:39, about 60:40, about 59:41, about 58:42, about 57:43, about 56:44, about 55:45, about 54:46, about 53:47, about 52:48, about 51:49, about 50:50, about 49:51, about 48:52, about 47:53, about 46:54, about 45:55, about 44:56, about 43:57, about 42:58, about 41:59, about 40:60, about 39:61, about 38:62, about 37:63, about 36:64, about 35:65, about 34:66, about 33:67, about 32:68, about 31:69, about 30:70, about 29:71, about 28:72, about 27:73, about 26:74, about 25:75, about 24:76, about 23:77, about 22:78, about 21:79, about 20:80, about 19:81, about 18:82, about 17:83, about 16:84, about 15:85, about 14:86, about 13:87, about 12:88, about 11:89, about 10:90, about 9:91, about 8:92, about 7:93, about 6:94, about 5:95, about 4:96, about 3:97, about 2:98, or about 1:99.

In an embodiment, a composition of the present disclosure includes silk fibroin-based protein fragments having low molecular weight and silk fibroin-based protein fragments having high molecular weight. In some embodiments, the w/w ratio between low molecular weight silk fibroin-based protein fragments and high molecular weight silk fibroin-based protein fragments is between about 99:1 to about 1:99, between about 95:5 to about 5:95, between about 90:10 to about 10:90, between about 75:25 to about 25:75, between about 65:35 to about 35:65, or between about 55:45 to about 45:55. In some embodiments, the w/w ratio between low molecular weight silk fibroin-based protein fragments and high molecular weight silk fibroin-based protein fragments is between about 99:1 to about 55:45, between about 95:5 to about 45:55, between about 90:10 to about 35:65, between about 75:25 to about 15:85, between about 65:35 to about 10:90, or between about 55:45 to about 1:99. In an embodiment, the w/w ratio between low molecular weight silk fibroin-based protein fragments and high molecular weight silk fibroin-based protein fragments is about 99:1, about 98:2, about 97:3, about 96:4, about 95:5, about 94:6, about 93:7, about 92:8, about 91:9, about 90:10, about 89:11, about 88:12, about 87:13, about 86:14, about 85:15, about 84:16, about 83:17, about 82:18, about 81:19, about 80:20, about 79:21, about 78:22, about 77:23, about 76:24, about 75:25, about 74:26, about 73:27, about 72:28, about 71:29, about 70:30, about 69:31, about 68:32, about 67:33, about 66:34, about 65:35, about 64:36, about 63:37, about 62:38, about 61:39, about 60:40, about 59:41, about 58:42, about 57:43, about 56:44, about 55:45, about 54:46, about 53:47, about 52:48, about 51:49, about 50:50, about 49:51, about 48:52, about 47:53, about 46:54, about 45:55, about 44:56, about 43:57, about 42:58, about 41:59, about 40:60, about 39:61, about 38:62, about 37:63, about 36:64, about 35:65, about 34:66, about 33:67, about 32:68, about 31:69, about 30:70, about 29:71, about 28:72, about 27:73, about 26:74, about 25:75, about 24:76, about 23:77, about 22:78, about 21:79, about 20:80, about 19:81, about 18:82, about 17:83, about 16:84, about 15:85, about 14:86, about 13:87, about 12:88, about 11:89, about 10:90, about 9:91, about 8:92, about 7:93, about 6:94, about 5:95, about 4:96, about 3:97, about 2:98, or about 1:99.

In an embodiment, a composition of the present disclosure includes silk fibroin-based protein fragments having medium molecular weight and silk fibroin-based protein fragments having high molecular weight. In some embodiments, the w/w ratio between medium molecular weight silk fibroin-based protein fragments and high molecular weight silk fibroin-based protein fragments is between about 99:1 to about 1:99, between about 95:5 to about 5:95, between about 90:10 to about 10:90, between about 75:25 to about 25:75, between about 65:35 to about 35:65, or between about 55:45 to about 45:55. In some embodiments, the w/w ratio between medium molecular weight silk fibroin-based protein fragments and high molecular weight silk fibroin-based protein fragments is between about 99:1 to about 55:45, between about 95:5 to about 45:55, between about 90:10 to about 35:65, between about 75:25 to about 15:85, between about 65:35 to about 10:90, or between about 55:45 to about 1:99. In an embodiment, the w/w ratio between medium molecular weight silk fibroin-based protein fragments and high molecular weight silk fibroin-based protein fragments is about 99:1, about 98:2, about 97:3, about 96:4, about 95:5, about 94:6, about 93:7, about 92:8, about 91:9, about 90:10, about 89:11, about 88:12, about 87:13, about 86:14, about 85:15, about 84:16, about 83:17, about 82:18, about 81:19, about 80:20, about 79:21, about 78:22, about 77:23, about 76:24, about 75:25, about 74:26, about 73:27, about 72:28, about 71:29, about 70:30, about 69:31, about 68:32, about 67:33, about 66:34, about 65:35, about 64:36, about 63:37, about 62:38, about 61:39, about 60:40, about 59:41, about 58:42, about 57:43, about 56:44, about 55:45, about 54:46, about 53:47, about 52:48, about 51:49, about 50:50, about 49:51, about 48:52, about 47:53, about 46:54, about 45:55, about 44:56, about 43:57, about 42:58, about 41:59, about 40:60, about 39:61, about 38:62, about 37:63, about 36:64, about 35:65, about 34:66, about 33:67, about 32:68, about 31:69, about 30:70, about 29:71, about 28:72, about 27:73, about 26:74, about 25:75, about 24:76, about 23:77, about 22:78, about 21:79, about 20:80, about 19:81, about 18:82, about 17:83, about 16:84, about 15:85, about 14:86, about 13:87, about 12:88, about 11:89, about 10:90, about 9:91, about 8:92, about 7:93, about 6:94, about 5:95, about 4:96, about 3:97, about 2:98, or about 1:99.

In an embodiment, a composition of the present disclosure includes silk fibroin-based protein fragments having low molecular weight, silk fibroin-based protein fragments having medium molecular weight, and silk fibroin-based protein fragments having high molecular weight. In an embodiment, the w/w ratio between low molecular weight silk fibroin-based protein fragments, medium molecular weight silk fibroin-based protein fragments, and high molecular weight silk fibroin-based protein fragments is about 1:1:8, about 1:2:7, about 1:3:6, about 1:4:5, about 1:5:4, about 1:6:3, about 1:7:2, about 1:8:1, about 2:1:7, about 2:2:6, about 2:3:5, about 2:4:4, about 2:5:3, about 2:6:2, about 2:7:1, about 3:1:6, about 3:2:5, about 3:3:4, about 3:4:3, about 3:5:2, about 3:6:1, about 4:1:5, about 4:2:4, about 4:3:3, about 4:4:2, about 4:5:1, about 5:1:4, about 5:2:3, about 5:3:2, about 5:4:1, about 6:1:3, about 6:2:2, about 6:3:1, about 7:1:2, about 7:2:1, or about 8:1:1.

In some embodiments, the silk compositions provided herein may be applied as mixtures to an article to be processed or in stepwise processes to the article. For example, a silk composition that includes low molecular weight silk and medium molecular weight silk may be applied to an article to be processed. Alternatively, a low molecular weight silk composition may be applied to an article to be processed, as provided by the processes described herein, and then a medium or high molecular weight silk may then be applied to the article. The low, medium, and high molecular weight silk compositions may be added in any order or any combination (e.g., low/med, low/high, med/high, low/med/high).

In some embodiments, the silk compositions provided herein may be applied as mixtures to an article to be coated or in stepwise processes to form coating layers on the article. For example, a silk composition that includes low molecular weight silk and medium molecular weight silk may be applied to an article to be coated. Alternatively, a low molecular weight silk composition may be applied to an article to be coated, as provided by the processes described herein, and then a medium or high molecular weight silk may then be applied to the article. The low, medium, and high molecular weight silk compositions may be added in any order or any combination (e.g., low/med, low/high, med/high, low/med/high).

In some embodiments, the silk compositions provided herein may be applied as mixtures to an article to be repaired or in stepwise processes to form fillings in or on the article. For example, a silk composition that includes low molecular weight silk and medium molecular weight silk may be applied to an article to be repaired. Alternatively, a low molecular weight silk composition may be applied to an article to be repaired, as provided by the processes described herein, and then a medium or high molecular weight silk may then be applied to the article. The low, medium, and high molecular weight silk compositions may be added in any order or any combination (e.g., low/med, low/high, med/high, low/med/high).

In some embodiments, where multiple layers of silk compositions are applied to an article to be coated, they may have at least one layer, or 1 layer to 1 million layers, or 1 layer to 100,000 layers, or 1 layer to 10,000 layers, or 1 layer to 1,000 layers of such silk compositions, wherein the layers may have the same or different thicknesses. For example, in some embodiments, the layers may have a thickness of from about 1 nm to about 1 mm, or about 1 nm to about 1 µm, or about 1 nm to about 500 nm, or about 1 nm to about 400 nm, or about 1 nm to about 300 nm, or about 1 nm to about 200 nm, or about 1 nm to about 100 nm, or about 1 nm to about 75 nm, or about 1 nm to about 50 nm, or about 1 nm to about 25 nm, or about 1 nm to about 20 nm, or about 1 nm to about 15 nm, or about 1 nm to about 10 nm, or about 1 nm to about 5 nm.

In an embodiment, a composition of the present disclosure having pure silk fibroin-based protein fragments has a polydispersity ranging from about 1 to about 5.0. In an embodiment, a composition of the present disclosure having pure silk fibroin-based protein fragments has a polydispersity ranging from about 1.5 to about 3.0. In an embodiment, a composition of the present disclosure having pure silk fibroin-based protein fragments has a polydispersity ranging from about 1 to about 1.5. In an embodiment, a composition of the present disclosure having pure silk fibroin-based protein fragments has a polydispersity ranging from about 1.5 to about 2.0. In an embodiment, a composition of the present disclosure having pure silk fibroin-based protein fragments has a polydispersity ranging from about 2.0 to about 2.5. In an embodiment, a composition of the present disclosure having pure silk fibroin-based protein fragments, has a polydispersity ranging from about is 2.0 to about 3.0. In an embodiment, a composition of the present disclosure having pure silk fibroin-based protein fragments, has a polydispersity ranging from about is 2.5 to about 3.0.

In an embodiment, a composition of the present disclosure having silk protein fragments has a polydispersity ranging from about 1 to about 5.0. In an embodiment, a composition of the present disclosure having silk protein fragments has a polydispersity ranging from about 1.5 to about 3.0. In an embodiment, a composition of the present disclosure having silk protein fragments has a polydispersity ranging from about 1 to about 1.5. In an embodiment, a composition of the present disclosure having silk protein fragments has a polydispersity ranging from about 1.5 to about 2.0. In an embodiment, a composition of the present disclosure having silk protein fragments has a polydispersity ranging from about 2.0 to about 2.5. In an embodiment, a composition of the present disclosure having silk protein fragments, has a polydispersity ranging from about is 2.0 to about 3.0. In an embodiment, a composition of the present disclosure having silk protein fragments, has a polydispersity ranging from about is 2.5 to about 3.0.

In some embodiments the polydispersity of low molecular weight silk protein fragments may be about 1 to about 5.0, or about 1.5 to about 3.0, or about 1 to about 1.5, or about 1.5 to about 2.0, or about 2.0 to about 2.5, or about 2.5 to about 3.0.

In some embodiments the polydispersity of medium molecular weight silk protein fragments may be about 1 to about 5.0, or about 1.5 to about 3.0, or about 1 to about 1.5, or about 1.5 to about 2.0, or about 2.0 to about 2.5, or about 2.5 to about 3.0.

In some embodiments the polydispersity of high molecular weight silk protein fragments may be about 1 to about 5.0, or about 1.5 to about 3.0, or about 1 to about 1.5, or about 1.5 to about 2.0, or about 2.0 to about 2.5, or about 2.5 to about 3.0.

In some embodiments, in compositions described herein having combinations of low, medium, and/or high molecular weight silk protein fragments, such low, medium, and/or high molecular weight silk proteins may have the same or different polydispersities.

In some embodiments, SFS may be supplied in a concentrated form suspended in water. In some embodiments, SFS may have a concentration by weight (% w/w or % w/v) or by volume (v/v) of less than about 50%, or less than about 45%, or less than about 40%, or less than about 35%, or less than about 30%, or less than about 25%, or less than about 20%, or less than about 15%, or less than about 10%, or less than about 5%, or less than about 4%, or less than about 3%, or less than about 2%, or less than about 1%, or less than about 0.1%, or less than about 0.01%, or less than about 0.001%, or less than about 0.0001%, or less than about 0.00001%. In some embodiments, SFS may have a concentration by weight (% w/w or % w/v) or by volume (v/v) of greater than about 50%, or greater than about 45%, or greater than about 40%, or greater than about 35%, or greater than about 30%, or greater than about 25%, or greater than about 20%, or greater than about 15%, or greater than about 10%, or greater than about 5%, or greater than about 4%, or greater than about 3%, or greater than about 2%, or greater than about 1%, or greater than about 0.1%, or greater than about 0.01%, or greater than about 0.001%, or greater than about 0.0001%, or greater than about 0.00001%.

In some embodiments, the solution concentration and the wet pick of the material determines the amount of silk fibroin solution (SFS), which may include silk-based proteins or fragments thereof, that may be fixed or otherwise adhered to the faux or bonded leather, or faux or bonded leather article being coated. The wet pick up may be expressed by the following formula:

$$\text{wet pick up (\%)} = \frac{\text{weigh of } \textit{SFS} \text{ applied}}{\text{weight of dry textile material}} \times 100$$

The total amount of SFS added to the faux or bonded leather, or faux or bonded leather article may be expressed by the following formula:

$$\text{SFS added (\%)} = \frac{\text{weigh of dry SFS coated material}}{\text{weight of dry material before coating}} \times 100$$

Regarding methods for applying SFS to faux or bonded leather, or faux or bonded leather articles more broadly, SFS may be applied to faux or bonded leather, or faux or bonded leather articles through a pad or roller application on process, a saturation and removal process, and/or a topical application process. Moreover, the methods of silk application (i.e., SFS application or coating) may include bath coating, kiss rolling, spray coating, and/or two-sided rolling. In some embodiments, the coating processes (e.g., bath coating, kiss rolling, spray coating, two-sided rolling, roller application, saturation and removal application, and/or topical application), drying processes, and curing processes may be varied as described herein to modify one or more selected faux or bonded leather, or faux or bonded leather article properties of the resulting coated faux or bonded leather, or faux or bonded leather article wherein such properties.

In an embodiment, the drying and/or curing temperature for the processes of the disclosure may be less than about 70° C., or less than about 75° C., or less than about 80° C., or less than about 85° C., or less than about 90° C., or less than about 95° C., or less than about 100° C., or less than about 110° C., or less than about 120° C., or less than about 130° C., or less than about 140° C., or less than about 150° C., or less than about 160° C., or less than about 170° C., or less than about 180° C., or less than about 190° C., or less than about 200° C., or less than about 210° C., or less than about 220° C., or less than about 230° C.

In an embodiment, the drying and/or curing temperature for the processes of the disclosure may be greater than about 70° C., or greater than about 75° C., or greater than about 80° C., or greater than about 85° C., or greater than about 90° C., or greater than about 95° C., or greater than about 100° C., or greater than about 110° C., or greater than about 120° C., or greater than about 130° C., or greater than about 140° C., or greater than about 150° C., or greater than about 160° C., or greater than about 170° C., or greater than about 180° C., or greater than about 190° C., or greater than about 200° C., or greater than about 210° C., or greater than about 220° C., or greater than about 230° C.

In an embodiment, the drying time for the processes of the disclosure may be less than about 10 seconds, or less than about 20 seconds, or less than about 30 seconds, or less than about 40 seconds, or less than about 50 seconds, or less than about 60 seconds, or less than about 2 minutes, or less than about, 3 minutes, or less than about 4 minutes, or less than about 5 minutes, or less than about 6 minutes, or less than about 7 minutes, or less than about 8 minutes, or less than about 9 minutes, or less than about 10 minutes, or less than about 20 minutes, or less than about 30 minutes, or less than about 40 minutes, or less than about 50 minutes, or less than about 60 minutes.

In an embodiment, the drying time for the processes of the disclosure may be greater than about 10 seconds, or greater than about 20 seconds, or greater than about 30 seconds, or greater than about 40 seconds, or greater than about 50 seconds, or greater than about 60 seconds, or greater than about 2 minutes, or greater than about, 3 minutes, or greater than about 4 minutes, or greater than about 5 minutes, or greater than about 6 minutes, or greater than about 7 minutes, or greater than about 8 minutes, or greater than about 9 minutes, or greater than about 10 minutes, or greater than about 20 minutes, or greater than about 30 minutes, or greater than about 40 minutes, or greater than about 50 minutes, or greater than about 60 minutes.

In an embodiment, the curing time for the processes of the disclosure may be less than about 1 second, or less than about 2 seconds, or less than about 3 seconds, or less than about 4 seconds, or less than about 5 seconds, or less than about 6 seconds, or less than about 7 seconds, or less than about 8 seconds, or less than about 9 seconds, or less than about 10 seconds, or less than about 20 seconds, or less than about 30 seconds, or less than about 40 seconds, or less than about 50 seconds, or less than about 60 seconds, or less than about 2 minutes, or less than about 3 minutes, or less than about 4 minutes, or less than about 5 minutes, or less than about 6 minutes, or less than about 7 minutes, or less than about 8 minutes, or less than about 9 minutes, or less than about 10 minutes, or less than about 20 minutes, or less than about 30 minutes, or less than about 40 minutes, or less than about 50 minutes, or less than about 60 minutes.

In an embodiment, the curing time for the processes of the disclosure may be greater than about 1 second, or greater than about 2 seconds, or greater than about 3 seconds, or greater than about 4 seconds, or greater than about 5 seconds, or greater than about 6 seconds, or greater than about 7 seconds, or greater than about 8 seconds, or greater than about 9 seconds, or greater than about 10 seconds, or greater than about 20 seconds, or greater than about 30 seconds, or greater than about 40 seconds, or greater than about 50 seconds, or greater than about 60 seconds, or greater than about 2 minutes, or greater than about 3 minutes, or greater than about 4 minutes, or greater than about 5 minutes, or greater than about 6 minutes, or greater than about 7 minutes, or greater than about 8 minutes, or greater than about 9 minutes, or greater than about 10 minutes, or greater than about 20 minutes, or greater than about 30 minutes, or greater than about 40 minutes, or greater than about 50 minutes, or greater than about 60 minutes.

In some embodiments, a silk fibroin processed or coated material may be heat resistant to a selected temperature where the selected temperature is chosen for drying, curing, and/or heat setting a dye that may be applied to the material (e.g., a coated faux or bonded leather, or faux or bonded leather article). As used herein, a "heat resistant" may refer to a property of the silk fibroin coating deposited on the material where the silk fibroin coating and/or silk fibroin protein does not exhibit a substantial modification (i.e., "substantially modifying") in silk fibroin coating performance as compared to a control material having a comparable silk fibroin coating that was not subjected to the selected temperature for drying, curing, wash cycling, and/or heat setting purposes. In some embodiments, the selected temperature is the glass transition temperature ($T_g$) for the material upon which the silk fibroin coating is applied. In some embodiments, the selected temperature is greater than about 65° C., or greater than about 70° C., or greater than about 80° C., or greater than about 90° C., or greater than about 100° C., or greater than about 110° C., or greater than about 120° C., or greater than about 130° C., or greater than about 140° C., or greater than about 150° C., or greater than about 160° C., or greater than about 170° C., or greater than about 180° C., or greater than about 190° C., or greater than about 200° C., or greater than about 210° C., or greater than about 220° C. In some embodiments, the selected temperature is less than about 65° C., or less than about 70° C., or less than about 80° C., or less than about 90° C., or less than about 100° C., or less than about 110° C., or less than about 120° C., or less than about 130° C., or less than about 140°

C., or less than about 150° C., or less than about 160° C., or less than about 170° C., or less than about 180° C., or less than about 190° C., or less than about 200° C., or less than about 210° C., or less than about 220° C. In some embodiments, the SFS processed, coated, or repaired article may be subjected to heat setting in order to set one or more dyes that may be applied to the SFS coated article in order to permanently set the one or more dyes on the SFS coated or repaired article. In some embodiments, the SFS processed, coated, or repaired article may be heat setting resistant, wherein the SFS coating on the SFS coated article may resist a heat setting temperature of greater than about 100° C., or greater than about 110° C., or greater than about 120° C., or greater than about 130° C., or greater than about 140° C., or greater than about 150° C., or greater than about 160° C., or greater than about 170° C., or greater than about 180° C., or greater than about 190° C., or greater than about 200° C., or greater than about 210° C., or greater than about 220° C. In some embodiments, the selected temperature is less than about 100° C., or less than about 110° C., or less than about 120° C., or less than about 130° C., or less than about 140° C., or less than about 150° C., or less than about 160° C., or less than about 170° C., or less than about 180° C., or less than about 190° C., or less than about 200° C., or less than about 210° C., or less than about 220° C.

In an embodiment, a material processed, coated, or repaired by the silk fibroin coating or filling composition as described herein may partially dissolved or otherwise partially incorporated within a portion of the material after the silk fibroin coated or repaired material is subjected to heating and/or curing as described herein.

Without being limited to any one theory of the disclosure, where the silk fibroin processed, coated, or repaired material is heated to greater than about the glass transition temperature (Tg) for the material that is processed, coated, or repaired, the silk fibroin coating may become partially dissolved or otherwise partially incorporated within a portion of the material.

In some embodiments, a material processed, coated, or repaired by the silk fibroin coating as described herein may be sterile or may be sterilized to provide a sterilized silk fibroin coated material. Alternatively, or in addition thereto, the methods described herein may include a sterile SFS prepared from sterile silk fibroin.

In some embodiments, SFS may be used in an SFS processing composition, coating, or repairing composition, where such composition or coating includes one or more chemical agents (e.g., a silicone). SFS may be provided in such an SFS coating at a concentration by weight (% w/w or % w/v) or by volume (v/v) of less than about 50%, or less than about 45%, or less than about 40%, or less than about 35%, or less than about 30%, or less than about 25%, or less than about 20%, or less than about 15%, or less than about 10%, or less than about 9%, or less than about 8%, or less than about 7%, or less than about 6%, or less than about 5%, or less than about 4%, or less than about 3%, or less than about 2%, or less than about 1%, or less than about 0.9%, or less than about 0.8%, or less than about 0.7%, or less than about 0.6%, or less than about 0.5%, or less than about 0.4%, or less than about 0.3%, or less than about 0.2%, or less than about 0.1%, or less than about 0.01%, or less than about 0.001%. In some embodiments, SFS may be provided in such an SFS coating at a concentration by weight (% w/w or % w/v) or by volume (v/v) of greater than about 25%, or greater than about 20%, or greater than about 15%, or greater than about 10%, or greater than about 9%, or greater than about 8%, or greater than about 7%, or greater than about 6%, or greater than about 5%, or greater than about 4%, or greater than about 3%, or greater than about 2%, or greater than about 1%, or greater than about 0.9%, or greater than about 0.8%, or greater than about 0.7%, or greater than about 0.6%, or greater than about 0.5%, or greater than about 0.4%, or greater than about 0.3%, or greater than about 0.2%, or greater than about 0.1%, or greater than about 0.01%, or greater than about 0.001%.

In some embodiments, chemical fabric softeners may include silicones as described herein.

In some embodiments, the chemical agents may include the following, which are supplied by CHT Bezema and are associated with certain selected faux or bonded leather's or faux or bonded leather article's properties, which may be used to strengthen SFS binding on coated or repaired surfaces and/or SFS may be used for enhancing the following chemical agents' properties:

ALPAPRINT CLEAR
  Silicone printing and coating
  Component B is mentioned in the technical leaflet Dry handle
  Good rubbing fastness
  Good washfastness
ALPAPRINT ELASTIC ADD
  Silicone printing and coating
  Component B is mentioned in the technical leaflet
  Good
  rubbing fastness
  Good washfastness
  Suited for yardage printing
ALPAPRINT WHITE
  Silicone printing and coating
  Component B is mentioned in the technical leaflet
  Dry handle
  Good rubbing fastness Good
  washfastness
ALPATEC 30142 A
  Textile finishing
  Coating
  Silicone printing and coating
  Component B is mentioned in the technical leaflet
  Suitable
  for narrow ribbon coating
  Good rubbing fastness
  Good washfastness
ALPATEC 30143 A
  Silicone printing and coating
  Component B is mentioned in the technical leaflet
  Good rubbing fastness Good
  washfastness
  Suited for yardage printing
ALPATEC 30191 A
  Silicone printing and coating
  Component B is mentioned in the technical leaflet
  Suitable for narrow ribbon coating
  High transparency Coating
ALPATEC 30203 A
  Silicone printing and coating
  Component B is mentioned in the technical leaflet
  Suitable
  for narrow ribbon coating
  High transparency Coating
ALPATEC 3040 LSR KOMP. A
  Functional coatings, Silicone printing and coating
  Component B is mentioned in the technical leaflet High abrasion resistance
  High transparency
  Coating ALPATEC 3060 LSR KOMP. A
  Functional coatings, Silicone printing and coating
  Component B is mentioned in the technical leaflet High abrasion resistance
  High transparency
  Coating
ALPATEC 530
  Silicone printing and coating Suitable for narrow ribbon coating
  High transparency Coating
  One component system
ALPATEC 540
  Silicone printing and coating Suitable for narrow ribbon coating High transparency
  Coating
  One component system
ALPATEC 545
  Silicone printing and coating Suitable for narrow ribbon coating High transparency
  Coating
  One component system
ALPATEC 550
  Silicone printing and coating Suitable for narrow ribbon coating High transparency
  Coating
  One component system
ALPATEC 730
  Silicone printing and coating Suitable for narrow ribbon coating
  Good washfastness High abrasion resistance High transparency
ALPATEC 740
  Silicone printing and coating
  Suitable for narrow ribbon coating Good washfastness
  High abrasion resistance High transparency
ALPATEC 745
  Silicone printing and coating Suitable for narrow ribbon coating Good washfastness
  High abrasion resistance
  High transparency
ALPATEC 750
  Silicone printing and coating Suitable for narrow ribbon coating Good washfastness
  High abrasion resistance High transparency
ALPATEC BANDAGE A
  Silicone printing and coating
  Component B is mentioned in the technical leaflet
  Suitable for narrow ribbon coating
  Coating
  Two component system
APYROL BASE2 E
  Flame retardants
  Liquid
  Soft handle
  For BS 5852/1+2
  Suited for paste coating
APYROL FCR-2
  Water repellency/oil repellency
  Cationic
  High effectiveness
  Water-based Liquid
APYROL FFD E Flame
  retardants Liquid
  Suited for polyester Suited
  for polyamide
  Flame inhibiting filler
APYROL FR CONC E
  Flame retardants, Functional coatings
  Liquid
  Suited for polyester Suited
  for polyamide Flame
  inhibiting filler
APYROL GBO-E
  Flame retardants, Functional coatings
  Suited for polyester
  Black-out coating For
  DIN 4102/B1 Containing
  halogen
APYROL LV 21
  Flame retardants, Functional coatings For
  DIN 4102/B1
  Suited for paste coating
  Suited for backcoating of black-out vertical blinds and roller blinds
  Containing halogen
APYROL PP 31
  Flame retardants Liquid
  Free from antimony Flame inhibiting filler
  For BS 5852/1+2
APYROL PP 46
  Flame retardants Powder
  Free from antimony
  Flame inhibiting filler Suited
  for paste coating
APYROL PREM E
  Flame retardants Soft
  handle
  For BS 5852/1+2
  Containing halogen Semi-permanent
APYROL PREM2 E
  Flame retardants Soft
  handle
  For BS 5852/1+2
  Containing halogen Semi-permanent
COLORDUR005 WHITE
  Flock adhesives, Functional coatings, Silicone printing and coating Based
  on silicone
  Dyestuff pigment suspension
COLORDUR 105 LEMON
  Flock adhesives, Functional coatings, Silicone printing and coating Based
  on silicone
  Dyestuff pigment suspension
COLORDUR 115 GOLDEN YELLOW
  Flock adhesives, Functional coatings, Silicone printing and coating
  Based on silicone
  Dyestuff pigment suspension
COLORDUR 185 ORANGE
  Flock adhesives, Functional coatings, Silicone printing and coating Based
  on silicone
  Dyestuff pigment suspension COLORDUR215 RED
  Flock adhesives, Functional coatings, Silicone printing and coating Based
  on silicone
  Dyestuff pigment suspension
COLORDUR 225 DARK RED
  Flock adhesives, Functional coatings, Silicone printing and coating Based
  on silicone
  Dyestuff pigment suspension
COLORDUR 285 VIOLET
  Flock adhesives, Functional coatings, Silicone printing and coating Based
  on silicone
  Dyestuff pigment suspension
COLORDUR 305 BLUE
  Flock adhesives, Functional coatings, Silicone printing and coating Based
  on silicone
  Dyestuff pigment suspension
COLORDUR 355 MARINE
  Flock adhesives, Functional coatings, Silicone printing and coating
  Based on silicone
  Dyestuff pigment suspension
COLORDUR 405 GREEN
  Flock adhesives, Functional coatings, Silicone printing and coating Based
  on silicone
  Dyestuff pigment suspension
COLORDUR 465 OLIVE GREEN
  Flock adhesives, Functional coatings, Silicone printing and coating Based
  on silicone
  Dyestuff pigment suspension
COLORDUR 705 BLACK
  Flock adhesives, Functional coatings, Silicone printing and coating Based
  on silicone
  Dyestuff pigment suspension
COLORDUR AM ADDITIVE
  Flock adhesives, Silicone printing and coating Based
  on silicone
  Migration prevention Dyestuff
  pigment suspension
COLORDUR FL 1015 YELLOW
  Flock adhesives, Functional coatings, Silicone printing and coating Based
  on silicone
  Dyestuff pigment suspension
COLORDUR FL 1815 ORANGE
  Flock adhesives, Functional coatings, Silicone printing and coating
  Based on silicone
  Dyestuff pigment suspension
COLORDUR FL 2415 PINK
  Flock adhesives, Functional coatings, Silicone printing and coating
  Based on silicone
  Dyestuff pigment suspension
COLORDUR FL 4015 GREEN
  Flock adhesives, Functional coatings, Silicone printing and coating Based
  on silicone
  Dyestuff pigment suspension
ECOPERL 1
  Water repellency/oil repellency
  Washfast
  Sprayable
  Based on special functionalised polymers/waxes
  Cationic
ECOPERL ACTIVE
  Water repellency/oil repellency
  Washfast
  Based on special functionalised polymers/waxes
  Cationic
  High effectiveness
LAMETHAN 1 ET 25 BR 160
  Functional coatings, Lamination
  Washfast
  Transparent 25 μm
  strong
  Film based on polyester urethane
LAMETHAN ADH-1
  Functional coatings, Lamination
  Breathable
  Suited for dry laminating
  Good stability to washing at 40° C. Stable foam adhesive LAMETHAN ADH-L
  Functional coatings, Lamination
  Washfast
  Transparent
  Suited forpaste coating Suited
  for wet laminating
LAMETHAN ALF-K
  Functional coatings, Lamination
  Adhesive additive for bondings
  Suited for dry laminating Stable foam adhesive
  Suited for stable foam coating
LAMETHAN LB 15-T BR 152DK
  Functional coatings, Lamination
  Transparent
  15 μm strong Breathable
  Suited for dry laminating
LAMETHAN LB 25 BR 155
  Functional coatings, Lamination
  Transparent
  25 μm strong
  Suited for dry laminating
  Good stability to washing at 40° C.
LAMETHAN LB 25 W BR 152
  Lamination 25 μm
  strong Breathable
  Suited for dry laminating
  Good stability to washing at 40° C.
LAMETHAN TAPE DE 80
  Functional coatings, Lamination
  Polymer base: polyurethane
  Transparent
  ood stability to washing at 40° C. Tape
  for seam sealing
LAMETHAN TAPE ME 160
  Functional coatings, Lamination
  Polymerbase: polyurethane
  Transparent
  Good stability to washing at 40° C. Tape
  for seam sealing LAMETHAN VL-H920 O BR150
  Functional coatings, Lamination
  Two coats with membrane and PES charmeuse
  Breathable
  Suited for dry laminating
  Good stability to washing at 40° C.
LAMETHAN VL-H920 S BR 150
  Functional coatings, Lamination
  Two coats with membrane and PES charmeuse
  Breathable
  Suited for dry laminating
  Good stability to washing at 40° C.
LAMETHAN VL-H920 W BR150
  Functional coatings, Lamination
  Two coats with membrane and PES charmeuse
  Breathable
  Suited for dry laminating
  Good stability to washing at 40° C.
TUBICOAT A 12 E
  Binders, Functional coatings
  Anionic
  Liquid
  Formaldehyde-free Polymer base:
  polyacrylate
TUBICOAT A 17
  Binders, Functional coatings
  Suitable for tablecloth coating
  Anionic
  Liquid
  Self-crosslinking
TUBICOAT A 19
  Binders, Functional coatings
  Washfast
  Anionic Formaldehyde-free
  Good stabilityto washing
TUBICOAT A 22
  Binders, Functional coatings
  Washfast
  Medium-hard film
  Anionic
  Liquid TUBICOAT A
  Binders
  Medium-hard film
  Anionic
  Liquid
  Application for varying the handle
TUBICOAT A 28
  Binders, Functional coatings
  Anionic
  Liquid Formaldehyde-free
  Good stability to washing
TUBICOAT A 36
  Binders, Functional coatings
  Washfast
  Anionic Liquid
  Low formaldehyde
TUBICOAT A 37
  Binders, Functional coatings
  Washfast
  Suitable for tablecloth coating
  Anionic
  Liquid TUBICOAT A
41
  Binders, Functional coatings
  Anionic
  Liquid
  Self-crosslinking Good
  fastnesses
TUBICOAT A 61
  Binders, Functional coatings
  Suitable for tablecloth coating
  Liquid
  Non-ionic
  Self-crosslinking TUBICOAT
A 94
  Binders, Functional coatings
  Anionic
  Liquid
  Self-crosslinking Good
  fastnesses
TUBICOAT AIB 20 Fashion
  coatings Transparent
  Suited for foam coating Pearl
  Gloss Finish
TUBICOAT AOS Foaming
  auxiliaries Non-ionic
  Foaming
  Suited for the fluorocarbon finishing
TUBICOAT ASK
  Functional coatings, Lamination
  Adhesive additive for bondings
  Transparent
  Suited forpaste coating Suited
  for dry laminating
TUBICOAT B-H
  Binders, Functional coatings Polymer
  base: Styrene butadiene
  Anionic
  Liquid Formaldehyde-free
TUBICOAT B 45
  Binders, Functional coatings
  Washfast
  Polymer base: Styrene butadiene
  Anionic
  Liquid TUBICOAT BO-NB
  Functional coatings
  Medium hard
  Suited for black-out coating
  Good flexibility at low temperatures Suited
  for stable foam coating
TUBICOAT BO-W Functional
  coatings
  Suited for black-out coating
  Impermeable for light
  Suited for stable foam coating
  Water vapourpermeable
TUBICOAT BOS
  Foaming auxiliaries Anionic
  Foaming
  Foam stabilizer TUBICOAT
DW-FI
  Functional coatings, Special products
  Anionic
  Suited forcoating pastes Suited
  for stable foam Foamable
TUBICOAT E 4
  Binders
  Anionic
  Self-crosslinking Low
  formaldehyde
  Polymer base: polyethylene vinyl acetate TUBICOAT ELC
  Functional coatings Suited for
  paste coating Black
  Electrically conductive Soft
TUBICOAT EMULGATOR HF
  Functional coatings, Special products
  Anionic
  Dispersing
  Suited for coating pastes
  Suited for stable foam
TUBICOAT ENTSCHAUMER N
  Defoamers and deaerators
  Liquid
  Non-ionic
  Silicone-free
  Suited for coating pastes
TUBICOAT FIX FC
  Fixing agents Cationic
  Water-based Liquid
  Formaldehyde-free
TUBICOAT FIX ICB CONC.
  Fixing agents
  Liquid Non-ionic
  Formaldehyde-free Suited for
  crosslinking
TUBICOATFIXIERERAZ
  Fixing agents Liquid
  Suited for crosslinking Based
  on polyaziridin
  Unblocked
TUBICOAT FIXIERER FA
  Fixing agents
  Anionic Water-based
  Liquid
  Low formaldehyde
TUBICOAT FIXIERER H 24
  Fixing agents Anionic
  Water-based Liquid
  Formaldehyde-free
TUBICOAT FIXIERER HT
  Fixing agents
  Water-based Liquid
  Non-ionic
  Suited for crosslinking
TUBICOAT FOAMER NY
  Foaming auxiliaries Non-ionic
  Foaming
  Suited for the fluorocarbon finishing
  Non-yellowing
TUB ICOAT GC PU
  Fashion coatings Washfast
  Soft handle
  Polymerbase: polyurethane
  Transparent
TUBICOAT GRIP
  Functional coatings Slip
  resistant
  Suited for stable foam coating Soft
TUBICOAT HEC
  Thickeners Powder
  Non-ionic
  Stable to electrolytes Stable
  to shear forces
TUBICOAT HOP-S
  Special products
  Anionic
  Suited for coating pastes
  Coating
  Adhesion promoter
TUBICOAT HS 8
  Binders
  Anionic Liquid
  Formaldehyde-free Hard film
TUBICOAT HWS-1
  Functional coatings Suited for
  paste coating Water-proof
  Suited for giant umbrellas and tents
TUBICOAT KL-TOP F
  Fashion coatings, Functional coatings
  Washfast
  Polymer base: polyurethane
  Transparent
  Suited for paste coating
TUBICOAT KLS-M
  Fashion coatings, Functional coatings
  Washfast
  Soft handle
  Polymer base: polyurethane
  Breathable
TUBICOAT MAF
  Fashion coatings
  Washfast
  Matrix effect
  Improves the rubbing fastnesses Soft
  handle
TUBICOAT MD TC 70
  Fashion coatings
  Vintage wax
  Suited for foam coating Suited
  for topcoats
TUBICOAT MEA
  Functional coatings
  Washfast
  Polymer base: polyurethane Suited
  for paste coating Suited for
  topcoat coatings
TUBICOAT MG-R
  Fashion coatings Washfast
  Soft handle
  Suited forpaste coating Duo
  Faux leather Finish
TUBICOAT MOP NEU
  Functional coatings, Special products
  Washfast
  Anionic
  Foamable Finish
TUBICOAT MP-D
  Fashion coatings, Functional coatings
  Washfast
  Soft handle Medium
  hard Breathable
TUBICOAT MP-W
  Functional coatings
  Washfast
  Polymer base: polyurethane
  Breathable
  Water-proof TUBICOAT NTC-SG Functional
  coatings Washfast
  Transparent
  Suited for paste coating
  Medium hard TUBICOAT
PERL A22-20
  Fashion coatings Suited for
  paste coating Suited for foam
  coating
  Pearl Gloss Finish
TUBICOAT PERL HS-1
  Functional coatings Suited for
  paste coating
  Suited forblack-out coating Suited
  for pearlescent coating Suited for
  topcoat coatings
TUBICOAT PERL PU SOFT
  Fashion coatings
  Washfast
  Scarabaeus effect Soft
  handle
  Polymer base: polyurethane
TUBICOAT PERL VC CONC.
  Fashion coatings, Functional coatings Soft
  handle
  Polymer base: polyurethane Suited
  for paste coating Suited for black-out coating
TUBICOAT PHV Functional
  coatings Medium hard
  Suited for three-dimensional dot coating
TUBICOAT PSA 1731
  Functional coatings, Lamination
  Transparent
  Suited for paste coating Suited
  for dry laminating Non-breathable
TUBICOAT PU-UV
  Binders Anionic
  Liquid
  Formaldehyde-free
  Good fastnesses TUBICOAT
PU 60
  Binders
  Anionic
  Liquid
  Application for varying the handle
  Formaldehyde-free
TUBICOAT PU 80
  Binders, Functional coatings
  Washfast
  Anionic Liquid
  Can be washed off
TUBICOAT PUH-BI
  Binders
  Anionic Liquid
  Formaldehyde-free Hard film
TUBICOAT PUL Functional
  coatings
  Polymer base: polyurethane Suited
  for paste coating
  Suited for three-dimensional dot coating
  Slip resistant
TUBICOAT PUS
  Binders, Functional coatings
  Anionic
  Liquid
  Formaldehyde-free Polymerbase:
  polyurethane
TUBICOAT PUW-M
  Binders
  Medium-hard film
  Anionic Liquid
  Formaldehyde-free
TUBICOAT PUW-S
  Binders
  Anionic Liquid
  Formaldehyde-free
  Good stability to washing
TUBICOAT PW 14
  Binders, Functional coatings
  Anionic
  Formaldehyde-free Heat-sealable
  Not wetting
TUBICOAT SA-M
  Functional coatings Washfast
  Suited for paste coating
  Suited for three-dimensional dot coating
TUBICOATSCHÄUMERHP
  Foaming auxiliaries, Functional coatings Non-ionic
  Foaming
  Suited for the fluorocarbon finishing
TUBICOAT SF-BASE
  Fashion coatings Washfast
  Soft handle
  Suited forfoam coating Silk
  gloss effect
TUBICOAT SHM
  Foaming auxiliaries Anionic
  Foam stabilizer TUBICOAT
SI 55
  Special products
  Pseudo-cationic
  Suited forcoating pastes
  Foamable
  Coating
TUBICOAT STABILISATOR RP
  Foaming auxiliaries
  Anionic
  Foam stabilizer TUBICOAT
STC 100
  Fashion coatings, Functional coatings
  Transparent
  Breathable
  Suited for stable foam coating
TUBICOAT STC 150
  Fashion coatings, Functional coatings
  Washfast
  Soft handle
  Transparent Breathable
TUBICOAT STL
  Functional coatings
  Washfast
  Slip resistant
  Suited for stable foam coating Soft
TUBICOAT TCT
  Fashion coatings, Functional coatings
  Washfast
  Polymer base: polyurethane
  Transparent
  Suited for paste coating
TUBICOAT VA 10
  Binders
  Anionic Liquid
  Formaldehyde-free Hard
  film TUBICOAT VCP
  Functional coatings Suited for
  paste coating
  Medium hard
  Suited for black-out coating
TUBICOAT VERDICKER 17
  Thickeners Anionic
  High efficiency
  Synthetic
TUBICOAT VERDICKER ASD
  Thickeners Anionic
  Quick swelling Stable to
  shear forces Pseudoplastic
TUBICOAT VERDICKER LP
  Thickeners
  Anionic
  Stable to shear forces
  Pseudoplastic Dispersible
TUBICOAT VERDICKER PRA
  Thickeners
  Anionic Liquid
  Stable to electrolytes
  Rheological additive
TUBICOAT WBH 36
  Special products Finish
  Application for preventing roller deposits
  TUBICOAT WBV Special
  products Non-ionic
  Finish
  Application for preventing roller deposits
TUBICOATWEISS EU
  Functional coatings, Special products Suited
  for coating pastes
  Suited for stable foam Suited for
  topcoat coatings
  Titanium dioxide paste TUBICOAT
WLI-LTKONZ
  Functional coatings Washfast
  Suited for paste coating
  Slip resistant Soft
TUBICOAT WLI
  Fashion coatings, Functional coatings
  Washfast
  Scarabaeus effect Soft
  handle
  Suited for paste coating
TUBICOAT WOT
  Fashion coatings
  Washfast
  Soft handle
  Suited for paste coating Wash-out effect
TUBICOAT WX-TCA 70
  Fashion coatings, Functional coatings
  Vintage wax
  Suited for paste coating Suited
  for topcoat coatings
TUBICOATWX BASE
  Fashion coatings
  Vintage wax Soft
  handle
  Suited for paste coating
  Application in the prime coat
TUBICOAT ZP NEU
  Water repellency/oil repellency
  Zircon-paraffine base
  Suited for aqueous systems
  Cationic
  Foamable TUBIGUARD 10-F
  Water repellency/oil repellency
  Washfast
  Sprayable
  Cationic Liquid
TUBIGUARD 21
  Water repellency/oil repellency
  Washfast
  Cationic
  High effectiveness
  Water-based
TUBIGUARD 25-F
  Water repellency/oil repellency
  Washfast
  Sprayable Cationic
  High effectiveness
TUBIGUARD 270
  Functional coatings, Water repellency/oil repellency
  Washfast
  Cationic
  High effectiveness
  Liquid
TUBIGUARD 30-F
  Water repellency/oil repellency
  Washfast
  Sprayable
  Cationic
  High effectiveness
TUBIGUARD 44 N
  Water repellency/oil repellency
  Washfast
  Sprayable
  Suited for aqueous systems
  Liquid
TUBIGUARD 44N-F
  Water repellency/oil repellency Suited
  for aqueous systems
  Non-ionic
  Suited for polyester
  Foamable
TUBIGUARD 66
  Water repellency/oil repellency
  Washfast
  Sprayable
  High effectiveness
  Liquid
TUBIGUARD 90-F
  Water repellency/oil repellency
  Washfast
  Cationic
  High effectiveness Liquid
TUBIGUARD AN-F
  Water repellency/oil repellency
  Washfast
  Sprayable Cationic
  High effectiveness
TUBIGUARD FA2-F
  Water repellency/oil repellency
  Sprayable
  Cationic
  Suited for polyester
  Foamable
TUBIGUARD PC3-F
  Functional coatings, Water repellency/oil repellency
  Washfast
  Cationic Liquid
  Paste TUBIGUARD SR 2010-F W
  Water repellency/oil repellency
  Cationic
  High effectiveness
  Foamable
  Based on C6 fluorocarbon In some embodiments, the chemical agents may include the following, which are supplied by CHT Bezema and are associated with certain selected faux or bonded leather or faux or bonded leather article) properties, which may be used to strengthen SFS binding to inkjet printing dye:

CHT-ALGINAT MVU
  Ink jet printing preparation, Thickeners
  Cationic
  Powder Anionic
  High colour brilliance
PRISULON CR-F 50
  Ink j et printing preparation, Thickeners Liquid
  Good outlines
  High surface levelness Good
  penetration
TUBIJET DU01
  Ink jet printing preparation
  Antimigrant
  Anionic Liquid
  Formaldehyde-free
TUBIJET NWA
  Ink jet printing preparation
  Liquid
  Non-ionic
  Without impact on the handle
  Formaldehyde-free
TUBIJET PUS
  Ink jet printing preparation Film
  forming
  Anionic
  Liquid Formaldehyde-free
TUBIJET VDK
  Ink jet printing preparation
  Liquid
  Formaldehyde-free
  Halogen-free
  Flame protection effect
TUBIJET WET
  Ink jet printing preparation
  Anionic
  Liquid
  Without impact on the handle
  Formaldehyde-free In some embodiments, the chemical agents of the disclosure may include the following inkjet printing dyes, which are supplied by CHT Bezema and are associated with certain selected faux or bonded leather, or faux or bonded leather article properties, which may be used in combination with SFS:

BEZAFLUOR BLUE BB
  Pigments
  High Performance
  BEZAFLUOR (fluorescent pigments)
BEZAFLUORGREEN BT
  Pigments
  High Performance
  BEZAFLUOR (fluorescent pigments)
BEZAFLUOR ORANGE R
  Pigments
  High Performance
  BEZAFLUOR (fluorescent pigments)
BEZAFLUOR PINK BB
  Pigments
  High Performance
  BEZAFLUOR (fluorescent pigments)
BEZAFLUOR RED R
  Pigments
  High Performance
  BEZAFLUOR (fluorescent pigments)
BEZAFLUORVIOLET BR
  Pigments
  High Performance
  BEZAFLUOR (fluorescent pigments)
BEZAFLUOR YELLOW BA
  Pigments
  High Performance
  BEZAFLUOR (fluorescent pigments)
BEZAPRINT BLACK BDC
  Pigments
  Advanced
  BEZAPRINT (classic pigments)
BEZAPRINT BLACK DT
  Pigments
  Advanced
  BEZAPRINT (classic pigments)
BEZAPRINT BLACK DW
  Pigments
  Advanced
  BEZAPRINT (classic pigments)
BEZAPRINT BLACK GOT
  Pigments
  High Performance
  BEZAKTIV GOT (GOTS)
BEZAPRINT BLUE BN
  Pigments Advanced
  BEZAPRINT (classic pigments)
BEZAPRINT BLUE BT
  Pigments Advanced
  BEZAPRINT (classic pigments)
BEZAPRINT BLUE GOT
  Pigments
  High Performance BEZAKTIV
  GOT (GOTS)
BEZAPRINT BLUE RR
  Pigments
  Advanced
  BEZAPRINT (classic pigments)
BEZAPRINT BLUE RT
  Pigments
  Advanced
  BEZAPRINT (classic pigments)
BEZAPRINT BLUE RTM
  Pigments Advanced
  BEZAPRINT (classic pigments)
BEZAPRINT BLUE TB
  Pigments Advanced
  BEZAPRINT (classic pigments)
BEZAPRINT BORDEAUX K2R
  Pigments
  Advanced
  BEZAPRINT (classic pigments)
BEZAPRINT BROWN RP
  Pigments
  Advanced
  BEZAPRINT (classic pigments)

BEZAPRINT BROWN TM
  Pigments
  Advanced
  BEZAPRINT (classic pigments)
BEZAPRINT CITRON 10G
  Pigments Advanced
  BEZAPRINT (classic pigments)
BEZAPRINT CITRON GOT
  Pigments
  High Performance BEZAKTIV GOT (GOTS)
BEZAPRINT GREEN 2B
  Pigments Advanced
  BEZAPRINT (classic pigments)
BEZAPRINT GREEN BS
  Pigments Advanced
  BEZAPRINT (classic pigments)
BEZAPRINT GREEN BT
  Pigments
  Advanced
  BEZAPRINT (classic pigments)
BEZAPRINT GREY BB
  Pigments
  Advanced
  BEZAPRINT (classic pigments)
BEZAPRINT NAVY GOT
  Pigments
  High Performance BEZAKTIV GOT (GOTS)
BEZAPRINT NAVY RRM
  Pigments Advanced
  BEZAPRINT (classic pigments)
BEZAPRINT NAVY TR
  Pigments Advanced
  BEZAPRINT (classic pigments)
BEZAPRINT OLIVE GREEN BT
  Pigments
  Advanced
  BEZAPRINT (classic pigments)
BEZAPRINT ORANGE 2G
  Pigments
  Advanced
  BEZAPRINT (classic pigments)
BEZAPRINT ORANGE GOT
  Pigments
  High Performance BEZAKTIV GOT (GOTS)
BEZAPRINT ORANGE GT
  Pigments Advanced
  BEZAPRINT (classic pigments)
BEZAPRINT ORANGE RG
  Pigments Advanced
  BEZAPRINT (classic pigments)
BEZAPRINT PINK BW
  Pigments Advanced
  BEZAPRINT (classic pigments)
BEZAPRINT RED 2BN
  Pigments
  Advanced
  BEZAPRINT (classic pigments)
BEZAPRINT RED GOT
  Pigments
  High Performance BEZAKTIV GOT (GOTS)
BEZAPRINT RED KF
  Pigments Advanced
  BEZAPRINT (classic pigments)
BEZAPRINT RED KGC
  Pigments Advanced
  BEZAPRINT (classic pigments)
BEZAPRINT SCARLET GRL
  Pigments Advanced
  BEZAPRINT (classic pigments)
BEZAPRINT SCARLET RR
  Pigments Advanced
  BEZAPRINT (classic pigments)
BEZAPRINT TURQUOISE GT
  Pigments
  Advanced
  BEZAPRINT (classic pigments)
BEZAPRINT VIOLET FB
  Pigments
  Advanced
  BEZAPRINT (classic pigments)
BEZAPRINT VIOLET KB
  Pigments Advanced
  BEZAPRINT (classic pigments)
BEZAPRINTVIOLETR
  Pigments Advanced
  BEZAPRINT (classic pigments)
BEZAPRINT VIOLET TN
  Pigments Advanced
  BEZAPRINT (classic pigments)
BEZAPRINT YELLOW 2GN
  Pigments
  Advanced
  BEZAPRINT (classic pigments)
BEZAPRINT YELLOW 3GT
  Pigments
  Advanced
  BEZAPRINT (classic pigments)
BEZAPRINT YELLOW 4RM
  Pigments
  Advanced
  BEZAPRINT (classic pigments)
BEZAPRINT YELLOW GOT
  Pigments
  High Performance BEZAKTIV GOT (GOTS)
BEZAPRINTYELLOW RR
  Pigments Advanced
  BEZAPRINT (classic pigments)

In some embodiments, the chemical agents of the disclosure may include the following, which are supplied by Lamberti SPA and are associated with certain selected faux or bonded leather, or faux or bonded leather article properties, which may be used to strengthen SFS binding on coated or repaired surfaces or SFS may be used for enhancing such chemical agent properties:

Pretreatment:
  Waterborne Polyurethanes Dispersions
    Rolflex AFP.
      Aliphatic polyether polyurethane dispersion in water. The product has high hydrolysis resistance, good breaking load resistance and excellent tear resistance.
    RolflexACF.
      Aliphatic polycarbonate polyurethane dispersion in water. The product shows good PU and PVC bonding properties, excellent abrasion resistance as well as chemical resistance, included alcohol.

Rolflex V 13.
: Aliphatic polyether/acrylic copolymer polyurethane dispersion in water. The product has good thermoadhesive properties and good adhesion properties on PVC.

Rolflex K 80.
: Aliphatic polyether/acrylic copolymer polyurethane dispersion in water. ROLFLEX K 80 is specifically designed as a high performing adhesive for textile lamination. The product has excellent perchloroethylene and water fastness.

RolflexABC.
: Aliphatic polyether polyurethane dispersion in water. Particularly, the product presents very high water column, excellent electrolytes resistance, high LOI index, high resistance to multiple bending.

RolflexADH.
: Aliphatic polyether polyurethane dispersion in water. The product has a very high water column resistance.

Rolflex W4.
: Aliphatic waterborned PU dispersion particularly suggested for the formulation of textile coatings for clothing, outwear where a full, soft and non sticky touch is required.

Rolflex ZB7.
: Aliphatic waterborned PU dispersion particularly suggested for the formulation oftextile coatings for clothing, outwear, sportswear, fashion and technical articles for industrial applications. The product has a very high charge digestion properties, electrolites stability and excellent mechanical and tear resistance. Can be also suitable for foam coating and printing application.

Rolflex BZ 78.
: Aliphatic waterborne PU dispersion particularly suggested for the formulation of textile coatings for clothing, outwear, sportswear, fashion and technical articles for industrial applications. The product has an excellent hydrolysis resistance, a very high charge digestion and electrolytes stability and an excellent mechanical and tear resistance. Can be also suitable for foam coating and printing application.

Rolflex PU 147.
: Aliphatic polyether polyurethane dispersion in water. This product shows good film forming properties at room temperature. It has high fastness to light and ultraviolet radiation and good resistance to water, solvent and chemical agents, as well as mechanical resistance.

Rolflex SG.
: Aliphatic polyether polyurethane dispersion in water. Due to its thermoplastic properties it is suggested to formulate heat activated adhesives at low temperatures.

Elafix PV 4.
: Aliphatic blocked isocyanate Nano-dispersion used in order to give antifelting and antipilling properties to pure wool fabrics and his blend.

Rolflex C 86.
: Aliphatic cationic waterborne PU dispersion particularly suggested for the formulation of textile coatings for clothing, outwear, fashion where medium-soft and pleasant full touch is required. Fabrics treated with the product can be dyed with a selection of dyes, to get double-color effects of different intensity.

Rolflex CN 29.
: Aliphatic cationic waterborne PU dispersion particularly suggested for the formulation oftextile coatings for clothing, outwear, fashion where soft and pleasant full touch is required. Fabrics treated with the product can be dyed with a selection of dyes, to get double-color effects of different intensity.

Oil and water repellents

Lamgard FT 60.
: General purpose fluorocarbon resin for water and oil repellency; by padding application.

Lamgard 48.
: High performance fluorocarbon resin for water and oil repellency;
: padding application. High rubbing fastness.

ImbitexNRW3
: Wetting agent for water-and oil repellent finishing.

Lamgard EXT.
: Crosslinker for fluorocarbon resins to improve washing fastness.

Flame retardants

Piroflam 712.
: Non-permanent flame retardant compound for padding and spray application.

Piroflam ECO.
: Alogen free flame retardant compound for back coating application for all kind of fibers.

Piroflam UBC.
: Flame retardant compound for back coating application for all kind of fibers.

Crosslinkers

Rolflex BK8.
: Aromatic blocked polyisocyanate in water dispersion. It is suggested as a cross-linking agent in coating pastes based of polyurethane resins to improve washing fastness.

Fissativo 05.
: Water dispersible aliphatic polyisocyanate suitable as crosslinking agent for acrylic and polyurethane dispersions to improve adhesion and wet and dry scrub resistance.

ResinaMEL.
: Melamine-formaldehyde resin.

Cellofix VLF.
: Low formaldehyde melamine resin.

Thickeners

Lambicol CL 60.
: Fully neutralized synthetic thickener for pigment printing in oil/water emulsion; medium viscosity type Viscolam PU conc.
: Nonionic polyurethane based thickener with pseudoplastic behavior Viscolam 115 new.
: Acrylic thickener not neutralized Viscolam PS 202.
: Nonionic polyurethane based thickener with newtonian behavior Dyeing
Viscolam 1022.
  Nonionic polyurethane based thickener with moderate pseudoplastic behavior.
Dispersing agents
  Lamegal BO.
    Liquid dispersing agent non ionic, suitable for direct, reactive, disperse dyeing and PES stripping
  Lamegal DSP.
    Dispersing/anti back-staining agent in preparation, dyeing and soaping of dyed and printed materials. Antioligomer agent.
  Lamegal 619.
    Effective low foam dispersing leveling agent for dyeing of PES
  Lamegal TLS.
    Multi-purpose sequestring and dispersing agent for all kind of textile process
Levelling agents
  Lamegal A 12.
    Leveling agent for dyeing on wool, polyamide and its blends with acid or metalcomplex dyes
Fixing agents
  Lamfix L.
    Fixing agent for direct and reactive dyestuffs, containing formaldheyde
  Lamfix LU conc.
    Formaldehyde free cationic fixing agent for direct and reactive dyes. It does not affect the shade and light fastness.
  Lamfix PA/TR.
    Fixing agent to improve the wet fastness of acid dyes on polyamide fabrics, dyed or printed and polyamide yarns. Retarding agent in dyeing of Polyamide/cellulosic blends with direct dyes.
Special resins
  Denifast TC. Special resin for cationization of cellulose fibers to obtain special effects ("DENIFAST system" and "DENISOL system").
  Cobral DD/50.
    Special resin for cationization of cellulose fibers to obtain special effect ("DENIFAST system" and "DENISOL system").
Antireducing agents
  Lamberti Redox L2S gra.
    Anti-reducing agent in grain form. 100% active content Lamberti Redox L2 S liq.
    Anti-reducing agent in liquid form for automatic dosage.
Anticreasing agent
  Lubisol AM.
    Lubricating and anti creasing agent for rope wet operation on all kind of fibers and machines.
Pigment dye
  Antimigrating agent
    Neopat Compound 96/m conc.
      Compound, developed as migration inhibitor for continuous dyeing process with pigments (pad-dry process).
  Binding agent
    Neopat Binder PM/S conc.
      Concentrated version of a specific binder used to prepare pad-liquor for dyeing with pigments (pad-dry process).
  All in One agent
    Neopat Compound PK1.
      High concentrated compound specifically developed as migration inhibitor with specific binder for continuous dyeing process with pigments (pad-dry process)all in one
  Delavê agent
    Neopat compound FTN.
      High concentrated compound of surfactants and polymers specifically developed for pigment dyeing and pigment-reactive dyeing process; especially for medium/dark shades for wash off effect
Traditional Finishing Agents
  Wrinkle free treatment
    Cellofix ULF conc.
      Anti-crease modified glyoxalic resin for finishing of cottons, cellulosics and blend with synthetics fibers.
    Poliflex P040.
      Polyethilenic resin for waxy, full and slippy handle by foulard applications.
    Rolflex WF.
      Aliphatic waterborned Nano-PU dispersion used as extender for wrinkle free treatments.
  Softeners
    Texamina C/FPN.
      Cationic softening agent with a very soft handle particularly recommended for application by exhaustion for all kind of fabrics. Suitable also for cone application.
    Texamina C SAL flakes.
      100% cationic softening agent in flakes form for all type of fabrics. Dispersible at room temperature.
    Texamina CL LIQ.
      Anphoteric softening agent for all types of fabrics. Not yellowing.
    Texamina HVO.
      Anphoteric softening agent for woven and knitted fabrics of cotton, other cellulosics and blends. Gives a soft, smooth and dry handle. Applied by padding.
    Texamina SIL.
      Nonionic silicon dispersion in water. Excellent softening, lubricating and anti-static properties for all fibre types by padding.
    Texamina SILK.
      Special cationic softener with silk protein inside. Gives a "swollen touch" particularly suitable for cellulosic, wool, silk.
    Lamfinish LW.
      All-in compound based on special polymeric hydrophilic softeners; by coating, foulard, and exhaustion.
    Elastolam E50.
      General purpose mono-component silicone elastomeric softener for textile finishing.
    Elastolam EC 100.
      Modified polysiloxane micro-emulsion which gives apermanent finishing, with extremely soft and silky handle.
  Handle modifier
    Poliflex CSW.
      Cationic anti-slipping agent.
    Poliflex R75.
      Parafine finishing agent to give waxy handle.
    Poliflex s.
      Compound specifically developed for special writing effects.

Poliflex m.
: Compound for special dry-waxy handle.

Lamsoft SW 24.
: Compound for special slippy handle specifically developed for coating application.

Lamfinish SLIPPY.
: All-in compound to get a slippy touch; by coating.

Lamfinish GUMMY.
: All-in compound to get a gummy touch; by coating.

Lamfinish OLDRY.
: All-in compound to get dry-sandy touch especially suitable for vintage effects; by coating Waterborne Polyurethanes Dispersions Rolflex LB 2.
: Aliphatic waterborned PU dispersion particularly suggested for the formulation of textile coatings where bright and rigid top finish is required. It is particularly suitable as a finishing agent for organza touch on silk fabrics. Transparent and shiny.

Rolflex HP 51.
: Aliphatic waterborned PU dispersion particularly suggested for the formulation of textile coatings for outwear, luggage, technical articles especially where hard and flexible touch is required. Transparent and shiny.

Rolflex PU 879.
: Aliphatic waterborned PU dispersion particularly suggested for the formulation of textile coatings for outwear, luggage, technical articles where a medium-hard and flexible touch is required.

Rolflex ALM.
: Aliphatic waterborned PU dispersion particularly suggested for the formulation of textile coatings for outwear, luggage, technical articles where a soft and flexible touch is required. Can be also suitable for printing application.

Rolflex AP.
: Aliphatic waterborned PU dispersion particularly suggested for the formulation of textile coatings for outwear, fashion where a soft and gummy touch is required.

Rolflex W4.
: Aliphatic waterborned PU dispersion particularly suggested for the formulation of textile coatings for clothing, outwear where a full, soft and non sticky touch is required.

Rolflex ZB7.
: Aliphatic waterborned PU dispersion particularly suggested for the formulation of textile coatings for clothing, outwear, sportswear, fashion and technical articles for industrial applications. The product has a very high charge digestion properties, electrolites stability and excellent mechanical and tear resistance. Can be also suitable for foam coating and printing application.

Rolflex BZ 78.
: Aliphatic waterborned PU dispersion particularly suggested for the formulation of textile coatings for clothing, outwear, sportswear, fashion and technical articles for industrial applications. The product has an excellent hydrolysis resistance, a very high charge digestion and electrolites stability and an excellent mechanical and tear resistance. Can be also suitable for foam coating and printing application.

Rolflex K 110.
: Gives to the coated fabric a full, soft, and slightly sticky handle with excellent fastness on all types of fabrics.

Rolflex OP 80.
: Aliphatic waterborned PU dispersion particularly suggested for the formulation of textile coatings for outwear, luggage and fashion finishes where an opaque non writing effect is desired.

Rolflex NBC.
: Aliphatic waterborned PU dispersion generally used by padding application as a filling and zero formaldheyde sizing agent. Can be used for outwear and fashion finishings where a full, elastic and non sticky touch is required.

Rolflex PAD.
: Aliphatic waterborned PU dispersion specifically designed for padding application for outwear, sportswear and fashion applications where a full, elastic and non sticky touch is required. Excellent washing and dry cleaning fastness as well as good bath stability.

Rolflex PN.
: Aliphatic waterborned PU dispersion generally applied by padding application for outerwear and fashion high quality applications where strong, elastic non sticky finishes are required.

Elafix PV 4.
: Aliphatic blocked isocyanate Nano-dispersion used in order to give antifelting and antipilling properties to pure wool fabrics and his blend.

Rolflex SW3.
: Aliphatic waterborned PU dispersion particularly suggested to be used by padding application for the finishing of outwear, sportswear and fashion where a slippery and elastic touch is required. It is also a good antipilling agent. Excellent in wool application.

Rolflex C 86.
: Aliphatic cationic waterborned PU dispersion particularly suggested for the formulation of textile coatings for clothing, outwear, fashion where medium-soft and pleasant full touch is required. Fabrics treated with the product can be dyed with a selection of dyes, to get double-color effects of different intensity.

Rolflex CN29.
: Aliphatic cationic waterborned PU dispersion particularly suggested for the formulation of textile coatings for clothing, outwear, fashion where soft and pleasant full touch is required.
: Fabrics treated with the product can be dyed with a selection of dyes, to get double-color effects of different intensity.

Other resins

Textol 110.
: Handle modifier with very soft handle for coating finishes

Textol RGD.
: Water emulsion of acrylic copolymer for textile coating, with very rigid handle.

Textol SB 21.
: Butadienic resin for finishing and binder for textile printing

Appretto PV/CC.
: Vinylacetate water dispersion for rigid stiffening

Amisolo B.
  CMS water dispersion for textile finishing as stiffening agent
Lamovil RP.
  PVOH stabilized solution as stiffening agent Technical Finishing Agents
  Waterborne Polyurethanes Dispersions
    Rolflex AFP.
      Aliphatic polyether polyurethane dispersion in water. The product has high hydrolysis resistance, good breaking load resistance and excellent tear resistance.
    Rolflex ACF.
      Aliphatic polycarbonate polyurethane dispersion in water. The product shows good PU and PVC bonding properties, excellent abrasion resistance as well as chemical resistance, included alcohol.
    Rolflex V 13.
      Aliphatic polyether/acrylic copolymer polyurethane dispersion in water. The product has good thermoadhesive properties and good adhesion properties on PVC.
    Rolflex K 80.
      Aliphatic polyether/acrylic copolymer polyurethane dispersion in water. ROLFLEX K 80 is specifically designed as a high performing adhesive for textile lamination. The product has excellent perchloroethylene and water fastness.
    Rolflex ABC.
      Aliphatic polyether polyurethane dispersion in water. Particularly, the product presents very high water column, excellent electrolytes resistance, high LOI index, high resistance to multiple bending.
    RolflexADH.
      Aliphatic polyether polyurethane dispersion in water. The product has a very high water column resistance.
    Rolflex W4.
      Aliphatic waterborned PU dispersion particularly suggested for the formulation of textile coatings for clothing, outwear where a full, soft and non sticky touch is required.
    Rolflex ZB7.
      Aliphatic waterborned PU dispersion particularly suggested for the formulation oftextile coatings for clothing, outwear, sportswear, fashion and technical articles for industrial applications. The product has a very high charge digestion properties, electrolites stability and excellent mechanical and tear resistance. Can be also suitable for foam coating and printing application.
    Rolflex BZ 78.
      Aliphatic waterborned PU dispersion particularly suggested for the formulation of textile coatings for clothing, outwear, sportswear, fashion and technical articles for industrial applications. The product has an excellent hydrolysis resistance, a very high charge digestion and electrolites stability and an excellent mechanical and tear resistance. Can be also suitable for foam coating and printing application.
    Rolflex PU 147.
      Aliphatic polyether polyurethane dispersion in water. This product shows good film forming properties at room temperature. It has high fastness to light and ultraviolet radiation and good resistance to water, solvent and chemical agents, as well as mechanical resistance.
    Rolflex SG.
      Aliphatic polyether polyurethane dispersion in water. Due to its thermoplastic properties it is suggested to formulate heat activated adhesives at low temperatures.
    Elafix PV 4.
      Aliphatic blocked isocyanate Nano-dispersion used in order to give antifelting and antipilling properties to pure wool fabrics and his blend.
    Rolflex C 86.
      Aliphatic cationic waterborned PU dispersion particularly suggested for the formulation oftextile coatings for clothing, outwear, fashion where medium-soft and pleasant full touch is required. Fabrics treated with the product can be dyed with a selection of dyes, to get double-color effects of different intensity.
    Rolflex CN 29.
      Aliphatic cationic waterborned PU dispersion particularly suggested for the formulation of textile coatings for clothing, outwear, fashion where soft and pleasant full touch is required. Fabrics treated with the product can be dyed with a selection of dyes, to get double-color effects of different intensity.
  Oil and water repellents
    Lamgard FT 60.
      General purpose fluorocarbon resin for water and oil repellency; by padding application.
    Lamgard 48.
      High performance fluorocarbon resin for water and oil repellency; by padding application. High rubbing fastness.
    Imbitex NRW3.
      Wetting agent for water-and oil repellent finishing.
    Lamgard EXT.
      Crosslinker for fluorocarbon resins to improve washing fastness.
  Flame retardants
    Piroflam 712.
      Non-permanent flame retardant compound for padding and spray application.
    Piroflam ECO.
      Alogen free flame retardant compound for back coating application for all kind of fibers.
    Piroflam UBC.
      Flame retardant compound for back coating application for all kind of fibers
  Crosslinkers
    Rolflex BK8.
      Aromatic blocked polyisocyanate in water dispersion. It is suggested as a cross-linking agent in coating pastes based of polyurethane resins to improve washing fastness.
    Fissativo 05.
      Water dispersible aliphatic polyisocyanate suitable as crosslinking agent for acrylic and polyurethane dispersions to improve adhesion and wet and dry scrub resistance.
    Re sina MEL.
      Melammine-formaldheyde resin.
    Cellofix VLF.
      Low formaldheyde malammine resin.

Thickeners
   Lambicol CL 60.
      Fully neutralized synthetic thickener for pigment printing in oil/water emulsion; medium viscosity type
   Viscolam PU conc.
      Nonionic polyurethane based thickener with pseudoplastic behavior
   Viscolam 115 new.
      Acrylic thickener not neutralized
   Viscolam PS202.
      Nonionic polyurethane based thickener with newtonian behavior
   Viscolam 1022.
      Nonionic polyurethane based thickener with moderate pseudoplastic behavior.

In some embodiments, the chemical agent may include one or more of a silicone, an acidic agent, a dyeing agent, a pigment dye, a traditional finishing agent, and a technical finishing agent. The dyeing agent may include one or more of a dispersing agent, a levelling agent, a fixing agent, a special resin, an antireducing agent, and an anticreasing agent. The pigment dye may include one or more of an antimigrating agent, a binding agent, an all in one agent, and a delave agent. The traditional finishing agent may include one or more of a wrinkle free treatment, a softener, a handle modifier, a waterborne polyurethanes dispersion, and other resins. The technical finishing agent may include one or more of a waterborne polyurethanes dispersion, an oil repellant, a water repellant, a crosslinker, and a thickener.

In some embodiments, certain chemical agents of the disclosure may be provided by one or more of the following chemical suppliers: Adrasa, AcHitex Minerva, Akkim, Archroma, Asutex, Avocet dyes, BCC India, Bozzetto group, CHT, Clariant, Clearity, Dilube, Dystar, Eksoy, Erca group, Genkim, Giovannelli e Figli, Graf Chemie, Huntsman, KDN Bio, Lamberti, LJ Specialties, Marlateks, Montegauno, Protex, Pulcra Chemicals, Ran Chemicals, Fratelli Ricci, Ronkimya, Sarex, Setas, Silitex, Soko Chimica, Tanatex Chemicals, Union Specialties, Zaitex, Zetaesseti, and Z Schimmer.

In some embodiments, the chemical agent may include an acidic agent. Accordingly, in some embodiments, SFS may include an acidic agent. In an embodiment, the acidic agent may be a Bronsted acid. In an embodiment, the acidic agent includes one or more of citric acid and acetic acid. In an embodiment, the acidic agent aids the deposition and coating of SPF mixtures (i.e., SFS coating) on the faux or bonded leather, or faux or bonded leather article to be coated as compared to the absence of such acidic agent. In an embodiment, the acidic agent improves crystallization of the SPF mixtures at the textile to be coated.

In an embodiment, the acidic agent is added at a concentration by weight (% w/w or % w/v) or by volume (v/v) of greater than about 0.001%, or greater than about 0.002%, or greater than about 0.003%, or greater than about 0.004%, or greater than about 0.005%, or greater than about 0.006%, or greater than about 0.007%, or greater than about 0.008%, or greater than about 0.009%, or greater than about 0.01%, or greater than about 0.02%, or greater than about 0.03%, or greater than about 0.04%, or greater than about 0.05%, or greater than about 0.06%, or greater than about 0.07%, or greater than about 0.08%, or greater than about 0.09%, or greater than about 0.1%, or greater than about 0.2%, or greater than about 0.3%, or greater than about 0.4%, or greater than about 0.5%, or greater than about 0.6%, or greater than about 0.7%, or greater than about 0.8%, or greater than about 0.9%, or greater than about 1.0% or greater than about 2.0%, or greater than about 3.0%, or greater than about 4.0%, or greater than about 5.0%. In an embodiment, the acidic agent is added at a concentration by weight (% w/w or % w/v) or by volume (v/v) of less than about 0.001%, or less than about 0.002%, or less than about 0.003%, or less than about 0.004%, or less than about 0.005%, or less than about 0.006%, or less than about 0.007%, or less than about 0.008%, or less than about 0.009%, or less than about 0.01%, or less than about 0.02%, or less than about 0.03%, or less than about 0.04%, or less than about 0.05%, or less than about 0.06%, or less than about 0.07%, or less than about 0.08%, or less than about 0.09%, or less than about 0.1%, or less than about 0.2%, or less than about 0.3%, or less than about 0.4%, or less than about 0.5%, or less than about 0.6%, or less than about 0.7%, or less than about 0.8%, or less than about 0.9%, or less than about 1.0% or less than about 2.0%, or less than about 3.0%, or less than about 4.0%, or less than about 5.0%.

In some embodiments, SFS may have a pH of less than about 9, or less than about 8.5, or less than about 8, or less than about 7.5, or less than about 7, or less than about 6.5, or less than about 6, or less than about 5.5, or less than about 5, or less than about 4.5, or less than about 4, or greater than about 3.5, or greater than about 4, or greater than about 4.5, or greater than about 5, or greater than about 5.5, or greater than about 6, or greater than about 6.5, or greater than about 7, or greater than about 7.5, or greater than about 8, or greater than about 8.5.

In some embodiments, SFS may include an acidic agent, and may have a pH of less than about 9, or less than about 8.5, or less than about 8, or less than about 7.5, or less than about 7, or less than about 6.5, or less than about 6, or less than about 5.5, or less than about 5, or less than about 4.5, or less than about 4, or greater than about 3.5, or greater than about 4, or greater than about 4.5, or greater than about 5, or greater than about 5.5, or greater than about 6, or greater than about 6.5, or greater than about 7, or greater than about 7.5, or greater than about 8, or greater than about 8.5.

In an embodiment, the chemical agent may include silicone. In some embodiments, a SFS may include silicone. In some embodiments, the faux or bonded leather, or faux or bonded leather article may be pretreated (i.e., prior to SFS application) or post-treated (i.e., after SFS application) with silicone.

In some embodiments, silicone may include a silicone emulsion.

The term "silicone," may generally refer to a broad family of synthetic polymers, mixtures of polymers, and/or emulsions thereof, that have a repeating silicon-oxygen backbone including, but not limited to, polysiloxanes. In some embodiments, a silicone may include any silicone species disclosed herein.

Describing the compositions and coatings more broadly, silicone may be used, for example to improve hand, but may also increase the water repellency (or reduce water transport properties) of a material coated with silicone.

In some embodiments, SFS may include silicone in a concentration by weight (% w/w or % w/v) or by volume (v/v) of less than about 25%, or less than about 20%, or less than about 15%, or less than about 10%, or less than about 9%, or less than about 8%, or less than about 7%, or less than about 6%, or less than about 5%, or less than about 4%, or less than about 3%, or less than about 2%, or less than about 1%, or less than about 0.9%, or less than about 0.8%, or less than about 0.7%, or less than about 0.6%, or less than about 0.5%, or less than about 0.4%, or less than about 0.3%, or less than about 0.2%, or less than about 0.1%, or less than about 0.01%, or less than about 0.001%.

In some embodiments, SFS may include silicone in a concentration by weight (% w/w or % w/v) or by volume (v/v) of greater than about 25%, or greater than about 20%, or greater than about 15%, or greater than about 10%, or greater than about 9%, or greater than about 8%, or greater than about 7%, or greater than about 6%, or greater than about 5%, or greater than about 4%, or greater than about 3%, or greater than about 2%, or greater than about 1%, or greater than about 0.9%, or greater than about 0.8%, or greater than about 0.7%, or greater than about 0.6%, or greater than about 0.5%, or greater than about 0.4%, or greater than about 0.3%, or greater than about 0.2%, or greater than about 0.1%, or greater than about 0.01%, or greater than about 0.001%.

In some embodiments, SFS may be supplied in a concentrated form suspended in water. In some embodiments, SFS may have a concentration by weight (% w/w or % w/v) or by volume (v/v) of less than about 50%, or less than about 45%, or less than about 40%, or less than about 35%, or less than about 30%, or less than about 25%, or less than about 20%, or less than about 15%, or less than about 10%, or less than about 5%, or less than about 4%, or less than about 3%, or less than about 2%, or less than about 1%, or less than about 0.1%, or less than about 0.01%, or less than about 0.001%, or less than about 0.0001%, or less than about 0.00001%. In some embodiments, SFS may have a concentration by weight (% w/w or % w/v) or by volume (v/v) of greater than about 50%, or greater than about 45%, or greater than about 40%, or greater than about 35%, or greater than about 30%, or greater than about 25%, or greater than about 20%, or greater than about 15%, or greater than about 10%, or greater than about 5%, or greater than about 4%, or greater than about 3%, or greater than about 2%, or greater than about 1%, or greater than about 0.1%, or greater than about 0.01%, or greater than about 0.001%, or greater than about 0.0001%, or greater than about 0.00001%.

In some embodiments, an SFS coating may include SFS, as described herein.

In some embodiments, SFS may include a silicone and/or an acidic agent. In some embodiments, SFS may include a silicone and an acidic agent. In some embodiments, the SFS may include a silicone, an acidic agent, and/or an additional chemical agent, wherein the additional chemical agent may be one or more of the chemical agents described herein. In some embodiments, SFS may include a silicone emulsion and an acidic agent, such as acetic acid or citric acid. In some embodiments, the coating processes of the disclosure may include a finishing step for the resulting coated materials. In some embodiments, the finishing or final finishing of the materials that are coated with SFS under the processes of the disclosure may include sueding, steaming, brushing, polishing, compacting, raising, tigering, shearing, heatsetting, waxing, air jet, calendaring, pressing, shrinking, treatment with polymerizer, coating, lamination, and/or laser etching. In some embodiments, finishing of the SFS coated materials may include treatment of the textiles with an AIRO® 24 dryer that may be used for continuous and open-width tumbling treatments of woven, non-woven, and knitted fabrics.

Silk bonded Layered or Spun Materials

In an embodiment, this disclosure provides an article comprising a plurality of fibers or yarns and a silk derived protein or fragments thereof. In some embodiments, the plurality of fibers are natural fibers, synthetic fibers, or a combination thereof.

In some embodiments, the fibers and yarns are sourced from post-industrial fibers and yarns. In some embodiments, the fibers and yarns are sourced from waste fabric materials.

Post-Industrial or Post-Consumer Waste Fabric Materials

In some embodiments, the source of the waste fabric materials are the post-industrial and/or post-consumer textile wastes. Post-industrial or post-consumer waste textile materials include, but are not limited to, beddings, garments, clothing, furniture, carpet, textile scraps, and the like.

In some embodiments, the waste fabric materials comprises natural fibers or yarns include one or more of silk, cotton, alpaca fleece, alpaca wool, lama fleece, lama wool, cashmere, sheep fleece, and sheep wool. In some embodiments, the natural fibers or yarns include one or more of alpaca fiber, alpaca fleece, alpaca wool, lama fiber, lama fleece, lama wool, cotton, cashmere and sheep fiber, sheep fleece, sheep wool, byssus, chiengora, quiviut, yak, rabbit, lambswool, mohair wool, camel hair, angora wool, silkworm silk, abaca fiber, coir fiber, flax fiber, jute fiber, kapok fiber, kenaf fiber, raffia fiber, bamboo fiber, hemp, modal fiber, pina, ramie, sisal, and soy protein fiber.

In some embodiments, the waste fabric materials comprises synthetic fibers include one or more of acrylic, anidex, aramid, fluorocarbon, modacrylic, novoloid, nylon, nytril, olefin, PBI, polycarbonate, polyester, rubber, saran, spandex, vinal vinvon.

In some embodiments, the source of the waste fabric materials are waste leather materials. In some embodiments, the source of the waste leather materials has been leather tanning scraps without surface coating. In some embodiments, the source of the waste leather materials are the post-industrial and/or post-consumer leather waste. Post-industrial or post-consumer waste leather materials include, but are not limited to, vegetable tanned leather, chrome tanned leather, bark tanned leather, and the like. Animals that are used for their leather include cows, goats, lambs, crocodiles, and alligators. The post-industrial and/or post-consumer waste leather is frequently from the shoe, automotive, apparel, personal leather goods, saddle making, or furniture businesses. A synthetic polymeric coating is commonly present, to give color or texture to the leather.

In some embodiments, the waste leather materials are subjected to a chemical treatment process to remove a given polymer coating from the scrap leather. In some embodiments, the treatment chemicals can include, for example, one or more organic solvents and/or one or more enzymes. Steam can also be used. The chemicals penetrate the leather materials. The types of organic chemicals and/or enzymes used to remove the surface finishes include, but not limited to, dilute acid or concentrated neutral salt solutions. Representative organic solvents include halogenated alcohols, fluorinated alcohols such as tetrafluoroethylene (TFE) and hexafluoro isopropanol (HFIP), hexafluoroacetone, chloro alcohols, dimethylacetamide (optionally combining with lithium chloride), ethyl acetate, 2-butanone (methyl ethyl ketone), diethyl ether, ethanol, cyclohexane, water, dichloromethane (methylene chloride), tetrahydrofuran, dimethylsulfoxide (DMSO), acetonitrile, methyl formate, and various solvent mixtures. HFIP and methylene chloride are particularly desirable solvents. In some embodiments, water is added to the solvents.

In some embodiments, the waste leather material is weighted and sorted based on fiber content. In some embodiments, the waste leather material is mixed to the desired fiber composition, chopped and ground into shoddy fibers.

In one embodiment, the waste fabric materials are reduced in size in two separate stages. In the first stage, the scraps are cut to a size in the range of between about 0.5 and about 3 inches in length and in width, and are generally square or rectangular.

The waste fabric material size reduction in the initial stage can be performed by a guillotine cutter, and all subsequent fibers produced from this action that are less than 3 mm long can be filtered out of the process. The segregated fibers that are less than 3 mm long can then be moved to a secondary process where they are used in an end-use application appropriate to their size. A secondary fiber reduction can occur by passing the materials through an enclosed tunnel equipped with a series or rotary knives. In some embodiments, the materials can be passed through pairs of cylinders with a coat of wire or small pins. The paired cylinders rotate inwardly in a manner that combs or extracts the fibers. In some embodiments, the waste fabric material can be passed under or through cylindrical cutting heads with spiral cutting edges. The edges of the cutting instrument have pointed projections along the spiral ridges that also acts in a combing and extraction method of the fibers. The resulting fibers can then be further refined, if necessary, through the rotary cutting blades allowing for even more accurate fiber length processing.

The focus of this fiber reduction station is to return fibers to the process which measure between 3 mm and 9 mm in length, dependent on the downstream application requirements. The optimum fiber length necessary for a quality non-woven leather replacement product measuring from 6 mm to 7 mm. If, for example, the final fiber application were leather yarn spinning, then the optimal fiber lengths would measure between 4 mm and 6 mm.

Binder System

In some embodiments, the silk bonded layered materials or the silk bonded spun materials further comprising a binder resin. In some embodiments, the binder resin is selected from the group consisting of thermoplastic resin, latex, polyvinyl chloride, polyurethane, butadiene acrylonitrile copolymer, anionic copolymer of ester and urethane, animal proteins, collagen, gelatin, albumin, silk fibroin, spider silk, and combinations thereof. In some embodiments, the polymer binder is polyvinyl chloride. In some embodiments, the polymer binder is polyurethane. In some embodiments, the polymer binder is butadiene acrylonitrile copolymer (Chemigum® Latex 6387). In some embodiments, the polymer binder is anionic copolymer of ester and urethane (Baybond PU 401). In some embodiments, the binder system comprises silk fibroin protein and a binder resin selected from the group consisting of resin, latex, polyvinyl chloride, polyurethane, butadiene acrylonitrile copolymer, anionic copolymer of ester and urethane.

In some embodiments, the binder system comprises silk fibroin protein and polyvinyl chloride. In some embodiments, the binder system comprises silk fibroin protein and polyurethane. In some embodiments, the binder system comprises silk fibroin protein and butadiene acrylonitrile copolymer (Chemigum® Latex 6387). In some embodiments, the binder system comprises silk fibroin protein and anionic copolymer of ester and urethane (Baybond PU 401).

Additives

In some embodiments, the silk bonded layered materials or the silk bonded spun materials further comprising an optional additive selected from the group consisting of pH adjusting agent, lubricant, emulsifier, antistatic agent, dispersant, flocculant, thickener, surfactant, inorganic filler, catalyst, film forming agent, coloring agent, and combinations thereof. The additives are applied to influence performance, quality and uniformity of process fibers.

In some embodiments, the silk bonded layered materials or the silk bonded spun materials further comprising a flocculant. In some embodiments, the flocculant is selected form cationic polyacrylamide, and nonionic polyacrylamide. In some embodiments, the flocculant is high molecular weight nonionic polyacrylamide (Percol® 351, also known as Magnafloc® 351).

In some embodiments, the thickener comprises highly water-soluble polymer that is capable of increasing viscosity. In some embodiments, the thickener is selected from the group consisting of sucrose, gelatin, polyacrylamide (Separan® AP-30, Dow Chemical), crosslinked polyacrylamide, acrylamide copolymer, carboxymethylcellulose (CMC), polyethylene oxide, polyvinyl alcohol, methyl cellulose, acrylamide-acrylic acid copolymer, ethylene oxide based urethane block copolymers (Mw 10 kDa to 200 kDa, or), hydroxyethyl cellulose ethers have a C10 to C24 alkyl side chain (Mw 50 kDa to 400 kDa), and various natural gums (deacetylated karaya gum). The use of thickeners for raising the viscosity of the water has been found useful for forming and maintaining dispersions of fibers. Thickeners are most effective way to reduce the tendency of long fibers to form ropes and fiber bundles.

In some embodiments, the thickener is present in the leather fiber dispersion at an amount between about 0.01 wt. % and 0.1% by the total weight of the leather fiber dispersion. In some embodiments, the thickener is present in the leather fiber dispersion at an amount ranging from about 0.03% to about 0.07% by the total weight of the leather fiber dispersion, wherein the thickener is Separan AP-30 polyacrylamide thickener, which provides a nascent viscosity of 10 cps to 50 cps., at a shear rate of $30.5^{s-1}$.

In some embodiments, the pH-adjusting agent is selected from the group consisting of hydrogen chloric acid, citric acid, sodium bicarbonate, sodium hydroxide, potassium hydroxide, and sodium carbonate.

In some embodiments, the lubricant is selected from the group consisting of animal oil, vegetable oil, mineral oil, fatty ester, methyl oleate, butyl stearate, and combinations thereof.

In some embodiments, surfactant is selected from the group consisting of nonionic surfactant (fatty acid ester of polyhydric alcohol, fatty acid and ethylene oxide adduct), anionic surfactant (alkyl sulfate, alkyl phosphate, and fatty acid alkaline soap), and cationic surfactant (fatty alkyl quaternary ammonium).

In some embodiments, the dispersant is selected from the group consisting of polyethylene oxide homopolymer having an average molecular weight of from about 1 million to about 7 million or higher; polyacrylamide homopolymer having an average molecular weight of form about 1 million up to about 15 million or higher; acrylamide-acrylic acid copolymers having an average molecular weight in the range of about 2-3 million, or higher; and polyamines having average molecular weight of from about 1 million to about 5 million or higher. In some embodiments, the dispersant is oxyalkylated fatty amine. In some embodiments, the dispersant in the leather fiber dispersion is of about 1 ppm to about 200 ppm.

In some embodiments, the emulsifier comprises ethoxylated castor oil that promotes fiber dispersion.

In some embodiments, the antistatic agent is selected from the group consisting of alkyl phosphate and alkyl sulfate.

In some embodiments, the lubricant is selected from the group consisting of polypropylene alcohol, and polyalkylene glycohol. Lubricating agents are used to modify fiber-to-fiber friction and are used to minimize falling-out of fibers during the drawing process.

In some embodiments, the film forming agent is used to forming coating on the silk bonded layered material or yarns. In some embodiments, the film forming agent is selected from the group consisting of polyglycolide (PGA), polyethylene glycols, copolymers of glycolide, glycolide/L-lactide copolymers (PGA/PLLA), glycolide/trimethylene carbonate copolymers (PGA/TMC), polylactides (PLA), stereocopolymers of PLA, poly-L-lactide (PLLA), poly-DL-lactide (PDLLA), L-lactide/DL-lactide copolymers, co-polymers of PLA, lactide/tetramethylglycolide copolymers, lactide/trimethylene carbonate copolymers, lactide/δ-valerolactone copolymers, lactide/ε-caprolactone copolymers, polydepsipeptides, PLA/polyethylene oxide copolymers, unsymmetrically 3,6-substituted poly-1,4-dioxane-2,5-diones, poly-β-hydroxybutyrate (PHBA), PHBA/β-hydroxyvalerate copolymers (PHBA/HVA), poly-β-hydroxypropionate (PHPA), poly-p-dioxanone (PDS), poly-δ-valerolactone, poly-ε-caprolactone, methylmethacrylate-N-vinyl pyrrolidine copolymers, polyesteramides, polyesters of oxalic acid, polydihydropyrans, polyalkyl-2-cyanoacrylates, polyurethanes (PU), polyvinylalcohols (PVA), polypeptides, poly-β-malic acid (PMLA), poly-β-alkanoic acids, polyvinylalcohol (PVA), polyethyleneoxide (PEO), chitine polymers, polyethylene, polypropylene, polyasetal, polyamides, polyesters, polysulphone, polyether ether ketone, polyethylene terephthalate, polycarbonate, polyaryl ether ketone, polyether ketone ketone, and combinations thereof.

Silk Bonded Leather Fibers

In an embodiment, this disclosure provides silk protein bonded leather fibers comprising the silk fibroin protein as described above, a binder resin and leather fibers. In some embodiments, this disclosure provides silk protein bonded leather fibers comprising leather fibers, binder resin, and silk fibroin protein fragments having an average weight average molecular weight selected from between about 1 kDa and about 5 kDa, between about 5 kDa and about 10 kDa, between about 6 kDa and about 17 kDa, between about 10 kDa and about 15 kDa, between about 15 kDa and about 20 kDa, between about 17 kDa and about 39 kDa, between about 20 kDa and about 25 kDa, between about 25 kDa and about 30 kDa, between about 30 kDa and about 35 kDa, between about 35 kDa and about 40 kDa, between about 39 kDa and about 80 kDa, between about 40 kDa and about 45 kDa, between about 45 kDa and about 50 kDa, between about 60 kDa and about 100 kDa, and between about 80 kDa and about 144 kDa, and a polydispersity between 1 and about 5.

In some embodiments, this disclosure provides silk protein bonded leather fibers comprising leather fibers and silk fibroin protein fragments having an average weight average molecular weight selected from between about 6 kDa and about 17 kDa, between about 17 kDa and about 39 kDa, between about 39 kDa and about 80 kDa, and a polydispersity between 1.5 and about 3.0.

In some embodiments, the silk fibroin fragments in the silk protein bonded leather fibers are obtained from a precursor solution comprising silk fibroin fragments having an average weight average molecular weight selected from between about 1 kDa and about 5 kDa, between about 5 kDa and about 10 kDa, between about 6 kDa and about 17 kDa, between about 10 kDa and about 15 kDa, between about 15 kDa and about 20 kDa, between about 17 kDa and about 39 kDa, between about 20 kDa and about 25 kDa, between about 25 kDa and about 30 kDa, between about 30 kDa and about 35 kDa, between about 35 kDa and about 40 kDa, between about 39 kDa and about 80 kDa, between about 40 kDa and about 45 kDa, between about 45 kDa and about 50 kDa, between about 60 kDa and about 100 kDa, and between about 80 kDa and about 144 kDa, and a polydispersity between 1.0 and about 5.0.

In some embodiments, the silk bonded leather fibers comprise low molecular weight silk fibroin protein fragments. In some embodiments, the silk bonded leather fibers comprise mid-molecular weight silk fibroin protein fragments. In some embodiments, the silk bonded leather fibers comprise a mixture of low molecular weight silk fibroin protein fragments and mid-molecular weight silk fibroin protein fragment.

In some embodiments, the silk bonded leather fibers comprise low molecular weight silk fibroin protein fragments having a weight average molecular weight selected from between about 5 kDa to about 20 kDa. In some embodiments, the silk bonded leather fibers comprise low molecular weight silk fibroin protein fragments having a weight average molecular weight selected from the group consisting of from about 5 kDa to 10 kDa, about 10 kDa to about 20 kDa, and about 20 kDa to about 25 kDa. In some embodiments, the silk bonded leather fibers comprise low molecular weight silk fibroin protein fragments having a weight average molecular weight selected from between about 10 kDa to about 20 kDa.

In some embodiments, the silk bonded leather fibers comprise mid-molecular weight silk fibroin protein fragments having an average weight average molecular weight selected from the group consisting of from about 25 kDa to about 30 kDa, about 30 kDa to about 35 kDa, from about 35 kDa to about 40 kDa, from about 17 kDa to about 39 kDa, from about 45 kDa to about 50 kDa, from about 50 kDa to about 55 kDa, from about 55 kDa to about 60 kDa, from about 60 kDa to about 65 kDa, from about 40 kDa to about 65 kDa, from 65 kDa to about 70 kDa, from about 70 kDa to about 75 kDa, from about 75 kDa to about 80 kDa, from about 39 kDa to about 80 kDa, from about 80 kDa to about 85 kDa, from about 85 kDa to about 90 kDa, from about 90 kDa to about 95 kDa, from about 95 kDa to about 100 kDa, from about 100 kDa to about 105 kDa, from about 105 kDa to about 110 kDa, from about 60 kDa to about 100 kDa, and from about 80 kDa to about 144 kDa. In some embodiments, the silk bonded leather fibers comprise mid-molecular weight silk fibroin protein fragments having a weight average molecular weight selected from between about 17 kDa to about 39 kDa. In some embodiments, the silk bonded leather fibers comprise mid-molecular weight silk fibroin protein fragments having a weight average molecular weight selected from between about 40 kDa to about 65 kDa. In some embodiments, the silk bonded leather fibers comprise mid-molecular weight silk fibroin protein fragments having a weight average molecular weight selected from between about 39 kDa to about 80 kDa. In some embodiments, the silk bonded leather fibers comprise mid-molecular weight silk fibroin protein fragments having a weight average molecular weight selected from between about 80 kDa to about 144 kDa.

In some embodiments, the silk bonded leather fibers comprise low molecular weight silk fibroin fragments (low-MW silk) having a weight average molecular weight (Mw)

selected from between about 6 kDa and about 17 kDa and a polydispersity between about 1.5 and about 3.0. In some embodiments, the silk bonded leather fibers comprise low molecular weight silk fibroin fragments (low-MW silk) having a weight average molecular weight (Mw) selected from between about 14 kDa and about 30 kDa and a polydispersity between about 1.5 and about 3.0. In some embodiments, silk bonded leather fibers comprise mid-molecular weight silk fibroin fragments (Med-MW silk) having a weight average molecular weight selected from between about 39 kDa and about 54 kDa and a polydispersity between about 1.5 and about 3.0. In some embodiments, silk bonded leather fibers comprise mid-molecular weight silk fibroin fragments (high-MW silk) having a weight average molecular weight selected from between about 55 kDa to about 150 kDa and a polydispersity between about 1.5 and about 3.0.

In some embodiments, the silk fibroin fragments in silk protein bonded leather fibers have a polydispersity between 1 and about 1.5. In some embodiments, the silk fibroin fragments in the silk protein bonded leather fibers have a polydispersity between about 1.5 and about 2.0. In some embodiments, the silk fibroin fragments in the silk protein bonded leather fibers have a polydispersity between about 1.5 and about 3.0. In some embodiments, the silk fibroin fragments in the silk protein bonded leather fibers have a polydispersity between about 2.0 and about 2.5. In some embodiments, the silk fibroin fragments in the silk protein bonded leather fibers have a polydispersity between about 2.5 and about 3.0.

In some embodiments, the binder resin is selected from the group consisting of thermoplastic resin, latex, polyvinyl chloride, polyurethane, butadiene acrylonitrile copolymer, anionic copolymer of ester and urethane, and combinations thereof. In some embodiments, the polymer binder is polyvinyl chloride. In some embodiments, the polymer binder is polyurethane. In some embodiments, the polymer binder is butadiene acrylonitrile copolymer (Chemigum® Latex 6387). In some embodiments, the polymer binder is anionic copolymer of ester and urethane (Baybond PU 401).

In some embodiments, the leather fibers has a weight ratio of leather fibers to Low-MW silk fibroin protein fragments selected from the group consisting of 0.5:1, 0.6:1, 0.7:1, 0.8:1, 0.9:1, 1:1, 1:0.9, 1:0.8, 1:0.7, 1:0.6 and 1:0.5. In some embodiments, the leather fibers has a weight ratio of leather fibers to Mid-MW silk fibroin protein fragments selected from the group consisting of 4.0:1, 3.9:1, 3.8:1, 3.7:1, 3.6:1, 3.5:1, 3.4:1, 3.3:1, 3.2:1, 3.1:1 and 3.0:1. In some embodiments, the leather fibers has a weight ratio of leather fibers to Low-MW silk fibroin protein fragments of 0.7:1. In some embodiments, the leather fibers has a weight ratio of leather fibers to Mid-MW silk fibroin protein fragments of 3.5:1.

In some embodiments, the leather fibers has a weight ratio of leather fibers to binder resin is of 1.17:1 (7:6). In some embodiments, the leather fibers in the aqueous suspension has a weight ratio of leather fibers to binder resin selected from the group consisting of 5:3, 3:1, 4:3, 7:6, 6:6, 6:7, 3:4, 1:3, and 3:5.

In some embodiments, the leather fibers has a weight ratio of leather fibers to binder resin and Low-MW silk fibroin protein fragments of 7:6:10. In some embodiments, the leather fibers has a weight ratio of leather fibers to binder resin and Mid-MW silk fibroin protein fragments of 7:6:12.

In some embodiments, the silk protein bonded leather fibers further comprising about 0.01% (w/w) to about 10% (w/w) sericin relative to the silk fibroin fragments.

In some embodiments, the silk fibroin fragments in the precursor solution do not spontaneously or gradually gelate and do not visibly change in color or turbidity when in the precursor solution for at least 10 days prior to obtaining the silk fibroin fragments in the substantially solid silk composition.

In an embodiment, this disclosure provides a process for making silk protein bonded leather fibers and filaments and yarns thereof from waste leather materials (e.g., leather tanning scraps, post-industrial or post-consumer waste leather materials). In some embodiments, this disclosure provides a method of making silk protein bonded leather fibers comprising the steps: (1) obtaining waste leather materials; (2) cutting the waste leather material to form ground leather having size ranging from 3 mm to 10 mm in length; (3) forming a suspension of the ground leather in water; (4) beating the suspension with a laboratory beater for at least 2 hours to form a ground leather fiber suspension; (5) adding a polymer binder and silk solution as described herein to the ground leather fiber suspension to form a blend of leather fibers with silk fibroin protein fragments; (6) adding a flocculant to the blend of leather fibers with silk fibroin protein fragments to form a flocked silk leather material; (7) adjusting pH in the leather fiber aqueous suspension with a pH adjusting agent to a value ranging from about 3 to 5; (8) feeding the flocked silk leather materials directly onto a screen for draining out water; (9) drying the flocked silk leather materials under heat to form silk bonded leather fibers.

In some embodiments, the pH value of the leather fiber aqueous suspension is selected from the group consisting of about 3.0, about 3.1, about 3.2, about 3.3, about 3.4, about 3.5, about 3.6, about 3.7, about 3.8, about 3.9, about 4.0, about 4.1, about 4.2, about 4.3, about 4.4, about 4.5, about 4.6, about 4.7, about 4.8, about 4.9, and about 5.0. In some embodiments, the pH-adjusting agent is hydrochloric acid.

In some embodiments, the leather fiber concentration in the leather fiber aqueous suspension is of about 0.1 wt. % to about 1.0 wt. % by the total weight of the leather fiber aqueous suspension. In some embodiments, the leather fiber concentration is of about 0.3 wt. % to about 0.5 wt. % by the total weight of the leather fiber aqueous suspension. In some embodiments, the leather fiber concentration is selected from the group consisting of about 0.1 wt. %, 0.2 wt. %, 0.3 wt. %, 0.4 wt. %, 0.5 wt. %, 0.6 wt. %, 0.7 wt. %, 0.8 wt. %, 0.9 wt. %, and 1.0 wt. % by the total weight of the leather fiber aqueous suspension. In some embodiments, the leather fiber concentration in the aqueous suspension is of about 0.42 wt. % by the total weight of the leather fiber aqueous suspension.

In some embodiments, the silk fibroin fragments have a concentration of about 0.05 wt. % to about 1.0 wt. % by the total weight of the leather fiber suspension. In some embodiments, the silk fibroin fragments have a concentration selected from the group consisting of about 0.1 wt. %, 0.2 wt. %, 0.3 wt. %, 0.4 wt. %, 0.5 wt. %, 0.6 wt. %, 0.7 wt. %, 0.8 wt. %, 0.9 wt. %, and 1.0 wt. % by the total weight of the leather fiber aqueous suspension. In some embodiments, the silk fibroin fragments have a concentration of about 0.6 wt. % by the total weight of the leather fiber aqueous suspension. In some embodiments, the silk fibroin fragments have a concentration of about 0.12 wt. % by the total weight of the leather fiber aqueous suspension.

In some embodiments, the binder resin has a concentration of about 0.05 wt. % to about 1.0 wt. % by the total weight of the leather fiber suspension. In some embodiments, the binder resin has a concentration selected from the group consisting of about 0.1 wt. %, 0.2 wt. %, 0.3 wt. %, 0.4 wt. %, 0.5 wt. %, 0.6 wt. %, 0.7 wt. %, 0.8 wt. %, 0.9 wt. %, and 1.0 wt. % by the total weight of the leather fiber aqueous suspension. In some embodiments, the binder resin has a concentration of about 0.36 wt. % by the total weight of the leather fiber aqueous suspension.

In some embodiments, the flocculant is present in the leather fiber aqueous suspension at a concentration ranging from 0.0005 wt. % to about 1.0 wt. % by the total weight of the leather fiber aqueous suspension. In some embodiments, the flocculant has a concentration of about 0.0005 wt. % to about 0.005 wt. % by the total weight of the leather fiber suspension. In some embodiments, the flocculant has a concentration selected from the group consisting of about 0.0005 wt. %, about 0.00075 wt. %, about 0.001 wt. %, 0.0015 wt. %, about 0.002 wt. %, about 0.0025 wt. %, about 0.003 wt. %, about 0.0035 wt. %, about 0.004 wt. %, about 0.0045 wt. %, and about 0.005 wt. % by the total weight of the leather fiber aqueous suspension. In some embodiments, the flocculant has a concentration of about 0.001 wt. % by the total weight of the leather fiber aqueous suspension.

The ground leather pulp is loosened during the beating process with the laboratory beater (e.g., Valley beater) to form dispersing collagen fibers with single strand and without interconnection. However, the collagen fibers obtained by the Valley beating method without more are short, poor in spinnability, only used for producing low-level textiles or as the raw materials for "waste textile".

Leather in its natural state is a nonwoven material where the fibrils of the fiber have grown together. After subjecting the virgin leather fibers to the Valley beating process as described above, the natural leather has been deconstructed to collagen fibers. To reconstruct the leather, it is advantageous to reconstruct the semblance of nature by returning the fibers to a natural non-woven material and strengthen the bond between the collagen fibers. This objective can be achieved by adding silk fibroin proteins fragments as binder as described above.

The silk fibroin protein and collagen fibers in the leather are natural proteins composed of 22 proteinogenic amino acids. The silk protein has high affinity to the leather fibers (collagen fibers) resulted from the presence of hydrophilic amino acid residue in the silk fibroin protein (e.g., physical entanglement due to forming hydrogen bonding between silk protein fragments and leather fibers), for example, —OH group from serine, guanidine group from arginine, free amine group from lysine, —COOH group from aspartic acid and glutamic acid.

This disclosure provides silk fibroin protein and beaten leather fiber composite materials that are good in spinnability and suitable for making filaments and yarns.

In some embodiment, the pure silk fibroin-based protein fragments in the silk solution are substantially devoid of sericin, have an average weight average molecular weight selected from between about 6 kDa to about 16 kDa, and have a polydispersity ranging from about 1.5 and about 3.0. In some embodiment, the pure silk fibroin-based protein fragments in the silk solution are substantially devoid of sericin, have an average weight average molecular weight selected from between about 14 kDa to about 30 kDa, and have a polydispersity ranging from about 1.5 and about 3.0. In an embodiment, the pure silk fibroin-based protein fragments in the solution are substantially devoid of sericin, have an average weight average molecular weight selected from between about 17 kDa to about 38 kDa, and have a polydispersity ranging from about 1.5 and about 3.0. In an embodiment, the pure silk fibroin-based protein fragments in the solution are substantially devoid of sericin, have an average weight average molecular weight selected from between about 39 kDa to about 54 kDa, and have a polydispersity selected from between about 1.5 and about 3.0. In an embodiment, the pure silk fibroin-based protein fragments in the solution are substantially devoid of sericin, have an average weight average molecular weight selected from between about 39 kDa to about 80 kDa, and have a polydispersity ranging from about 1.5 and about 3.0. In an embodiment, the pure silk fibroin-based protein fragments in the solution are substantially devoid of sericin, have an average weight average molecular weight selected from between about 55 kDa to about 150 kDa, and have a polydispersity selected from between about 1.5 and about 3.0.

Silk Bonded Layered or Spun Materials

In an embodiment, this disclosure provides an article comprising a plurality of fibers or yarns and a silk derived protein or fragments thereof. In some embodiments, the plurality of fibers are natural fibers, synthetic fibers, or a combination thereof. In some embodiments, the natural fibers or yarns include one or more of silk, cotton, alpaca fleece, alpaca wool, lama fleece, *lama* wool, cashmere, sheep fleece, and sheep wool. In some embodiments, the natural fibers or yarns include one or more of alpaca fiber, alpaca fleece, alpaca wool, lama fiber, lama fleece, lama wool, cotton, cashmere and sheep fiber, sheep fleece, sheep wool, byssus, chiengora, quiviut, yak, rabbit, lambswool, mohair wool, camel hair, angora wool, silkworm silk, abaca fiber, coir fiber, flax fiber, jute fiber, kapok fiber, kenaf fiber, raffia fiber, bamboo fiber, hemp, modal fiber, pina, ramie, sisal, and soy protein fiber.

In some embodiments, the synthetic fibers or yarns include one or more of polyester, nylon, and polyester-polyurethane copolymer. In some embodiments, the synthetic fibers or yarns include one or more of acrylic, anidex, aramid, fluorocarbon, modacrylic, novoloid, nylon, nytril, olefin, PBI, polycarbonate, polyester, rubber, saran, spandex, vinal vinvon.

In some embodiments, the article further comprising one or more materials selected from ground up leather, ground up faux or bonded leather, rubber, a polymer, a pigment, a dye, or any combinations thereof.

In some embodiments, the article further comprising a coating.

In some embodiments, the coating includes one or more polymers selected from polyglycolide (PGA), polyethylene glycols, copolymers of glycolide, glycolide/L-lactide copolymers (PGA/PLLA), glycolide/trimethylene carbonate copolymers (PGA/TMC), polylactides (PLA), stereocopolymers of PLA, poly-L-lactide (PLLA), poly-DL-lactide (PDLLA), L-lactide/DL-lactide copolymers, co-polymers of PLA, lactide/tetramethylglycolide copolymers, lactide/trimethylene carbonate copolymers, lactide/δ-valerolactone copolymers, lactide/ε-caprolactone copolymers, polydepsipeptides, PLA/polyethylene oxide copolymers, unsymmetrically 3,6-substituted poly-1,4-dioxane-2,5-diones, poly-β-hydroxybutyrate (PHBA), PHBA/β-hydroxyvalerate copolymers (PHBA/HVA), poly-β-hydroxypropionate (PHPA), poly-p-dioxanone (PDS), poly-δ-valerolactone, poly-ε-caprolactone, methylmethacrylate-N-vinyl pyrrolidine copolymers, polyesteramides, polyesters of oxalic acid, polydihydropyrans, polyalkyl-2-cyanoacrylates, polyurethanes (PU), polyvinylalcohols (PVA), polypeptides, poly-β-malic acid (PMLA), poly-β-alkanoic acids, polyvinylalcohol (PVA), polyethyleneoxide (PEO), chitine polymers, polyethylene, polypropylene, polyasetal, polyamides, polyesters, polysulphone, polyether ether ketone, polyethylene terephthalate, polycarbonate, polyaryl ether ketone, and polyether ketone ketone.

In some embodiments, the article further comprising one or more materials selected from ground up leather, ground up faux or bonded leather, rubber, a polymer, a pigment, a dye, or any combinations thereof.

In some embodiments, the article further comprising a coating.

In some embodiments, the coating includes one or more polymers selected from polyglycolide (PGA), polyethylene glycols, copolymers of glycolide, glycolide/L-lactide copolymers (PGA/PLLA), glycolide/trimethylene carbonate copolymers (PGA/TMC), polylactides (PLA), stereocopolymers of PLA, poly-L-lactide (PLLA), poly-DL-lactide (PDLLA), L-lactide/DL-lactide copolymers, co-polymers of PLA, lactide/tetramethylglycolide copolymers, lactide/trimethylene carbonate copolymers, lactide/δ-valerolactone copolymers, lactide/ε-caprolactone copolymers, polydepsipeptides, PLA/polyethylene oxide copolymers, unsymmetrically 3,6-substituted poly-1,4-dioxane-2,5-diones, poly-β-hydroxybutyrate (PHBA), PHBA/β-hydroxyvalerate copolymers (PHBA/HVA), poly-β-hydroxypropionate (PHPA), poly-p-dioxanone (PDS), poly-δ-valerolactone, poly-ε-caprolactone, methylmethacrylate-N-vinyl pyrrolidine copolymers, polyesteramides, polyesters of oxalic acid, polydihydropyrans, polyalkyl-2-cyanoacrylates, polyurethanes (PU), polyvinylalcohols (PVA), polypeptides, poly-β-malic acid (PMLA), poly-β-alkanoic acids, polyvinylalcohol (PVA), polyethyleneoxide (PEO), chitine polymers, polyethylene, polypropylene, polyasetal, polyamides, polyesters, polysulphone, polyether ether ketone, polyethylene terephthalate, polycarbonate, polyaryl ether ketone, and polyether ketone ketone.

In some embodiments, the coating includes silk fibroin proteins or fragments thereof having an average weight average molecular weight in a range selected from between about 1 kDa and about 5 kDa, between about 5 kDa and about 10 kDa, between about 6 kDa and about 17 kDa, between about 10 kDa and about 15 kDa, between about 15 kDa and about 20 kDa, between about 17 kDa and about 39 kDa, between about 20 kDa and about 25 kDa, between about 25 kDa and about 30 kDa, between about 30 kDa and about 35 kDa, between about 35 kDa and about 40 kDa, between about 39 kDa and about 80 kDa, between about 40 kDa and about 45 kDa, between about 45 kDa and about 50 kDa, between about 60 kDa and about 100 kDa, and between about 80 kDa and about 144 kDa, and a polydispersity between 1 and about 5.

In some embodiments, the silk derived proteins or fragments thereof do not spontaneously or gradually gelate and do not visibly change in color or turbidity when in an aqueous solution for at least 10 days prior to being added to the article.

In some embodiments, the article further comprises one or more polysaccharides selected from starch, cellulose, gum arabic, guar gum, xanthan gum, alginate, pectin, chitin, chitosan, carrageenan, inulin, and gellan gum.

In an embodiment, this disclosure provides silk bonded layered materials comprising the silk fibroin protein as described above and leather fibers. In an embodiment, this disclosure provides silk bonded spun materials comprising the silk fibroin protein as described above and leather fibers.

In some embodiments, this disclosure provides silk bonded layered materials comprising leather fibers and silk fibroin protein fragments having an average weight average molecular weight selected from between about 1 kDa and about 5 kDa, between about 5 kDa and about 10 kDa, between about 6 kDa and about 17 kDa, between about 10 kDa and about 15 kDa, between about 15 kDa and about 20 kDa, between about 17 kDa and about 39 kDa, between about 20 kDa and about 25 kDa, between about 25 kDa and about 30 kDa, between about 30 kDa and about 35 kDa, between about 35 kDa and about 40 kDa, between about 39 kDa and about 80 kDa, between about 40 kDa and about 45 kDa, between about 45 kDa and about 50 kDa, between about 60 kDa and about 100 kDa, and between about 80 kDa and about 144 kDa, and a polydispersity between 1 and about 5.

In some embodiments, this disclosure provides silk bonded layered materials comprising leather fibers and silk fibroin protein fragments having an average weight average molecular weight selected from between about 6 kDa and about 17 kDa, between about 17 kDa and about 39 kDa, between about 39 kDa and about 80 kDa, and a polydispersity between 1.5 and about 3.0.

In an embodiment, this disclosure provides silk bonded spun materials comprising leather fibers and silk fibroin protein fragments having an average weight average molecular weight selected from between about 1 kDa and about 5 kDa, between about 5 kDa and about 10 kDa, between about 6 kDa and about 17 kDa, between about 10 kDa and about 15 kDa, between about 15 kDa and about 20 kDa, between about 17 kDa and about 39 kDa, between about 20 kDa and about 25 kDa, between about 25 kDa and about 30 kDa, between about 30 kDa and about 35 kDa, between about 35 kDa and about 40 kDa, between about 39 kDa and about 80 kDa, between about 40 kDa and about 45 kDa, between about 45 kDa and about 50 kDa, between about 60 kDa and about 100 kDa, and between about 80 kDa and about 144 kDa, and a polydispersity between 1 and about 5.

In some embodiments, this disclosure provides silk bonded spun materials comprising leather fibers and silk fibroin protein fragments having an average weight average molecular weight selected from between about 6 kDa and about 17 kDa, between about 17 kDa and about 39 kDa, between about 39 kDa and about 80 kDa, and a polydispersity between 1.5 and about 3.0.

In some embodiments, the silk fibroin fragments in the silk bonded layered materials or spun materials are obtained from a precursor solution comprising silk fibroin fragments having an average weight average molecular weight selected from between about 1 kDa and about 5 kDa, between about 5 kDa and about 10 kDa, between about 6 kDa and about 17 kDa, between about 10 kDa and about 15 kDa, between about 15 kDa and about 20 kDa, between about 17 kDa and about 39 kDa, between about 20 kDa and about 25 kDa, between about 25 kDa and about 30 kDa, between about 30 kDa and about 35 kDa, between about 35 kDa and about 40 kDa, between about 39 kDa and about 80 kDa, between about 40 kDa and about 45 kDa, between about 45 kDa and about 50 kDa, between about 60 kDa and about 100 kDa, and between about 80 kDa and about 144 kDa, and a polydispersity between 1.0 and about 5.0.

In some embodiment, the pure silk fibroin-based protein fragments in the silk solution used to make the silk bonded layered material or spun yarns are substantially devoid of sericin, have an average weight average molecular weight selected from between about 6 kDa to about 16 kDa, and have a polydispersity ranging from about 1.5 and about 3.0. In some embodiment, the pure silk fibroin-based protein fragments in the silk solution used to make the silk bonded layered material or spun yarns are substantially devoid of sericin, have an average weight average molecular weight selected from between about 14 kDa to about 30 kDa, and have a polydispersity ranging from about 1.5 and about 3.0. In an embodiment, the pure silk fibroin-based protein fragments in the silk solution are substantially devoid of sericin, have an average weight average molecular weight selected from between about 17 kDa to about 38 kDa, and have a polydispersity ranging from about 1.5 and about 3.0. In some embodiment, the pure silk fibroin-based protein fragments in the silk solution used to make the silk bonded layered material or spun yarns are substantially devoid of sericin, have an average weight average molecular weight selected from between about 39 kDa to about 54 kDa, and have a polydispersity ranging from about 1.5 and about 3.0. In an embodiment, the pure silk fibroin-based protein fragments in the silk solution are substantially devoid of sericin, have an average weight average molecular weight selected from between about 39 kDa to about 80 kDa, and have a polydispersity ranging from about 1.5 and about 3.0. In some embodiment, the pure silk fibroin-based protein fragments in the silk solution used to make the silk bonded layered material or spun yarns are substantially devoid of sericin, have an average weight average molecular weight selected from between about 55 kDa to about 150 kDa, and have a polydispersity ranging from about 1.5 and about 3.0.

In some embodiments, the silk fibroin fragments in the silk bonded layered materials or spun materials have a polydispersity between 1 and about 1.5. In some embodiments, the silk fibroin fragments in the silk bonded layered materials or spun materials have a polydispersity between about 1.5 and about 2.0. In some embodiments, the silk fibroin fragments in the silk bonded layered materials or spun materials have a polydispersity between about 1.5 and about 3.0. In some embodiments, the silk fibroin fragments in the silk bonded layered materials or spun materials have a polydispersity between about 2.0 and about 2.5. In some embodiments, the silk fibroin fragments in the silk bonded layered materials or spun materials have a polydispersity between about 2.5 and about 3.0.

In some embodiments, the binder resin is selected from the group consisting of thermoplastic resin, latex, polyvinyl chloride, polyurethane, butadiene acrylonitrile copolymer, anionic copolymer of ester and urethane, and combinations thereof. In some embodiments, the polymer binder is polyvinyl chloride. In some embodiments, the polymer binder is polyurethane. In some embodiments, the polymer binder is butadiene acrylonitrile copolymer (Chemigum® Latex 6387). In some embodiments, the polymer binder is anionic copolymer of ester and urethane (Baybond PU 401).

In some embodiments, the weight ratio of the leather fibers to the silk fibroin protein fragments in the silk bonded leather fibers ranges from about 1.5:1, 1.4:1, 1.3:1, 1.2:1, 1.1:1, 1:1, 1:1.1, 1:1.2, 1:1.3, 1:1.4 and 1:1.5. In some embodiments, the weight ratio of the leather fibers to the silk fibroin protein fragments is of 1:1.4.

In some embodiments, the in the silk bonded layered materials or spun materials further comprising about 0.01% (w/w) to about 10% (w/w) sericin relative to the silk fibroin fragments.

In some embodiments, the silk fibroin fragments in the precursor solution do not spontaneously or gradually gelate and do not visibly change in color or turbidity when in the precursor solution for at least 10 days prior to obtaining the silk fibroin fragments in the substantially solid silk composition.

In some embodiments, this disclosure provides a method making silk protein boned layered or spun materials comprising the step of (1) providing the silk bonded leather fibers as described above; and (2) carding, wet-laid nonwoven processing, drawing and/or twisting the silk bonded leather fibers to form yarns, layered or sheet materials.

In some embodiments, the silk bonded layered resulted from wet-laid nonwoven processing is further subjected to milling and or heat pressing to the silk leather.

In some embodiments, the silk bonded leather fibers are carded into sliver that is spun into a yarn. The spun silk bonded leather fiber yarns is then drawn and textured.

In some embodiments, a drawing machine is used in the drawing step to draw and level fibers one to three times, each fiber is continuously extended to achieve the object for improving the uniformity of the fibers.

In some embodiments, based on diameter and length of the silk leather fibers and requirements of spinning yarns, appropriate operational parameters in twisting, such as correct roller, abrasion, ring spindle and process for spinning yarns, are selected to twist the silk leather fibers and textile fibers to form yarns.

In some embodiments, the silk bonded layered material or silk bonded spun material has a weight ranging from 200 gsm to 700 gsm. GSM (also known as $g/m^{-2}$)=grams per square meter and is the metric measurement of the weight of a fabric. In some embodiments, the silk bonded layered material or silk bonded spun material has a weight selected from the group consisting of 200 gsm, 250 gsm, 300 gsm, 350 gsm, 400 gsm, 450 gsm, 460 gsm, 470 gsm, 480 gsm, 490 gsm, 500 gsm, 510 gsm, 520 gsm, 530 gsm, 540 gsm, 550 gsm, 560 gsm, 570 gsm, 580 gsm, 590 gsm, 600 gsm, 610 gsm, 620 gsm, 630 gsm, 640 gsm, 650 gsm, 660 gsm, 670 gsm, 680 gsm, 690 gsm, and 700 gsm. In some embodiments, the silk bonded layered material or silk bonded spun material has a weight of 650 gsm. In some embodiments, the silk bonded layered material or silk bonded spun material has a weight of 620 gsm. In some embodiments, the silk bonded layered material or silk bonded spun material has a weight of 600 gsm. In some embodiments, the silk bonded layered material or silk bonded spun material has a weight of 550 gsm. In some embodiments, the silk bonded layered material or silk bonded spun material has a weight of 500 gsm. In some embodiments, the silk bonded layered material or silk bonded spun material has a weight of 510 gsm. In some embodiments, the silk bonded layered material or silk bonded spun material has a weight of 460 gsm. In some embodiments, the silk bonded layered material or silk bonded spun material has a weight of 450 gsm.

In some embodiments, the article is a single or multilayered faux or bonded leather article.

In some embodiments, the plurality of fibers or yarns are assembled in one or more of a nonwoven mat or fabric; a woven, knitted, or crochet fabric; or a combination thereof.

In some embodiments, the plurality of fibers or yarns and the silk derived protein or fragments thereof are included in a layer having a thickness of about 0.1 mm, about 0.2 mm, about 0.3 mm, about 0.4 mm, about 0.5 mm, about 0.6, mm, about 0.7 mm, about 0.8 mm, about 0.9 mm, about 1.0 mm, about 1.1 mm, about 1.2 mm, about 1.3 mm, about 1.4 mm, about 1.5 mm, about 1.6, mm, about 1.7 mm, about 1.8 mm, about 1.9 mm, about 2.0 mm, about 2.1 mm, about 2.2 mm, about 2.3 mm, about 2.4 mm, about 2.5 mm, about 2.6, mm, about 2.7 mm, about 2.8 mm, about 2.9 mm, about 3.0 mm, about 3.1 mm, about 3.2 mm, about 3.3 mm, about 3.4 mm, about 3.5 mm, about 3.6, mm, about 3.7 mm, about 3.8 mm, about 3.9 mm, about 4.0 mm, about 4.1 mm, about 4.2 mm, about 4.3 mm, about 4.4 mm, about 4.5 mm, about 4.6, mm, about 4.7 mm, about 4.8 mm, about 4.9 mm, or about 5.0 mm.

In some embodiments, the plurality of fibers or yarns and the silk derived protein or fragments thereof are included in a layer having a thickness of about 1 mm, about 2 mm, about 3 mm, about 4 mm, about 5 mm, about 6, mm, about 7 mm, about 8 mm, about 9 mm, or about 10 mm.

In some embodiments, the article further comprising a laminated film. In some embodiments, the laminated film includes one or more polymers selected from polyglycolide (PGA), polyethylene glycols, copolymers of glycolide, glycolide/L-lactide copolymers (PGA/PLLA), glycolide/trimethylene carbonate copolymers (PGA/TMC), polylactides (PLA), stereocopolymers of PLA, poly-L-lactide (PLLA), poly-DL-lactide (PDLLA), L-lactide/DL-lactide copolymers, co-polymers of PLA, lactide/tetramethylglycolide copolymers, lactide/trimethylene carbonate copolymers, lactide/δ-valerolactone copolymers, lactide/ε-caprolactone copolymers, polydepsipeptides, PLA/polyethylene oxide copolymers, unsymmetrically 3,6-substituted poly-1,4-dioxane-2,5-diones, poly-β-hydroxybutyrate (PHBA), PHBA/β-hydroxyvalerate copolymers (PHBA/HVA), poly-β-hydroxypropionate (PHPA), poly-p-dioxanone (PDS), poly-δ-valerolactone, poly-ε-caprolactone, methylmethacrylate-N-vinyl pyrrolidine copolymers, polyesteramides, polyesters of oxalic acid, polydihydropyrans, polyalkyl-2-cyanoacrylates, polyurethanes (PU), polyvinylalcohols (PVA), polypeptides, poly-β-malic acid (PMLA), poly-β-alkanoic acids, polyvinylalcohol (PVA), polyethyleneoxide (PEO), chitine polymers, polyethylene, polypropylene, polyasetal, polyamides, polyesters, polysulphone, polyether ether ketone, polyethylene terephthalate, polycarbonate, polyaryl ether ketone, and polyether ketone ketone.

In some embodiments, the method further comprising one or more additional steps selected from dyeing, drying, water annealing, mechanical stretching, trimming, performing one or more polishing steps, applying a pigment, applying a colorant, applying an acrylic formulation, chemical fixing, stamping, applying a silicone finish, providing a Uniflex treatment, and/or providing a Finiflex treatment.

EXAMPLES

The following examples are put forth so as to provide those of ordinary skill in the art with a complete disclosure and description of how to make and use the described embodiments, and are not intended to limit the scope of what the inventors regard as their invention nor are they intended to represent that the experiments below are all or the only experiments performed. Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Silk formulations

| Type of Silk | Titration Agent (TA) | Formulation Process |
|---|---|---|
| 6% 1:1 (L:M) pH 8 | Ammonium Hydroxide | Mix 1 part low MW with 1 part med MW; Titrate stepwise with dilute TA (1:100 stock) |
| 6% 2:1 (L:M) pH 8 | Ammonium Hydroxide | Mix 2 parts low MW with 1 part med MW; Titrate stepwise with dilute TA (1:100 stock) |
| 6% 3:1 (L:M) pH 8 | Ammonium Hydroxide | Mix 3 parts low MW with 1 part med MW; Titrate stepwise with dilute TA (1:100 stock) |
| 6% 4:1 (L:M) pH 8 | Ammonium Hydroxide | Mix 4 parts low MW with 1 part med MW; Titrate stepwise with dilute TA (1:100 stock) |
| 6% 5:1 (L:M) pH 8 | Ammonium Hydroxide | Mix 5 parts low MW with 1 part med MW; Titrate stepwise with dilute TA (1:100 stock) |
| 6% 6:1 (L:M) pH 8 | Ammonium Hydroxide | Mix 6 parts low MW with 1 part med MW; Titrate stepwise with dilute TA (1:100 stock) |
| 6% 7:1 (L:M) pH 8 | Ammonium Hydroxide | Mix 7 parts low MW with 1 part med MW; Titrate stepwise with dilute TA (1:100 stock) |
| 6% 8:1 (L:M) pH 8 | Ammonium Hydroxide | Mix 8 parts low MW with 1 part med MW; Titrate stepwise with dilute TA (1:100 stock) |
| 6% 9:1 (L:M) pH 8 | Ammonium Hydroxide | Mix 9 parts low MW with 1 part med MW; Titrate stepwise with dilute TA (1:100 stock) |
| 6% 1:2 (L:M) pH 8 | Ammonium Hydroxide | Mix 1 part low MW with 2 parts med MW; Titrate stepwise with dilute TA (1:100 stock) |
| 6% 1:3 (L:M) pH 8 | Ammonium Hydroxide | Mix 1 part low MW with 3 parts med MW; Titrate stepwise with dilute TA (1:100 stock) |
| 6% 1:4 (L:M) pH 8 | Ammonium Hydroxide | Mix 1 part low MW with 4 parts med MW; Titrate stepwise with dilute TA (1:100 stock) |
| 6% 1:5 (L:M) pH 8 | Ammonium Hydroxide | Mix 1 part low MW with 5 parts med MW; Titrate stepwise with dilute TA (1:100 stock) |
| 6% 1:6 (L:M) pH 8 | Ammonium Hydroxide | Mix 1 part low MW with 6 parts med MW; Titrate stepwise with dilute TA (1:100 stock) |
| 6% 1:7 (L:M) pH 8 | Ammonium Hydroxide | Mix 1 part low MW with 7 parts med MW; Titrate stepwise with dilute TA (1:100 stock) |
| 6% 1:8 (L:M) pH 8 | Ammonium Hydroxide | Mix 1 part low MW with 8 parts med MW; Titrate stepwise with dilute TA (1:100 stock) |
| 6% 1:9 (L:M) pH 8 | Ammonium Hydroxide | Mix 1 part low MW with 9 parts med MW; Titrate stepwise with dilute TA (1:100 stock) |

| | | |
|---|---|---|
| 6% 1:1 (L:M) pH 4 | Acetic Acid | Mix 1 part low MW with 1 part med MW; Titrate stepwise with stock TA |
| 6% 2:1 (L:M) pH 4 | Acetic Acid | Mix 2 parts low MW with 1 part med MW; Titrate stepwise with stock TA |
| 6% 3:1 (L:M) pH 4 | Acetic Acid | Mix 3 parts low MW with 1 part med MW; Titrate stepwise with stock TA |
| 6% 4:1 (L:M) pH 4 | Acetic Acid | Mix 4 parts low MW with 1 part med MW; Titrate stepwise with stock TA |
| 6% 5:1 (L:M) pH 4 | Acetic Acid | Mix 5 parts low MW with 1 part med MW; Titrate stepwise with stock TA |
| 6% 6:1 (L:M) pH 4 | Acetic Acid | Mix 6 parts low MW with 1 part med MW; Titrate stepwise with stock TA |
| 6% 7:1 (L:M) pH 4 | Acetic Acid | Mix 7 parts low MW with 1 part med MW; Titrate stepwise with stock TA |
| 6% 8:1 (L:M) pH 4 | Acetic Acid | Mix 8 parts low MW with 1 part med MW; Titrate stepwise with stock TA |
| 6% 9:1 (L:M) pH 4 | Acetic Acid | Mix 9 parts low MW with 1 part med MW; Titrate stepwise with stock TA |
| 6% 1:2 (L:M) pH 4 | Acetic Acid | Mix 1 part low MW with 2 parts med MW; Titrate stepwise with stock TA |
| 6% 1:3 (L:M) pH 4 | Acetic Acid | Mix 1 part low MW with 3 parts med MW; Titrate stepwise with stock TA |
| 6% 1:4 (L:M) pH 4 | Acetic Acid | Mix 1 part low MW with 4 parts med MW; Titrate stepwise with stock TA |
| 6% 1:5 (L:M) pH 4 | Acetic Acid | Mix 1 part low MW with 5 parts med MW; Titrate stepwise with stock TA |
| 6% 1:6 (L:M) pH 4 | Acetic Acid | Mix 1 part low MW with 6 parts med MW; Titrate stepwise with stock TA |
| 6% 1:7 (L:M) pH 4 | Acetic Acid | Mix 1 part low MW with 7 parts med MW; Titrate stepwise with stock TA |
| 6% 1:8 (L:M) pH 4 | Acetic Acid | Mix 1 part low MW with 8 parts med MW; Titrate stepwise with stock TA |
| 6% 1:9 (L:M) pH 4 | Acetic Acid | Mix 1 part low MW with 9 parts med MW; Titrate stepwise with stock TA |
| 1% 1:1 (L:M) pH 8 | Ammonium Hydroxide | Dilute silk stocks to 1% w/v; Mix 1 part low MW with 1 part med MW; Titrate stepwise with dilute TA (1:100 stock) |
| 1% 2:1 (L:M) pH 8 | Ammonium Hydroxide | Dilute silk stocks to 1% w/v; Mix 2 parts low MW with 1 part med MW; Titrate stepwise with dilute TA (1:100 stock) |
| 1% 3:1 (L:M) pH 8 | Ammonium Hydroxide | Dilute silk stocks to 1% w/v; Mix 3 parts low MW with 1 part med MW; Titrate stepwise with dilute TA (1:100 stock) |
| 1% 4:1 (L:M) pH 8 | Ammonium Hydroxide | Dilute silk stocks to 1% w/v; Mix 4 parts low MW with 1 part med MW; Titrate stepwise with dilute TA (1:100 stock) |
| 1% 5:1 (L:M) pH 8 | Ammonium Hydroxide | Dilute silk stocks to 1% w/v; Mix 5 parts low MW with 1 part med MW; Titrate stepwise with dilute TA (1:100 stock) |
| 1% 6:1 (L:M) pH 8 | Ammonium Hydroxide | Dilute silk stocks to 1% w/v; Mix 6 parts low MW with 1 part med MW; Titrate stepwise with dilute TA (1:100 stock) |
| 1% 7:1 (L:M) pH 8 | Ammonium Hydroxide | Dilute silk stocks to 1% w/v; Mix 7 parts low MW with 1 part med MW; Titrate stepwise with dilute TA (1:100 stock) |
| 1% 8:1 (L:M) pH 8 | Ammonium Hydroxide | Dilute silk stocks to 1% w/v; Mix 8 parts low MW with 1 part med MW; Titrate stepwise with dilute TA (1:100 stock) |
| 1% 9:1 (L:M) pH 8 | Ammonium Hydroxide | Dilute silk stocks to 1% w/v; Mix 9 parts low MW with 1 part med MW; Titrate stepwise with dilute TA (1:100 stock) |
| 1% 1:2 (L:M) pH 8 | Ammonium Hydroxide | Dilute silk stocks to 1% w/v; Mix 1 part low MW with 2 parts med MW; Titrate stepwise with dilute TA (1:100 stock) |
| 1% 1:3 (L:M) pH 8 | Ammonium Hydroxide | Dilute silk stocks to 1% w/v; Mix 1 part low MW with 3 parts med MW; Titrate stepwise with dilute TA (1:100 stock) |
| 1% 1:4 (L:M) pH 8 | Ammonium Hydroxide | Dilute silk stocks to 1% w/v; Mix 1 part low MW with 4 parts med MW; Titrate stepwise with dilute TA (1:100 stock) |
| 1% 1:5 (L:M) pH 8 | Ammonium Hydroxide | Dilute silk stocks to 1% w/v; Mix 1 part low MW with 5 parts med MW; Titrate stepwise with dilute TA (1:100 stock) |
| 1% 1:6 (L:M) pH 8 | Ammonium Hydroxide | Dilute silk stocks to 1% w/v; Mix 1 part low MW with 6 parts med MW; Titrate stepwise with dilute TA (1:100 stock) |
| 1% 1:7 (L:M) pH 8 | Ammonium Hydroxide | Dilute silk stocks to 1% w/v; Mix 1 part low MW with 7 parts med MW; Titrate stepwise with dilute TA (1:100 stock) |

| | | |
|---|---|---|
| 1% 1:8 (L:M) pH 8 | Ammonium Hydroxide | Dilute silk stocks to 1% w/v; Mix 1 part low MW with 8 parts med MW; Titrate stepwise with dilute TA (1:100 stock) |
| 1% 1:9 (L:M) pH 8 | Ammonium Hydroxide | Dilute silk stocks to 1% w/v; Mix 1 part low MW with 9 parts med MW; Titrate stepwise with dilute TA (1:100 stock) |
| 6% med pH 13 | Ammonium Hydroxide | Titrate 6% Med MW silk stepwise with dilute TA (1:100 stock) |
| 6% med pH 12 | Ammonium Hydroxide | Titrate 6% Med MW silk stepwise with dilute TA (1:100 stock) |
| 6% med pH 11 | Ammonium Hydroxide | Titrate 6% Med MW silk stepwise with dilute TA (1:100 stock) |
| 6% med pH 10 | Ammonium Hydroxide | Titrate 6% Med MW silk stepwise with dilute TA (1:100 stock) |
| 6% med pH 9 | Ammonium Hydroxide | Titrate 6% Med MW silk stepwise with dilute TA (1:100 stock) |
| 6% med pH 8 | Ammonium Hydroxide | Titrate 6% Med MW silk stepwise with dilute TA (1:100 stock) |
| 6% med pH 7 | Ammonium Hydroxide and/or Acetic Acid | Titrate 6% Med MW silk stepwise with dilute TA (1:100 stock) |
| pH 6 6% low | Acetic Acid | Titrate 6% low MW silk stepwise with stock TA |
| 6% low pH 5 | Acetic Acid | Titrate 6% low MW silk stepwise with stock TA |
| 6% low pH 4 | Acetic Acid | Titrate 6% low MW silk stepwise with stock TA |
| 6% med pH 3 | Acetic Acid | Titrate 6% med MW silk stepwise with stock TA |
| 6% low pH 2 | Acetic Acid | Titrate 6% low MW silk stepwise with stock TA |
| 1% low pH 6 | Acetic Acid | Dilute 6% silk low MW stock to 1% w/v; Titrate stepwise with stock TA |
| 1% low pH 5 | Acetic Acid | Dilute 6% silk low MW stock to 1% w/v; Titrate stepwise with stock TA |
| 1% low pH 4 | Acetic Acid | Dilute 6% silk low MW stock to 1% w/v; Titrate stepwise with stock TA |
| 1% low pH 3 | Acetic Acid | Dilute 6% silk low MW stock to 1% w/v; Titrate stepwise with stock TA |
| 1% low pH 2 | Acetic Acid | Dilute 6% silk low MW stock to 1% w/v; Titrate stepwise with stock TA |
| 1% med pH 6 | Acetic Acid | Dilute 6% silk med MW stock to 1% w/v; Titrate stepwise with stock TA |
| 1% med pH 5 | Acetic Acid | Dilute 6% silk med MW stock to 1% w/v; Titrate stepwise with stock TA |
| 1% med pH 4 | Acetic Acid | Dilute 6% silk med MW stock to 1% w/v; Titrate stepwise with stock TA |
| 1% med pH 3 | Acetic Acid | Dilute 6% silk med MW stock to 1% w/v; Titrate stepwise with stock TA |
| 1% med pH 2 | Acetic Acid | Dilute 6% silk med MW stock to 1% w/v; Titrate stepwise with stock TA |

Silk-based coatings formulated with GG and GLY

| Additive | Concentration (% wt. OR % vol.) | pH | Wet Coating Thickness (μm) | Titrants |
|---|---|---|---|---|
| GG | 0.1-1.0 % wt. | 5-10 | 4- | NH4OH (5%) Citric Acid w/v) |
| GLY | 0.1 -25 % vol. | 5-10 | 4- | NH4OH (5%) Citric Acid w/v) |

Silk-fibroin formulations

| Additive | Concentration | Descriptor |
|---|---|---|
| Gellan Gum Carrageenan | 0.1-1.0 % w/v | Rheology Modifier |
| Glycerol Sorbitol Glucose Sucrose | 0.0-100 mg/mL | Plasticizer |
| Kollasol LOK Stahl DF-13- | 0.0-1.0 g/L | De-foaming agent |

All patents, patent applications, and published references cited herein are hereby incorporated by reference in their entirety. While the methods of the present disclosure have been described in connection with the specific embodiments thereof, it will be understood that it is capable of further modification. Further, this application is intended to cover any variations, uses, or adaptations of the methods of the present disclosure, including such departures from the present disclosure as come within known or customary practice in the art to which the methods of the present disclosure pertain.

Example 1: Preparation of Aqueous Silk Solution

Silk solutions of various molecular weights and/or combinations of molecular weights can be optimized for specific applications. The following provides an example of this process but it not intended to be limiting in application or formulation.

Methods of making silk fibroin or silk fibroin fragments and their applications in various fields are known and are described for example in U.S. Pat. Nos. 9,187,538, 9,511,012, 9,517,191, 9,522,107, 9,522,108, 9,545,369, and 10,166,177, 10,287,728 and 10,301,768, all of which are incorporated herein in their entireties.

The raw silk cocoons from the silkworm *Bombyx mori* was cut into pieces. The pieces silk cocoons were processed in an aqueous solution of $Na_2CO_3$ at about 100° C. for about 60 minutes to remove sericin (degumming). The volume of the water used equals about 0.4×raw silk weight and the amount of $Na_2CO_3$ is about 0.848×the weight of the raw silk cocoon pieces. The resulting degummed silk cocoon pieces were rinsed with deionized water three times at about 60° C. (20 minutes per rinse). The volume of rinse water for each cycle was 0.2 L×the weight of the raw silk cocoon pieces. The excess water from the degummed silk cocoon pieces was removed. After the DI water washing step, the wet degummed silk cocoon pieces were dried at room temperature. The degummed silk cocoon pieces were mixed with a LiBr solution, and the mixture was heated to about 100° C. The warmed mixture was placed in a dry oven and was heated at about 100° C. for about 60 minutes to achieve complete dissolution of the native silk protein. The resulting silk fibroin solution was filtered and dialyzed using Tangential Flow Filtration (TFF) and a 10 kDa membrane against deionized water for 72 hours. The resulting silk fibroin aqueous solution has a concentration of about 8.5 wt. %. Then, 8.5% silk solution was diluted with water to result in a 1.0% w/v silk solution. TFF can then be used to further concentrate the pure silk solution to a concentration of 20.0% w/w silk to water.

Each process step from raw cocoons to dialysis is scalable to increase efficiency in manufacturing. Whole cocoons are currently purchased as the raw material, but pre-cleaned cocoons or non-heat treated cocoons, where worm removal leaves minimal debris, have also been used. Cutting and cleaning the cocoons is a manual process, however for scalability this process could be made less labor intensive by, for example, using an automated machine in combination with compressed air to remove the worm and any particulates, or using a cutting mill to cut the cocoons into smaller pieces.

The degumming step, currently performed in small batches, could be completed in a larger vessel, for example an industrial washing machine where temperatures at or in between 60° C. to 100° C. can be maintained. The rinsing step could also be completed in the industrial washing machine, eliminating the manual rinse cycles.

Dissolution of the silk in LiBr solution could occur in a vessel other than a convection oven, for example a stirred tank reactor.

Varying degumming conditions (i.e., time and temperature), LiBr solution parameters (i.e., concentration) and dissolution parameters (i.e., duration and temperature) results in aqueous silk solutions with different viscosities, homogeneities, and colors. Increasing the temperature for degumming process, lengthening the degumming time, using a higher temperature LiBr solution at emersion and over time when dissolving the silk and increasing the time at temperature (e.g., in an oven as shown here, or an alternative heat source) all resulted in less viscous and more homogeneous solvent and silk solutions. While almost all parameters resulted in a viable silk solution, methods that allow complete dissolution to be achieved in fewer than 4 to 6 hours are preferred for process scalability.

In some preparation examples, the degumming process are carried out as conditions in heated $Na_2CO_3$ solution: 90° C. 30 min, 90° C. 60 min, 100° C. 30 min, and 100° C. 60 min. The dissolution of degummed silk fibroin was carried using LiBr aqueous solution as solvent. Briefly, 9.3 M LiBr was prepared and allowed to sit at room temperature for at least 30 minutes. 5 mL of LiBr solution was added to 1.25 g of silk and placed in the 60° C. oven. Samples from each set were removed at 4, 6, 8, 12, 24, 168 and 192 hours.

In some preparation examples, the degumming process are carried out as conditions in heated $Na_2CO_3$ solution: 90° C. 30 min, 90° C. 60 min, 100° C. 30 min, and 100° C. 60 min. The dissolution of degummed silk fibroin was carried using LiBr aqueous solution as solvent. Briefly, 9.3 M LiBr solution was heated to one of four temperatures: 60° C., 80° C., 100° C. or boiling. 5 mL of hot LiBr solution was added to 1.25 g of silk and placed in the 60° C. oven. Samples from each set were removed at 1, 4 and 6 hours.

In some preparation examples, the degumming process are carried out as conditions in heated $Na_2CO_3$ solution: 90° C. 30 min, 90° C. 60 min, 100° C. 30 min, and 100° C. 60 min. The dissolution of degummed silk fibroin was carried using LiBr aqueous solution as solvent. Briefly, 9.3 M LiBr solution was heated to one of four temperatures: 60° C., 80° C., 100° C. or boiling. 5 mL of hot LiBr solution was added to 1.25 g of silk and placed in the oven at the same temperature of the LiBr. Samples from each set were removed at 1, 4 and 6 hours. 1 mL of each sample was added to 7.5 mL of 9.3 M LiBr and refrigerated for viscosity testing.

Molecular weight of the silk protein fragments may be controlled based upon the specific parameters utilized during the extraction step, including extraction time and temperature; specific parameters utilized during the dissolution step, including the LiBr temperature at the time of submersion of the silk in to the lithium bromide and time that the solution is maintained at specific temperatures; and specific parameters utilized during the filtration step. By controlling process parameters using the disclosed methods, it is possible to create SPF mixture solutions with polydispersity equal to or lower than 2.5 at a variety of different molecular weight selected from between 5 kDa to 200 kDa, more preferably between 10 kDa and 80 kDa. By altering process parameters to achieve silk solutions with different molecular weights, a range of fragment mixture end products, with desired polydispersity of equal to or less than 2.5 may be targeted based upon the desired performance requirements. For example, a lower molecular weight silk film containing a drug may have a faster release rate compared to a higher molecular weight film making it ideal for a daily delivery vehicle in consumer cosmetics. Additionally, SPF mixture solutions with a polydispersity of greater than 2.5 can be achieved. Further, two solutions with different average molecular weights and polydispersities can be mixed to create combination solutions. Alternatively, a liquid silk gland (100% sericin free silk protein) that has been removed directly from a worm could be used in combination with any of the SPF mixture solutions of the present disclosure. Molecular weight of the pure silk fibroin-based protein fragment composition was determined using High Pressure Liquid Chromatography (HPLC) with a Refractive Index Detector (RID). Polydispersity was calculated using Cirrus GPC Online GPC/SEC Software Version 3.3 (Agilent).

Parameters were varied during the processing of raw silk cocoons into silk solution. Varying these parameters affected the MW of the resulting silk solution. Parameters manipulated included (i) time and temperature of extraction, (ii) temperature of LiBr, (iii) temperature of dissolution oven, and (iv) dissolution time.

The raw silk cocoons from the silkworm *Bombyx mori* was cut into pieces. The pieces of raw silk cocoons were boiled in an aqueous solution of $Na_2CO_3$ (about 100° C.) for a period of time between about 30 minutes to about 60 minutes to remove sericin (degumming). The volume of the water used equals about 0.4×raw silk weight and the amount of $Na_2CO_3$ is about 0.848×the weight of the raw silk cocoon pieces. The resulting degummed silk cocoon pieces were rinsed with deionized water three times at about 60° C. (20 minutes per rinse). The volume of rinse water for each cycle was 0.2 L×the weight of the raw silk cocoon pieces. The excess water from the degummed silk cocoon pieces was removed. After the DI water washing step, the wet degummed silk cocoon pieces were dried at room temperature. The degummed silk cocoon pieces were mixed with a LiBr solution, and the mixture was heated to about 100° C. The warmed mixture was placed in a dry oven and was heated at a temperature ranging from about 60° C. to about 140° C. for about 60 minutes to achieve complete dissolution of the native silk protein. The resulting solution was allowed to cool to room temperature and then was dialyzed to remove LiBr salts using a 3,500 Da MWCO membrane. Multiple exchanges were performed in Di water until $Br^-$ ions were less than 1 ppm as determined in the hydrolyzed fibroin solution read on an Oakton Bromide ($Br^-$) double-junction ion-selective electrode.

The resulting silk fibroin aqueous solution has a concentration of about 8.0% w/v containing pure silk fibroin-based protein fragments having an average weight average molecular weight selected from about 6 kDa to about 16 kDa, about 17 kDa to about 39 kDa, and about 39 kDa to about 80 kDa and a polydispersity of between about 1.5 and about 3.0. The 8.0% w/v was diluted with DI water to provide a 1.0% w/v, 2.0% w/v, 3.0% w/v, 4.0% w/v, 5.0% w/v by the coating solution.

Three (3) silk solutions were utilized in standard silk structures in accordance with standard methods in the literature with the following results:

Solution #1 is a silk concentration of 5.9%, average MW of 19.8 kDa and 2.2 PDI (made with a 60 min boil extraction, 100° C. LiBr dissolution for 1 hr).

Solution #2 is a silk concentration of 6.4% (made with a 30 min boil extraction, 60° C. LiBr dissolution for 4 hrs).

Solution #3 is a silk concentration of 6.17% (made with a 30 min boil extraction 100° C. LiBr dissolution for 1 hour).

Example 2: Wet-Laid Nonwoven

Materials

Ground leather was prepared according to the process described above. Silk solutions were prepared according to the process in Example 1.

The binder resins used include High Stretch V95, butadiene-acrylonitrile copolymer (Chemigum® Latex 6387), and anionic polyester urethane polymer dispersion (Baybond® PU 401). The Chemigum® Latex 6387 resin was identified as a preferred resin binder.

High molecular weight nonionic polyacrylamide (Percol® 351, or Magnafloc® 351) was used as flocculant. Hydrogen chloric acid was used as pH adjusting agent.

Wet-laid Nonwoven Making Process

9 L pure water and 42 gram of ground leather was added to a Valley Beater. The ground leather suspension in water was subject to beating for at least 2 hours to give beaten leather fiber aqueous suspension. After the Valley beating process, 36 gram of resin binder, silk solution, and 1 mL of Percol® 351 was added sequentially to the beaten leather fiber aqueous suspension and a wand was used to stir the mixture to allow thorough mixing of all ingredients until flocking took place.

The water content is allowed to drain out leaving the flocked material on a screen. A cotton mat is placed on top of the screen material, and the pack (screen, flocked material and mat) is aspirated in X and Y motion from any excess water, the pack is flipped over and some more aspiration is completed.

The screen is manually separated from the flocked material while replaced by an absorbent mat on both side. The new pack is passed through pad roller to remove as much as possible moisture and the absorbent mats are replaced by cotton mats. The pack is placed in an oven at 135-125° C. with a screen as weight to reduce uncontrolled shrinkage of the flocked material.

Control samples contained resin binder only without silk fibroin protein fragments. Control Sample 1 contains only High Stretch V95 as resin binder. Control Sample 5 contains only Chemigum® Latex 6387 as resin binder. Control Sample 6 contains only Baybond® PU 401 as resin binder. Sample 2, Sample 3, Sample 4 and Sample 7 are working samples. The sample formulations for the silk bonded leather fiber composition are summarized in Tables 1-2 below.

TABLE 1

| Silk Bonded Leather Fiber Aqueous Suspension Formulations | | | | | | | |
|---|---|---|---|---|---|---|---|
| | Sample 1 | Sample 2 | Sample 3 | Sample 4 | Sample 5 | Sample 6 | Sample 7 |
| Water (L) | 10 | 9 | 9 | 9 | 10 | 10 | 9 |
| Ground leather (g) | 42 | 42 | 42 | 42 | 42 | 42 | 42 |

TABLE 1-continued

Silk Bonded Leather Fiber Aqueous Suspension Formulations

| resin binder | High Stretch V95 36 g | High Stretch V95 36 g | High Stretch V95 36 g | Chemigum ® Latex 6387 36 g | Chemigum ® Latex 6387 36 g | Baybond ® PU 401 36 g | High Stretch V95 36 g |
|---|---|---|---|---|---|---|---|
| silk solution A (L) | — | 1[a] | 1[a] | 1[a] | — | — | — |
| silk solution B (L) | — | — | — | — | — | — | 0.2[b] |
| Percol 351 (mL) | 1 | 1 | 1 | 1 | 1 | 1 | 1 |
| 1M HCl[c] (mL) | 1 | 1 | 1 | 1 | 1 | 1 | 1 |
| Dry Product weight (gsm) | 620 | 550 | 650 | 500 | 650 | 450 | 510 |

[a]0.6 wt. % silk fibroin protein fragments concentration in the entire liquid suspension.
[b]0.12 wt. % silk fibroin protein fragments concentration in the entire liquid suspension.
[c]pH adjusting agent and the pH of the entire liquid suspension during processing is adjusted to pH 3-5.

TABLE 2

Silk Bonded Leather Fiber Aqueous Suspension Formulations

|  | Sample 1 | Sample 5 | Sample 6 | Sample 8 | Sample 9 |
|---|---|---|---|---|---|
| Water (L) | 10 | 10 | 10 | 9 | 9 |
| Ground leather (g) | 42 | 42 | 42 | 42 | 42 |
| Cotton Fiber (g) | — | — | — | — | 7 |

| resin binder | High Stretch V95 36 g | Chemigum ® Latex 6387 36 g | Baybond ® PU 401 36 g | High Stretch V95 36 g | High Stretch V95 36 g |
|---|---|---|---|---|---|
| silk solution B (L) | — | — | — | 0.2[b] | 0.2[b] |
| Percol 351 (mL) | 1 | 1 | 1 | 1 | 1 |
| 1M HCl[c] (mL) | 1 | 1 | 1 | 1 | 1 |
| Dry Product weight (gsm) | 620 | 650 | 450 | 460 | — |

[b]0.12 wt. % silk fibroin protein fragments concentration in the entire liquid suspension.
[c]pH adjusting agent and the pH of the entire liquid suspension during processing is adjusted to pH 3-5.

Example 3: Data Summary for Leather Compositions

This Example describes the recycling of leather waste using silk fibroin fragments described herein as an ingredient to create novel materials with improved mechanical, optical and haptic properties.

Leather waste was used for the preparation of leather compositions of the disclosure. Leather waste can be recycled as described herein; otherwise, such leather waste is added to the waste generated in the leather industry. This waste was utilized to create a final product with application in different industries where natural or faux or bonded leather is used. Generally, in bonded leather products, resins are added to keep the leather scraps together. However, with the addition of silk protein fragments described herein, part or all of the resins can be replaced, thereby creating a petrochemical free alternative with an improved eco-friendly impact to the environment when compared to the standard leather bonded products.

In some embodiments, leather articles and compositions consisting of leather raw materials, silk protein fragments, and optionally at least one type of natural yarn (such as cotton, cashmere, wool, etc.) can be recycled continuously using the processes described herein. As would be understood by one of ordinary skill in the art, leather articles and compositions containing man-made contaminants (such as synthetic resins) could not be recycled continuously because the amount of contaminants in the article or composition would increase with each round of recycling.

Figure 3:
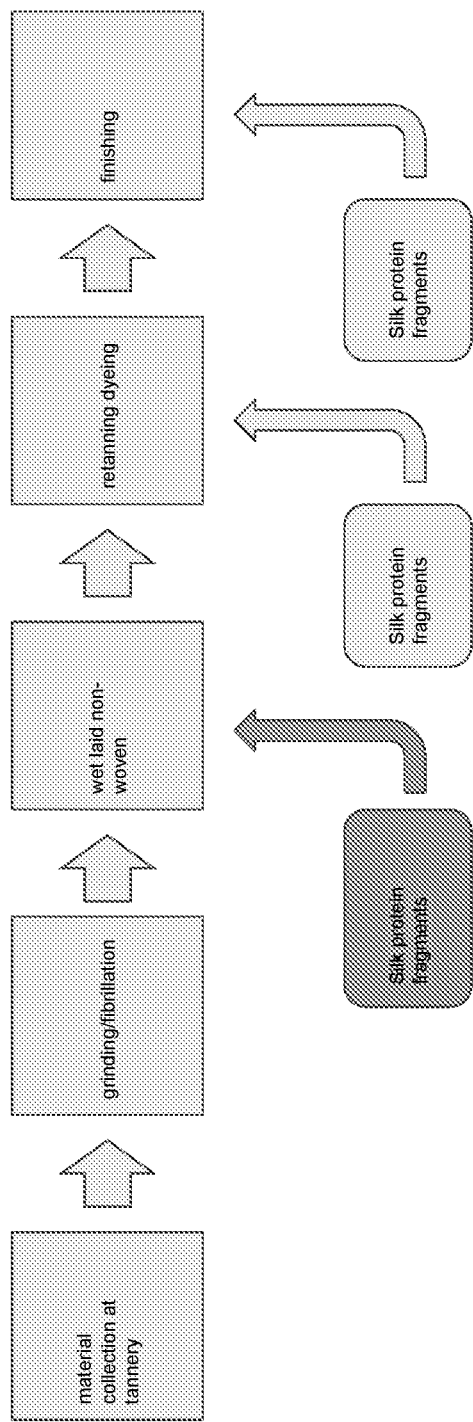
FIG. 3 is a flow chart showing an exemplary process for preparing leather compositions of the disclosure.

FIG. 3 illustrates a flow chart of an exemplary process for preparing leather compositions of the disclosure.

Samples were prepared using the following:
Range of ingredients used:
Leather waste:
Bovine wet blue shaving from tannery processing
Bovine post-industrial waste
Sheep post-industrial waste
Silk protein fragments:
Activated Silk 104-LS (comprising low molecular weight silk fibroin fragments (low-MW silk))
Activated Silk 105-LS (comprising medium molecular weight silk fibroin fragments (medium-MW silk))
Sericin (post industrial waste collected from the degumming process)
Resin:
HYSTRETCH™ V95
Chemigum Latex 6387
BayBond PU 401
Holden HX-200
Fiber material:
Cashmere
Cotton
Lyocell 1.5 Tdpf×10 mm
Other ingredients:
Percol as flocculant
Hydrochloric acid as pH correction
Table 3 below shows the composition of the prepared samples. Holden HX-200 is a HX-200 is a pre-vulcanized casting Latex produced by Holden's Latex. HYSTRETCH™ V-95 is a fully saturated elastomeric terpolymer, designed as the APE-free equivalent to Hystretch™ V-29. HYSTRETCH™ V-95 and Hystretch™ V-29 are produced by Lubrizol. Lyocell is a form of is a form of rayon that consists of cellulose fiber.

Refined leather generally includes shreds and small pieces of leather. In some embodiments, leather scraps are chopped into squares no larger than 1 cm$^2$; the chopped leather is converted into small pieces using a grinding process; and then the small pieces undergo fibrillation using a hammer-mill.

TABLE 3

Compositions of samples

| Sample ID | Refined solid Leather (grams) | Sericin Recycled (grams) | Activated Silk 104-LS (grams) | Activated Silk 105-LS (grams) | Recycled fibers/ (grams) | Percol (mL) | resin/ (grams) | Heat Press | Calender |
|---|---|---|---|---|---|---|---|---|---|
| 1 | 42 | | | | | | | | |
| 2 | 42 | | | | | | | | |
| 3A | 42 | | | | | | | | |
| 3B | 42 | | | | | | | | |
| 4A | 42 | | 36 | | | | | | |
| 4B | 42 | | 36 | | | | | | |
| 5A | 42 | | | | | | HX-200/56 | | |
| 5B | 42 | | | | | | HX-200/56 | | |
| 6 | 42 | | | 36 | | | | | |
| 7 | 42 | 36 | | | | | | | |
| 8 | 42 | 7 | | | cotton/5 | | | | |
| 9 | 42 | 7 | | | cashmere/5 | | | | |
| 10 | 42 | | | | | | HX-200/56 | | |
| 11 | 42 | | | 12 | | | HX-200/18 | | |
| 12 | 42 | | | 24 | | | HX-200/36 | | |
| 13 | 42 | | 12 | | | | HX-200/24 | | |
| | 42 | | | | | | | | |
| 13 | 42 | | | | | | | | |
| 14 | 42 | | | | | | | | |
| 15 | 42 | | | | | | | | |
| 16 | 42 | | | | | | Hystretch 95/15 | | |
| 17 | 42 | | | | | | Hystretch 95/22.5 | | |
| | 42 | | | | | | | | |
| 18 | 42 | | | | | 3 | Hystretch 95/42 | 2.5 min on each side, 250 F. | 90 C. 15PSI, 1.5 speed |
| 19 | 42 | | | | | 3 | Hystretch 95/42 | 2.5 min on each side, 250 F. | 90 C. 15PSI, 1.5 speed |
| 20 | 42 | | | | | 1 | | 2.5 min on each side, 250 F. | 90 C. 15PSI, 1.5 speed |
| 21 | 42 | | | | | 1 | | 2.5 min on each side, 250 F. | 90 C. 15PSI, 1.5 speed |
| 22 | 42 | | | | | 3 | Hystretch 95/21 | 2.5 min on each side, 250 F. | 90 C. 15PSI, 1.5 speed |
| 23 | 42 | | | | | 2 | Hystretch 95/21 | 2.5 min on each side, 250 F. | 90 C. 15PSI, 1.5 speed |
| 24 | 42 | | | | Lyocell/10 | 0.5 | | 2.5 min on each side, 250 F. | 90 C. 15PSI, 1.5 speed |
| 25 | 42 | | | | Lyocell/10 | 1 | Hystretch 95/21 | 2.5 min on each side, 250 F. | 90 C. 15PSI, 1.5 speed |
| 26 | 42 | | | | Lyocell/10 | 2 | Hystretch 95/42 | 2.5 min on each side, 250 F. | 90 C. 15PSI, 1.5 speed |
| | 42 | | | | | | | | |
| 27 | 42 | | 5 | | | 1 | | 3 min on each side | 90 C. 15PSI, 1.5 speed |
| 28 | 42 | | | 5 | | | | 3 min on each side | 90 C. 15PSI, 1.5 speed |
| 29 | 42 | 5 | | | | | | 3 min on each side | 90 C. 15PSI, 1.5 speed |
| 30 | 42 | | 5 | | Lyocell/10 | 1 | Hystretch 95/21 | 3 min on each side | 90 C. 15PSI, 1.5 speed |
| 31 | 42 | | | 5 | Lyocell/10 | 1 | Hystretch 95/21 | 3 min on each side | 90 C. 15PSI, 1.5 speed |
| 32 | 42 | 5 | | | Lyocell/10 | 1 | Hystretch 95/21 | 3 min on each side | 90 C. 15PSI, 1.5 speed |
| | 42 | | | | | | | | |
| 32-1 | 42 | 5 | | | Lyocell/10 | 1 | Hystretch 95/21 | 3 min on each side | 90 C. 15PSI, 1.5 speed |
| 32-2 | 42 | 5 | | | Lyocell/10 | 1 | Hystretch 95/21 | 3 min on each side | 90 C. 15PSI, 1.5 speed |
| 32-3 | 42 | 5 | | | Lyocell/10 | 1 | Hystretch 95/21 | 3 min on each side | 90 C. 15PSI, 1.5 speed |
| 32-4 | 42 | 5 | | | Lyocell/10 | 1 | Hystretch 95/21 | 3 min on each side | 90 C. 15PSI, 1.5 speed |
| 30-1 | 42 | | 5 | | Lyocell/10 | 1 | Hystretch 95/21 | 3 min on each side | 90 C. 15PSI, 1.5 speed |
| 30-2 | 42 | | 5 | | Lyocell/10 | 1 | Hystretch 95/21 | 3 min on each side | 90 C. 15PSI, 1.5 speed |
| 30-3 | 42 | | 5 | | Lyocell/10 | 1 | Hystretch 95/21 | 3 min on each side | 90 C. 15PSI, 1.5 speed |
| 25-1 | 42 | | | | Lyocell/10 | 1 | Hystretch 95/21 | 3 min on each side | 90 C. 15PSI, 1.5 speed |
| 33 | 42 | 5 | | | Lyocell/5 | 1 | Hystretch 95/21 | 3 min on each side | 90 C. 15PSI, 1.5 speed |
| 34 | 17 | 2.5 | | | Lyocell/5 | 1 | Hystretch 95/10.5 | 3 min on each side | 90 C. 15PSI, 1.5 speed |

After identifying the desired silk fibroin solution concentration of 6%, dye recipes were modified accordingly and Carteggio application was verified.

The samples of the disclosure, commercially available bonded leather, and natural leather were benchmarked with selected test used in the leather industry. Tables 4-9 show experimental data demonstrating the physical properties of the samples produced.

TABLE 4

Composition of Samples and Experimentally-Measured Physical Properties of Same

| Source Units | Sample Name | Sample ID | Stiffness (Torsion Wire) ASTM D 2821 Degree | Softness (BLC softness guage) IUP 36/ISO 17235 mm | Permeability to water vapour (MVTR) ASTM D 5052 g/cm2/24 hours |
|---|---|---|---|---|---|
| Comerrcial Bonded Leather | | | | | |
| Prodetti Alfa | Chiaro Corium | A | 50 | 19 | 29 |
| Prodetti Alfa | Chiaro Corium | B | 130 | 12 | 1 |
| Prodetti Alfa | Impasto Chiaro Soft | C | 135 | 15 | 178 |
| Prodetti Alfa | Impasto Scurio Soft | D | 135 | 8.3 | 179 |
| RELEA | Relea Décor Pure B | E | 100 | 14.7 | 16 |
| RELEA | Soft Pure B | F | 40 | 24.3 | 106 |
| RELEA | Soft Pure L | G | 105 | 18.3 | 245 |
| 100% Natural Leather | | | | | |
| Chanel | Lambskin | LE-002-LR-BK-0001 | 130 | 45.7 | 1124 |
| Michael Kors | Cow skin | LE047G2-BK-L 1/1-0001 | 235 | 23 | 51 |
| EBN Made | | | | | |
| EBN | RL-050-BC-NC-02-P1 | 14P | 95 | — | 1011 |
| EBN | RL-050-BC-NC-03-P2 | 15P | 95 | — | 899 |
| EBN | RL-050-BC-NC-04-P3 | 16P | 95 | — | 919 |
| EBN | RL-050-BC-NC-05-P4 | 17P | 105 | — | 900 |
| EBN | RL-050-BC-NC-02 | 14 | 85 | — | 993 |
| EBN | RL-050-BC-NC-03 | 15 | 95 | — | 1043 |
| EBN | RL-050-BC-NC-04 | 16 | 100 | — | 907 |
| EBN | RL-050-BC-NC-05 | 17 | 95 | — | 929 |
| EBN | RL-050-BC-NC-06 | 21 | 110 | 1 | — |
| EBN | RL-050-BC-NC-07 | 24 | 110 | 1.4 | — |
| EBN | RL-050-BC-NC-01 | 25 | 135 | 1.2 | — |
| EBN | SRL-050-BL-NC-01 | 30 | 125 | — | — |
| EBN | SRL-050-BM-NC-01 | 31 | 125 | — | — |
| EBN | SRL-050-BS-NC-01 | 32 | 125 | — | — |

| Sample ID | GSM g/m2 | Thickness mm | Tear Strength g/force | Tensile Strength N/mm2 | Residual Moisture % | Environmental Data | Abrasion Test |
|---|---|---|---|---|---|---|---|
| A | 1080 | 0.8 | | 11 | | Leather Standard | |
| B | 1080 | 1.6 | | 11 | | OEKO TEX | |
| C | 850 | 1 | | ≥9 | | REACH Conformity | |
| D | 850 | 1.6 | | ≥9 | | | |
| E | 1000 | 0.8 | | 9.5-11.5 | 8-12 Wt % | Leather Standard | >15 Tours |
| F | 960 | 0.6 | | 8.5 | | OEKO TEX | |
| G | 960 | 1.2 | | 8.5 | | REACH Conformity | |
| LE-002-LR-BK-0001 | | | | | | | |
| LE047G2-BK-L 1/1-0001 | | | | | | | |
| 14P | | | | | | | |
| 15P | | | | | | | |
| 16P | | | | | | | |
| 17P | | | | | | | |
| 14 | | | | | | | |
| 15 | | | | | | | |
| 16 | | | | | | | |
| 17 | | | | | | | |
| 21 | | | 157.3 | | | | |
| 24 | | | 290.7 | 10 | | | |
| 25 | | | 498.7 | | | | |
| 30 | 720 | 1.7 | 432 | 19.4 | | | |
| 31 | 710 | 1.5 | 560 | 25.4 | | | |
| 32 | 675 | 1.4 | 698.7 | 44 | | | |

TABLE 4-continued

Composition of Samples and Experimentally-Measured Physical Properties of Same

| Sample ID | Color Fastness | Chemical Resistance | Soiling Behaviour | Soiling Behaviour | Soiling Behaviour | Soiling Behaviour | Soiling Behaviour |
|---|---|---|---|---|---|---|---|
| A | | | | | | | |
| B | | | | | | | |
| C | | | | | | | |
| D | | | | | | | |
| E | Blue Scale: ≥5 | not resistant to alkalis (long term); No change with dilute acids, oils&grease | Coffee: 5/5 | Red Wine: 5/5 | Ketchup: 5/5 | Olive and Mustard oil: 5/5 | Alcohol 48%: 5/5 |
| F | Grey Scale: ≥4 | | | | | | |
| G | | | | | | | |
| LE-002-LR-BK-0001 | | | | | | | |
| LE047G2-BK-L1/1-0001 | | | | | | | |
| 14P | | | | | | | |
| 15P | | | | | | | |
| 16P | | | | | | | |
| 17P | | | | | | | |
| 14 | | | | | | | |
| 15 | | | | | | | |
| 16 | | | | | | | |
| 17 | | | | | | | |
| 21 | | | | | | | |
| 24 | | | | | | | |
| 25 | | | | | | | |
| 30 | | | | | | | |
| 31 | | | | | | | |
| 32 | | | | | | | |

| Sample ID | Avg. Elongation | Dimensional Stability % | Acc. Weathering Test |
|---|---|---|---|
| A | ≥40 | | 4 |
| B | | | |
| C | ≥30 | 1% | |
| D | | | |
| E | | | |
| F | | | |
| G | | | |
| LE-002-LR-BK-0001 | | | |
| LE047G2-BK-L1/1-0001 | | | |
| 14P | | | |
| 15P | | | |
| 16P | | | |
| 17P | | | |
| 14 | | | |
| 15 | | | |
| 16 | | | |
| 17 | | | |
| 21 | | | |
| 24 | | | |
| 25 | | | |
| 30 | 11 | | |
| 31 | 17 | | |
| 32 | 28 | | |

TABLE 5

Tensile strength of samples and comparative examples

| Sample ID | Sample Name | Tensile Strength N/mm2 |
|---|---|---|
| A | Chiaro Corium | 11 |
| B | Chiaro Corium | 11 |
| C | Impasto Chiara Soft | 9 |
| D | Impasto Scurio Soft | 9 |
| E | Relea Décor Pure B | 11.5 |
| F | Soft Pure B | 8.5 |
| G | Soft Pure L | 8.5 |
| 24 | RL-050-BC-NC-07 | 8.33 |
| 25 | RL-050-BC-NC-01 | 12.8 |
| 30 | SRL-050-BL-NC-01 | 11.41 |

TABLE 5-continued

Tensile strength of samples and comparative examples

| Sample ID | Sample Name | Tensile Strength N/mm2 |
|---|---|---|
| 31 | SRL-050-BM-NC-01 | 16.93 |
| 32 | SRL-050-BS-NC-01 | 31.42 |

Test Method for Tensile Strength of Leather: ASTM D2209

Tensile strength properties determine the onset of grain crack.

Figure 4:
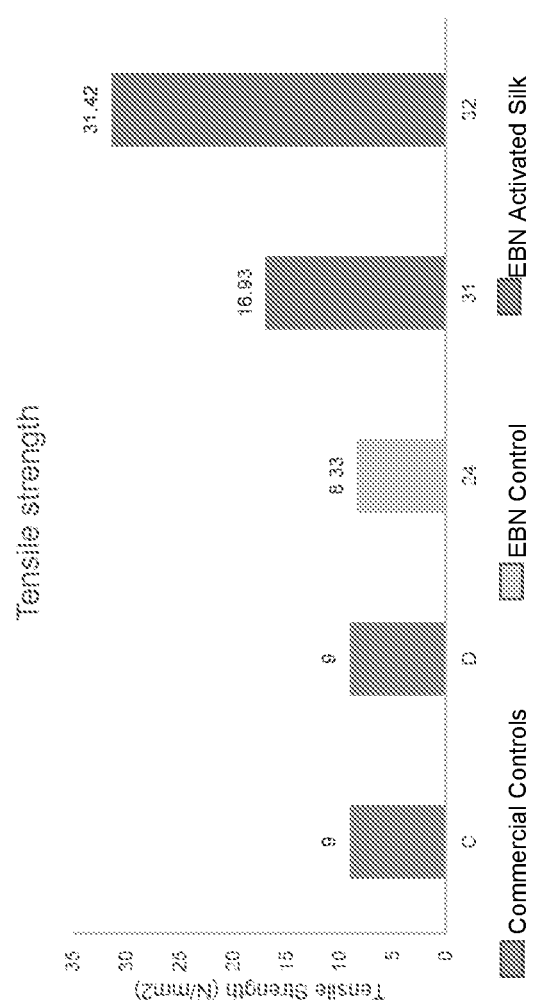
FIG. 4 is a graph of experimental data showing the tensile strength of compositions of the disclosure and comparative examples.
Figure 5:
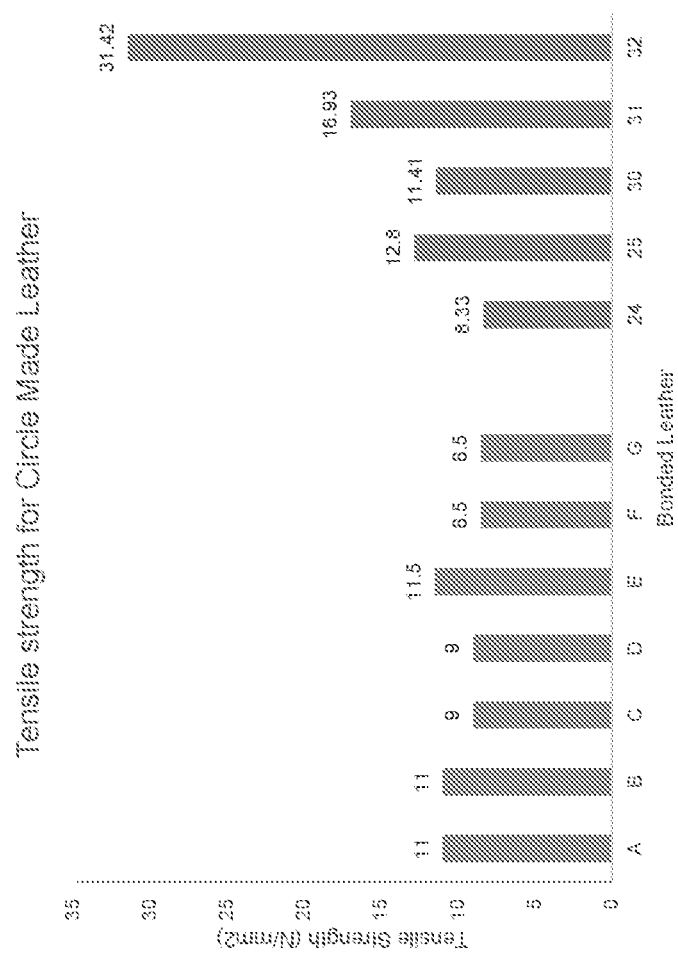
FIG. 5 is a graph of experimental data showing the tensile strength of compositions of the disclosure and comparative examples.

Samples of the disclosure demonstrate up to 250% increased tensile strength compared to commercially available bonded leather and control. FIG. 4 and FIG. 5 graphically depict the tensile strength of samples of the disclosure and comparative examples.

TABLE 6

Tear strength of samples and comparative examples

| Sample ID | Sample Name | Tear Strength g/force |
|---|---|---|
| 21 | RL-050-BC-NC-06 | 157.3 |
| 24 | RL-050-BC-NC-07 | 290.7 |
| 25 | RL-050-BC-NC-01 | 498.7 |
| 30 | SRL-050-BL-NC-01 | 432 |
| 31 | SRL-050-BM-NC-01 | 560 |
| 32 | SRL-050-BS-NC-01 | 698.7 344% |

Test Method for Tearing Strength of Fabrics by Falling Pendulum Type (Elmendorf): ASTM D1424

Figure 6:
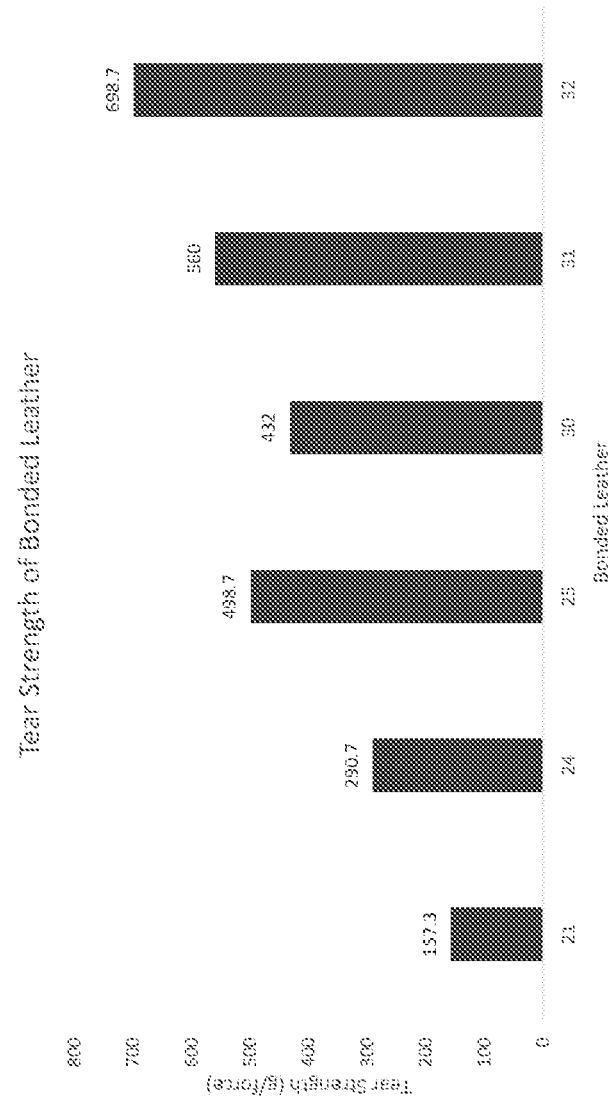
FIG. 6 is a graph of experimental data showing the tear strength of compositions of the disclosure and comparative examples.
Figure 7:
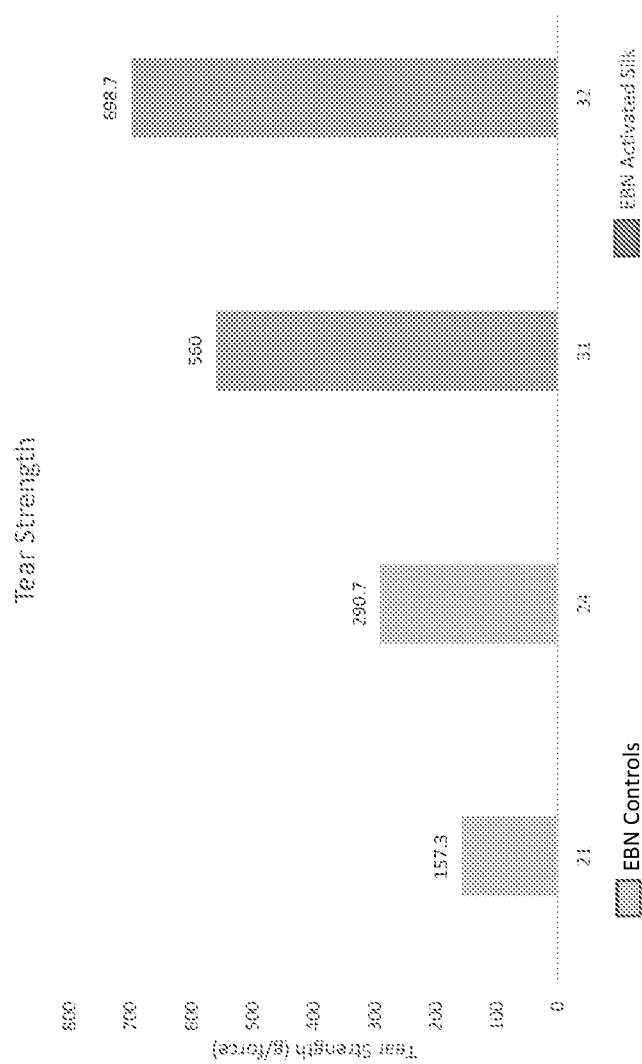
FIG. 7 is a graph of experimental data showing the tear strength of compositions of the disclosure and comparative examples.

Tear strength properties determines the resistance to propagate a tear in the specimen. Samples of the disclosure containing silk protein fragments demonstrate up to 340% improved tear strength properties relative to the controls. FIG. 6 and FIG. 7 graphically depict the tensile strength of samples of the disclosure and comparative examples.

TABLE 7

Stiffness of samples and comparative examples

| Sample ID | Sample Name | Stiffness (Torsion Wire) ASTM D 2821 Degree |
|---|---|---|
| A | Chiaro Corium | 50 |
| B | Chiaro Corium | 130 |
| C | Impasto Chiaro Soft | 135 |
| D | Impasto Scurio Soft | 135 |
| E | Relea Décor Pure B | 100 |
| F | Soft Pure B | 40 |
| G | Soft Pure L | 105 |
| 14P | RL-050-BC-NC-02-P1 | 95 |
| 15P | RL-050-BC-NC-03-P2 | 95 |
| 16P | RL-050-BC-NC-04-P3 | 95 |
| 17P | RL-050-BC-NC-05-P4 | 105 |
| 14 | RL-050-BC-NC-02 | 85 |
| 15 | RL-050-BC-NC-03 | 95 |
| 16 | RL-050-BC-NC-04 | 100 |
| 17 | RL-050-BC-NC-05 | 95 |
| 21 | RL-050-BC-NC-06 | 110 |
| 24 | RL-050-BC-NC-07 | 110 |
| 25 | RL-050-BC-NC-01 | 135 |
| 30 | SRL-050-BL-NC-01 | 125 |

TABLE 7-continued

Stiffness of samples and comparative examples

| Sample ID | Sample Name | Stiffness (Torsion Wire) ASTM D 2821 Degree |
|---|---|---|
| 31 | SRL-050-BM-NC-01 | 125 |
| 32 | SRL-050-BS-NC-01 | 125 |

Figure 8:
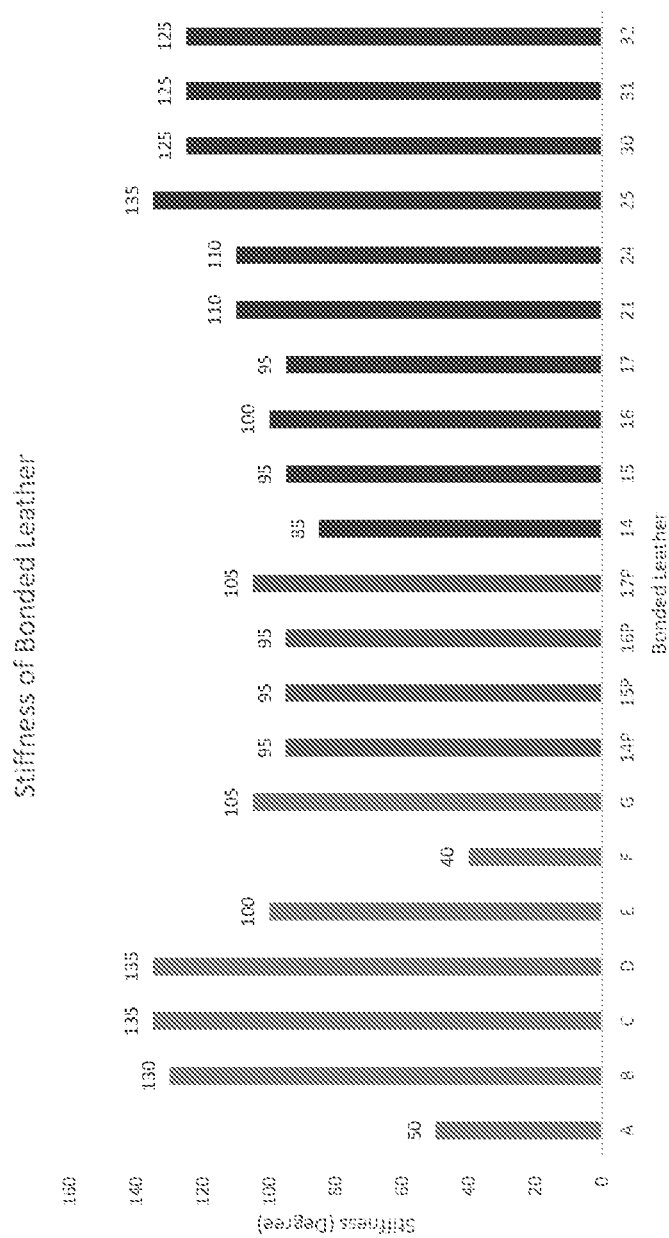
FIG. 8 is a graph of experimental data showing the stiffness of compositions of the disclosure and comparative examples.
Figure 9:
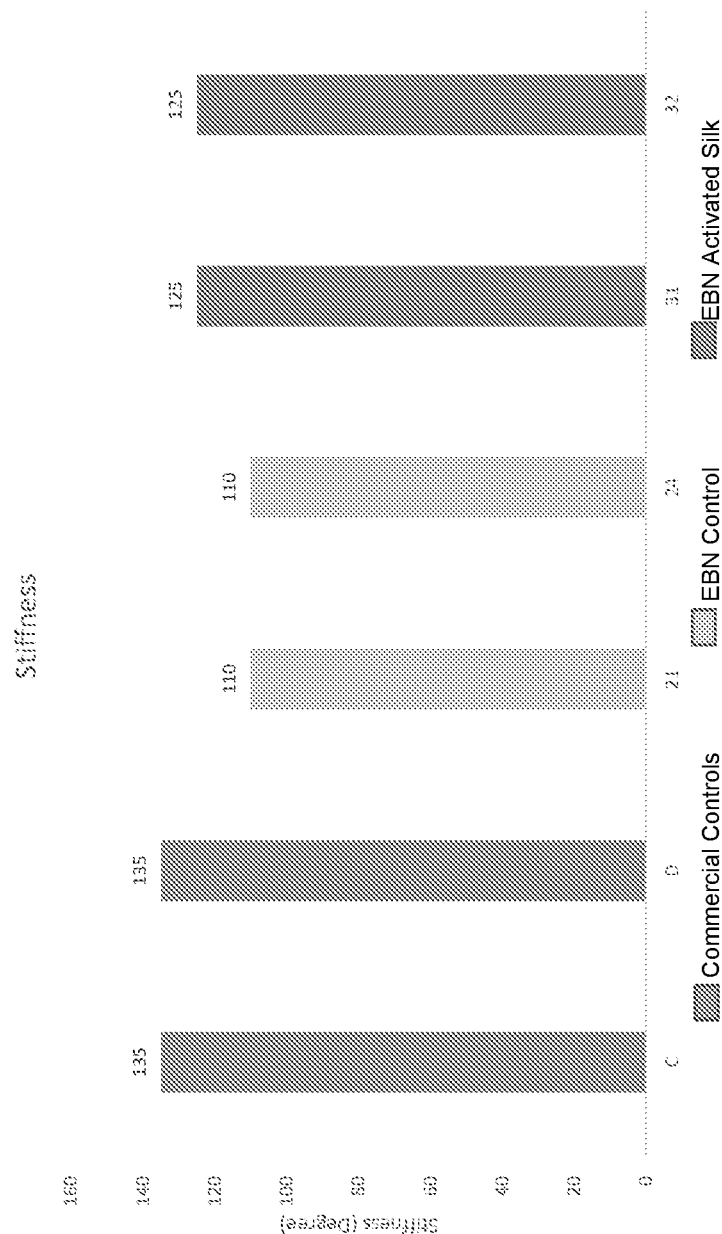
FIG. 9 is a graph of experimental data showing the stiffness of compositions of the disclosure and comparative examples.

FIG. 8 and FIG. 9 graphically depict the tensile strength of samples of the disclosure and comparative examples.

TABLE 8

Elongation of samples and comparative examples

| Sample ID | Sample Name | Avg. Elongation |
|---|---|---|
| A | Chiaro Corium | 40 |
| B | Chiaro Corium | 40 |
| C | Impasto Chiaro Soft | 30 |
| D | Impasto Scurio Soft | 30 |
| 30 | SRL-050-BL-NC-01 | 11 |
| 31 | SRL-050-BM-NC-01 | 17 |
| 32 | SRL-050-BS-NC-01 | 28 |

Figure 10:
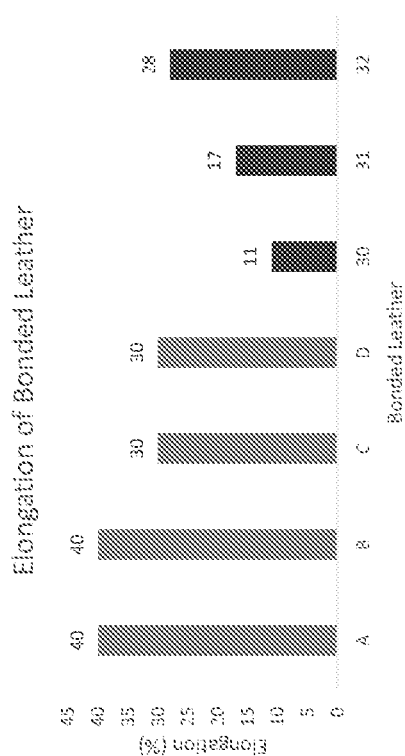
FIG. 10 is a graph of experimental data showing the elongation of compositions of the disclosure and comparative examples.
Figure 11:
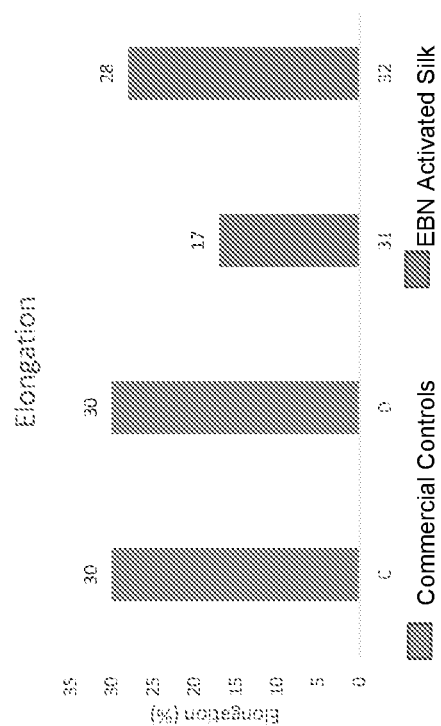
FIG. 11 is a graph of experimental data showing the elongation of compositions of the disclosure and comparative examples.

FIG. 10 and FIG. 11 graphically depict the elongation of samples of the disclosure and comparative examples.

TABLE 9

Permeability to water vapor of samples and comparative examples

| Sample ID | Sample Name | Permeability to water vapour (MVTR) ASTM D 5052 g/cm2/24 hours |
|---|---|---|
| A | Chiaro Corium | 29 |
| B | Chiaro Corium | 1 |
| C | Impasto Chiaro Soft | 178 |
| D | Impasto Scurio Soft | 179 |
| E | Relea Décor Pure B | 16 |
| F | Soft Pure B | 106 |
| G | Soft Pure L | 245 |
| 14P | RL-050-BC-NC-02-P1 | 1011 |
| 15P | RL-050-BC-NC-03-P2 | 899 |
| 16P | RL-050-BC-NC-04-P3 | 919 |
| 17P | RL-050-BC-NC-05-P4 | 900 |
| 14 | RL-050-BC-NC-02 | 993 |
| 15 | RL-050-BC-NC-03 | 1043 |
| 16 | RL-050-BC-NC-04 | 907 |
| 17 | RL-050-BC-NC-05 | 929 |

MVTR = moisture vapor transmission rate;

Test Method for permeability to water vapor (MVTR): ASTM D 5052

Figure 12:
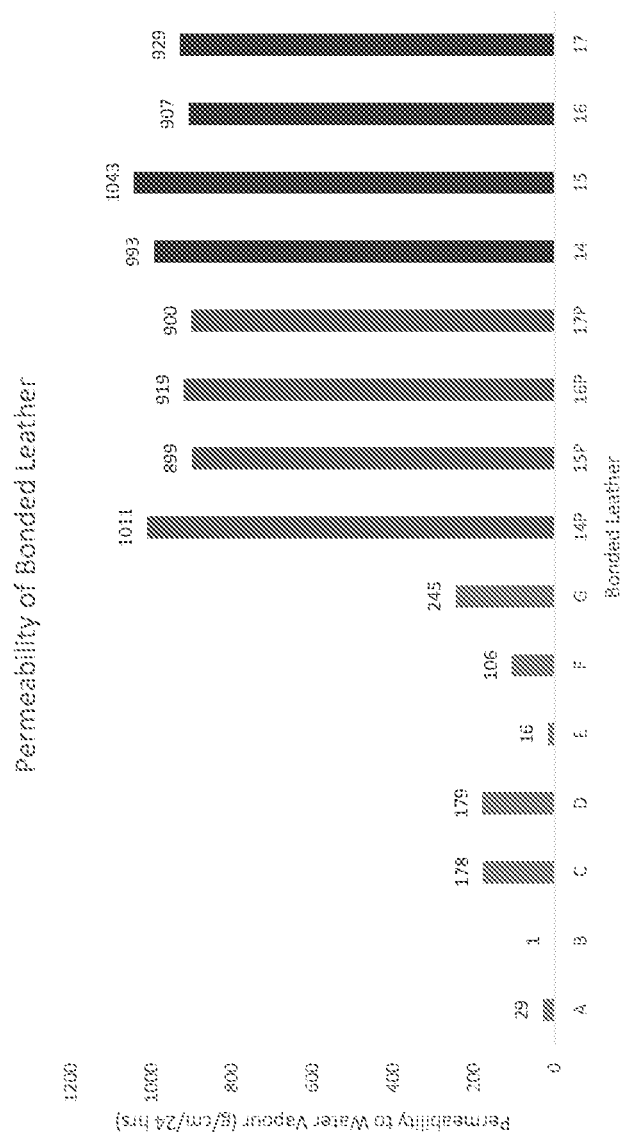
FIG. 12 is a graph of experimental data showing the permeability to water vapor of compositions of the disclosure and comparative examples.
Figure 13:
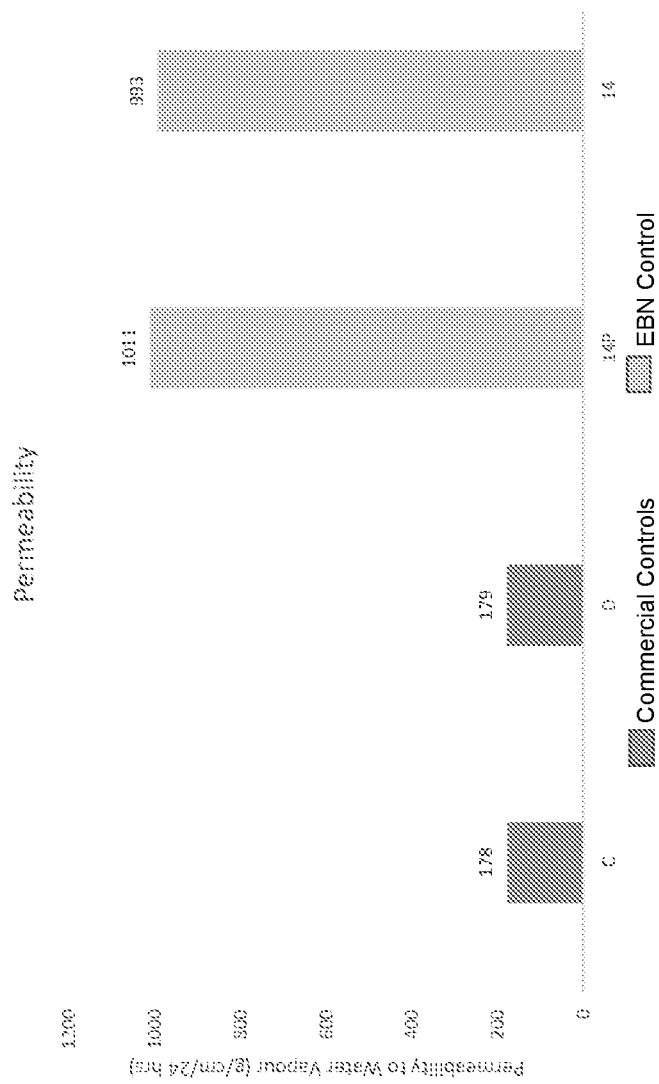
FIG. 13 is a graph of experimental data showing the permeability to water vapor of compositions of the disclosure and comparative examples.

Permeability to water vapor determines the breathability of the specimen. Samples of the disclosure demonstrate an improvement of greater than 400% in breathability compared to the commercially available bonded leather samples. FIG. 12 and FIG. 13 graphically depict the tensile strength of samples of the disclosure and comparative examples.

Dyeing Process for Leather Samples

An Optidye RS Basic Plus 5 lbs dyeing machine was used for the dyeing process. After recording the initial weight of the samples, images of each sample were recorded for both sides. Before dying, the samples of the disclosure were prepared by removing all dirt and impurities with a soaking in DI water for 2 hours. After soaking, the excess DI water was removed, and the samples were weighted. A pre-wet sample can also aid a better pickup of dye.

A 1000 ml warm water bath was prepared for the dye solution. 20 g of Acid Dye was added to 10 ml of warm water to make a smooth paste. The paste was added to the 1000 ml warm water for a 1:50 material to liquor ratio.

The dye was completely dissolved in the water bath and make sure no lumps of dye exist.

To this dye solution, 10 g of NaCl dissolved in water was added for better exhaustion of the dye on the leather sample. The solution was stirred for some time until the salt and dye were completely dissolved in water. The pH was checked, and ammonium sulphate was added as needed to create pH 3-4

The dye solution was placed in the mixing tanks for dyeing. The program was set such that the temperature rose to 60° C. at a rate of 1° C. per minute. The drum was rotated at 10 rev/min.

The samples were run at the temperature of 60° C. for 1 hour, and then 10 g of citric acid was added to fix the dye and achieve a level color on the sample. The samples were run for another 30 mins, and then washed in cold water to remove the superficial excess dye.

Figure 14:
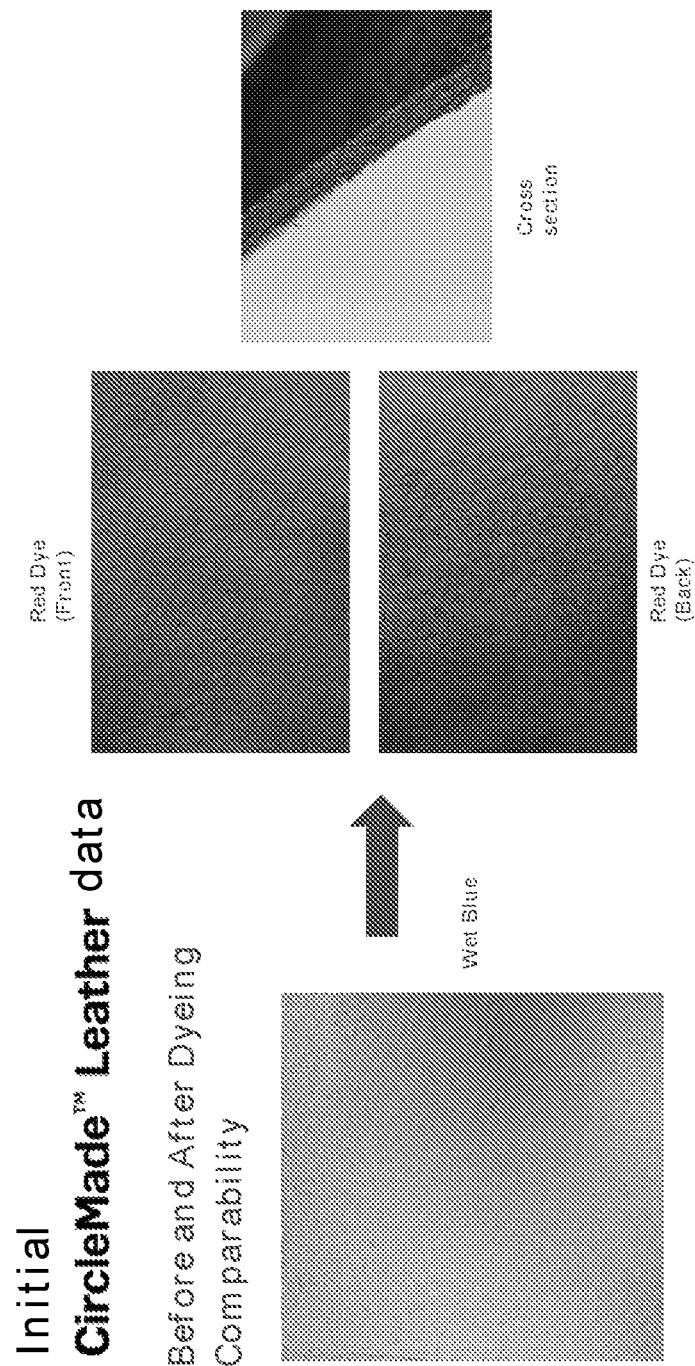
FIG. 14 is a series of images comparing a wet blue sample of the disclosure before dyeing and after dyeing.
Figure 15:
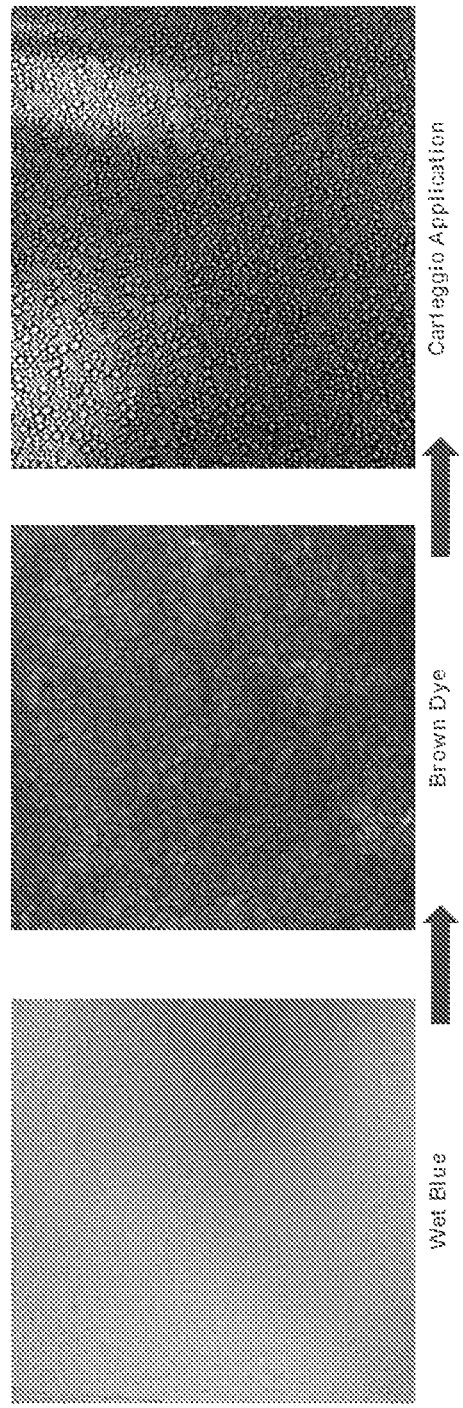
FIG. 15 is a series of images comparing a wet blue sample of the disclosure before dyeing, after dyeing, and after Carteggio application.

The samples were dried in the oven at 60° C. with a mesh weight on top to prevent non homogenous drying rate. At 10 minutes interval, the samples were removed from the oven and weighed to verify if the sample is dried. Samples were allowed to further equilibrate at room temperature on the bench for at least 12 hours before recording the final weight and recording the images on both sides of each sample. FIG. 14 and FIG. 15 depict images of dyed samples of the disclosure.

Process for Dyeing of Recycled Leather Using Acid Dyes

The process includes a dyeing recipe used on full sheet recycled leather samples. The process describes a scale-up recycled dyeing process from bench top dyeing machine to lab scale dyeing machine. The process can achieve comparable dyeing color distribution as the bench top dyeing machine.

1. Materials:
    1.1 20% Lyocell+15% HS (control) (RL-050-BC-NC-01) (sample #25)
    1.2 5% Silk C+20% lyocell+15% HS (SRL-050-BL-NC-01) (sample #30)
    1.3 5% Silk D+20% lyocell+15% HS (SRL-050-BM-NC-01) (sample #31)
    1.4 2.5% Silk Sericin+20% lyocell+15% HS (SRL-050-BS-NC-01) (sample #32)
    1.5 Pre-Metallized Acid Dye 428-Chocolate Brown (Dharma Trading Co.)
    1.6 Pre-Metallized Acid Dye 440-Ox Blood Red (Dharma Trading Co.)
    1.7 Pre-Metallized Acid Dye 434-Pistachio (Dharma Trading Co.)
    1.8 Ammonium Sulfate
    1.9 Acetic Acid
    1.10 Sodium Chloride
    1.11 Distilled Water
2. Equipment:
    2.1 Optidye RS Basic Plus 5 lbs dyeing machien
    2.2 Hot stir plate
    2.3 Dye canisters
    2.4 Thermometer
    2.5 Glass beaker
    2.6 Stir bars
    2.7 3 ml pipette
    2.8 Weigh boats
    2.9 Weighing balance
    2.10 Camera
3. Tests:
    3.1 Visual test for appearance of dyed sample
    3.2 % Wet pick up of Dye of Sample
    3.3 Mass calculation of sample
4. Methods:
    4.1 The initial weight of the samples was recorded.
    4.2 Images of each sample on both sides were recorded
    4.3 The leather was prepared to remove all dirt and impurities by soaking in DI water for 2 hours.
    4.4 After soaking, the excess water was squeezed out and the sample was weighed (Pre-wet sample can be used for dyeing for better pickup of dye).
    4.5 A 1000 ml warm water bath was prepared for preparation of the dye solution.
    4.6 20 g of Acid Dye to was added 10 ml of warm water to make a smooth paste.
    4.7 The paste was added to the 1000 ml warm water for a 1:50 material to liquor ratio.
    4.8 The dye was completely dissolved in the water bath and it was made sure that sure no lumps of dye exist.
    4.9 To this dye solution, 10 g of NaCl dissolved in water was added for better exhaustion of the dye on the leather sample.
    4.10 The solution was stirred for some time till the salt and dye were completely dissolved in water.
    4.11 The pH was checked and ammonium sulphate was added as needed to create pH 3-4
    4.12 This dye solution was put in the cannister for dyeing in the Ahiba IR
    4.13 The program was set such that the temperature rose to 60° C. at a rate of 1° C. per minute.
    4.14 The canister was rotated at 10 rev/min
    4.15 The samples were run at this temperature of 60° C. for 1 hour and 10 g citric acid was added to fix the dye and achieve a level color on the sample.
    4.16 The samples were run for another 30 mins and then washed in cold water to remove the superficial excess dye.
    4.17 The samples were dried in the oven at 60° C. with a mesh weight on top to prevent waviness. At 10 minutes interval, the samples were removed from the oven and weighed to verify if the sample was dry.
    4.18 Samples were allowed to further equilibrate at room temperature on the bench for at least 12 hours before recording the final weight and recording the images on both sides of each sample.

Table 10 below shows the formulations for dyeing

TABLE 10

| Formulations for dyeing | | |
|---|---|---|
| Sample ID | Sample No. | Ingredients |
| 25 | RL-050-BC-NC-01 | 500 ml Water + 10 g |
| 30 | SRL-050-BL-NC-01 | Acid Dye + 10 g NaCl + |
| 31 | SRL-050-BM-NC-01 | Ammonium Sulfate + |
| 32 | SRL-050-BS-NC-01 | 10 g Citric Acid |

Example 4: Data Summary for Yarn

This Example describes a method for recycling fabric waste using silk protein fragments of the disclosure as an ingredient to create novel yarn with improved mechanical, optical and haptics.

For raw material, fabric waste was used as the feedstock; otherwise, such fabric wastet would be added to the waste generated in the textile industry. The fabric waste was used to create a final yarn with applications in different industries where virgin yarn is used. The feedstock is made from industrial and post-consumer textile waste. After the waste is chopped into small lengths, the fibers are mechanically opened to create a shoddy fiber mix.

The shoddy fibers are refined with a Shirley machine to the correct length of fibers before they can be carded. After drawing and rowing, the fibers are transformed into a yarn using a spinning process.

Figure 16:
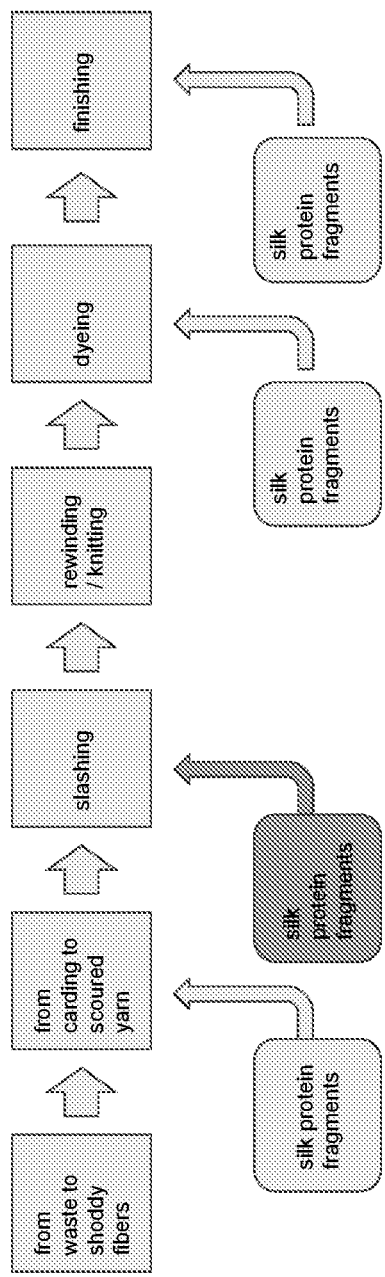
FIG. 16 is a flow chart showing an exemplary process for preparing yarn compositions of the disclosure.

FIG. 16 illustrates a flow chart of an exemplary process for preparing yarn samples of the disclosure.

Samples were prepared using the following:

Range of ingredients used:

Yarn waste:

Silk protein fragments:

Activated Silk 504-LS (comprising low molecular weight silk fibroin fragments (low-MW silk))

Activated Silk 505-LS (comprising medium molecular weight silk fibroin fragments (medium-MW silk))

A slashing machine was used for the application of silk protein fragments to the recycled yarn. A concentration range of 0%-0.1%-1%-50% 100% with AS-504-LS was tested with a wet pick up between 40%-100%. The silk protein fragment bath was maintained at a temperature of 50° C., while the drying was completed with forced air drying at 86° C. temperature.

Yarn Count Characterization

Figure 17:
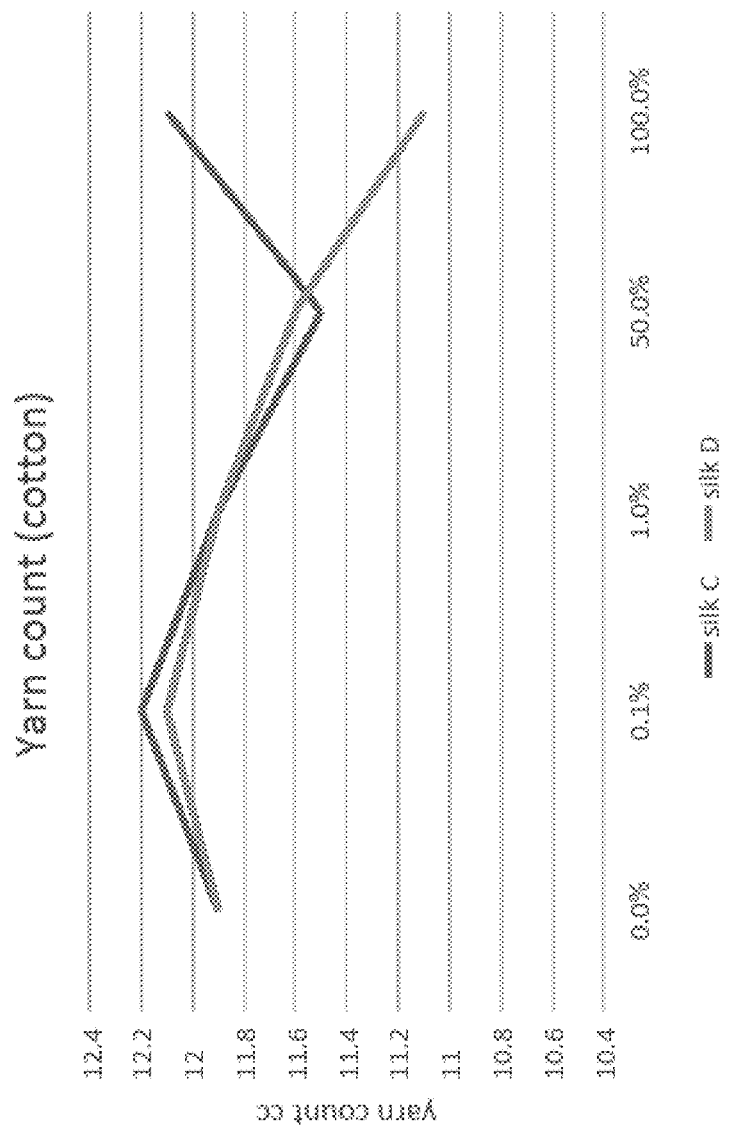
FIG. 17 is a graph of experimental data showing the yarn count of yarn of the disclosure. Silk c: Activated Silk 504-LS; silk d: Activated Silk 505-LS.

A proportional decrease in cotton yarn count with an increase of silk concentration demonstrated that SPFs were incorporated into the yarn. The experimental data for Activated Silk 504-LS (silk c) and Activated Silk 505-LS (silk d) is graphically depicted in FIG. 17.

Yarn Mechanical Properties Characterization

Figure 18:
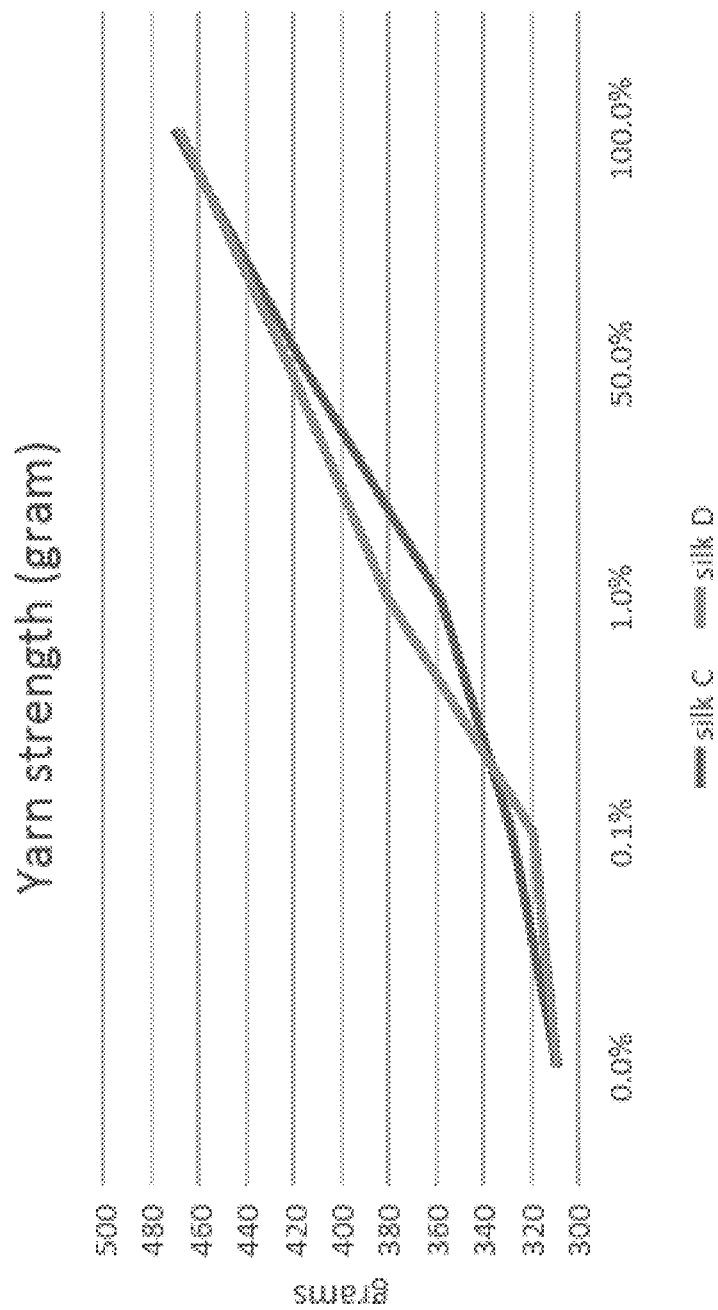
FIG. 18 is a graph of experimental data showing the yarn strength of yarn of the disclosure. Silk c: Activated Silk 504-LS; silk d: Activated Silk 505-LS.

A proportional increase in yarn strength was associated with SPF percentage concentration increase. At 100% silk concentration (100% concentration of 6% solution), yarn strength increased up to 52%. The experimental data for Activated Silk 504-LS (silk c) and Activated Silk 505-LS (silk d) is graphically depicted in FIG. 18.

Figure 19:
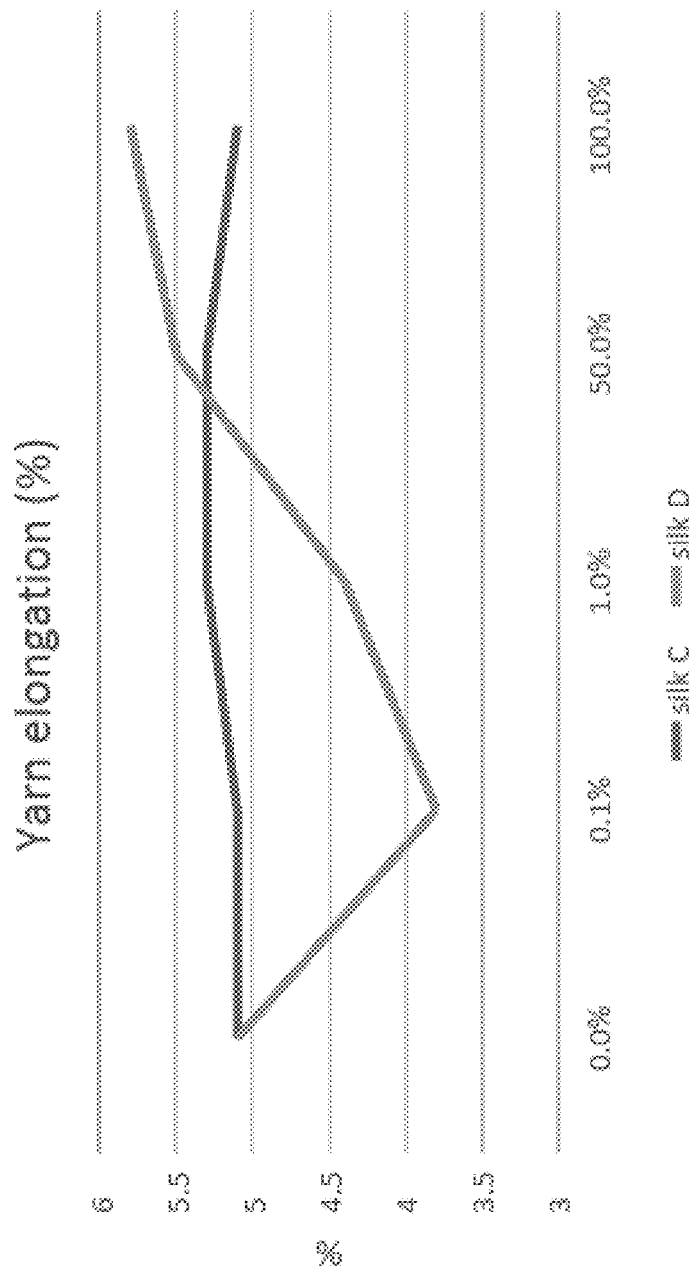
FIG. 19 is a graph of experimental data showing the yarn elongation of of yarn of the disclosure. Silk c: Activated Silk 504-LS; silk d: Activated Silk 505-LS.

Even with the increased with mechanical strength in yarn the yarn elongation is minimally impacted. The experimental data for Activated Silk 504-LS (silk c) and Activated Silk 505-LS (silk d) is graphically depicted in FIG. 19.

Yarn Evenness Characterization

Figure 20:
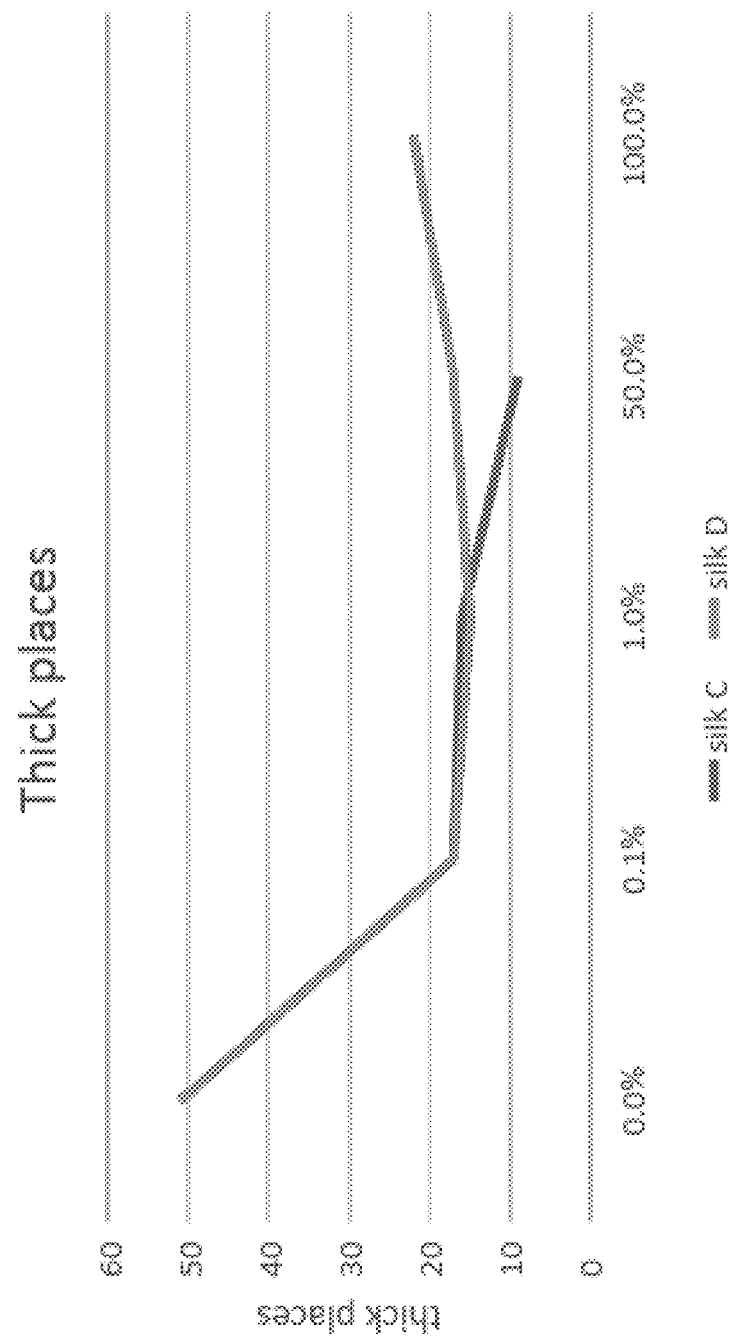
FIG. 20 is a graph of experimental data showing the yarn evenness characterization of thick places in the yarn of the disclosure. Silk c: Activated Silk 504-LS; silk d: Activated Silk 505-LS.
Figure 21:
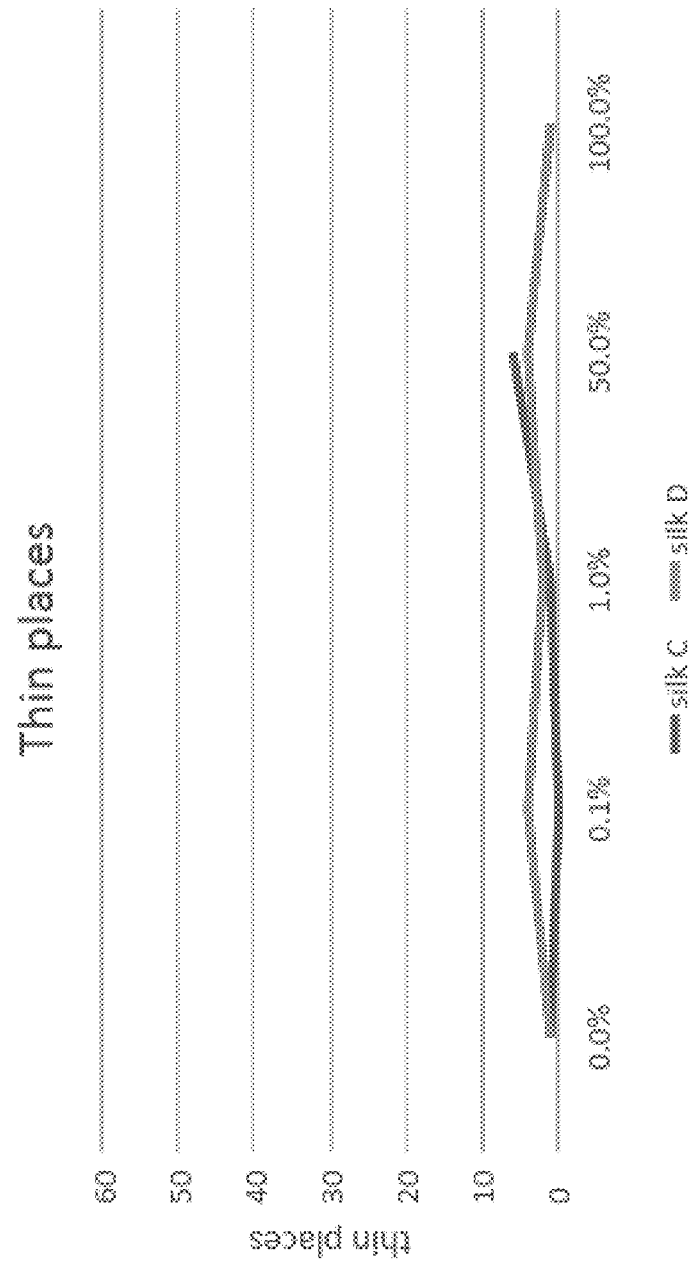
FIG. 21 is a graph of experimental data showing the yarn evenness characterization of thin places in the yarn of the disclosure. Silk c: Activated Silk 504-LS; silk d: Activated Silk 505-LS.

Depending on silk concentration the thick places in the yarn can be reduced up to 82%. To be noted that while thick places are reduced, the thin places section are maintained consistent. The experimental data for Activated Silk 504-LS (silk c) and Activated Silk 505-LS (silk d) is graphically depicted in FIG. 20 and FIG. 21.

Application on Recycled Yarn

Recycled material feedstock from weaving salvages was mainly composed of polyester, acrylic, polypropylene and nylon yarn.

Yarn Processing

Recycled material was selected at Material Returns according to recipe. The feedstock was chopped at Leigh Fibers. Shoddy fibers were processed into yarn at Gaston Technical Textile. The recycled yarn had a yarn count of approximately 1/11 cotton count.

The solution selected for the first experiment was Activated Silk 505-LS at 50% concentration (50% concentration of a 6% silk solution).

After the yarn has been coated, it was rewound to apply wax at a rate of 1-3% to aid the knitting process.

A 7 gg knitting machine was selected to prepare the first prototypes and to demonstrate compatibility of the yarn of the disclosure with the knitting process.

Figure 22:
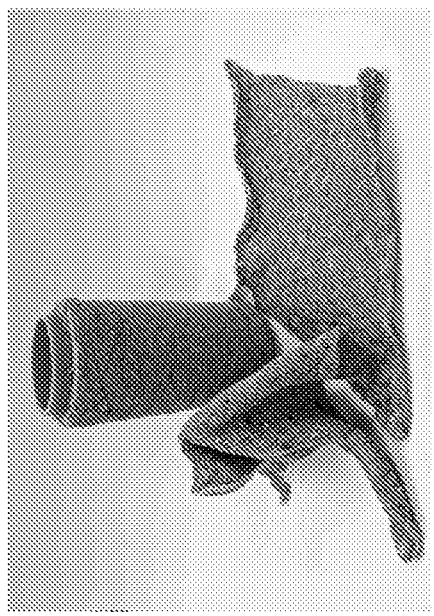
FIG. 22 is an image showing control yarn and knitted panels prepared from same.

6×6 inches panels with untreated control yarn and Activated Silk coated yarn were produced. FIG. 22 depicts an image of the control yarn and panels prepared from same.

Microscopy Analysis

Figure 23:
FIG. 23 is an image taken with a microscope showing the surface of a panel prepared from control yarn. Lens: MX(G)-5040Z; Normal: ×50; H-View: 0.239 inch; Resolve: 0.000 inch.
Figure 24:
FIG. 24 is an image taken with a microscope showing the surface of a panel prepared from yarn of the disclosure. Lens: MX(G)-5040Z; Normal: ×50; H-View: 0.239 inch; Resolve: 0.000 inch.

Analysis with a microscope of the knitted fabric samples characterized a surface fuzziness. Activated Silk treated yarn has less amount of fuzziness (FIG. 24) in comparison to the control yarn (FIG. 23).

Dyeing Compatibility

Figure 25:
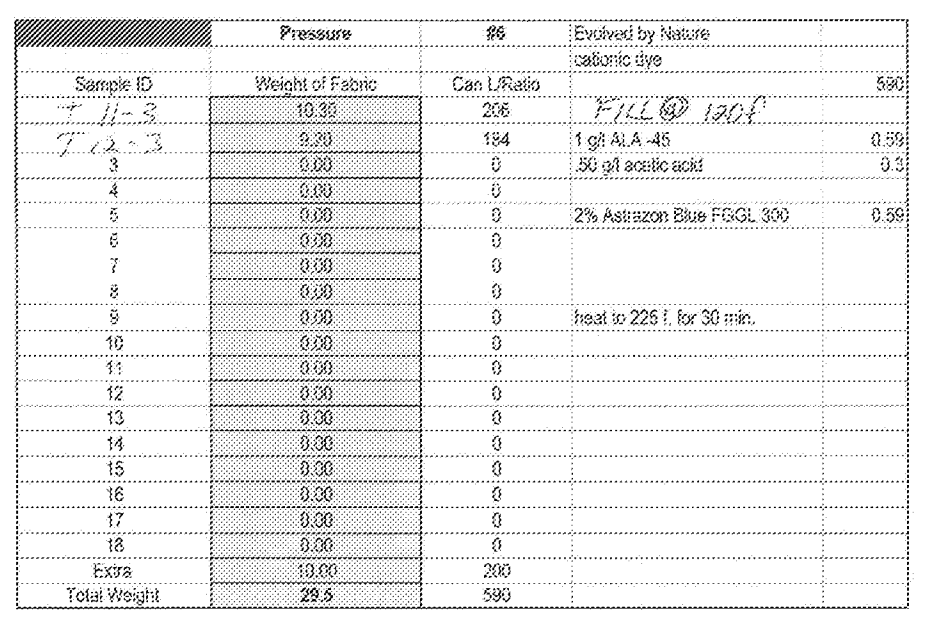

The knitted sample untreated control and Activated Silk treated are dyed with a cationic dye Astrazon Blue FGGL 300 from Dyestar according to the procedure shown in FIG. 25.

Fabric Color Characterization

Figure 26:
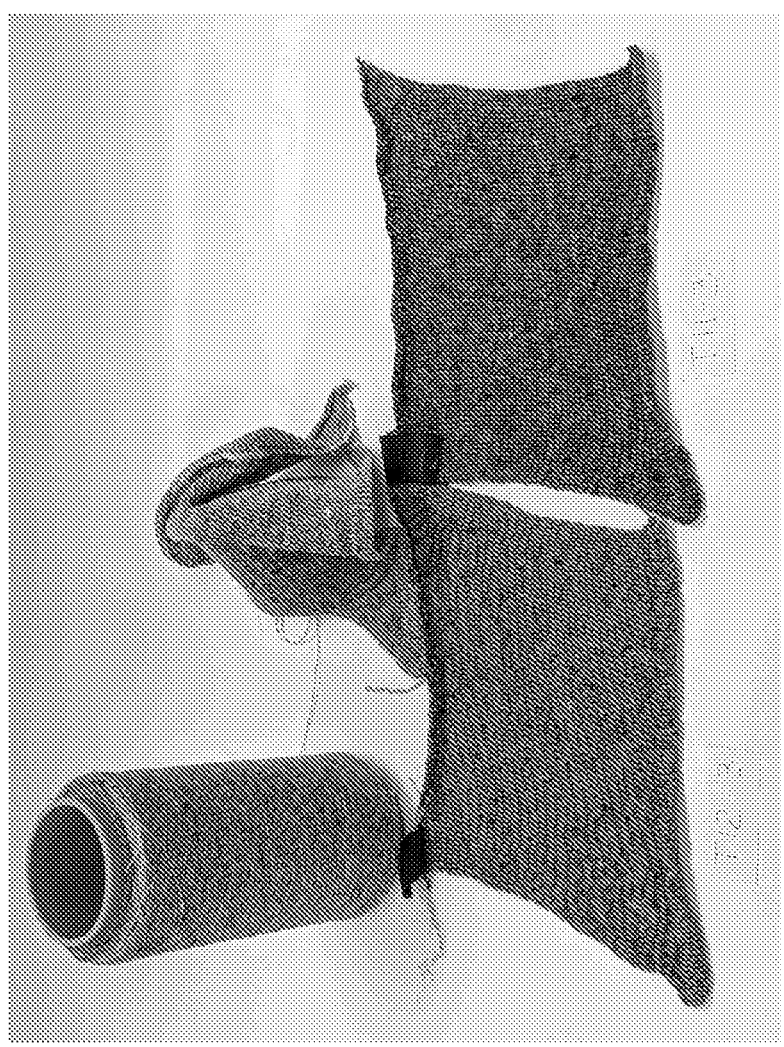
FIG. 26 is an image showing dyed panels prepared from control yarn (T-12-3) and yarn of the disclosure (T11-3).

The color was characterized with a Precise Color Reader model #WR-10QC. Tables 11 and 12 show the recordings. T11-3 refers to yarn treated with the Activated Silk 505-LS, and T12-3 refers to the untreated control. FIG. 26 shows images of the dyed panels.

TABLE 11

| Baseline recording of control sample | | | |
|---|---|---|---|
| | L | a | b |
| T12 control baseline | 53.01 | −0.22 | 4.54 |

TABLE 12

| Color difference in samples | | | | |
|---|---|---|---|---|
| cationic dye | ΔL | Δa | Δb | ΔE |
| T11-3 | −16.62 | 2.12 | −11.55 | 20.35 |
| T12-3 | −11.23 | 3.4 | −7.07 | 13.7 |

ΔL (L sample minus L standard) = difference in lightness and darkness (+ = lighter, − = darker)
Δa (a sample minus a standard) = difference in red and green (+ = redder, − = greener)
Δb (b sample minus b standard) = difference in yellow and blue (+ = yellower, − = bluer)

The invention claimed is:

1. A single or multilayered material comprising a plurality of fibers, filaments, powders, particles, or yarns, and a silk derived protein,
wherein the silk derived protein comprises silk fibroin proteins or fragments thereof having an average weight average molecular weight selected from between about 1 kDa and about 5 kDa, between about 5 kDa and about 10 kDa, between about 6 kDa and about 17 kDa, between about 10 kDa and about 15 kDa, between about 15 kDa and about 20 kDa, between about 17 kDa and about 39 kDa, between about 20 kDa and about 25 kDa, between about 25 kDa and about 30 kDa, between about 30 kDa and about 35 kDa, between about 35 kDa and about 40 kDa, between about 39 kDa and about 80 kDa, between about 40 kDa and about 45 kDa, between about 45 kDa and about 50 kDa, between about 60 kDa and about 100 kDa, and between about 80 kDa, and a polydispersity between 1 and about 5.

2. The material of claim 1, wherein the material is a bonded leather or a faux leather.

3. The material of claim 1, wherein the plurality of fibers, filaments, powders, particles, or yarns comprises natural or synthetic fibers, filaments, powders, particles, or yarns.

4. The material of claim 1, wherein the plurality of fibers, filaments, powders, particles, or yarns comprises one or more of natural leather, leather waste, recycled leather, fibrillated leather, grounded leather, synthetic leather, bovine wet blue shaving, bovine post-industrial waste, sheep post-industrial waste, silk, cotton, alpaca fleece, alpaca wool, lama fleece, lama wool, cotton, cashmere, sheep fiber, sheep fleece, sheep wool, byssus, chiengora, quiviut, yak, rabbit, lambswool, mohair wool, camel hair, angora wool, spider silk, silkworm silk, abaca fiber, coir fiber, flax fiber, jute fiber, kapok fiber, kenaf fiber, raffia fiber, bamboo fiber, hemp, modal fiber, pina, ramie, sisal, soy protein fiber, polyester, nylon, polyester-polyurethane copolymer, acrylic, anidex, aramid, fluorocarbon, modacrylic, novoloid, nylon, nytril, olefin, PBI, polycarbonate, polyester, rubber, saran, spandex, vinal vinvon, Lyocell, cellulose, non-woven or woven fibers or filaments, non-woven or woven mat or fabric, a woven, knitted, or crochet fabric, or any combination thereof.

5. The material of claim 1, wherein the silk derived protein comprises sericin.

6. The material of claim 5, wherein the silk fibroin proteins or fragments thereof do not spontaneously or gradually gelate and do not visibly change in color or turbidity when in an aqueous solution for at least 10 days prior to being formulated into the material.

7. The material of claim 1, wherein the relative amount of the plurality of fibers, filaments, powders, particles, or yarns in the material is between about 40% and about 95%.

8. The material of claim 1, wherein the relative amount of the silk derived protein in the material is between about 0.01% and about 25%.

9. The material of claim 1, further comprising one or more of a polymer, a pigment, a dye, a silicone, a polyurethane or any combinations thereof.

10. An article comprising a layer of the material of claim 1, the layer having a thickness between about 0.01 mm and about 10 mm.

11. An article comprising a layer of the material of claim 1, the layer having a thickness of about 1 mm, about 2 mm, about 3 mm, about 4 mm, about 5 mm, about 6, mm, about 7 mm, about 8 mm, about 9 mm, or about 10 mm.

12. The article of claim 10, further comprising one or more of a coating, a laminated film, or a combination thereof.

13. The article of claim 12, wherein the coating or the laminated film comprises silk fibroin proteins or fragments thereof having an average weight average molecular weight in a range selected from between about 1 kDa and about 5 kDa, between about 5 kDa and about 10 kDa, between about 6 kDa and about 17 kDa, between about 10 kDa and about 15 kDa, between about 15 kDa and about 20 kDa, between about 17 kDa and about 39 kDa, between about 20 kDa and about 25 kDa, between about 25 kDa and about 30 kDa, between about 30 kDa and about 35 kDa, between about 35 kDa and about 40 kDa, between about 39 kDa and about 80 kDa, between about 40 kDa and about 45 kDa, between about 45 kDa and about 50 kDa, between about 60 kDa and about 100 kDa, and between about 80 kDa and about 144 kDa, and a polydispersity between 1 and about 5.

14. A spun yarn comprising a plurality of fibers and a silk derived protein or fragments thereof, wherein a portion of the silk derived protein or fragments thereof are coated onto the plurality of fibers, wherein
the plurality of fibers are natural fibers, synthetic fibers, or a combination thereof, and
the silk derived protein or fragments thereof includes silk fibroin proteins or fragments thereof having an average weight average molecular weight in a range selected from between about 1 kDa and about 5 kDa, between about 5 kDa and about 10 kDa, between about 6 kDa and about 17 kDa, between about 10 kDa and about 15 kDa, between about 15 kDa and about 20 kDa, between about 17 kDa and about 39 kDa, between about 20 kDa and about 25 kDa, between about 25 kDa and about 30 kDa, between about 30 kDa and about 35 kDa, between about 35 kDa and about 40 kDa, between about 39 kDa and about 80 kDa, between about 40 kDa and about 45 kDa, between about 45 kDa and about 50 kDa, between about 60 kDa and about 100 kDa, and between about 80 kDa and about 144 kDa, and a polydispersity between 1 and about 5.

15. The spun yarn of claim 14, wherein the natural fibers include one or more of silk, cotton, alpaca fleece, alpaca wool, lama fleece, lama wool, cashmere, sheep fleece, sheep wool, alpaca fiber, lama fiber, sheep fiber, byssus, chiengora, quiviut, yak, rabbit, mohair wool, camel hair, angora wool, silkworm silk, abaca fiber, coir fiber, flax fiber, jute fiber, kapok fiber, kenaf fiber, raffia fiber, bamboo fiber, hemp, modal fiber, pina, ramie, sisal, and soy protein fiber.

16. The spun yarn of claim 14, wherein the synthetic fibers include one or more of polyester, nylon, polyester-polyurethane copolymer acrylic, anidex, aramid, fluorocarbon, modacrylic, novoloid, nylon, nytril, olefin, PBI, polycarbonate, rubber, saran, spandex, vinal vinvon.

17. The spun yarn of claim 14, wherein the silk derived protein includes sericin.

18. The spun yarn of claim 14, further comprising one or more slivers comprising the plurality of fibers.

* * * * *

SEQUENCE LISTING

<160> NUMBER OF SEQ ID NOS: 53

<210> SEQ ID NO 1
<211> LENGTH: 6
<212> TYPE: PRT
<213> ORGANISM: Artificial Sequence

```
<220> FEATURE:
<223> OTHER INFORMATION: Synthetic protein-like multiblock polymer
      hexapeptide
<220> FEATURE:
<221> NAME/KEY: MISC_FEATURE
<222> LOCATION: (6)..(6)
<223> OTHER INFORMATION: X can be is alanine, tyrosine, valine, or
      serine

<400> SEQUENCE: 1

Gly Ala Gly Ala Gly Xaa
1               5

<210> SEQ ID NO 2
<211> LENGTH: 6
<212> TYPE: PRT
<213> ORGANISM: Artificial Sequence
<220> FEATURE:
<223> OTHER INFORMATION: Synthetic protein-like multiblock polymer
      hexapeptide

<400> SEQUENCE: 2

Gly Ala Gly Ala Gly Ser
1               5

<210> SEQ ID NO 3
<211> LENGTH: 5
<212> TYPE: PRT
<213> ORGANISM: Artificial Sequence
<220> FEATURE:
<223> OTHER INFORMATION: Synthetic mammalian elastin

<400> SEQUENCE: 3

Val Pro Gly Val Gly
1               5

<210> SEQ ID NO 4
<211> LENGTH: 5
<212> TYPE: PRT
<213> ORGANISM: Artificial Sequence
<220> FEATURE:
<223> OTHER INFORMATION: Synthetic mammalian elastin

<400> SEQUENCE: 4

Gly Val Gly Val Pro
1               5

<210> SEQ ID NO 5
<211> LENGTH: 6
<212> TYPE: PRT
<213> ORGANISM: Artificial Sequence
<220> FEATURE:
<223> OTHER INFORMATION: Synthetic linker repetitve fragment

<400> SEQUENCE: 5

Gly Ala Gly Ala Gly Ser
1               5

<210> SEQ ID NO 6
<211> LENGTH: 44
<212> TYPE: PRT
<213> ORGANISM: Artificial Sequence
<220> FEATURE:
<223> OTHER INFORMATION: Synthetic protein

<400> SEQUENCE: 6

Ser Gly Phe Gly Pro Val Ala Asn Gly Gly Ser Gly Glu Ala Ser Ser
1               5                   10                  15
```

Glu Ser Asp Phe Gly Ser Ser Gly Phe Gly Pro Val Ala Asn Ala Ser
            20                  25                  30

Ser Gly Glu Ala Ser Ser Glu Ser Asp Phe Ala Gly
        35                  40

<210> SEQ ID NO 7
<211> LENGTH: 5
<212> TYPE: PRT
<213> ORGANISM: Artificial Sequence
<220> FEATURE:
<223> OTHER INFORMATION: Synthetic consensus peptide
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: MISC_FEATURE
<222> LOCATION: (5)..(6)
<223> OTHER INFORMATION: X can be alanine, serine, glycine, tyrocine, or
      proline

<400> SEQUENCE: 7

Gly Pro Gly Xaa Xaa
1               5

<210> SEQ ID NO 8
<211> LENGTH: 9
<212> TYPE: PRT
<213> ORGANISM: Artificial Sequence
<220> FEATURE:
<223> OTHER INFORMATION: Synthetic pro-resilin elastomeric protein

<400> SEQUENCE: 8

Gly Gly Arg Pro Ser Asp Thr Tyr Gly
1               5

<210> SEQ ID NO 9
<211> LENGTH: 9
<212> TYPE: PRT
<213> ORGANISM: Artificial Sequence
<220> FEATURE:
<223> OTHER INFORMATION: Synthetic pro-resilin elastomeric protein

<400> SEQUENCE: 9

Gly Gly Arg Pro Ser Ser Ser Tyr Gly
1               5

<210> SEQ ID NO 10
<211> LENGTH: 35
<212> TYPE: PRT
<213> ORGANISM: Araneus diadematus

<400> SEQUENCE: 10

Gly Ser Ser Ala Ala Ala Ala Ala Ala Ala Ala Ser Gly Pro Gly Gly
1               5                   10                  15

Tyr Gly Pro Glu Asn Gln Gly Pro Ser Gly Pro Gly Tyr Gly Pro
            20                  25                  30

Gly Gly Pro
        35

<210> SEQ ID NO 11
<211> LENGTH: 5
<212> TYPE: PRT
<213> ORGANISM: Artificial Sequence
<220> FEATURE:
<223> OTHER INFORMATION: Synthetic recombinant silk protein repetitve -continued

```
      unit

<400> SEQUENCE: 11

Gly Pro Gly Ala Ser
1               5

<210> SEQ ID NO 12
<211> LENGTH: 5
<212> TYPE: PRT
<213> ORGANISM: Artificial Sequence
<220> FEATURE:
<223> OTHER INFORMATION: Synthetic recombinant silk protein repetitve
      unit

<400> SEQUENCE: 12

Gly Pro Gly Ser Gly
1               5

<210> SEQ ID NO 13
<211> LENGTH: 5
<212> TYPE: PRT
<213> ORGANISM: Artificial Sequence
<220> FEATURE:
<223> OTHER INFORMATION: Synthetic recombinant silk protein repetitve
      unit

<400> SEQUENCE: 13

Gly Pro Gly Gly Tyr
1               5

<210> SEQ ID NO 14
<211> LENGTH: 5
<212> TYPE: PRT
<213> ORGANISM: Artificial Sequence
<220> FEATURE:
<223> OTHER INFORMATION: Synthetic recombinant silk protein repetitve
      unit

<400> SEQUENCE: 14

Gly Pro Gly Gly Pro
1               5

<210> SEQ ID NO 15
<211> LENGTH: 5
<212> TYPE: PRT
<213> ORGANISM: Artificial Sequence
<220> FEATURE:
<223> OTHER INFORMATION: Synthetic recombinant silk protein repetitve
      unit

<400> SEQUENCE: 15

Gly Pro Gly Gly Ala
1               5

<210> SEQ ID NO 16
<211> LENGTH: 5
<212> TYPE: PRT
<213> ORGANISM: Artificial Sequence
<220> FEATURE:
<223> OTHER INFORMATION: Synthetic recombinant silk protein repetitve
      unit

<400> SEQUENCE: 16

Gly Pro Gly Gln Gln
1               5

<210> SEQ ID NO 17
```

```
<211> LENGTH: 5
<212> TYPE: PRT
<213> ORGANISM: Artificial Sequence
<220> FEATURE:
<223> OTHER INFORMATION: Synthetic recombinant silk protein repetitve
      unit

<400> SEQUENCE: 17

Gly Pro Gly Gly Gly
1               5

<210> SEQ ID NO 18
<211> LENGTH: 5
<212> TYPE: PRT
<213> ORGANISM: Artificial Sequence
<220> FEATURE:
<223> OTHER INFORMATION: Synthetic recombinant silk protein repetitve
      unit

<400> SEQUENCE: 18

Gly Pro Gly Gln Gly
1               5

<210> SEQ ID NO 19
<211> LENGTH: 5
<212> TYPE: PRT
<213> ORGANISM: Artificial Sequence
<220> FEATURE:
<223> OTHER INFORMATION: Synthetic recombinant silk protein repetitve
      unit

<400> SEQUENCE: 19

Gly Pro Gly Gly Ser
1               5

<210> SEQ ID NO 20
<211> LENGTH: 5
<212> TYPE: PRT
<213> ORGANISM: Artificial Sequence
<220> FEATURE:
<223> OTHER INFORMATION: Synthetic recombinant silk protein repetitve
      unit

<400> SEQUENCE: 20

Ala Ala Ala Ala Ala
1               5

<210> SEQ ID NO 21
<211> LENGTH: 6
<212> TYPE: PRT
<213> ORGANISM: Artificial Sequence
<220> FEATURE:
<223> OTHER INFORMATION: Synthetic recombinant silk protein repetitve
      unit

<400> SEQUENCE: 21

Ala Ala Ala Ala Ala Ala
1               5

<210> SEQ ID NO 22
<211> LENGTH: 7
<212> TYPE: PRT
<213> ORGANISM: Artificial Sequence
<220> FEATURE:
<223> OTHER INFORMATION: Synthetic recombinant silk protein repetitve
      unit

<400> SEQUENCE: 22
```

Ala Ala Ala Ala Ala Ala Ala
1               5

<210> SEQ ID NO 23
<211> LENGTH: 8
<212> TYPE: PRT
<213> ORGANISM: Artificial Sequence
<220> FEATURE:
<223> OTHER INFORMATION: Synthetic recombinant silk protein repetitve
      unit

<400> SEQUENCE: 23

Ala Ala Ala Ala Ala Ala Ala Ala
1               5

<210> SEQ ID NO 24
<211> LENGTH: 9
<212> TYPE: PRT
<213> ORGANISM: Artificial Sequence
<220> FEATURE:
<223> OTHER INFORMATION: Synthetic recombinant silk protein repetitve
      unit

<400> SEQUENCE: 24

Ala Ala Ala Ala Ala Ala Ala Ala Ala
1               5

<210> SEQ ID NO 25
<211> LENGTH: 10
<212> TYPE: PRT
<213> ORGANISM: Artificial Sequence
<220> FEATURE:
<223> OTHER INFORMATION: Synthetic recombinant silk protein repetitve
      unit

<400> SEQUENCE: 25

Ala Ala Ala Ala Ala Ala Ala Ala Ala Ala
1               5                   10

<210> SEQ ID NO 26
<211> LENGTH: 9
<212> TYPE: PRT
<213> ORGANISM: Artificial Sequence
<220> FEATURE:
<223> OTHER INFORMATION: Synthetic recombinant silk protein repetitve
      unit

<400> SEQUENCE: 26

Gly Gly Arg Pro Ser Asp Thr Tyr Gly
1               5

<210> SEQ ID NO 27
<211> LENGTH: 9
<212> TYPE: PRT
<213> ORGANISM: Artificial Sequence
<220> FEATURE:
<223> OTHER INFORMATION: Synthetic recombinant silk protein repetitve
      unit

<400> SEQUENCE: 27

Gly Gly Arg Pro Ser Ser Ser Tyr Gly
1               5

<210> SEQ ID NO 28
<211> LENGTH: 24
<212> TYPE: PRT
<213> ORGANISM: Artificial Sequence
<220> FEATURE:

<223> OTHER INFORMATION: Synthetic recombinant silk protein repetitve
       unit

<400> SEQUENCE: 28

Gly Pro Tyr Gly Pro Gly Ala Ser Ala Ala Ala Ala Ala Gly Gly
1               5                   10                  15

Tyr Gly Pro Gly Ser Gly Gln Gln
            20

<210> SEQ ID NO 29
<211> LENGTH: 35
<212> TYPE: PRT
<213> ORGANISM: Artificial Sequence
<220> FEATURE:
<223> OTHER INFORMATION: Synthetic recombinant silk protein repetitve
       unit

<400> SEQUENCE: 29

Gly Ser Ser Ala Ala Ala Ala Ala Ala Ala Ser Gly Pro Gly Gly
1               5                   10                  15

Tyr Gly Pro Glu Asn Gln Gly Pro Ser Gly Pro Gly Tyr Gly Pro
            20                  25                  30

Gly Gly Pro
        35

<210> SEQ ID NO 30
<211> LENGTH: 20
<212> TYPE: PRT
<213> ORGANISM: Artificial Sequence
<220> FEATURE:
<223> OTHER INFORMATION: Synthetic recombinant silk protein repetitve
       unit

<400> SEQUENCE: 30

Gly Pro Gly Gln Gln Gly Pro Gly Gln Gln Gly Pro Gly Gln Gln Gly
1               5                   10                  15

Pro Gly Gln Gln
            20

<210> SEQ ID NO 31
<211> LENGTH: 27
<212> TYPE: PRT
<213> ORGANISM: Artificial Sequence
<220> FEATURE:
<223> OTHER INFORMATION: Synthetic recombinant silk protein repetitve
       unit

<400> SEQUENCE: 31

Gly Pro Gly Gly Ala Gly Gly Pro Tyr Gly Pro Gly Ala Gly Gly
1               5                   10                  15

Pro Tyr Gly Pro Gly Gly Ala Gly Gly Pro Tyr
            20                  25

<210> SEQ ID NO 32
<211> LENGTH: 28
<212> TYPE: PRT
<213> ORGANISM: Artificial Sequence
<220> FEATURE:
<223> OTHER INFORMATION: Synthetic recombinant silk protein repetitve
       unit

<400> SEQUENCE: 32

Gly Gly Thr Thr Ile Ile Glu Asp Leu Asp Ile Thr Ile Asp Gly Ala
1               5                   10                  15

```
Asp Gly Pro Ile Thr Ile Ser Glu Glu Leu Thr Ile
            20                  25
```

<210> SEQ ID NO 33
<211> LENGTH: 34
<212> TYPE: PRT
<213> ORGANISM: Artificial Sequence
<220> FEATURE:
<223> OTHER INFORMATION: Synthetic recombinant silk protein repetitve
      unit

<400> SEQUENCE: 33

```
Pro Gly Ser Ser Ala Ala Ala Ala Ala Ala Ala Ser Gly Pro Gly
1               5                   10                  15

Gln Gly Gln Gly Gln Gly Gln Gly Gln Gly Gly Arg Pro Ser Asp Thr
            20                  25                  30

Tyr Gly
```

<210> SEQ ID NO 34
<211> LENGTH: 39
<212> TYPE: PRT
<213> ORGANISM: Artificial Sequence
<220> FEATURE:
<223> OTHER INFORMATION: Synthetic recombinant silk protein repetitve
      unit

<400> SEQUENCE: 34

```
Ser Ala Ala Ala Ala Ala Ala Ala Ala Gly Pro Gly Gly Gly Asn Gly
1               5                   10                  15

Gly Arg Pro Ser Asp Thr Tyr Gly Ala Pro Gly Gly Gly Asn Gly Gly
            20                  25                  30

Arg Pro Ser Ser Ser Tyr Gly
        35
```

<210> SEQ ID NO 35
<211> LENGTH: 18
<212> TYPE: PRT
<213> ORGANISM: Artificial Sequence
<220> FEATURE:
<223> OTHER INFORMATION: Synthetic recombinant silk protein repetitve
      unit

<400> SEQUENCE: 35

```
Gly Gly Ala Gly Gly Ala Gly Gly Ala Gly Gly Ser Gly Gly Ala Gly
1               5                   10                  15

Gly Ser
```

<210> SEQ ID NO 36
<211> LENGTH: 30
<212> TYPE: PRT
<213> ORGANISM: Artificial Sequence
<220> FEATURE:
<223> OTHER INFORMATION: Synthetic recombinant silk protein repetitve
      unit

<400> SEQUENCE: 36

```
Gly Pro Gly Gly Ala Gly Pro Gly Gly Tyr Gly Pro Gly Gly Ser Gly
1               5                   10                  15

Pro Gly Gly Tyr Gly Pro Gly Gly Ser Gly Pro Gly Gly Tyr
            20                  25                  30
```

<210> SEQ ID NO 37
<211> LENGTH: 24
<212> TYPE: PRT

```
<213> ORGANISM: Artificial Sequence
<220> FEATURE:
<223> OTHER INFORMATION: Synthetic recombinant silk protein repetitve
      unit

<400> SEQUENCE: 37

Gly Pro Tyr Gly Pro Gly Ala Ser Ala Ala Ala Ala Ala Ala Gly Gly
1               5                   10                  15

Tyr Gly Pro Gly Cys Gly Gln Gln
            20

<210> SEQ ID NO 38
<211> LENGTH: 24
<212> TYPE: PRT
<213> ORGANISM: Artificial Sequence
<220> FEATURE:
<223> OTHER INFORMATION: Synthetic recombinant silk protein repetitve
      unit

<400> SEQUENCE: 38

Gly Pro Tyr Gly Pro Gly Ala Ser Ala Ala Ala Ala Ala Ala Gly Gly
1               5                   10                  15

Tyr Gly Pro Gly Lys Gly Gln Gln
            20

<210> SEQ ID NO 39
<211> LENGTH: 35
<212> TYPE: PRT
<213> ORGANISM: Artificial Sequence
<220> FEATURE:
<223> OTHER INFORMATION: Synthetic recombinant silk protein repetitve
      unit

<400> SEQUENCE: 39

Gly Ser Ser Ala Ala Ala Ala Ala Ala Ala Ser Gly Pro Gly Gly
1               5                   10                  15

Tyr Gly Pro Glu Asn Gln Gly Pro Cys Gly Pro Gly Tyr Gly Pro
            20                  25                  30

Gly Gly Pro
        35

<210> SEQ ID NO 40
<211> LENGTH: 35
<212> TYPE: PRT
<213> ORGANISM: Artificial Sequence
<220> FEATURE:
<223> OTHER INFORMATION: Synthetic recombinant silk protein repetitve
      unit

<400> SEQUENCE: 40

Gly Ser Ser Ala Ala Ala Ala Ala Ala Ala Ser Gly Pro Gly Gly
1               5                   10                  15

Tyr Gly Pro Lys Asn Gln Gly Pro Ser Gly Pro Gly Tyr Gly Pro
            20                  25                  30

Gly Gly Pro
        35

<210> SEQ ID NO 41
<211> LENGTH: 35
<212> TYPE: PRT
<213> ORGANISM: Artificial Sequence
<220> FEATURE:
<223> OTHER INFORMATION: Synthetic recombinant silk protein repetitve
      unit
```

```
<400> SEQUENCE: 41

Gly Ser Ser Ala Ala Ala Ala Ala Ala Ala Ser Gly Pro Gly Gly
1               5                   10                  15

Tyr Gly Pro Lys Asn Gln Gly Pro Ser Gly Pro Gly Gly Tyr Gly Pro
                20                  25                  30

Gly Gly Pro
        35

<210> SEQ ID NO 42
<211> LENGTH: 15
<212> TYPE: PRT
<213> ORGANISM: Artificial Sequence
<220> FEATURE:
<223> OTHER INFORMATION: Synthetic silk protein-like multiblock peptide
<220> FEATURE:
<221> NAME/KEY: MISC_FEATURE
<222> LOCATION: (1)..(1)
<223> OTHER INFORMATION: X can be tyrosine or glutamine
<220> FEATURE:
<221> NAME/KEY: MISC_FEATURE
<222> LOCATION: (4)..(4)
<223> OTHER INFORMATION: X can be tyrosine or glutamine
<220> FEATURE:
<221> NAME/KEY: MISC_FEATURE
<222> LOCATION: (8)..(8)
<223> OTHER INFORMATION: X can be tyrosine or glutamine

<400> SEQUENCE: 42

Xaa Gly Gly Xaa Gly Ala Gly Xaa Gly Ala Gly Ala Gly Ala Gly
1               5                   10                  15

<210> SEQ ID NO 43
<211> LENGTH: 14
<212> TYPE: PRT
<213> ORGANISM: Artificial Sequence
<220> FEATURE:
<223> OTHER INFORMATION: Synthetic silk protein-like multiblock peptide
<220> FEATURE:
<221> NAME/KEY: MISC_FEATURE
<222> LOCATION: (11)..(12)
<223> OTHER INFORMATION: X can be amino acid sequence GPS or GPG

<400> SEQUENCE: 43

Gly Pro Gly Gly Tyr Gly Pro Gly Gln Gln Xaa Xaa Ser Ala
1               5                   10

<210> SEQ ID NO 44
<211> LENGTH: 11
<212> TYPE: PRT
<213> ORGANISM: Artificial Sequence
<220> FEATURE:
<223> OTHER INFORMATION: Synthetic silk protein-like multiblock peptide
<220> FEATURE:
<221> NAME/KEY: MISC_FEATURE
<222> LOCATION: (8)..(8)
<223> OTHER INFORMATION: X can be tyrosine, glutamine, or alanine

<400> SEQUENCE: 44

Gly Arg Gly Ala Ala Gly Gly Xaa Gly Ala Ala
1               5                   10

<210> SEQ ID NO 45
<211> LENGTH: 15
<212> TYPE: PRT
<213> ORGANISM: Artificial Sequence
<220> FEATURE:
<223> OTHER INFORMATION: Synthetic silk protein-like multiblock peptide
<220> FEATURE:
<221> NAME/KEY: MISC_FEATURE
```

```
<222> LOCATION: (1)..(1)
<223> OTHER INFORMATION: X can be tyrosine or glutamine
<220> FEATURE:
<221> NAME/KEY: MISC_FEATURE
<222> LOCATION: (4)..(4)
<223> OTHER INFORMATION: X can be tyrosine or glutamine
<220> FEATURE:
<221> NAME/KEY: MISC_FEATURE
<222> LOCATION: (8)..(8)
<223> OTHER INFORMATION: X can be tyrosine or glutamine

<400> SEQUENCE: 45

Xaa Gly Gly Xaa Gly Ala Gly Xaa Gly Ala Gly Ala Gly Ala Gly
1               5                   10                  15

<210> SEQ ID NO 46
<211> LENGTH: 8
<212> TYPE: PRT
<213> ORGANISM: Artificial Sequence
<220> FEATURE:
<223> OTHER INFORMATION: Synthetic modified amino acid sequence

<400> SEQUENCE: 46

Gly Cys Gly Gly Gly Gly Gly Gly
1               5

<210> SEQ ID NO 47
<211> LENGTH: 8
<212> TYPE: PRT
<213> ORGANISM: Artificial Sequence
<220> FEATURE:
<223> OTHER INFORMATION: Synthetic modified amino acid sequence

<400> SEQUENCE: 47

Gly Lys Gly Gly Gly Gly Gly Gly
1               5

<210> SEQ ID NO 48
<211> LENGTH: 14
<212> TYPE: PRT
<213> ORGANISM: Artificial Sequence
<220> FEATURE:
<223> OTHER INFORMATION: Synthetic modified amino acid sequence

<400> SEQUENCE: 48

Gly Cys Gly Gly Ser Gly Gly Gly Gly Ser Gly Gly Gly Gly
1               5                   10

<210> SEQ ID NO 49
<211> LENGTH: 13
<212> TYPE: PRT
<213> ORGANISM: Artificial Sequence
<220> FEATURE:
<223> OTHER INFORMATION: Synthetic modified amino acid sequence

<400> SEQUENCE: 49

Gly Lys Gly Gly Gly Gly Gly Gly Ser Gly Gly Gly Gly
1               5                   10

<210> SEQ ID NO 50
<211> LENGTH: 13
<212> TYPE: PRT
<213> ORGANISM: Artificial Sequence
<220> FEATURE:
<223> OTHER INFORMATION: Synthetic modified amino acid sequence

<400> SEQUENCE: 50

Gly Cys Gly Gly Gly Gly Gly Gly Ser Gly Gly Gly Gly
```

```
<210> SEQ ID NO 51
<211> LENGTH: 33
<212> TYPE: PRT
<213> ORGANISM: Araneus diadematus

<400> SEQUENCE: 51

Gly Ser Ser Ala Ala Ala Ala Ala Ala Ala Ser Gly Pro Gly Gln
1               5                   10                  15

Gly Gln Gly Gln Gly Gln Gly Gln Gly Gly Arg Pro Ser Asp Thr Tyr
                20                  25                  30

Gly

<210> SEQ ID NO 52
<211> LENGTH: 39
<212> TYPE: PRT
<213> ORGANISM: Araneus diadematus

<400> SEQUENCE: 52

Ser Ala Ala Ala Ala Ala Ala Ala Ala Gly Pro Gly Gly Gly Asn Gly
1               5                   10                  15

Gly Arg Pro Ser Asp Thr Tyr Gly Ala Pro Gly Gly Gly Asn Gly Gly
                20                  25                  30

Arg Pro Ser Ser Ser Tyr Gly
        35

<210> SEQ ID NO 53
<211> LENGTH: 30
<212> TYPE: PRT
<213> ORGANISM: Artificial Sequence
<220> FEATURE:
<223> OTHER INFORMATION: Synthetic recombinant silk protein repetitve
      fragment

<400> SEQUENCE: 53

Gly Pro Gly Gly Ala Gly Pro Gly Gly Tyr Gly Pro Gly Gly Ser Gly
1               5                   10                  15

Pro Gly Gly Tyr Gly Pro Gly Gly Ser Gly Pro Gly Gly Tyr
                20                  25                  30
```